(12) United States Patent
Da Silva Conceicao et al.

(10) Patent No.: US 11,104,911 B2
(45) Date of Patent: *Aug. 31, 2021

(54) **EMBRYO-PREFERRED *ZEA MAYS* PROMOTERS AND METHODS OF USE**

(71) Applicant: PIONEER HI-BRED INTERNATIONAL, INC., Johnston, IA (US)

(72) Inventors: Alexandre Da Silva Conceicao, Wilmington, DE (US); William James Gordon-Kamm, Urbandale, IA (US); Theodore Mitchell Klein, Wilmington, DE (US); Carlos M. La Rota, Johnston, IA (US); Keith S. Lowe, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

This patent is subject to a terminal disclaimer.

(21) Appl. No.: 16/062,646

(22) PCT Filed: Aug. 26, 2016

(86) PCT No.: PCT/US2016/049128
§ 371 (c)(1),
(2) Date: Jun. 15, 2018

(87) PCT Pub. No.: WO2017/112006
PCT Pub. Date: Jun. 29, 2017

(65) Prior Publication Data
US 2018/0371480 A1    Dec. 27, 2018

Related U.S. Application Data

(60) Provisional application No. 62/271,230, filed on Dec. 22, 2015.

(51) Int. Cl.
*C12N 15/82*    (2006.01)

(52) U.S. Cl.
CPC ............................... *C12N 15/8234* (2013.01)

(58) Field of Classification Search
None
See application file for complete search history.

(56) References Cited

U.S. PATENT DOCUMENTS

| | | | |
|---|---|---|---|
| 8,022,275 B2 * | 9/2011 | Crane | C12N 15/8233 435/320.1 |
| 2006/0123505 A1 | 6/2006 | Kikuchi et al. | |
| 2011/0167516 A1 * | 7/2011 | Gordon-Kamm | C12N 15/8213 800/278 |
| 2013/0152231 A1 * | 6/2013 | Wang | C07K 14/415 800/287 |
| 2013/0254935 A1 * | 9/2013 | Gordon-Kamm | C07K 14/415 800/281 |
| 2015/0096083 A1 | 4/2015 | Wu et al. | |
| 2017/0121722 A1 * | 5/2017 | Anand | A01H 4/008 |
| 2021/0062203 A1 * | 3/2021 | Anand | C12N 15/8205 |

FOREIGN PATENT DOCUMENTS

| | | |
|---|---|---|
| WO | 2003/008540 A2 | 1/2003 |
| WO | 2013/005152 A1 | 1/2013 |

OTHER PUBLICATIONS

Canevascini et al. Tissue-specific expression and promoter analysis of the Tobacco Ltp1 gene. (1996) Plant Physiology; vol. 112; pp. 513-524 (Year: 1996).*
Substantial—Definition (2019) downloaded from https://www.google.com/search?source=hp&ei=F6m4Xb2FN4uo_QaNYHADg&q=definition+substantial&oq=definition+substantial&gs_l=psyab.3..0l2j0i22i30l8.674.6068..10716...0.0..0.138.1389.22j1....2..0....1..gwswiz.....6..0i362i308i154i357j0i131j0i 10.tBbKSCe (Year: 2019).*
Lv et al. Construction vascular-specific expression bi-directional promoters in plants. (2009) J. of Biotech.; vol. 141; pp. 104-108 (Year: 2009).*
Federico et al. The complex developmental expression of a novel stress-responsive barley Ltp gene is determined by a shortened promoter sequence. (2005) Plant Molecular Biology; vol. 57; pp. 35-51 (Year: 2005).*
Benfey et al. The cauliflower mosaic virus 35S promoter: combinatorial regulation of transcription in plants. (1990) Science; vol. 250; pp. 959-966 (Year: 1990).*
Kim et al. A 20 nucleotide upstream element is essential for the nopaline synthase (nos) promoter activity. (1994) Plant Mol. Biol.; vol. 24; pp. 105-117 (Year: 1994).*
Alexandrov et al. *Zea mays* clone 1062364 nonspecific lipid-transfer protein 2. (2008) GenBank Accession EU951912; p. 1 of 1. (Year: 2008).*
Wilson, R.K. *Zea mays* cultivar B73 chromosome 10 clone CH201-210M14. (2014) GenBank Accession AC198290; pp. 1-46 (Year: 2014).*
Database XP-002763124, Accession: AC198290, "*Zea mays* chromosome 10 clone CH201-210M14", Feb. 16, 2007 (Feb. 16, 2007).
International Search Report and Written Opinion, International Application No. PCT/US2016/049128 dated Jan. 30, 2017.

\* cited by examiner

*Primary Examiner* — Cathy Kingdon Worley

(57) ABSTRACT

Compositions and methods for regulating expression of heterologous nucleotide sequences in a plant are provided. Compositions include nucleotide sequences for regulatory regions. Phospholipid transfer protein (PLTP) promoters from maize are provided. Also provided is a method for expressing a heterologous nucleotide sequence in a plant using a promoter sequence, such as a maize PLTP promoter, disclosed herein. DNA constructs comprising a promoter operably linked to a heterologous nucleotide sequence of interest are also provided.

39 Claims, 26 Drawing Sheets
Specification includes a Sequence Listing.

EMBRYO-PREFERRED ZEA MAYS PROMOTERS AND METHODS OF USE

CROSS-REFERENCE TO RELATED APPLICATIONS

This application is the 371 national stage entry of International Application Number PCT/US2016/049128 filed on Aug. 26, 2016, which claims priority to U.S. Provisional Application No. 62/271,230, filed Dec. 22, 2015, which are hereby incorporated herein in their entirety by reference.

REFERENCE TO SEQUENCE LISTING SUBMITTED ELECTRONICALLY

The official copy of the sequence listing is submitted electronically via EFS-Web as an ASCII formatted sequence listing with a file named "20181221_6870USPCTSubtituteSequenceListing.TXT" created on Dec. 21, 2018, and having a size of 164 kilobytes. The sequence listing contained in this ASCII formatted document is part of the specification and is herein incorporated by reference in its entirety.

FIELD OF THE DISCLOSURE

The present disclosure relates to the field of plant molecular biology, more particularly to regulation of gene expression in plants.

BACKGROUND OF THE DISCLOSURE

Expression of heterologous DNA sequences in a plant host is dependent upon the presence of operably linked regulatory elements that are functional within the plant host. Choice of the promoter sequence will determine when and where within the organism the heterologous DNA sequence is expressed. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from the core promoter sequence may be included in the expression constructs of transformation vectors to bring about varying levels of expression of heterologous nucleotide sequences in a plant, such as a transgenic plant.

Frequently it is desirable to express a DNA sequence in particular tissues or organs of a plant. For example, use of tissue-preferred promoters operably linked to morphogenic genes that promote cell proliferation are useful for efficient recovery of transgenic events during the transformation process. Such tissue-preferred promoters also have utility in expressing trait genes and/or pathogen-resistance proteins in the desired plant tissue in order to enhance plant yield and resistance to pathogens. Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Additionally, it may be desirable to express a DNA sequence in plant tissues that are in a particular growth or developmental phase such as, for example, cell division or elongation. Such a DNA sequence may be used to promote or inhibit plant growth processes, thereby affecting the growth rate or architecture of the plant.

Isolation and characterization of tissue-preferred promoters, particularly promoters that can serve as regulatory elements for the controlled expression of growth stimulating genes are needed.

BRIEF SUMMARY OF THE DISCLOSURE

Compositions and methods for regulating gene expression in a plant are provided. Compositions comprise novel nucleotide sequences for a promoter active in tissues before, during, and after pollination. More particularly, the promoters confer tissue-preferred expression. More particularly, Phospholipid Transfer Protein (PLTP) promoters are provided herein. Certain aspects of the disclosure comprise the nucleotide sequence set forth in at least one of SEQ ID NOS: 1-27 and fragments of the nucleotide sequence set forth in at least one of SEQ ID NOS: 1-27. Also included are functional fragments of the sequence set forth in at least one of SEQ ID NOS: 1-27, which drive tissue-preferred expression of an operably-linked nucleotide sequence. Aspects of the disclosure also include DNA constructs comprising a promoter, such as a PLTP promoter, operably linked to a heterologous nucleotide sequence of interest, wherein the promoter is capable of driving expression of the nucleotide sequence in a plant cell and the promoter comprises one of the nucleotide sequences disclosed herein. Aspects of the disclosure further provide expression vectors, and plants or plant cells having stably incorporated into their genomes a DNA construct as is described above. Additionally, compositions include seed of such plants.

Further aspects comprise a means for selectively expressing a nucleotide sequence in a plant, comprising transforming a plant cell with a DNA construct, and regenerating a transformed plant from said plant cell, said DNA construct comprising a promoter of the disclosure, such as a PLTP promoter, and a heterologous nucleotide sequence operably linked to the promoter, wherein the promoter initiates transcription of the nucleotide sequence in specific tissues or cell types such as the embryo and leaf cells, while precluding expression in such organs as roots, tassel, and the immature ear. In this manner, the promoter sequences are useful for controlling the expression of operably linked coding sequences in a tissue-preferred manner.

Downstream from the transcriptional initiation region of the promoter is sequence of interest is positioned that produces a modified phenotype in the plant. Such modification includes modulating the production of an endogenous product as to amount, relative distribution, or the like, or production of an exogenous expression product, to provide for a novel or modulated function or product in the plant. For example, a heterologous nucleotide sequence that encodes a gene product that confers resistance or tolerance to herbicide, salt, cold, drought, pathogen, nematodes or insects is encompassed.

In a further aspect, a method for modulating expression of a gene in a stably transformed plant is provided, comprising the steps of (a) transforming a plant cell with a DNA construct comprising the promoter of the disclosure operably linked to at least one nucleotide sequence; (b) growing the plant cell under plant growing conditions and (c) regenerating a stably transformed plant from the plant cell wherein expression of the linked nucleotide sequence alters the phenotype of the plant.

In an aspect, the present disclosure provides a nucleic acid molecule comprising a tissue preferred regulatory element having a nucleotide sequence selected from the group consisting of (a) a sequence with at least 70% identity to at least one of SEQ ID NOS: 1-27; (b) a fragment or variant of the nucleotide sequence of at least one of SEQ ID NOS: 1-27, wherein the sequence initiates transcription in a plant cell; (c) a polynucleotide which is complementary to the polynucleotide of (a) or (b); and (d) a polynucleotide that comprises at least 100 contiguous nucleotides of a sequence selected from the group consisting of at least one of SEQ ID NOS: 1-27; and wherein the regulatory element is operably linked to a heterologous polynucleotide of interest. In an aspect, an expression cassette comprising the regulatory element of the disclosed nucleic acid molecule comprising a tissue preferred regulatory element is provided. In an aspect, a vector comprising the expression cassette is provided. In an aspect, a plant cell comprising the expression cassette is provided. In an aspect, the expression cassette is stably integrated into the genome of the plant cell. In an aspect, the expression cassette is transiently expressed in the plant cell. In an aspect, the plant cell is from a monocot or a dicot. In an aspect, the monocot or the dicot is selected from the group consisting of: maize, sorghum, rice, soybean, wheat, cotton, and Brassica. In an aspect, a plant comprising the expression cassette is provided. In an aspect, the plant is a monocot or a dicot. In an aspect, the monocot or the dicot is selected from the group consisting of: maize, sorghum, rice, soybean, wheat, cotton, and Brassica. In an aspect, the expression cassette is stably incorporated into the genome of the plant. In an aspect, the expression cassette is transiently expressed in the plant cell. In an aspect, a seed of the plant is provided, wherein the seed comprises the expression cassette. In an aspect, the heterologous polynucleotide of interest encodes a transcription factor. In an aspect, the heterologous polynucleotide encodes a gene product that confers drought tolerance, cold tolerance, herbicide tolerance, pathogen resistance, or insect resistance. In an aspect, the heterologous polynucleotide of interest encodes a gene product that confers drought tolerance, cold tolerance, herbicide tolerance, pathogen resistance, or insect resistance. In an aspect, the heterologous polynucleotide encodes a gene product that is involved in plant metabolism, organ development, stem cell development, cell growth stimulation, organogenesis, somatic embryogenesis initiation and development of the apical meristem. In an aspect, the heterologous polynucleotide encodes a gene product that is involved in plant metabolism, organ development, stem cell development, cell growth stimulation, organogenesis, somatic embryogenesis initiation and development of the apical meristem. In an aspect, the heterologous polynucleotide is Wuschel (WUS) or BABYBOOM (ODP2 (BBM)). In an aspect, expression of the polynucleotide alters the phenotype of said plant. In an aspect, an expression cassette is provided comprising a recombinant polynucleotide comprising a functional fragment having promoter activity, wherein the fragment is derived from a nucleotide sequence selected from the group consisting of at least one of SEQ ID NOS: 1-27. In an aspect, the regulatory element of is expressed in an embryo. In an aspect, a plant cell is provided, wherein the regulatory element is expressed in a leaf. In an aspect, a plant cell is provided, wherein the regulatory element is expressed in an embryo and a leaf.

In a further aspect, the present disclosure provides a method for expressing a polynucleotide in a plant or a plant cell, the method comprising introducing into the plant or the plant cell an expression cassette comprising a regulatory element, wherein the regulatory element comprises a nucleotide sequence selected from the group consisting of: (a) a nucleotide sequence comprising the nucleotide sequence of at least one of SEQ ID NOS: 1-27 or a sequence that is at least 70% identical to at least one of SEQ ID NOS: 1-27; (b) a nucleotide sequence comprising a fragment or variant of the nucleotide sequence of at least one of SEQ ID NOS: 1-27, wherein the sequence initiates transcription in a plant cell; and (c) a nucleotide sequence which is complementary to (a) or (b). In an aspect, the regulatory element is operably associated with a heterologous polynucleotide. In an aspect, the heterologous polynucleotide of interest encodes a gene product that is involved in drought tolerance, plant metabolism, organ development, stem cell development, cell growth stimulation, organogenesis, somatic embryogenesis initiation and development of the apical meristem. In an aspect, the gene product is involved in abiotic stress tolerance. In an aspect, the heterologous polynucleotide of interest encodes a gene product that confers drought tolerance, cold tolerance, herbicide tolerance, pathogen resistance, or insect resistance. In an aspect, the plant is a monocot or a dicot. In an aspect, the monocot or the dicot is selected from the group consisting of: maize, sorghum, rice, soybean, wheat, cotton, and Brassica.

In a further aspect, the present disclosure provides a method for expressing a polynucleotide of interest in a plant, the method comprising introducing into a plant cell a heterologous regulatory element capable of increasing expression of the polynucleotide of interest, wherein the heterologous regulatory element comprises a polynucleotide sequence selected from the group consisting of: (a) a nucleotide sequence comprising the nucleotide sequence of at least one of SEQ ID NOS: 1-27 or a sequence that is at least 95% identical to at least one of SEQ ID NOS: 1-27; (b) a nucleotide sequence comprising at least a 100-bp fragment of the nucleotide sequence of at least one of SEQ ID NOS: 1-27, wherein the nucleotide sequence initiates transcription in a plant cell; and (c) a nucleotide sequence which is complementary to (a) or (b). In an aspect, the polynucleotide of interest encodes a polypeptide that is involved in organ development, stem cell development, cell growth stimulation, organogenesis, somatic embryogenesis initiation, development of the apical meristem, and a combination thereof. In an aspect, the polynucleotide of interest is an endogenous gene of the plant. In an aspect, the polynucleotide of interest encodes a polypeptide that confers drought tolerance, cold tolerance, herbicide tolerance, pathogen resistance, or insect resistance. In an aspect, the plant is a dicot or a monocot. In an aspect, the monocot or the dicot is selected from the group consisting of: maize, sorghum, rice, soybean, wheat, cotton, and Brassica.

DETAILED DESCRIPTION OF THE FIGURES

FIG. 1 illustrates a longitudinal cross section of a maize immature embryo under an epifluorescence stereo-microscope, with the embryo axis on the bottom and the scutellum above. In embryos expressing PLTP PRO::Zs-GREEN1:: pinII, strong green fluorescence was observed in cells on the scutellar surface.

FIG. 2A and FIG. 2B illustrate maize leaf epidermis in a plant containing a transgenic cassette with the maize PLTP promoter driving expression of ZS-GREEN1 fluorescent protein. Fluorescence was observed in only two cell types; the accessory cells which flank the guard cells of the stomata (indicated by arrows in FIG. 2A) and in short cells (also referred to as cork cells, indicated by arrows in FIG. 2B). The image was taken using a compound epifluorescence microscope.

Figure 25:
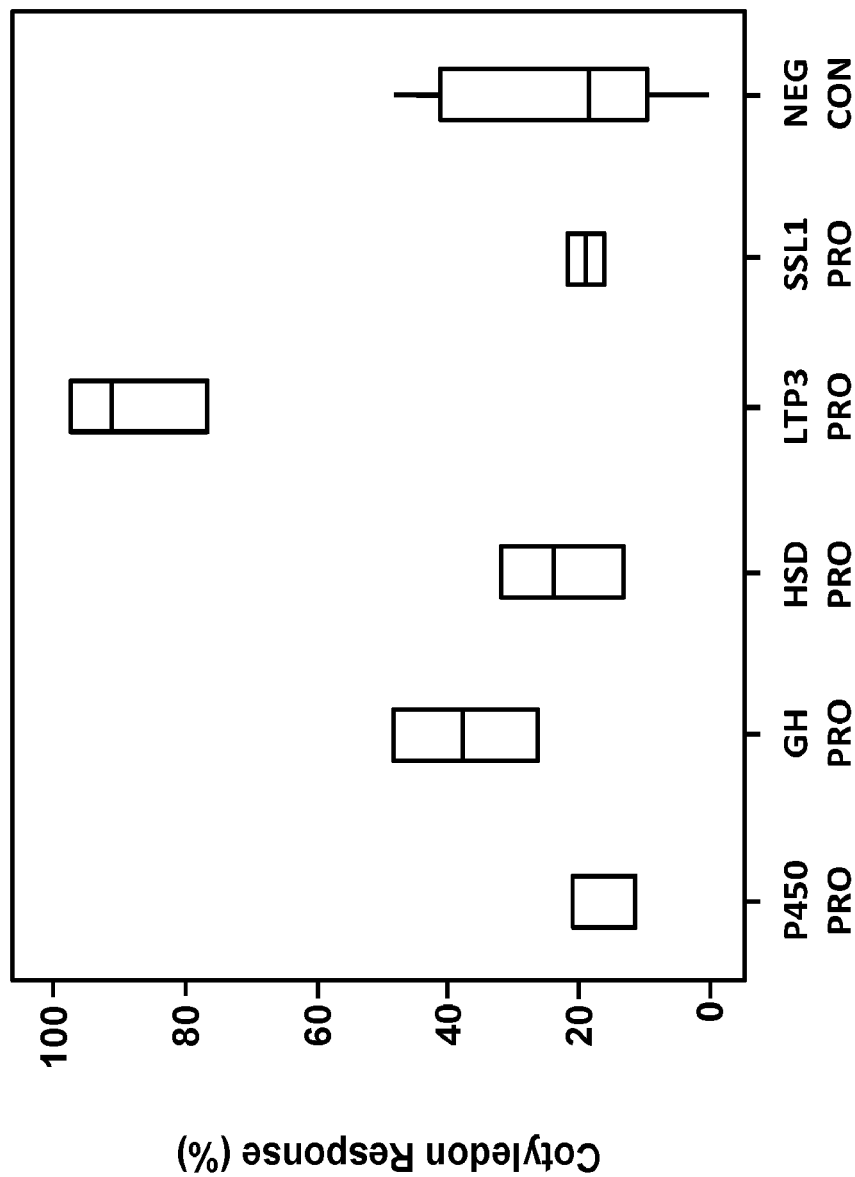

FIG. 25 shows transformation response as measured by the frequency of treated immature cotyledons that produced somatic embryos after *Agrobacterium*-mediated transformation to introduce a T-DNA containing an expression cassette with the *Arabidopsis* WUS gene behind one of five promoters; Gm-Phytochrome P450 promoter (P450 PRO); Gm-Glycosyl Hydrolase promoter (GH PRO); Gm-Homeodomain/Start-domain protein promoter (HSD PRO); Gm-LTP3 promoter (LTP3 PRO); Gm-Strictosidine Synthase-Like1 promoter (SSL1 PRO); the negative control with no WUS expression (NEG CON). For each promoter, the upper and lower ends of the box indicate the upper and lower quartile for the distribution of the data, while the line within the box represents the median. For the P450 PRO only two replicates were included in this analysis and thus no median was calculated.

Figure 26A:
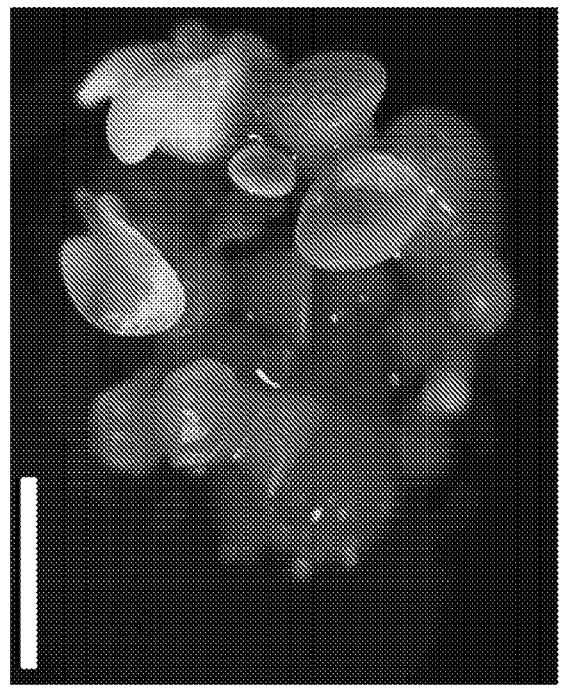
Figure 26B:

FIG. 26A shows a light micrograph and FIG. 26B shows the corresponding epifluorescence image of somatic embryos that were moved onto maturation medium to complete embryo development (shown on maturation medium 35 days after the underlying immature cotyledon was transformed with a T-DNA containing Gm-LTP3 PRO::At-WUS). Arrow points to one of the red fluorescing somatic cotyledons; the scale bars represent 2 mm in length.

DETAILED DESCRIPTION

The disclosure relates to compositions and methods drawn to plant promoters and methods of their use. The compositions of the disclosure comprise nucleotide sequences for tissue-preferred promoters known as ZM-PLTP (SEQ ID NO: 1), ZM-PLTP1 (SEQ ID NO: 3), ZM-PLTP2 (SEQ ID NO: 4), SB-PLTP1 (SEQ ID NO: 2), SBPLTP2 (SEQ ID NO: 5), SB-PLTP3 (SEQ ID NO: 6), OS-PLTP1 (SEQ ID NO: 8), OS-PLTP2 (SEQ ID NO: 9), SI-PLTP1 (SEQ ID NO: 7), ZM-FBP1 (SEQ ID NO: 10), ZM-RFP (SEQ ID NO: 11), ZM-APMP (SEQ ID NO: 12), ZM-RfeSP (SEQ ID NO: 13), ZM-CRR6 (SEQ ID NO: 14), ZM-G3K (SEQ ID NO: 15), ZM-CAB7 (SEQ ID NO: 16), ZM-UBR (SEQ ID NO: 17), ZM-HBP (SEQ ID NO: 18), ZM-PS1-N(SEQ ID NO: 19), ZM-SDR (SEQ ID NO: 20), OS-SDR (SEQ ID NO: 23), SB-SDR (SEQ ID NO: 24), ZM-SDR(long) (SEQ ID NO: 22), ZM-LGL (SEQ ID NO: 25), ZM-LEA14-A (SEQ ID NO: 26), ZM-LEA34-D (SEQ ID NO: 27) and GM-LTP3 (SEQ ID NO: 21). The compositions further comprise DNA constructs comprising a nucleotide sequence for the above promoters operably linked to a heterologous nucleotide sequence of interest. In particular, the present disclosure provides for nucleic acid molecules comprising at least one of the nucleotide sequence set forth in SEQ ID NOS: 1-27, and fragments, variants and complements thereof. A summary of SEQ ID NOS: 1-32 is presented in Table 1.

TABLE 1

Summary of SEQ ID NOS: 1-32.

| SEQ ID NO. | Polynucleotide or Polypeptide | Name | Description |
|---|---|---|---|
| 1 | DNA | ZM-PLTP | *Zea mays* PLTP promoter sequence |
| 2 | DNA | SB-PLTP1 | *Sorghum biocolor* PLTP1 promoter sequence |
| 3 | DNA | ZM-PLTP1 | *Zea mays* PLTP1 promoter sequence |
| 4 | DNA | ZM-PLTP2 | *Zea mays* PLTP2 promoter sequence |
| 5 | DNA | SB-PLTP2 | *Sorghum biocolor* PLTP2 promoter sequence |
| 6 | DNA | SB-PLTP3 | *Sorghum biocolor* PLTP3 promoter sequence |
| 7 | DNA | SI-PLTP1 | *Setaria italica* PLTP1 promoter sequence |
| 8 | DNA | OS-PLTP1 | *Oryza sativa* PLTP1 promoter sequence |
| 9 | DNA | OS-PLTP2 | *Oryza sativa* PLTP2 promoter sequence |
| 10 | DNA | ZM-FBP1 | *Zea mays* promoter for fructose-1,6-bisphosphatase |
| 11 | DNA | ZM-RFP | *Zea mays* promoter for NAD(P)-binding Rossmann-Fold protein |
| 12 | DNA | ZM-APMP | *Zea mays* promoter for adipocyte plasma membrane-associated protein-like protein |
| 13 | DNA | ZM-RfeSP | *Zea mays* promoter for Rieske [2Fe—2S] iron-sulphur domain protein |
| 14 | DNA | ZM-CRR6 | *Zea mays* promoter for chlororespiratory reduction 6 gene |
| 15 | DNA | ZM-G3K | *Zea mays* promoter for D-glycerate 3-kinase, chloroplastic-like protein gene |
| 16 | DNA | ZM-CAB7 | *Zea mays* promoter for chlorophyll a-b binding protein 7, chloroplastic-like protein |
| 17 | DNA | ZM-UBR | *Zea mays* promoter for ultraviolet-B-repressible protein gene |
| 18 | DNA | ZM-HBP | *Zea mays* promoter for Soul heme-binding family protein |
| 19 | DNA | ZM-PS1-N | *Zea mays* promoter for photosystem I reaction center subunit psi-N |
| 20 | DNA | ZM-SDR | *Zea mays* promoter for short-chain dehydrogenase/reductase |
| 21 | DNA | GM-LTP3 | *Glycine max* lipid transfer protein 3 promoter sequence |
| 22 | DNA | ZM-SDR (long) | *Zea mays* promoter for short-chain dehydrogenase/reductase (long) |
| 23 | DNA | OS-SDR | *Oryza sativa* promoter for short-chain dehydrogenase/reductase (long) |
| 24 | DNA | SB-SDR | *Sorghum bicolor* promoter for short-chain dehydrogenase/reductase (long) |
| 25 | DNA | ZM-LGL | *Zea mays* promoter for lactoylglutathione lyase |
| 26 | DNA | ZM-LEA14-A | *Zea mays* promoter for late embryogenic abundant protein Lea-14-A |
| 27 | DNA | ZM-LEA34-D | *Zea mays* promoter for late embryogenic abundant protein Lea-34-D |
| 28 | DNA | PHP77833 | Synthetic construct comprising the T-DNA (LB to RB) |
| 29 | DNA | PHP79024 | Synthetic construct comprising the T-DNA (LB to RB) |

TABLE 1-continued

Summary of SEQ ID NOS: 1-32.

| SEQ ID NO. | Polynucleotide or Polypeptide | Name | Description |
|---|---|---|---|
| 30 | DNA | PHP80730 | Synthetic construct comprising the T-DNA (LB to RB) |
| 31 | DNA | ZM-UBI | *Zea mays* Ubiquitin promoter sequence |
| 32 | DNA | GM-EF1A | *Glycine max* Elongation Factor 1A promoter sequence |

The regulatory sequences of the present disclosure include nucleotide constructs that allow initiation of transcription in a plant. In specific aspects, the PLTP promoters and other promoters allow initiation of transcription in a tissue-preferred manner. Such constructs of the disclosure comprise regulated transcription initiation regions associated with plant developmental regulation. Thus, the compositions of the present disclosure include DNA constructs comprising a nucleotide sequence of interest operably linked to a plant promoter, more particularly a PLTP promoter and/or other promoters described herein, and a 5'UTR sequence. Sequences comprising PLTP promoters from maize, sorghum, rice and *Setaria* are set forth herein as SEQ ID NOS: 1-9.

The promoters of the disclosure are useful for expressing sequences. In specific aspects, the promoter sequences of the disclosure are useful for expressing sequences of interest, particularly in a tissue-preferred manner. The nucleotide sequences of the disclosure also find use in the construction of expression vectors for subsequent expression of a heterologous nucleotide sequence in a plant of interest or as probes for the isolation of other promoters. In particular, the present disclosure provides for isolated DNA constructs comprising the promoter nucleotide sequences set forth in at least one of SEQ ID NOS: 1-27 operably linked to a nucleotide sequence of interest.

Aspects of the disclosure include a nucleic acid molecule comprising a regulatory element having a nucleotide sequence selected from the group consisting of: a sequence with at least 70% identity to at least one of SEQ ID NOS: 1-27; a fragment or variant of the nucleotide sequence of at least one of SEQ ID NOS:1-27, wherein the sequence initiates transcription in a plant cell; a polynucleotide which is complementary to the polynucleotide of (a) or (b); and a polynucleotide that comprises at least 100 contiguous nucleotides of a sequence selected from the group consisting of at least one of SEQ ID NOS: 1-27; and wherein the regulatory element is operably linked to a heterologous polynucleotide of interest. Also embodied is an expression cassette comprising the regulatory element containing the nucleic acid, a vector comprising the expression cassette, and a plant cell comprising the expression cassette. Further aspects include the plant cell wherein said expression cassette is stably integrated into the genome of the plant cell, from monocot or dicot plants, and the plant comprising the described expression cassette, whether monocot or dicot plant, including maize, sorghum, rice, soybean, wheat, cotton, or *Brassica*. Also embodied is a tissue preferred regulatory element.

Also embodied is a plant with the described expression cassette stably incorporated into the genome of the plant, a seed of the plant, wherein the seed comprises the expression cassette, and a plant wherein the heterologous polynucleotide of interest encodes a transcription factor. Further embodied is a plant wherein said gene or gene product confers drought tolerance, cold tolerance, herbicide tolerance, pathogen resistance, or insect resistance. A plant wherein expression of said polynucleotide alters the phenotype of said plant is also embodied. Also embodied is an expression cassette comprising a recombinant polynucleotide comprising a functional fragment having promoter activity, wherein the fragment is derived from a nucleotide sequence selected from the group consisting of SEQ ID NOS: 1-27. Also embodied is a plant, wherein said expression cassette is transiently expressed in the plant cell. Further embodied is a plant, wherein the heterologous polynucleotide is WUS or ODP2 (BBM). Further embodied is a plant cell, wherein the regulatory element is expressed in an embryo, a leaf, or an embryo and a leaf.

A further aspect includes a method for expressing a polynucleotide in a plant or a plant cell, said method comprising introducing into the plant or the plant cell an expression cassette comprising a regulatory element, wherein said regulatory element comprises a nucleotide sequence selected from the group consisting of:
a nucleotide sequence comprising the nucleotide sequence of at least one of SEQ ID NOS: 1-27 or a sequence that is at least 70% identical to at least one of SEQ ID NOS: 1-27;
a nucleotide sequence comprising a fragment or variant of the nucleotide sequence of at least one of SEQ ID NOS: 1-27, wherein the sequence initiates transcription in a plant cell; and a nucleotide sequence which is complementary to (a) or (b).

Aspects also include: the method wherein the regulatory element is operably associated with a heterologous polynucleotide, the method wherein the heterologous polynucleotide of interest encodes a gene product that is involved in drought tolerance, plant metabolism, organ development, stem cell development, cell growth stimulation, organogenesis, somatic embryogenesis, initiation and development of the apical meristem, the method wherein said gene product is involved in abiotic stress tolerance, the method wherein the heterologous polynucleotide of interest encodes a gene product that confers drought tolerance, cold tolerance, herbicide tolerance, pathogen resistance, or insect resistance, and the method wherein said plant is a monocot or a dicot.

Additional aspects include a method for expressing a polynucleotide of interest in a plant, said method comprising introducing into a plant cell a regulatory element capable of increasing expression of a polynucleotide of interest, wherein the heterologous regulatory element comprises a polynucleotide sequence selected from the group consisting of: a nucleotide sequence comprising the nucleotide sequence of at least one of SEQ ID NOS: 1-27 or a sequence that is at least 95% identical to at least one of SEQ ID NOS: 1-27; a nucleotide sequence comprising at least a 100-bp fragment of the nucleotide sequence of at least one of SEQ ID NOS: 1-27, and a nucleotide sequence which is complementary to (a) or (b), wherein the sequence initiates transcription in a plant cell.

Also embodied are: a method wherein the polynucleotide of interest encodes a polypeptide that is involved in organ development, stem cell development, cell growth stimulation, organogenesis, somatic embryogenesis initiation, development of the apical meristem, and a combination thereof, the method wherein the polynucleotide of interest is an endogenous gene of the plant, the method wherein the polynucleotide of interest encodes a polypeptide that confers drought tolerance, cold tolerance, herbicide tolerance, pathogen resistance, or insect resistance, the method wherein said plant is a dicot or a monocot, and the method wherein the monocot or dicot is selected from the group consisting of: maize, sorghum, rice, soybean, wheat, cotton, and *Brassica*.

The disclosure encompasses isolated or substantially purified nucleic acid compositions. An "isolated" or "purified" nucleic acid molecule or biologically active portion thereof is substantially free of other cellular material or culture medium when produced by recombinant techniques or substantially free of chemical precursors or other chemicals when chemically synthesized. An "isolated" nucleic acid is substantially free of sequences (including protein encoding sequences) that naturally flank the nucleic acid (i.e., sequences located at the 5' and 3' ends of the nucleic acid) in the genomic DNA of the organism from which the nucleic acid is derived. For example, in various aspects, the isolated nucleic acid molecule can contain less than about 5 kb, 4 kb, 3 kb, 2 kb, 1 kb, 0.5 kb or 0.1 kb of nucleotide sequences that naturally flank the nucleic acid molecule in genomic DNA of the cell from which the nucleic acid is derived. The sequences of the disclosure may be isolated from the 5' untranslated region flanking their respective transcription initiation sites.

Fragments and variants of the disclosed promoter nucleotide sequences are also encompassed by the present disclosure. In particular, fragments and variants of the promoter sequences of at least one of SEQ ID NOS: 1-27 may be used in the DNA constructs of the disclosure. As used herein, the term "fragment" refers to a portion of the nucleic acid sequence. Fragments of regulatory sequences retain the biological activity of initiating transcription, such as driving transcription in a constitutive manner. Alternatively, fragments of a nucleotide sequence that are useful as hybridization probes may not necessarily retain biological activity. Fragments of a nucleotide sequence for the regulatory regions disclosed herein may range from at least about 20 nucleotides, about 50 nucleotides, about 100 nucleotides, and up to the full length of at least one of SEQ ID NOS: 1-27.

A biologically active portion of a promoter can be prepared by isolating a portion of the promoter sequences of the disclosure, and assessing the promoter activity of the portion. Nucleic acid molecules that are fragments of a promoter nucleotide sequence comprise at least about 16, 50, 75, 100, 150, 200, 250, 300, 350, 400, 450, 500, 550, 600, 650, 700 or 800 nucleotides or up to the number of nucleotides present in a full-length regulatory sequence disclosed herein.

As used herein, the term "variants" is intended to mean sequences having substantial similarity with a promoter sequence disclosed herein. A variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, such as, for example, with polymerase chain reaction (PCR) and hybridization techniques as outlined herein.

Variant nucleotide sequences also include synthetically derived nucleotide sequences, such as those generated, for example, by using site-directed mutagenesis. Generally, variants of a particular nucleotide sequence of the aspects will have at least 40%, 50%, 60%, 65%, 70%, 75%, 80%, 85%, 90%, 91%, 92%, 93%, 94%, to 95%, 96%, 97%, 98%, 99% or more sequence identity to that particular nucleotide sequence as determined by sequence alignment programs described elsewhere herein using default parameters. Biologically active variants are also encompassed by the aspects. Biologically active variants include, for example, the native promoter sequences of the aspects having one or more nucleotide substitutions, deletions or insertions. Promoter activity may be measured by using techniques such as Northern blot analysis, reporter activity measurements taken from transcriptional fusions, and the like. See, for example, Sambrook, et al., (1989) Molecular Cloning: A Laboratory Manual (2d ed., Cold Spring Harbor Laboratory Press, Cold Spring Harbor, N.Y.), hereinafter "Sambrook," herein incorporated by reference in its entirety. Alternatively, levels of a reporter gene such as green fluorescent protein (GFP) or yellow fluorescent protein (YFP) or the like produced under the control of a promoter fragment or variant can be measured. See, for example, Matz et al. (1999) Nature Biotechnology 17:969-973; U.S. Pat. No. 6,072,050, herein incorporated by reference in its entirety; Nagai, et al., (2002) Nature Biotechnology 20(1):87-90. Variant nucleotide sequences also encompass sequences derived from a mutagenic and recombinogenic procedure such as DNA shuffling. With such a procedure, one or more different nucleotide sequences for the promoter can be manipulated to create a new promoter. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, (1994) Proc. Natl. Acad. Sci. USA 91:10747-10751; Stemmer, (1994) Nature 370:389 391; Crameri, et al., (1997) Nature Biotech. 15:436-438; Moore, et al., (1997) J. Mol. Biol. 272:336-347; Zhang, et al., (1997) Proc. Natl. Acad. Sci. USA 94:4504-4509; Crameri, et al., (1998) Nature 391:288-291 and U.S. Pat. Nos. 5,605,793 and 5,837,458, herein incorporated by reference in their entirety.

Methods for mutagenesis and nucleotide sequence alterations are well known in the art. See, for example, Kunkel, (1985) *Proc. Natl. Acad. Sci. USA* 82:488-492; Kunkel, et al., (1987) *Methods in Enzymol.* 154:367-382; U.S. Pat. No. 4,873,192; Walker and Gaastra, eds. (1983) Techniques in Molecular Biology (MacMillan Publishing Company, New York) and the references cited therein, herein incorporated by reference in their entirety.

The nucleotide sequences of the disclosure can be used to isolate corresponding sequences from other organisms, particularly other plants, more particularly other monocots or dicots. In this manner, methods such as PCR, hybridization and the like can be used to identify such sequences based on their sequence homology to the sequences set forth herein. Sequences isolated based on their sequence identity to the entire sequences set forth herein or to fragments thereof are encompassed by the present disclosure.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in, Sambrook, supra. See also, Innis, et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York), herein incorporated by reference in their entirety. Known methods of PCR include, but are not limited to, methods using paired primers, nested primers, single specific primers, degenerate primers, gene-specific primers, vector-specific primers, partially-mismatched primers and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides and may be labeled with a detectable group such as $^{32}$P or any other detectable marker. Thus, for example, probes for hybridization can be made by labeling synthetic oligonucleotides based on the regulatory sequences of the disclosure. Methods for preparation of probes for hybridization and for construction of genomic libraries are generally known in the art and are disclosed in Sambrook, supra.

For example, the entire regulatory sequence disclosed herein, or one or more portions thereof, may be used as a probe capable of specifically hybridizing to corresponding dicot regulatory sequences and messenger RNAs. To achieve specific hybridization under a variety of conditions, such probes include sequences that are unique among regulatory sequences and are generally at least about 10 nucleotides in length or at least about 20 nucleotides in length. Such probes may be used to amplify corresponding regulatory sequences from a chosen plant by PCR. This technique may be used to isolate additional coding sequences from a desired organism or as a diagnostic assay to determine the presence of coding sequences in an organism. Hybridization techniques include hybridization screening of plated DNA libraries (either plaques or colonies, see, for example, Sambrook, supra).

Hybridization of such sequences may be carried out under stringent conditions. The terms "stringent conditions" or "stringent hybridization conditions" are intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C. and a wash in 1 times to 2 times SSC (20 times SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C. and a wash in 0.5 times to 1 times SSC at 55 to 60° C. Exemplary high stringency conditions include hybridization in 50% formamide, 1 M NaCl, 1% SDS at 37° C., and a final wash in 0.1 times SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl, (1984) *Anal. Biochem* 138:267 284: $T_m$=81.5° C.+16.6 (log M)+0.41 (% GC)—0.61 (% form)—500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching, thus, $T_m$, hybridization, and/or wash conditions can be adjusted to hybridize to sequences of the desired identity. For example, if sequences with 90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3 or 4° C. lower than the $T_m$; moderately stringent conditions can utilize a hybridization and/or wash at 6, 7, 8, 9 or 10° C. lower than the $T_m$; low stringency conditions can utilize a hybridization and/or wash at 11, 12, 13, 14, 15 or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, (1993) Laboratory Techniques in Biochemistry and Molecular Biology—Hybridization with Nucleic Acid Probes, Part I, Chapter 2 (Elsevier, New York); and Ausubel, et al., eds. (1995) Current Protocols in Molecular Biology, Chapter 2 (Greene Publishing and Wiley-Interscience, New York), herein incorporated by reference in their entirety. See also, Sambrook.

Thus, isolated sequences that have constitutive promoter activity and which hybridize under stringent conditions to the regulatory sequences disclosed herein or to fragments thereof, are encompassed by the present disclosure.

In general, sequences that have promoter activity and hybridize to the promoter sequences disclosed herein will be at least 40% to 50% homologous, about 60%, 70%, 80%, 85%, 90%, 95% to 98% homologous or more with the disclosed sequences. That is, the sequence similarity of sequences may range, sharing at least about 40% to 50%, about 60% to 70%, and about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity" and (e) "substantial identity".

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 4:11-17; the algorithm of Smith, et al., (1981) *Adv. Appl. Math.* 2:482; the algorithm of Needleman and Wunsch, (1970) *J. Mol. Biol.* 48:443-453; the algorithm of Pearson and Lipman, (1988) *Proc. Natl. Acad. Sci.* 85:2444-2448; the algorithm of Karlin and Altschul, (1990) *Proc. Natl. Acad. Sci. USA* 872:264, modified as in Karlin and Altschul, (1993) *Proc. Natl. Acad. Sci. USA* 90:5873-5877, herein incorporated by reference in their entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA and TFASTA in the GCG Wisconsin Genetics Software Package®, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65; and Pearson, et al., (1994) *Meth. Mol. Biol.* 24:307-331, herein incorporated by reference in their entirety. The ALIGN program is based on the algorithm of Myers and Miller, (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403, herein incorporated by reference in its entirety, are based on the algorithm of Karlin and Altschul, (1990) supra. BLAST nucleotide searches can be performed with the BLASTN program, score=100, word length=12, to obtain nucleotide sequences homologous to a nucleotide sequence encoding a protein of the disclosure. BLAST protein searches can be performed with the BLASTX program, score=50, word length=3, to obtain amino acid sequences homologous to a protein or polypeptide of the disclosure. To obtain gapped alignments for comparison purposes, Gapped BLAST (in BLAST 2.0) can be utilized as described in Altschul, et al., (1997) *Nucleic Acids Res.* 25:3389, herein incorporated by reference in its entirety. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, the web site for the National Center for Biotechnology Information on the World Wide Web at ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. As used herein, "equivalent program" is any sequence comparison program that, for any two sequences in question, generates an alignment having identical nucleotide or amino acid residue matches and an identical percent sequence identity when compared to the corresponding alignment generated by GAP Version 10.

The GAP program uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package® for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package® is BLOSUM62 (see, Henikoff and Henikoff, (1989) *Proc. Natl. Acad. Sci. USA* 89:10915, herein incorporated by reference in its entirety).

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of one and a non-conservative substitution is given a score of zero, a conservative substitution is given a score between zero and one. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, optimally at least 80%, more optimally at least 90% and most optimally at least 95%, compared to a reference sequence using an alignment program using standard parameters. One of skill in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, 70%, 80%, 90% and at least 95%.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The regulatory sequences disclosed herein, as well as variants and fragments thereof, are useful for genetic engineering of plants, e.g. for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part or plant the genotype of which has been altered by the presence of heterologous nucleic acid including those transgenics initially so altered as well as those created by sexual crosses or asexual propagation from the initial transgenic.

A transgenic "event" is produced by transformation of plant cells with a heterologous DNA construct, including a nucleic acid expression cassette that comprises a gene of interest, the regeneration of a population of plants resulting from the insertion of the transferred gene into the genome of the plant and selection of a particular plant characterized by insertion into a particular genome location. An event is characterized phenotypically by the expression of the inserted gene. At the genetic level, an event is part of the genetic makeup of a plant. The term "event" also refers to progeny produced by a sexual cross between the transformant and another plant wherein the progeny include the heterologous DNA.

As used herein, the term plant includes whole plants, plant organs (e.g., leaves, stems, roots, etc.), plant cells, plant protoplasts, plant cell tissue cultures from which plants can be regenerated, plant calli, plant clumps and plant cells that are intact in plants or parts of plants such as embryos, pollen, ovules, seeds, leaves, flowers, branches, fruit, kernels, ears, cobs, husks, stalks, roots, root tips, anthers and the like. Grain is intended to mean the mature seed produced by commercial growers for purposes other than growing or reproducing the species. Progeny, variants and mutants of the regenerated plants are also included within the scope of the disclosure, provided that these parts comprise the introduced polynucleotides.

The present disclosure may be used for transformation of any plant species, including, but not limited to, monocots and dicots. Examples of plant species include corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana taba-* cum), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), *Setaria italica*, oats, barley, vegetables, ornamentals and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*) and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*) and *chrysanthemum*.

Conifers that may be employed in practicing the present disclosure include, for example, pines such as loblolly pine (*Pinus taeda*), slash pine (*Pinus elliotii*), ponderosa pine (*Pinusponderosa*), lodgepole pine (*Pinus contorta*) and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*) and cedars such as Western red cedar (*Thuja plicata*) and Alaska yellow-cedar (*Chamaecyparis nootkatensis*). In specific aspects, plants of the present disclosure are crop plants (for example, corn, alfalfa, sunflower, *Brassica*, soybean, cotton, safflower, peanut, sorghum, wheat, millet, tobacco, etc.). In other aspects, corn and soybean plants are optimal, and in yet other aspects corn plants are optimal.

Other plants of interest include grain plants that provide seeds of interest, oil-seed plants and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

As used herein, PLTP refers to "Phospholipid Transfer Protein" gene, which corresponds to the gene GRZM2G101958_T01 in the public unigene set 5b.60 and is located on maize chromosome 10 at a genetic position of 28.95 cM and a physical position of 3833396-3834547 bases. This gene is expressed in the embryo, in callus, in the accessory cells flanking the guard cells of the stomates, in silk hairs, and under drought stress, under chilling and after a frost. Herein, expression does not occur in roots, in the tassel (including the anthers and pollen), in the immature ear, or in kernels. Herein, PLTP sequences as disclosed here are ZM-PLTP (SEQ ID NO: 1), ZM-PLTP1 (SEQ ID NO: 3), ZM-PLTP2 (SEQ ID NO: 4), SB-PLTP1 (SEQ ID NO: 2), SB-PLTP2 (SEQ ID NO: 5), SB-PLTP3 (SEQ ID NO: 6), OS-PLTP1 (SEQ ID NO: 8), OS-PLTP2 (SEQ ID NO: 9), and SI-PLTP1 (SEQ ID NO: 7), and variants and fragments thereof.

As used herein, LTP3 refers to the Lipid Transfer Protein3 gene which corresponds to Genbank accession number XM-0066066884.2 located at physical position 47778536 to 4776537 on the soy chromosome 20. This gene is expressed in the embryo, in the developing seed, and in cultured cells. Herein, expression does not occur in roots, stems, meristems, or reproductive structures (flower or pod). Herein, LTP3 sequence is GM-LTP3 (SEQ ID NO: 21), and variants and fragments thereof.

The disclosure relates to compositions and methods drawn to plant promoters, such as PLTP promoters, and methods of their use. Compositions comprise nucleotide sequences for tissue-preferred promoters known as ZM-PLTP, ZM-PLTP1, ZM-PLTP2, SB-PLTP, SBPLTP2, SB-PLTP3, OS-PLTP, OS-PLTP2, SI-PLTP, ZM-FBP1, ZM-RFP, ZM-APMP, ZM-RfeSP, ZM-CRR6, ZM-G3K, ZM-CAB7, ZM-UBR, ZM-HBP, ZM-PS1-N, ZM-SDR, GM-LTP3, OS-SDR, SB-SDR, ZM-SDR(long), ZM-LGL, ZM-LEA-14-A and LEA-34-D. (see Table 1 herein). Certain aspects of the disclosure comprise the nucleotide sequence set forth in at least one of SEQ ID NOS: 1-27 and fragments of the nucleotide sequence set forth in at least one of SEQ ID NOS: 1-27. Also included are functional fragments of the sequence set forth in at least one of SEQ ID NOS: 1-27, which drive tissue-preferred expression of an operably-linked nucleotide sequence. Table 1 provides a summary of SEQ ID NOS: 1-27. Certain aspects of the disclosure comprise using more than one of the nucleotide sequences set forth in SEQ ID NOS: 1-27 in the same expression cassette and in the methods described herein for expressing a polynucleotide of interest in a plant or a plant cell.

Heterologous coding sequences expressed by a regulatory sequence of the disclosure may be used for varying the phenotype of a plant. Various changes in phenotype are of interest including modifying expression of a gene in a plant, altering a plant's pathogen or insect defense mechanism, increasing a plant's tolerance to herbicides, altering plant development to respond to environmental stress, modulating the plant's response to salt, temperature (hot and cold), drought and the like. These results can be achieved by the expression of a heterologous nucleotide sequence of interest comprising an appropriate gene product. In specific aspects, the heterologous nucleotide sequence of interest is an endogenous plant sequence whose expression level is increased in the plant or plant part. Results can be achieved by providing for altered expression of one or more endogenous gene products, particularly hormones, receptors, signaling molecules, enzymes, transporters or cofactors or by affecting nutrient uptake in the plant. Tissue-preferred expression as provided by the promoters disclosed herein can alter expression. These changes result in a change in phenotype of the transformed plant. In certain aspects, since the expression pattern is tissue-preferred, the expression patterns are useful for many types of screening.

General categories of nucleotide sequences of interest for the present disclosure include, for example, those genes involved in information, such as zinc fingers, those involved in communication, such as kinases and those involved in housekeeping, such as heat shock proteins. More specific categories of transgenes, for example, include genes encoding important traits for agronomics, insect resistance, disease resistance, herbicide resistance, environmental stress resistance (altered tolerance to cold, salt, drought, etc) and grain characteristics. Still other categories of transgenes include genes for inducing expression of exogenous products such as enzymes, cofactors, and hormones from plants and other eukaryotes as well as prokaryotic organisms. It is recognized that any gene of interest can be operably linked to the promoter of the disclosure and expressed in the plant.

Agronomically important traits that affect quality of grain, such as levels and types of oils, saturated and unsaturated, quality and quantity of essential amino acids, levels of cellulose, starch and protein content can be genetically altered using the methods of the aspects. Modifications to grain traits include, but are not limited to, increasing content of oleic acid, saturated and unsaturated oils, increasing levels of lysine and sulfur, providing essential amino acids, and modifying starch. Hordothionin protein modifications in corn are described in U.S. Pat. Nos. 5,990,389; 5,885,801; 5,885,802 and 5,703,049; herein incorporated by reference in their entirety. Another example is lysine and/or sulfur rich seed protein encoded by the soybean 2S albumin described in U.S. Pat. No. 5,850,016, filed Mar. 20, 1996 and the chymotrypsin inhibitor from barley, Williamson, et al., (1987) *Eur. J. Biochem* 165:99-106, the disclosures of which are herein incorporated by reference in their entirety.

Insect resistance genes may encode resistance to pests that have great yield drag such as rootworm, cutworm, European corn borer and the like. Such genes include, for example, *Bacillus thuringiensis* toxic protein genes, U.S. Pat. Nos. 5,366,892; 5,747,450; 5,736,514; 5,723,756; 5,593,881 and Geiser, et al., (1986) *Gene* 48:109, the disclosures of which are herein incorporated by reference in their entirety. Genes encoding disease resistance traits include, for example, detoxification genes, such as those which detoxify fumonisin (U.S. Pat. No. 5,792,931); avirulence (avr) and disease resistance (R) genes (Jones, et al., (1994) *Science* 266:789; Martin, et al., (1993) *Science* 262:1432; and Mindrinos, et al., (1994) *Cell* 78:1089), herein incorporated by reference in their entirety.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), genes coding for resistance to glyphosate (e.g., the EPSPS gene and the GAT gene; see, for example, US Patent Application Publication Number 2004/0082770 and WO 03/092360, herein incorporated by reference in their entirety) or other such genes known in the art. The bar gene encodes resistance to the herbicide basta, the nptII gene encodes resistance to the antibiotics kanamycin and geneticin and the ALS-gene mutants encode resistance to the herbicide chlorsulfuron.

Glyphosate resistance is imparted by mutant 5-enolpyruvl-3-phosphikimate synthase (EPSP) and aroA genes. See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and international publications WO 97/04103; WO 97/04114; WO 00/66746; WO 01/66704; WO 00/66747 and WO 00/66748, which are incorporated herein by reference in their entirety. Glyphosate resistance is also imparted to plants that express a gene that encodes a glyphosate oxidoreductase enzyme as described more fully in U.S. Pat. Nos. 5,776,760 and 5,463,175, which are incorporated herein by reference in their entirety. In addition glyphosate resistance can be imparted to plants by the over expression of genes encoding glyphosate N-acetyltransferase. See, for example, U.S. patent application Ser. Nos. 11/405,845 and 10/427, 692, herein incorporated by reference in their entirety.

Sterility genes can also be encoded in a DNA construct and provide an alternative to physical detasseling. Examples of genes used in such ways include male tissue-preferred genes and genes with male sterility phenotypes such as QM, described in U.S. Pat. No. 5,583,210, herein incorporated by reference in its entirety. Other genes include kinases and those encoding compounds toxic to either male or female gametophytic development.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321, herein incorporated by reference in its entirety. Genes such as β-Ketothiolase, PHBase (polyhydroxybutyrate synthase), and acetoacetyl-CoA reductase (see, Schubert, et al., (1988) *J. Bacteriol.* 170:5837-5847, herein incorporated by reference in its entirety) facilitate expression of polyhydroxyalkanoates (PHAs).

Exogenous products include plant enzymes and products as well as those from other sources including prokaryotes and other eukaryotes. Such products include enzymes, cofactors, hormones and the like.

Examples of other applicable genes and their associated phenotype include the gene which encodes viral coat protein and/or RNA, or other viral or plant genes that confer viral resistance; genes that confer fungal resistance; genes that promote yield improvement; and genes that provide for resistance to stress, such as cold, dehydration resulting from drought, heat and salinity, toxic metal or trace elements or the like.

In one aspect, the promoter is used to express transgenes involved in organ development, stem cells, initiation and development of the apical meristem, such as the Wuschel (WUS) gene; see U.S. Pat. Nos. 7,348,468 and 7,256,322 and United States Patent Application publication 20070271628 published Nov. 22, 2007, by Pioneer Hi-Bred International; Laux et al. (1996) Development 122:87-96; and Mayer et al. (1998) Cell 95:805-815. Modulation of WUS is expected to modulate plant and/or plant tissue phenotype including cell growth stimulation, organogenesis, and somatic embryogenesis. WUS may also be used to improve transformation via somatic embryogenesis. Expression of *Arabidopsis* WUS can induce stem cells in vegetative tissues, which can differentiate into somatic embryos (Zuo, et al. (2002) Plant J 30:349-359). Also of interest in this regard would be a MYB118 gene (see U.S. Pat. No. 7,148,402), MYB115 gene (see Wang et al. (2008) Cell Research 224-235), BABYBOOM gene (BBM; see Boutilier et al. (2002) Plant Cell 14:1737-1749),CLAVATA gene (see, for example, U.S. Pat. No. 7,179,963) or WOX genes (van der Graaff et al., 2009, Genome Biology 10:248; Dolzblasz et al., 2016, Mol. Plant 19:1028-39).

By way of illustration, without intending to be limiting, the following is a list of other examples of the types of genes which can be used in connection with the regulatory sequences of the disclosure.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones, et al., (1994) *Science* 266:789 (cloning of the tomato Cf-9 gene for resistance to *Cladosporium flavum*); Martin, et al., (1993) *Science* 262: 1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*); McDowell and Woffenden, (2003) *Trends Biotechnol.* 21(4):178-83 and Toyoda, et al., (2002) *Transgenic Res.* 11(6):567-82, herein incorporated by reference in their entirety. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Numbers 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880, 275; WO 91/14778; WO 99/31248; WO 01/12731; WO 99/24581; WO 97/40162 and U.S. application Ser. Nos. 10/032,717; 10/414,637 and 10/606,320, herein incorporated by reference in their entirety.

(C) An insect-specific hormone or pheromone such as an ecdysteroid and juvenile hormone, a variant thereof, a mimetic based thereon, or an antagonist or agonist thereof. See, for example, the disclosure by Hammock, et al., (1990) *Nature* 344:458, of baculovirus expression of cloned juvenile hormone esterase, an inactivator of juvenile hormone, herein incorporated by reference in its entirety.

(D) An insect-specific peptide which, upon expression, disrupts the physiology of the affected pest. For example, see the disclosures of Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847- 853 and Vasconcelos and Oliveira, (2004) *Toxicon* 44(4): 385-403, herein incorporated by reference in their entirety. See also, U.S. Pat. No. 5,266,317 to Tomalski, et al., who disclose genes encoding insect-specific toxins, herein incorporated by reference in its entirety.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application Number WO 93/02197 in the name of Scott, et al., which discloses the nucleotide sequence of a callase gene, herein incorporated by reference in its entirety. DNA molecules which contain chitinase-encoding sequences can be obtained, for example, from the ATCC under Accession Numbers 39637 and 67152. See also, Kramer, et al., (1993) *Insect Biochem. Molec. Biol.* 23:691, who teach the nucleotide sequence of a cDNA encoding tobacco hookworm chitinase, and Kawalleck, et al., (1993) *Plant Molec. Biol.* 21:673, who provide the nucleotide sequence of the parsley ubi4-2 polyubiquitin gene, U.S. patent application Ser. Nos. 10/389,432, 10/692,367 and U.S. Pat. No. 6,563,020, herein incorporated by reference in their entirety.

(G) A molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone, herein incorporated by reference in their entirety.

(H) A hydrophobic moment peptide. See, PCT Application Number WO 95/16776 and U.S. Pat. No. 5,580,852 (disclosure of peptide derivatives of Tachyplesin which inhibit fungal plant pathogens) and PCT Application Number WO 95/18855 and U.S. Pat. No. 5,607,914) (teaches synthetic antimicrobial peptides that confer disease resistance), herein incorporated by reference in their entirety.

(I) A membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*, herein incorporated by reference in its entirety.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451, herein incorporated by reference in its entirety. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments), herein incorporated by reference in its entirety.

(L) A virus-specific antibody. See, for example, Tavladoraki, et al., (1993) *Nature* 366:469, who show that transgenic plants expressing recombinant antibody genes are protected from virus attack, herein incorporated by reference in its entirety.

(M) A developmental-arrestive protein produced in nature by a pathogen or a parasite. Thus, fungal endo alpha-1,4- D-polygalacturonases facilitate fungal colonization and plant nutrient release by solubilizing plant cell wall homoalpha-1,4-D-galacturonase. See, Lamb, et al., (1992) *Bio/Technology* 10:1436, herein incorporated by reference in its entirety. The cloning and characterization of a gene which encodes a bean endopolygalacturonase-inhibiting protein is described by Toubart, et al., (1992) *Plant J.* 2:367, herein incorporated by reference in its entirety.

(N) A developmental-arrestive protein produced in nature by a plant. For example, Logemann, et al., (1992) *Bio/Technology* 10:305, herein incorporated by reference in its entirety, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2):128-131, Pieterse and Van Loon, (2004) *Curr. Opin. Plant Bio.* 7(4):456-64 and Somssich, (2003) *Cell* 113(7):815-6, herein incorporated by reference in their entirety.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. No. 09/950,933, herein incorporated by reference in their entirety.

(Q) Detoxification genes, such as for fumonisin, beauvericin, moniliformin and zearalenone and their structurally related derivatives. For example, see, U.S. Pat. No. 5,792,931, herein incorporated by reference in its entirety.

(R) Cystatin and cysteine proteinase inhibitors. See, U.S. application Ser. No. 10/947,979, herein incorporated by reference in its entirety.

(S) Defensin genes. See, WO03/000863 and U.S. application Ser. No. 10/178,213, herein incorporated by reference in their entirety.

(T) Genes conferring resistance to nematodes. See, WO 03/033651 and Urwin, et. al., (1998) *Planta* 204:472-479, Williamson (1999) *Curr Opin Plant Bio.* 2(4):327-31, herein incorporated by reference in their entirety.

(U) Genes such as rcglconferring resistance to Anthracnose stalk rot, which is caused by the fungus *Colletotrichum graminiola*. See, Jung, et al., Generation-means analysis and quantitative trait locus mapping of Anthracnose Stalk Rot genes in Maize, *Theor. Appl. Genet.* (1994) 89:413-418, as well as, U.S. Provisional Patent Application No. 60/675,664, herein incorporated by reference in their entirety.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824 and international publication WO 96/33270, which are incorporated herein by reference in their entirety.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes) and pyridinoxy or phenoxy proprionic acids and cycloshexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and international publications EP1173580; WO 01/66704; EP1173581 and EP1173582, which are incorporated herein by reference in their entirety. Glyphosate resistance is also imparted to plants that express a gene that encodes a glyphosate oxido-reductase enzyme as described more fully in U.S. Pat. Nos. 5,776,760 and 5,463,175, which are incorporated herein by reference in their entirety. In addition glyphosate resistance can be imparted to plants by the over expression of genes encoding glyphosate N-acetyltransferase. See, for example, U.S. patent application Ser. Nos. 11/405,845 and 10/427,692 and PCT Application Number US01/46227, herein incorporated by reference in their entirety. A DNA molecule encoding a mutant aroA gene can be obtained under ATCC Accession Number 39256 and the nucleotide sequence of the mutant gene is disclosed in U.S. Pat. No. 4,769,061 to Comai, herein incorporated by reference in its entirety. EP Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin, herein incorporated by reference in their entirety. The nucleotide sequence of a phosphinothricin-acetyl-transferase gene is provided in EP Patent Numbers 0 242 246 and 0 242 236 to Leemans, et al., De Greef, et al., (1989) *Bio/Technology* 7:61 which describe the production of transgenic plants that express chimeric bar genes coding for phosphinothricin acetyl transferase activity, herein incorporated by reference in their entirety. See also, U.S. Pat. Nos. 5,969,213; 5,489,520; 5,550,318; 5,874,265; 5,919,675; 5,561,236; 5,648,477; 5,646,024; 6,177,616 B1 and 5,879,903, herein incorporated by reference in their entirety. Exemplary genes conferring resistance to phenoxy proprionic acids and cycloshexones, such as sethoxydim and haloxyfop, are the Acc1-S1, Acc1-S2 and Acc1-S3 genes described by Marshall, et al., (1992) *Theor. Appl. Genet.* 83:435, herein incorporated by reference in its entirety.

(C) A herbicide that inhibits photosynthesis, such as a triazine (psbA and gs+ genes) and a benzonitrile (nitrilase gene). Przibilla, et al., (1991) *Plant Cell* 3:169, herein incorporated by reference in its entirety, describe the transformation of *Chlamydomonas* with plasmids encoding mutant psbA genes. Nucleotide sequences for nitrilase genes are disclosed in U.S. Pat. No. 4,810,648 to Stalker, herein incorporated by reference in its entirety, and DNA molecules containing these genes are available under ATCC Accession Numbers 53435, 67441 and 67442. Cloning and expression of DNA coding for a glutathione S-transferase is described by Hayes, et al., (1992) *Biochem. J.* 285:173, herein incorporated by reference in its entirety.

(D) Acetohydroxy acid synthase, which has been found to make plants that express this enzyme resistant to multiple types of herbicides, has been introduced into a variety of plants (see, e.g., Hattori, et al., (1995) *Mol Gen Genet* 246:419, herein incorporated by reference in its entirety). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol.* 106(1):17-23), genes for glutathione reductase and superoxide dismutase (Aono, et al., (1995) *Plant Cell Physiol* 36:1687, and genes for various phosphotransferases (Datta, et al., (1992) *Plant Mol Biol* 20:619), herein incorporated by reference in their entirety.

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1 and 5,767,373; and international publication number WO 01/12825, herein incorporated by reference in their entirety.

3. Transgenes that Confer or Contribute to an Altered Grain Characteristic, Such as:

(A) Altered fatty acids, for example, by
   (1) Down-regulation of stearoyl-ACP desaturase to increase stearic acid content of the plant. See, Knultzon, et al., (1992) *Proc. Natl. Acad. Sci. USA* 89:2624 and WO99/64579 (Genes for Desaturases to Alter Lipid Profiles in Corn), herein incorporated by reference in their entirety,
   (2) Elevating oleic acid via FAD-2 gene modification and/or decreasing linolenic acid via FAD-3 gene modification (see, U.S. Pat. Nos. 6,063,947; 6,323, 392; 6,372,965 and WO 93/11245, herein incorporated by reference in their entirety),
   (3) Altering conjugated linolenic or linoleic acid content, such as in WO 01/12800, herein incorporated by reference in its entirety,
   (4) Altering LEC1, AGP, Dek1, Superal1, mi1ps, various lpa genes such as lpa1, lpa3, hpt or hggt. For example, see, WO 02/42424, WO 98/22604, WO 03/011015, U.S. Pat. Nos. 6,423,886, 6,197,561, 6,825,397, US Patent Application Publication Numbers 2003/0079247, 2003/0204870, WO02/057439, WO03/011015 and Rivera-Madrid, et. al., (1995) *Proc. Natl. Acad. Sci.* 92:5620-5624, herein incorporated by reference in their entirety.

(B) Altered phosphorus content, for example, by the
   (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene, herein incorporated by reference in its entirety.
   (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) *Maydica* 35:383 and/or by altering inositol kinase activity as in WO 02/059324, US Patent Application Publication Number 2003/ 0009011, WO 03/027243, US Patent Application Publication Number 2003/0079247, WO 99/05298, U.S. Pat. Nos. 6,197,561, 6,291,224, 6,391,348, WO2002/059324, US Patent Application Publication Number 2003/0079247, WO98/45448, WO99/ 55882, WO01/04147, herein incorporated by reference in their entirety.

(C) Altered carbohydrates effected, for example, by altering a gene for an enzyme that affects the branching pattern of starch or a gene altering thioredoxin such as NTR and/or TRX (see, U.S. Pat. No. 6,531,648, which is incorporated by reference in its entirety) and/or a gamma zein knock out or mutant such as cs27 or TUSC27 or en27 (see, U.S. Pat. No. 6,858,778 and US Patent Application Publication Numbers 2005/0160488 and 2005/0204418; which are incorporated by reference in its entirety). See, Shiroza, et al., (1988) *J. Bacteriol.* 170:810 (nucleotide sequence of *Streptococcus mutans* fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268: 22480 (site-directed mutagenesis of barley alpha-amylase gene) and Fisher, et al., (1993) *Plant Physiol.* 102:1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)), herein incorporated by reference in their entirety. The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US Patent Application Publication Number 2004/0034886 and WO 00/68393 involving the manipulation of antioxidant levels through alteration of a phytl prenyl transferase (ppt), WO 03/082899 through alteration of a homogentisate geranyl geranyl transferase (hggt), herein incorporated by reference in their entirety.

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441, 274 (plant tryptophan synthase beta subunit), U.S. Pat. No. 6,346,403 (methionine metabolic enzymes), U.S. Pat. No. 5,939,599 (high sulfur), U.S. Pat. No. 5,912, 414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication Number 2003/0163838, US Patent Application Publication Number 2003/0150014, US Patent Application Publication Number 2004/ 0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication Number 2004/ 0025203 (UDPGdH), U.S. Pat. No. 6,194,638 (RGP), herein incorporated by reference in their entirety.

4. Genes that Create a Site for Site Specific DNA Integration

This includes the introduction of FRT sites that may be used in the FLP/FRT system and/or Lox sites that may be used in the Cre/Loxp system. For example, see Lyznik, et al., (2003) *Plant Cell Rep* 21:925-932 and WO 99/25821, which are hereby incorporated by reference in their entirety. Other systems that may be used include the Gin recombinase of phage Mu (Maeser, et al., 1991; Vicki Chandler, *The Maize Handbook* ch. 118 (Springer-Verlag 1994), the Pin recombinase of *E. coli* (Enomoto, et al., 1983), and the R/RS system of the pSR1 plasmid (Araki, et al., 1992), herein incorporated by reference in their entirety.

5. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see, WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US Patent Application Publication Number 2004/0148654 and WO01/36596 where abscisic acid is altered in plants resulting in improved plant phenotype such as increased yield and/or increased tolerance to abiotic stress; WO2000/006341, WO04/090143, U.S. patent application Ser. No. 10/817,483 and U.S. Pat. No. 6,992,237, where cytokinin expression is modified resulting in plants with increased stress tolerance, such as drought tolerance, and/or increased yield, herein incorporated by reference in their entirety. Also see WO0202776, WO2003052063, JP2002281975, U.S. Pat. No. 6,084,153, WO0164898, U.S. Pat. Nos. 6,177,275 and 6,107,547 (enhancement of nitrogen utilization and altered nitrogen responsiveness), herein incorporated by reference in their entirety. For ethylene alteration, see US Patent Application Publication Number 2004/0128719, US Patent Application Publication Number 2003/0166197 and WO200032761, herein incorporated by reference in their entirety. For plant transcription factors or transcriptional regulators of abiotic stress, see, e.g., US Patent Application Publication Number 2004/0098764 or US Patent Application Publication Number 2004/0078852, herein incorporated by reference in their entirety.

Other genes and transcription factors that affect plant growth and agronomic traits such as yield, flowering, plant growth and/or plant structure, can be introduced or introgressed into plants, see, e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht) and WO2004076638 and WO2004031349 (transcription factors), herein incorporated by reference in their entirety.

The heterologous nucleotide sequence operably linked to regulatory sequences and its related biologically active fragments or variants disclosed herein may be an antisense sequence for a targeted gene. The terminology "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, 80%, 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides or greater may be used. Thus, the promoter sequences disclosed herein may be operably linked to antisense DNA sequences to reduce or inhibit expression of a native protein in the plant.

"RNAi" refers to a series of related techniques to reduce the expression of genes (see, for example, U.S. Pat. No. 6,506,559, herein incorporated by reference in its entirety). Older techniques referred to by other names are now thought to rely on the same mechanism, but are given different names in the literature. These include "antisense inhibition," the production of antisense RNA transcripts capable of suppressing the expression of the target protein and "co-suppression" or "sense-suppression," which refer to the production of sense RNA transcripts capable of suppressing the expression of identical or substantially similar foreign or endogenous genes (U.S. Pat. No. 5,231,020, incorporated herein by reference in its entirety). Such techniques rely on the use of constructs resulting in the accumulation of double stranded RNA with one strand complementary to the target gene to be silenced. The regulatory sequences of the aspects may be used to drive expression of constructs that will result in RNA interference including microRNAs and siRNAs.

As used herein, the terms "promoter" or "transcriptional initiation region" mean a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Additionally, chimeric promoters may be provided. Such chimeras include portions of the promoter sequence fused to fragments and/or variants of heterologous transcriptional regulatory regions. Thus, the promoter regions disclosed herein can comprise upstream regulatory elements such as, those responsible for tissue and temporal expression of the coding sequence, enhancers and the like. In the same manner, the promoter elements, which enable expression in the desired tissue such as reproductive tissue, can be identified, isolated and used with other core promoters to confer early-endosperm-preferred expression.

In this aspect of the disclosure, "core promoter" is intended to mean a promoter without promoter elements.

As used herein, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements that modify gene expression. It is to be understood that nucleotide sequences, located within introns or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. In the context of the present disclosure a post-transcriptional regulatory element may include elements that are active following transcription initiation, for example translational and transcriptional enhancers, translational and transcriptional repressors and mRNA stability determinants.

The regulatory elements or variants or fragments thereof, of the present disclosure may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or either enhancing or repressing transcriptional activity of the heterologous regulatory element and modulating post-transcriptional events. For example, one or more regulatory elements or fragments thereof of the present disclosure may be operatively associated with constitutive, inducible or tissue specific promoters or fragments thereof, to modulate the activity of such promoters within desired tissues in plant cells.

The regulatory sequences of the present disclosure or variants or fragments thereof, when operably linked to a heterologous nucleotide sequence of interest can drive constitutive or transient expression, of the heterologous nucleotide sequence in the tissue of the plant expressing this construct. The term "constitutive expression" means that expression of the heterologous nucleotide sequence is found throughout the plant.

A "heterologous nucleotide sequence," as used throughout the disclosure, is a sequence that is not naturally occurring with or operably linked to the promoter sequence of the disclosure. While this nucleotide sequence is heterologous to the promoter sequence, it may be homologous or native or heterologous or foreign to the plant host. Likewise, the promoter sequence may be homologous or native or heterologous or foreign to the plant host and/or the polynucleotide of interest.

The isolated promoter sequences of the present disclosure can be modified to provide for a range of expression levels of the heterologous nucleotide sequence. Thus, less than the entire promoter region may be utilized and the ability to drive expression of the nucleotide sequence of interest retained. It is recognized that expression levels of the mRNA may be altered in different ways with deletions of portions of the promoter sequences. The mRNA expression levels may be decreased, or alternatively, expression may be increased as a result of promoter deletions if, for example, there is a negative regulatory element (for a repressor) that is removed during the truncation process. Generally, at least about 20 nucleotides of an isolated promoter sequence will be used to drive expression of a nucleotide sequence.

Heterologous nucleotide sequences can include plant transcription factors, sequences whose encoded proteins can bind to promoter, enhancer or other regulatory sequences and in the process either stimulate or repress transcription of the related endogenous gene. Examples of transcription factors include members of the AP2/EREBP family (including the BBM (ODP2), plethora and aintegumenta subfamilies, CAAT-box binding proteins such as LEC1 and HAP3, and homeobox-containing proteins such as WUS1, WUS2, WUS3, WOX2, WOX2a, WOX4, WOX5) as well as members of the MYB, bHLH, NAC, MADS, bZIP and WRKY families. Of the total of approximately 26,000 genes in *Arabidopsis*, over 1500 of these are transcriptional regulators, of which about 45% are unique to plants (Reichmann et al., 2000. Science 290:2105-2110).

It is recognized that to increase transcription levels, enhancers may be utilized in combination with the promoter regions of the disclosure. Enhancers are nucleotide sequences that act to increase the expression of a promoter region. Enhancers are known in the art and include the SV40 enhancer region, the 35S enhancer element and the like. Some enhancers are also known to alter normal promoter expression patterns, for example, by causing a promoter to be expressed constitutively when without the enhancer, the same promoter is expressed only in one specific tissue or a few specific tissues.

Modifications of the isolated promoter sequences of the present disclosure can provide for a range of expression of the heterologous nucleotide sequence. Thus, they may be modified to be weak promoters or strong promoters. Generally, a "weak promoter" means a promoter that drives expression of a coding sequence at a low level. A "low level" of expression is intended to mean expression at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

It is recognized that the promoters of the disclosure, such as the PLTP promoters, may be used with their native coding sequences to increase or decrease expression, thereby resulting in a change in phenotype of the transformed plant. The nucleotide sequences disclosed in the present disclosure, such as the PLTP promoters and the LTP3 promoter (see Table 1 herein), as well as variants and fragments thereof, are useful in the genetic manipulation of any plant. The regulatory sequences are useful in this aspect when operably linked with a heterologous nucleotide sequence whose expression is to be controlled to achieve a desired phenotypic response. The term "operably linked" means that the transcription or translation of the heterologous nucleotide sequence is under the influence of the promoter sequence. In this manner, the nucleotide sequences for the promoters of the disclosure may be provided in expression cassettes along with heterologous nucleotide sequences of interest for expression in the plant of interest, more particularly for expression in the reproductive tissue of the plant.

In one aspect of the disclosure, expression cassettes comprise a transcriptional initiation region comprising one of the promoter nucleotide sequences of the present disclosure, such as the PLTP and LTP3 promoters, or variants or fragments thereof, operably linked to the heterologous nucleotide sequence. Such an expression cassette can be provided with a plurality of restriction sites for insertion of the nucleotide sequence to be under the transcriptional regulation of the regulatory regions. The expression cassette may additionally contain selectable marker genes as well as 3' termination regions.

The expression cassette can include, in the 5'-3' direction of transcription, a transcriptional initiation region (i.e., a promoter, or variant or fragment thereof, of the disclosure), a translational initiation region, a heterologous nucleotide sequence of interest, a translational termination region and optionally, a transcriptional termination region functional in the host organism. The regulatory regions (i.e., promoters, transcriptional regulatory regions, and translational termination regions) and/or the polynucleotide of the aspects may be native/analogous to the host cell or to each other. Alternatively, the regulatory regions and/or the polynucleotide of the aspects may be heterologous to the host cell or to each other. As used herein, "heterologous" in reference to a sequence is a sequence that originates from a foreign species or, if from the same species, is substantially modified from its native form in composition and/or genomic locus by deliberate human intervention. For example, a promoter operably linked to a heterologous polynucleotide is from a species different from the species from which the polynucleotide was derived or, if from the same/analogous species, one or both are substantially modified from their original form and/or genomic locus or the promoter is not the native promoter for the operably linked polynucleotide.

While it may be preferable to express a heterologous nucleotide sequence using the promoters of the disclosure, such as the PLTP and LTP3 promoters, the native sequences may be expressed. Such constructs would change expression levels of the protein in the plant or plant cell. Thus, the phenotype of the plant or plant cell is altered.

The termination region may be native with the transcriptional initiation region, may be native with the operably linked DNA sequence of interest, may be native with the plant host, or may be derived from another source (i.e., foreign or heterologous to the promoter, the DNA sequence being expressed, the plant host, or any combination thereof). Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acid Res.* 15:9627-9639, herein incorporated by reference in their entirety.

The expression cassette comprising the sequences of the present disclosure may also contain at least one additional nucleotide sequence for a gene to be cotransformed into the organism. Alternatively, the additional sequence(s) can be provided on another expression cassette.

Where appropriate, the nucleotide sequences whose expression is to be under the control of the early-endosperm-tissue-preferred promoter sequence of the present disclosure and any additional nucleotide sequence(s) may be optimized for increased expression in the transformed plant. That is, these nucleotide sequences can be synthesized using plant preferred codons for improved expression. See, for example, Campbell and Gowri, (1990) *Plant Physiol.* 92:1-11, herein incorporated by reference in its entirety, for a discussion of host-preferred codon usage. Methods are available in the art for synthesizing plant-preferred genes. See, for example, U.S. Pat. Nos. 5,380,831, 5,436,391 and Murray, et al., (1989) *Nucleic Acids Res.* 17:477-498, herein incorporated by reference in their entirety.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include, without limitation: picornavirus leaders, for example, EMCV leader (Encephalomyocarditis 5' noncoding region) (Elroy-Stein, et al., (1989) *Proc. Nat. Acad. Sci. USA* 86:6126-6130); potyvirus leaders, for example, TEV leader (Tobacco Etch Virus) (Allison, et al., (1986) *Virology* 154:9-20); MDMV leader (Maize Dwarf Mosaic Virus); human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) *Molecular Biology of RNA*, pages 237-256) and maize chlorotic mottle virus leader (MCMV) (Lommel, et al., (1991) *Virology* 81:382-385), herein incorporated by reference in their entirety. See, also, Della-Cioppa, et al., (1987) *Plant Physiology* 84:965-968, herein incorporated by reference in its entirety. Methods known to enhance mRNA stability can also be utilized, for example, introns, such as the maize Ubiquitin intron (Christensen and Quail, (1996) *Transgenic Res.* 5:213-218; Christensen, et al., (1992) *Plant Molecular Biology* 18:675-689) or the maize AdhI intron (Kyozuka, et al., (1991) *Mol. Gen. Genet.* 228:40-48; Kyozuka, et al., (1990) *Maydica* 35:353-357) and the like, herein incorporated by reference in their entirety.

The DNA constructs of the aspects can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA. It is recognized that to increase transcription levels enhancers may be utilized in combination with the promoter regions of the aspects. Enhancers are known in the art and include the SV40 enhancer region, the 35S enhancer element, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, for example, transitions and transversions, may be involved.

Reporter genes or selectable marker genes may also be included in the expression cassettes of the present disclosure. Examples of suitable reporter genes known in the art can be found in, for example, Jefferson, et al., (1991) in Plant Molecular Biology Manual, ed. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain, et al., (1995) *Bio Techniques* 19:650-655 and Chiu, et al., (1996) *Current Biology* 6:325-330, herein incorporated by reference in their entirety.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213; Meijer, et al., (1991) *Plant Mol. Biol.* 16:807-820); hygromycin (Waldron, et al., (1985) *Plant Mol. Biol.* 5:103-108 and Zhijian, et al., (1995) *Plant Science* 108:219-227); streptomycin (Jones, et al., (1987) *Mol. Gen. Genet.* 210:86-91); spectinomycin (Bretagne-Sagnard, et al., (1996) *Trans genic Res.* 5:131-137); bleomycin (Hille, et al., (1990) *Plant Mol. Biol.* 7:171-176); sulfonamide (Guerineau, et al., (1990) *Plant Mol. Biol.* 15:127-36); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518), herein incorporated by reference in their entirety.

Other genes that could serve utility in the recovery of transgenic events would include, but are not limited to, examples such as GUS (beta-glucuronidase; Jefferson, (1987) *Plant Mol. Biol. Rep.* 5:387), GFP (green fluorescence protein; Chalfie, et al., (1994) *Science* 263:802), luciferase (Riggs, et al., (1987) *Nucleic Acids Res.* 15(19): 8115 and Luehrsen, et al., (1992) *Methods Enzymol.* 216: 397-414) and the maize genes encoding for anthocyanin production (Ludwig, et al., (1990) *Science* 247:449), herein incorporated by reference in their entirety.

The expression cassette comprising the regulatory sequences of the present disclosure operably linked to a nucleotide sequence of interest can be used to transform any plant. In this manner, genetically modified plants, plant cells, plant tissue, seed, root and the like can be obtained.

As used herein, "vector" refers to a DNA molecule such as a plasmid, cosmid or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

The methods of the disclosure involve introducing a polypeptide or polynucleotide into a plant. As used herein, "introducing" is intended to mean presenting to the plant the polynucleotide or polypeptide in such a manner that the sequence gains access to the interior of a cell of the plant. The methods of the disclosure do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods and virus-mediated methods.

A "stable transformation" is a transformation in which the nucleotide construct introduced into a plant integrates into the genome of the plant and is capable of being inherited by the progeny thereof. "Transient transformation" means that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (Townsend, et al., U.S. Pat. No. 5,563,055 and Zhao, et al., U.S. Pat. No. 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244; 5,932,782; Tomes, et al., (1995) in Plant Cell, Tissue, and Organ Culture: Fundamental Methods, ed. Gamborg and Phillips (Springer-Verlag, Berlin); McCabe, et al., (1988) *Biotechnology* 6:923-926) and Led 1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in The Experimental Manipulation of Ovule Tissues, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*), all of which are herein incorporated by reference in their entirety. Methods and compositions for rapid plant transformation are also found in U.S. Provisional Appl. No. 62/248,578, herein incorporated in entirety by reference.

In specific aspects, the DNA constructs comprising the promoter sequences of the disclosure, such as the PLTP promoters, can be provided to a plant using a variety of transient transformation methods. Such transient transformation methods include, but are not limited to, viral vector systems and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

In other aspects, the polynucleotide of the disclosure may be introduced into plants by contacting plants with a virus or viral nucleic acids. Generally, such methods involve incorporating a nucleotide construct of the disclosure within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931 and Porta, et al., (1996) *Molecular Biotechnology* 5:209-221, herein incorporated by reference in their entirety.

Methods are known in the art for the targeted insertion of a polynucleotide at a specific location in the plant genome. In one aspect, the insertion of the polynucleotide at a desired genomic location is achieved using a site-specific recombination system. See, for example, WO99/25821, WO99/25854, WO99/25840, WO99/25855 and WO99/25853, all of which are herein incorporated by reference in their entirety. Briefly, the polynucleotide of the disclosure can be contained in transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84, herein incorporated by reference in its entirety. These plants may then be grown, and either pollinated with the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a nucleotide construct of the disclosure, for example, an expression cassette of the disclosure, stably incorporated into its genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif., herein incorporated by reference in its entirety). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the aspects containing a desired polynucleotide is cultivated using methods well known to one skilled in the art.

The aspects provide compositions for screening compounds that modulate expression within plants. The vectors, cells and plants can be used for screening candidate molecules for agonists and antagonists of the regulatory sequences disclosed herein. For example, a reporter gene can be operably linked to a regulatory sequence and expressed as a transgene in a plant. Compounds to be tested are added and reporter gene expression is measured to determine the effect on promoter activity.

Methods to Introduce Genome Editing Technologies into Plants

In an aspect, the disclosed methods and compositions can be used to introduce into somatic embryos with increased efficiency and speed polynucleotides useful to target a specific site for modification in the genome of a plant derived from the somatic embryo. Site specific modifications that can be introduced with the disclosed methods and compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. For example, the disclosed methods and compositions can be used to introduce a CRISPR-Cas system into somatic embryos, for the purpose of genome modification of a target sequence in the genome of a plant or plant cell derived from the somatic embryo, for selecting plants, for deleting a base or a sequence, for gene editing, and for inserting a polynucleotide of interest into the genome of a plant derived from a somatic embryo. Thus, the disclosed methods and compositions can be used together with a CRISPR-Cas system to provide for an effective system for modifying or altering target sites and nucleotides of interest within the genome of a plant, plant cell or seed.

In an aspect, the present disclosure comprises methods and compositions for producing a somatic embryo, wherein the method comprises introducing a polynucleotide of interest into a target site in the genome of a plant cell, the method comprising (a) transforming one or more cells of an explant with an expression construct comprising: (i) a nucleotide sequence encoding a WUS/WOX homeobox polypeptide; (ii) a nucleotide sequence encoding a polypeptide comprising two AP2-DNA binding domains; or (iii) a combination of (i) and (ii); and (b) allowing expression of the polypeptide of (a) in each transformed cell to form one or more somatic embryos, wherein no callus is formed; and wherein no meristem proliferation occurs; and wherein transformation further comprises a first expression construct capable of expressing a guide nucleotide and a second recombinant DNA construct capable of expressing a Cas endonuclease, wherein the guide nucleotide and Cas endonuclease are capable of forming a complex that enables the Cas endonuclease to introduce a double strand break at the target site. Alternatively, the expression construct comprising the nucleotide sequence encoding a WUS/WOX homeobox polypeptide and/or nucleotide sequence encoding a polypeptide comprising two AP2-DNA binding domains can also comprise a nucleotide sequence capable of expressing the guide nucleotide and a nucleotide sequence capable of expressing the Cas endonuclease.

In an aspect, the Cas endonuclease gene is a plant optimized Cas9 endonuclease, wherein the plant optimized Cas9 endonuclease is capable of binding to and creating a double strand break in a genomic target sequence the plant genome.

The Cas endonuclease is guided by the guide nucleotide to recognize and optionally introduce a double strand break at a specific target site into the genome of a cell. The CRISPR-Cas system provides for an effective system for modifying target sites within the genome of a plant, plant cell or seed. Further provided are methods and compositions employing a guide polynucleotide/Cas endonuclease system to provide an effective system for modifying target sites within the genome of a cell and for editing a nucleotide sequence in the genome of a cell. Once a genomic target site is identified, a variety of methods can be employed to further modify the target sites such that they contain a variety of polynucleotides of interest. The disclosed compositions and methods can be used to introduce a CRISPR-Cas system for editing a nucleotide sequence in the genome of a cell. The nucleotide sequence to be edited (the nucleotide sequence of interest) can be located within or outside a target site that is recognized by a Cas endonuclease.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

CRISPR loci were first recognized in *E. coli* (Ishino et al. (1987) J. Bacterial. 169:5429-5433; Nakata et al. (1989) J. Bacterial. 171:3553-3556). Similar interspersed short sequence repeats have been identified in *Haloferax mediterranei, Streptococcus pyogenes, Anabaena*, and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307: 26-30; Mojica et al. (1995) Mol. Microbiol. 17:85-93). The CRISPR loci differ from other SSRs by the structure of the repeats, which have been termed short regularly spaced repeats (SRSRs) (Janssen et al. (2002) OMICS J. Integ. Biol. 6:23-33; Mojica et al. (2000) Mol. Microbiol. 36:244-246). The repeats are short elements that occur in clusters, that are always regularly spaced by variable sequences of constant length (Mojica et al. (2000) Mol. Microbiol. 36:244-246).

Cas gene includes a gene that is generally coupled, associated or close to or in the vicinity of flanking CRISPR loci. The terms "Cas gene" and "CRISPR-associated (Cas) gene" are used interchangeably herein. A comprehensive review of the Cas protein family is presented in Haft et al. (2005) Computational Biology, PLoS Comput Biol 1 (6): e60. doi:10.1371/journal.pcbi.0010060.

Figure 2A:
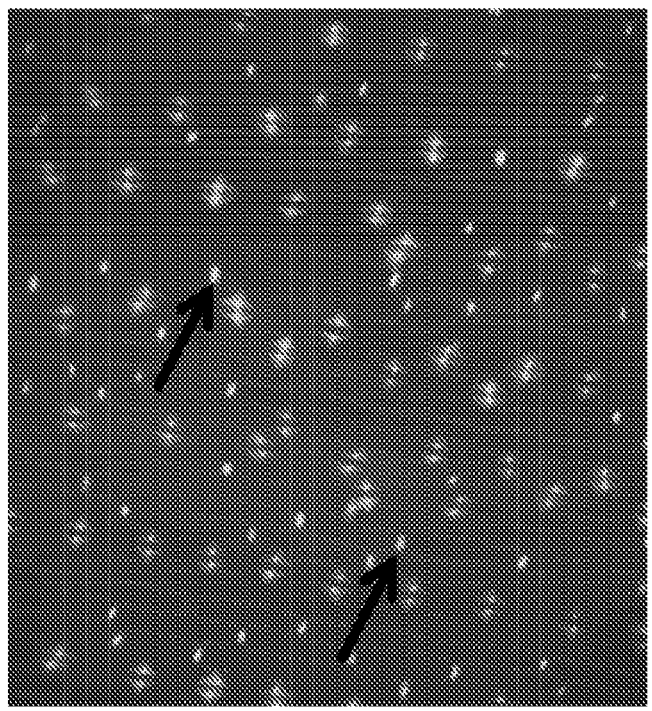
Figure 2B:
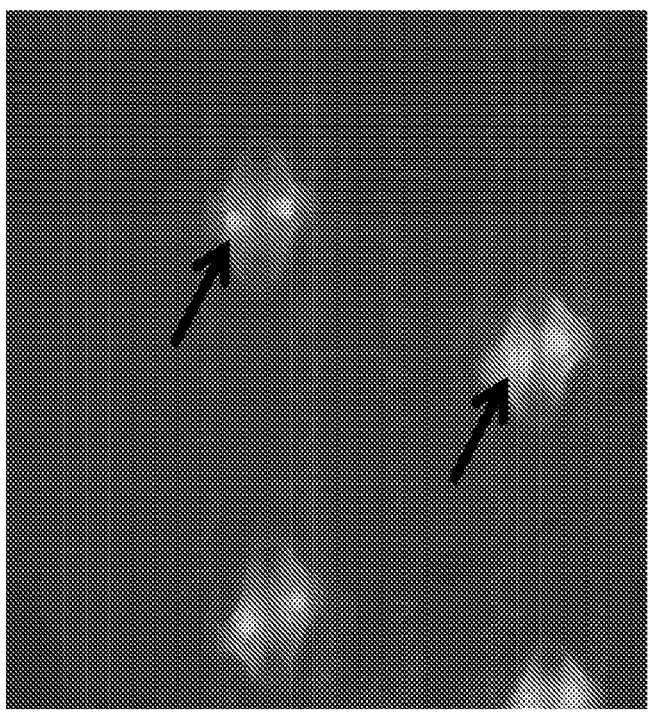

In addition to the four initially described gene families, an additional 41 CRISPR-associated (Cas) gene families have been described in WO/2015/026883, which is incorporated herein by reference. This reference shows that CRISPR systems belong to different classes, with different repeat patterns, sets of genes, and species ranges. The number of Cas genes at a given CRISPR locus can vary between species. Cas endonuclease relates to a Cas protein encoded by a Cas gene, wherein the Cas protein is capable of introducing a double strand break into a DNA target sequence. The Cas endonuclease is guided by the guide polynucleotide to recognize and optionally introduce a double strand break at a specific target site into the genome of a cell. As used herein, the term "guide polynucleotide/Cas endonuclease system" includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide nucleotide, but only if the correct protospacer-adjacent motif (PAM) is approximately oriented at the 3' end of the target sequence (see FIG. 2A and FIG. 2B of WO/2015/026883, published Feb. 26, 2015).

Figure 1:
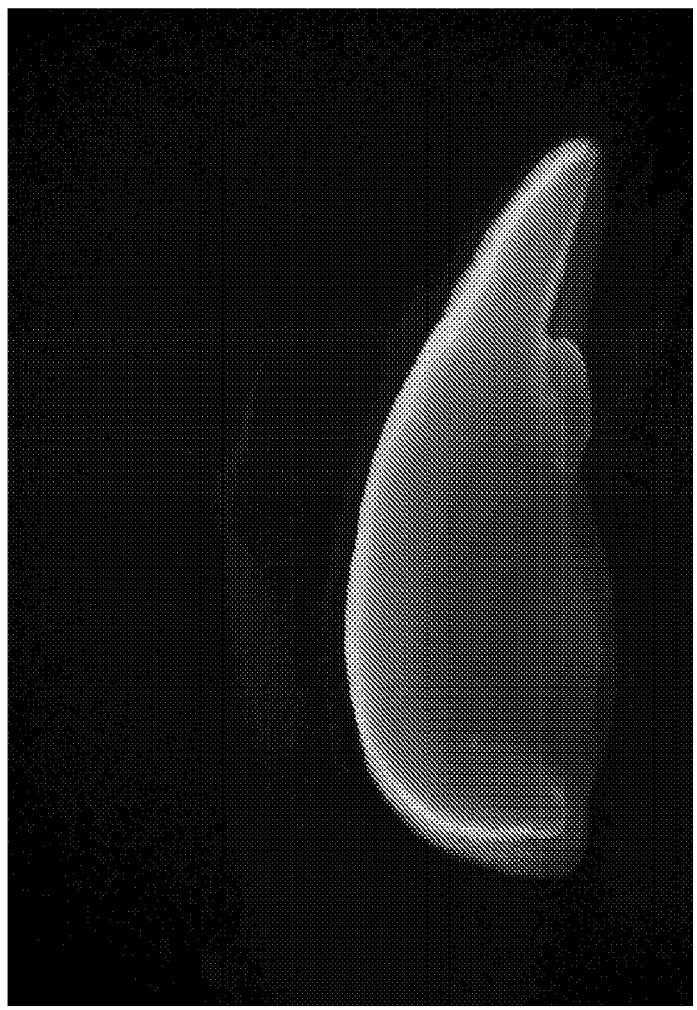

In an aspect, the Cas endonuclease gene is a Cas9 endonuclease, such as, but not limited to, Cas9 genes listed in SEQ ID NOs: 462, 474, 489, 494, 499, 505, and 518 of WO2007/025097, published Mar. 1, 2007, and incorporated herein by reference. In another aspect, the Cas endonuclease gene is plant, maize or soybean optimized Cas9 endonuclease, such as, but not limited to those shown in FIG. 1A of WO/2015/026883. In another aspect, the Cas endonuclease gene is operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region.

In an aspect, the Cas endonuclease gene is a Cas9 endonuclease gene of SEQ ID NO:1, 124, 212, 213, 214, 215, 216, 193 or nucleotides 2037-6329 of SEQ ID NO:5, or any functional fragment or variant thereof, of WO/2015/026883.

As related to the Cas endonuclease, the terms "functional fragment," "fragment that is functionally equivalent," and "functionally equivalent fragment" are used interchangeably herein. These terms refer to a portion or subsequence of the Cas endonuclease sequence of the present disclosure in which the ability to create a double-strand break is retained.

As related to the Cas endonuclease, the terms "functional variant," "variant that is functionally equivalent" and "functionally equivalent variant" are used interchangeably herein. These terms refer to a variant of the Cas endonuclease of the present disclosure in which the ability to create a double-strand break is retained. Fragments and variants can be obtained via methods such as site-directed mutagenesis and synthetic construction.

In an aspect, the Cas endonuclease gene is a plant codon optimized *Streptococcus pyogenes* Cas9 gene that can recognize any genomic sequence of the form N(12-30)NGG can in principle be targeted.

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more (Patent application PCT/US 12/30061 filed on Mar. 22, 2012). Meganucleases have been classified into four families based on conserved sequence motifs, the families are the LAGLI- DADG, GIY-YIG, H-N-H, and His-Cys box families. These motifs participate in the coordination of metal ions and hydrolysis of phosphodiester bonds. Meganucleases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families. TAL effector nucleases are a new class of sequence-specific nucleases that can be used to make double-strand breaks at specific target sequences in the genome of a plant or other organism. (Miller, et al. (2011) Nature Biotechnology 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a nonspecific endonuclease domain, for example nuclease domain from a Type Ms endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Bacteria and archaea have evolved adaptive immune defenses termed clustered regularly interspaced short palindromic repeats (CRISPR)/CRISPR-associated (Cas) systems that use short RNA to direct degradation of foreign nucleic acids ((WO2007/025097 published Mar. 1, 2007). The type II CRISPR/Cas system from bacteria employs a crRNA and tracrRNA to guide the Cas endonuclease to its DNA target. The crRNA (CRISPR RNA) contains the region complementary to one strand of the double strand DNA target and base pairs with the tracrRNA (trans-activating CRISPR RNA) forming a RNA duplex that directs the Cas endonuclease to cleave the DNA target.

As used herein, the term "guide nucleotide" relates to a synthetic fusion of two RNA molecules, a crRNA (CRISPR RNA) comprising a variable targeting domain, and a tracrRNA. In an aspect, the guide nucleotide comprises a variable targeting domain of 12 to 30 nucleotide sequences and a RNA fragment that can interact with a Cas endonuclease.

As used herein, the term "guide polynucleotide" relates to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide nucleotide".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In an aspect, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In an aspect, the size of the fragment of the cRNA naturally occurring in Bacteria and Archaea that is present in a crNucleotide disclosed herein can range from, but is not limited to, 2, 3, 4, 5, 6, 7, 8, 9,10, 11, 12, 13, 14, 15, 16, 17, 18, 19, 20 or more nucleotides.

In an aspect, the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides In an aspect, the RNA that guides the RNA Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In an aspect the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide nucleotide" (when composed of a contiguous stretch of RNA nucleotides) or "single guide DNA" (when composed of a contiguous stretch of DNA nucleotides) or "single guide nucleotide-DNA" (when composed of a combination of RNA and DNA nucleotides). In an aspect of the disclosure, the single guide nucleotide comprises a cRNA or cRNA fragment and a tracrRNA or tracrRNA fragment of the type II CRISPR/Cas system that can form a complex with a type II Cas endonuclease, wherein the guide nucleotide Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In an aspect, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In an aspect, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another aspect, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

In an aspect, the guide nucleotide and Cas endonuclease are capable of forming a complex that enables the Cas endonuclease to introduce a double strand break at a DNA target site.

In an aspect of the disclosure the variable target domain is 12, 13, 14, 15, 16, 17, 18, 19, 20, 21, 22, 23, 24, 25, 26, 27, 28, 29 or 30 nucleotides in length.

In an aspect of the disclosure, the guide nucleotide comprises a cRNA (or cRNA fragment) and a tracrRNA (or tracrRNA fragment) of the type II CRISPR/Cas system that can form a complex with a type II Cas endonuclease, wherein the guide nucleotide Cas endonuclease complex can direct the Cas endonuclease to a plant genomic target site, enabling the Cas endonuclease to introduce a double strand break into the genomic target site. In an aspect the guide nucleotide can be introduced into a plant or plant cell directly using any method known in the art such as, but not limited to, particle bombardment or topical applications.

In an aspect, the guide nucleotide can be introduced indirectly by introducing a recombinant DNA molecule comprising the corresponding guide DNA sequence operably linked to a plant specific promoter that is capable of transcribing the guide nucleotide in the plant cell. The term "corresponding guide DNA" includes a DNA molecule that is identical to the RNA molecule but has a "T" substituted for each "U" of the RNA molecule.

In an aspect, the guide nucleotide is introduced via particle bombardment or using the disclosed methods and compositions for *Agrobacterium* transformation of a recombinant DNA construct comprising the corresponding guide DNA operably linked to a plant U6 polymerase III promoter.

In an aspect, the RNA that guides the RNA Cas9 endonuclease complex, is a duplexed RNA comprising a duplex crRNA-tracrRNA. One advantage of using a guide nucleotide versus a duplexed crRNA-tracrRNA is that only one expression cassette needs to be made to express the fused guide nucleotide.

The terms "target site," "target sequence," "target DNA," "target locus," "genomic target site," "genomic target sequence," and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature.

As used herein, terms "endogenous target sequence" and "native target sequence" are used interchangeably herein to refer to a target sequence that is endogenous or native to the genome of a plant and is at the endogenous or native position of that target sequence in the genome of the plant. In an aspect, the target site can be similar to a DNA recognition site or target site that that is specifically recognized and/or bound by a double-strand break inducing agent such as a LIG3-4 endonuclease (US patent publication 2009-0133152 A1 (published May 21, 2009) or a MS26++ meganuclease (U.S. patent application Ser. No. 13/526,912 filed Jun. 19, 2012).

An "artificial target site" or "artificial target sequence" are used interchangeably herein and refer to a target sequence that has been introduced into the genome of a plant. Such an artificial target sequence can be identical in sequence to an endogenous or native target sequence in the genome of a plant but be located in a different position (i.e., a non-endogenous or non-native position) in the genome of a plant.

An "altered target site," "altered target sequence" "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

The following examples are offered by way of illustration and not by way of limitation.

EXAMPLES

The aspects are further defined in the following Examples, in which parts and percentages are by weight and degrees are Celsius, unless otherwise stated. It should be understood that these Examples, while indicating aspects of the disclosure, are given by way of illustration only. From the above discussion and these Examples, one skilled in the art can ascertain the essential characteristics of the aspects, and without departing from the spirit and scope thereof, can make various changes and modifications of them to adapt to various usages and conditions. Thus, various modifications of the aspects in addition to those shown and described herein will be apparent to those skilled in the art from the foregoing description. Such modifications are also intended to fall within the scope of the appended claims.

Example 1. Identification of the PLTP Promoter

Promoters were identified to improve transformation methods using the maize WUS2 and ODP2 genes. High levels of expression of ODP2 (for example, using the maize UBI PRO; SEQ ID NO: 31) and lower levels of expression of WUS2 (for example, using the *Agrobacterium* NOS PRO) have been reported and both expressed immediately after *Agrobacterium*-mediated transformation and throughout callus growth to provide optimal growth and rates of event recovery (see U.S. Pub. No. US20140157453 herein incorporated by reference in its entirety). However, continuing to express these transcription factors at this level resulted in severe pleiotropic abnormalities, including swollen, stunted roots, severe twisting and deformity of the vegetative portion of the plant, and also resulted in sterility. One previous solution was to excise these genes before regeneration of plantlets, using a RAB17 PRO-driven CRE recombinase. However, the desiccation process necessary to stimulate CRE expression was deleterious to the subsequent health of many inbreds, and an alternative solution was required.

From previous studies it is known that corn plants were particularly sensitive to ectopic expression of ODP2 and WUS2 in the roots, tassel and ear. Based on this information, new promoters were sought that expressed in the embryo (and thus callus), with no expression in the roots (at all developmental stages), tassel or ear—also anticipating that early expression in the leaf would be acceptable.

Figure 5:
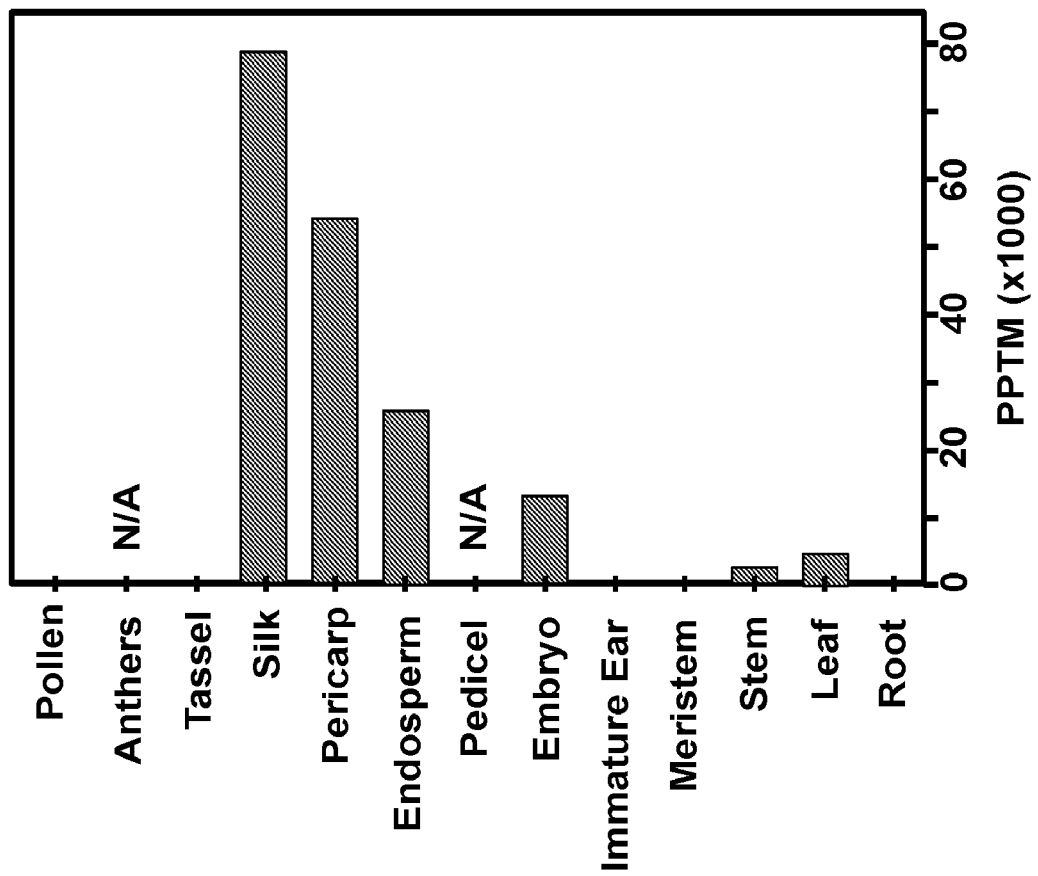
FIG. 5 illustrates expression of the endogenous maize Phospholipid Transfer Protein gene by its native promoter (ZM-PLTP) (SEQ ID NO: 1). Transcript levels based on Massively Parallel Signature Sequencing (MPSS) are shown in Parts Per Ten Million (PPTM).
Figure 19:
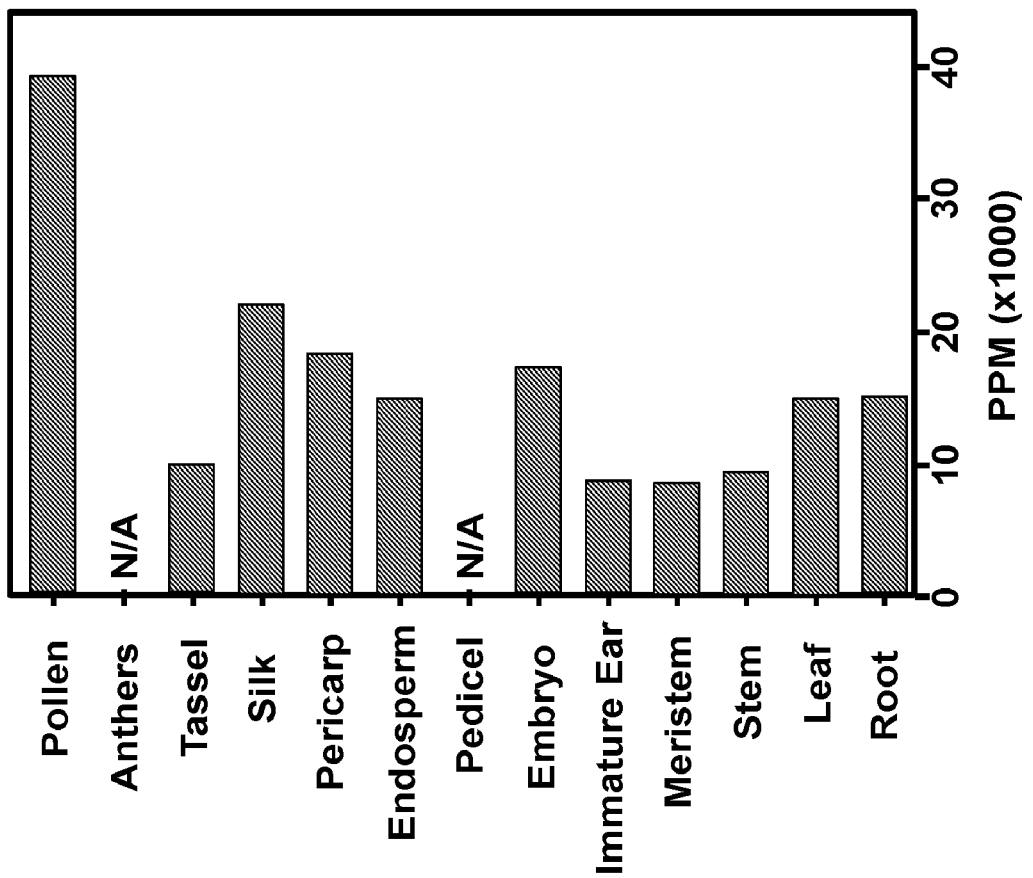
FIG. 19 illustrates expression of the endogenous maize ubiquitin gene by its native promoter (ZM-UBI) (SEQ ID NO: 31). Transcript levels based on Massively Parallel Signature Sequencing (MPSS) are shown in Parts Per Ten Million (PPTM).

Once the above expression criteria were established, 73,268 gene-candidates from DuPont Pioneer's database were analyzed (using Illumina RNA-Seq data) to determine which maize genes met this expression profile. Based on this analysis, eleven candidate promoters were identified that met these criteria. One identified promoter, ZM-PLTP (SEQ ID NO: 1), from a previously unidentified maize phospholipid transferase gene was more highly expressed in the embryo. As shown in FIG. 5, when compared to the constitutive expression of the UBI PRO (FIG. 19), expression of PLTP (FIG. 5) was i) very strong in silks, pericarp, and endosperm, ii) strong in the embryo, iii) moderate in the leaf and stem, and iv) off in the root, meristem, immature ear, tassel, anthers and pollen, while as the name implies, expression of UBI was observed in all tissues, being particularly strong in pollen. Expression of both PLTP and UBI were in a similar range, at approximately 13,000 and 17,000 PPM, respectively.

Example 2. Alignment of the Maize and Sorghum PLTP Promoters

The promoter sequences for the maize and sorghum promoters (SEQ ID NO:1 and SEQ ID NO:2, respectively) were aligned to distinguish shared elements (7-bases or longer) within the promoters, and to determine which of these elements shared the structure of known plant promoter elements in the literature. Based on this analysis, SEQ ID NO:1 and SEQ ID NO:2 promoter sequences shared a large number of elements, including a number of elements that match known plant promoter elements.

TABLE 2

Shared elements between the maize PLTP promoter sequence (SEQ ID NO: 1) and the sorghum PLTP promoter sequence (SEQ ID NO: 2). Table 2 includes the consensus sequences for known plant promoter elements that match SEQ ID NO: 1 and SEQ ID NO: 2. SE in Table 2 represents shared elements. Y represents a pyrimidine and W represents a weak preference for A or T.

| Shared Element | SE Length | Distance from 3'-end of seq1 | Assorted Plant Promoter Elements |
|---|---|---|---|
| AGAGTATGT | 9 | 986 | |
| AGAGAGAG | 8 | 912 | |
| CAGGAAGAG | 9 | 843 | |
| ATGTGTTT | 8 | 799 | |
| GTTTATTGT | 9 | 795 | |
| AATTAACT | 8 | 363 | |
| AACACCCAACCACCTCCTGCTC (SEQ ID NO: 33) | 22 | 326 | CCWACCCCTCCT (SEQ ID NO: 34) |

TABLE 2-continued

Shared elements between the maize PLTP promoter sequence (SEQ ID NO: 1) and the sorghum PLTP promoter sequence (SEQ ID NO: 2). Table 2 includes the consensus sequences for known plant promoter elements that match SEQ ID NO: 1 and SEQ ID NO: 2. SE in Table 2 represents shared elements. Y represents a pyrimidine and W represents a weak preference for A or T.

| Shared Element | SE Length | Distance from 3'-end of seq1 | Assorted Plant Promoter Elements |
|---|---|---|---|
| GGAACATCCA (SEQ ID NO: 35) | 10 | 244 | |
| TGCATCCA | 8 | 201 | |
| CATCCACCATT (SEQ ID NO: 36) | 11 | 191 | |
| TTCCACCGA | 9 | 171 | |
| GCCTATTTAAGGAGC (SEQ ID NO: 37) | 15 | 148 | TATTTAA |
| ACTCTCCTC | 9 | 119 | |
| TCCTCACCA | 9 | 115 | |
| TCACCAGC | 8 | 102 | |
| GCTAGCTC | 8 | 96 | |
| AGCACTTG | 8 | 82 | CANNTGYACT (SEQ ID NO: 38) |
| GCATTCCAAA (SEQ ID NO: 39) | 10 | 58 | |
| GTATGTA | 7 | 983 | |
| ATGTATG | 7 | 981 | |
| TATTGTG | 7 | 938 | |
| GAGAGTG | 7 | 909 | |
| AGAGAGT | 7 | 838 | |
| AGAGCCA | 7 | 820 | |
| CCAACTT | 7 | 816 | |
| GTGTTTA | 7 | 797 | |
| TGTTTAT | 7 | 796 | |
| CTTTAGA | 7 | 783 | |
| TAATTAA | 7 | 722 | |
| ATGTACG | 7 | 609 | ATGTACGAAGCGTAC (SEQ ID NO: 40) |
| CGTGTTA | 7 | 604 | |
| CGAAAGT | 7 | 443 | AAAG |
| GTATCTA | 7 | 408 | |
| TAGTCTA | 7 | 403 | |
| AGTCTAG | 7 | 402 | |
| AGTTAGT | 7 | 393 | AGTTAGTTAC AGTTAGTTAA AAGA (SEQ ID NO: 41) |
| TAGTATA | 7 | 390 | |
| GATGATG | 7 | 370 | |
| ATGAATT | 7 | 366 | |
| ACTCTGC | 7 | 358 | |
| TGCCTCC | 7 | 337 | |
| CCAACAC | 7 | 328 | CNAACACCAACA (SEQ ID NO: 42) |
| CAACACC | 7 | 327 | CAACA |
| CGACGGA | 7 | 248 | CGACG |
| CATGCAA | 7 | 233 | CATGCA |
| CGTGCAT | 7 | 203 | |
| CACTTGC | 7 | 80 | CANNTGYACT (SEQ ID NO: 43) |
| AGCTAGC | 7 | 38 | |
| GCTAGCA | 7 | 37 | |
| CTCCTCA | 7 | 13 | |

Example 3. Patterns of Transgene Expression Driven by the Maize PLTP Promoter

Figure 3:
FIG. 3 illustrates that green fluorescence was observed in silk hairs in maize plants expressing PLTP PRO::ZS-GREEN1::pinII. The image was taken using an epifluorescence stereo-microscope.

To evaluate spatial and temporal patterns of expression driven by the PLTP promoter, the following expression cassette was constructed: PLTP PRO::DS-GREEN::pinII TERM. Transgenic maize events containing this expression cassette were produced. Tissues from developing zygotic embryos, from roots and leaves of germinating plants (and during subsequent stages of vegetative growth), from tassel and ear were observed under epifluorescence illumination using a stereomicroscope and using a compound epifluorescence microscope. Expression in the zygotic embryo was strong, but was confined to the secretory epithelium of the scutellum (the surface contacting the endosperm, see FIG. 1). In leaves, the expression pattern was not uniform, but was very specifically restricted to the accessory cells flanking the guard cells and the short cells in the epidermis (see FIG. 2). While expression in the silks was also very strong, it was not uniform, with bright green fluorescence being observed in the silk hairs and the tip of the silk (see FIG. 3).

After *Agrobacterium*-mediated transformation of wild-type immature embryos using a Pioneer inbred line, green fluorescence was observed in early, developing transgenic somatic embryos (see FIG. 4) and continued to be expressed into regeneration (in the leaves but not in the roots).

Example 4. Plasmids

Plasmids comprising T-DNA described in Table 1 were used in experiments described herein.

TABLE 3

Plasmids comprising T-DNA described in Table 1 were used in experiments described herein below. The listed plasmids in Table 1 harbor a T-DNA containing the indicated components.

| Plasmid ID | T-DNA |
|---|---|
| PHP77833 | RB + NOS PRO:Top2:ZM-WUS2::IN2-1 TERM + ZM-PLTP PRO::ZM-ODP2::OS-T28 TERM + GZ-W64A TERM + UBI PRO:UBI1ZM INTRON:ESR::SB-SAG12 TERM + SB-ALS PRO:: HRA::SB-PEPC1 TERM + LTP2 PRO::ZS-YELLOW::PINII TERM-LB (SEQ ID NO: 28). |
| PHP79024 | RB + ZM-AXIG1 PRO:Top1:ZM-WUS2::IN2-1 TERM + ZM-PLTP PRO::ZM-ODP2::OS-T28 TERM + GZ-W64A TERM + UBI PRO:UBI1ZM INTRON:ESR::SB-SAG12 TERM + SB-ALS PRO:: HRA::SB-PEPC1 TERM + UBI PRO::ZS-GREEN1::PINII TERM:SB-ACTIN TERM-LB (SEQ ID NO: 29). |
| PHP80730 | OVERDRIVE + RB (OCTOPINTE) + GM-LTP3 PRO::AT-WUS::UBQ14 TERM + GM-UBQ PRO::GM-UBQ INTRON1::TAG-RFP::UBQ3 TERM + GM-SAMS PRO::GM-SAMS INTRON1::GM-HRA::GM-ALS TERM + LB (OCTOPINE) + LB (AGROPINE) + LB (SEQ ID NO: 30) |

Example 5: Culture Media

Various media are referenced in the Examples for use in transformation and cell culture. The descriptions of these media are described below in Tables 4-11.

TABLE 4

Media compositions for *sorghum* transformation.
Medium Composition

PHI-I: 4.3 g/l MS salts (Phytotechnology Laboratories, Shawnee Mission, KS, catalog number M524), 0.5 mg/l nicotinic acid, 0.5 mg/l pyridoxine HCl, 1 mg/l thiamine HCl, 0.1 g/l myo-inositol, 1 g/l casamino acids (Becton Dickinson and Company, BD Diagnostic Systems, Sparks, MD, catalog number 223050), 1.5 mg/l 2,4-dichlorophenoxyacetic acid (2,4-D), 68.5 g/l sucrose, 36 g/l glucose, pH 5.2; with 100 µM acetosyringone added before using.
PHI-T: PHI-I with 20 g/l sucrose, 10 g/l glucose, 2 mg/l 2,4-D, no casamino acids, 0.5 g/l MES buffer, 0.7 g/l L-proline, 10 mg/l ascorbic acid, 100 µM acetosyringone, 8 g/l agar, pH 5.8.
PHI-U: PHI-T with 1.5 mg/l 2,4-D 100 mg/l carbenicillin, 30 g/l sucrose, no glucose and acetosyringone; 5 mg/l PPT, pH 5.8.
PHI-UM: PHI-U with12.5 g/l mannose and 5 g/l maltose, no sucrose, no PPT, pH 5.8
PHI-V: PHI-U with 10 mg/l PPT
DBC3: 4.3 g/l MS salts, 0.25 g/l myo-inositol, 1.0 g/l casein hydrolysate, 1.0 mg/l thiamine HCL, 1.0 mg/l 2,4-D, 30 g/l maltose, 0.69 g/l L-proline, 1.22 mg/l cupric sulfate, 0.5 mg/l BAP, 3.5 g/l phytagel, pH 5.8
PHI-X: 4.3 g/l MS salts, 0.1 g/l myo-inositol, 5.0 ml MS vitamins stock[b], 0.5 mg/l zeatin, 700 mg/l L-proline, 60 g/l sucrose, 1 mg/l indole-3-acetic acid, 0.1 µM abscisic acid, 0.1 mg/l thidiazuron, 100 mg/l carbenicillin, 5 mg/l PPT, 8 g/l agar, pH 5.6.
PHI-XM: PHI-X with no PPT; added 1.25 mg/l cupric sulfate, pH 5.6.
PHI-Z: 2.15 g/l MS salts, 0.05 g/l myo-inositol, 2.5 ml MS vitamins stock[b], 20 g/l sucrose, 3 g/l phytagel, pH 5.6

[a]PHI-I, PHI-T, PHI-U, PHI-V, PHI-X, and PHI-Z media from Zhao et al. 2000
[b]MS vitamins stock: 0.1 g/l nicotinic acid, 0.1 g/l pyridoxine HCl, 0.02 g/l thiamine HCl, 0.4 g/l glycine.

TABLE 5

Composition of wheat liquid infection medium WI 4.

| WI 4 | |
|---|---|
| DI water | 1000 mL |
| MS salt + Vitamins (M519) | 4.43 g |
| Maltose | 30 g |
| Glucose | 10 g |
| MES | 1.95 g |
| 2,4-D (.5 mg/L) | 1 ml |
| Picloram (10 mg/ml) | 200 µl |
| BAP (1 mg/L) | .5 ml |
| Adjust PH to 5.8 with KOH | |
| Post sterilization add: | |
| Acetosyringone (400 µM) | 400 µl |

TABLE 6

Composition of wheat co-cultivation medium WC#10.

| WC # 10 | |
|---|---|
| DI water | 1000 mL |
| MS salt + Vitamins (M519) | 4.43 g |
| Maltose | 30 g |
| Glucose | 1 g |
| MES | 1.95 g |
| 2,4-D (.5 mg/L) | 1 ml |
| Picloram (10 mg/ml) | 200 µl |
| BAP (1 mg/L) | .5 ml |
| 50X CuSO4 (.1M) | 49 µl |
| Adjust PH to 5.8 with KOH and add 2.5 g/L of Phytagel. | |
| Post sterilization add: | |
| Acetosyringone (400 µM) | 400 µl |

TABLE 7

Composition of wheat Green Tissue culture medium DBC4.

DBC4

| | |
|---|---|
| dd H20 | 1000 mL |
| MS salt | 4.3 g |
| Maltose | 30 g |
| Myo-inositol | 0.25 g |
| N-Z-Amine-A | 1 g |
| Proline | 0.69 g |
| Thiamine-HCl (0.1 mg/mL) | 10 mL |
| 50X CuSO4 (0.1M) | 49 µL |
| 2,4-D (0.5 mg/mL) | 2 mL |
| BAP | 1 mL |
| Adjust PH to 5.8 with KOH and then add 3.5 g/L of Phytagel. | |
| Post sterilization add: | |
| Cef (100 mg/ml) | 1 ml |

TABLE 8

Composition of wheat Green Tissue induction medium DBC6.

DBC6

| | |
|---|---|
| dd H20 | 1000 mL |
| MS salt | 4.3 g |
| Maltose | 30 g |
| Myo-inositol | 0.25 g |
| N-Z-Amine-A | 1 g |
| Proline | 0.69 g |
| Thiamine-HCl (0.1 mg/mL) | 10 mL |
| 50X CuSO4 (0.1M) | 49 µL |
| 2,4-D (0.5 mg/mL) | 1 mL |
| BAP | 2 mL |
| Adjust PH to 5.8 with KOH and then add 3.5 g/L of Phytagel. | |
| Post sterilization add: | |
| Cef (100 mg/ml) | 1 ml |

TABLE 9

Composition of wheat regeneration medium MSA.

MSA

| | |
|---|---|
| dd H20 | 1000 mL |
| MS salt + Vitamins (M519) | 4.43 g |
| Sucorse | 20 g |
| Myo-Inositol | 1 g |
| Adjust PH to 5.8 with KOH and then add 3.5 g/L of Phytagel. | |
| Post sterilization add: | |
| Cef (100 mg/ml) | 1 ml |

TABLE 10

Composition of wheat regeneration medium MSB.

MSB

| | |
|---|---|
| dd H20 | 1000 mL |
| MS salt + Vitamins (M519) | 4.43 g |
| Sucorse | 20 g |
| Myo-Inositol | 1 g |
| Adjust PH to 5.8 with KOH and then add 3.5 g/L of Phytagel. | |
| Post sterilization add: | |
| Cef (100 mg/ml) | 1 ml |
| IBA | .5 ml |

TABLE 11

Media formations for maize transformation, selection and regeneration.

| Medium components | Units per liter | 12V | 810I | 700 | 710I | 605J | 605T | 289Q |
|---|---|---|---|---|---|---|---|---|
| MS BASAL SALT MIXTURE | g | | | 4.3 | 4.3 | 4.3 | 4.3 | 4.3 |
| N6 MACRONUTRIENTS 10X | ml | | | | | 60.0 | 60.0 | |
| POTASSIUM NITRATE | g | | | | | 1.7 | 1.7 | |
| B5H MINOR SALTS 1000X | ml | | | | | 0.6 | 0.6 | |
| NaFe EDTA FOR B5H 100X | ml | | | | | 6.0 | 6.0 | |
| ERIKSSON'S VITAMINS 1000X | ml | | | | | 0.4 | 0.4 | |
| S&H VITAMIN STOCK 100X | ml | | | | | 6.0 | 6.0 | |
| THIAMINE•HCL | mg | | | 10.0 | 10.0 | 0.5 | 0.5 | |
| L-PROLINE | g | | | | 0.7 | 2.0 | 2.0 | 0.7 |
| CASEIN HYDROLYSATE (ACID) | g | | | | | 0.3 | 0.3 | |
| SUCROSE | g | | | 68.5 | 20.0 | 20.0 | 20.0 | 60.0 |
| GLUCOSE | g | 5.0 | | 36.0 | 10.0 | 0.6 | 0.6 | |
| MALTOSE | g | | | | | | | |
| 2,4-D | mg | | | 1.5 | 2.0 | 0.8 | 0.8 | |
| AGAR | g | 15.0 | 15.0 | | 8.0 | 6.0 | 6.0 | 8.0 |
| PHYTAGEL | g | | | | | | | |
| DICAMBA | g | | | | | 1.2 | 1.2 | |

TABLE 11-continued

Media formations for maize transformation, selection and regeneration.

| Medium components | Units | | | | | | |
|---|---|---|---|---|---|---|---|
| SILVER NITRATE | mg | | | | | 3.4 | 3.4 |
| AGRIBIO Carbenicillin | mg | | | | 100.0 | | |
| Timentin | mg | | | | | 150.0 | 150.0 |
| Cefotaxime | mg | | | | | 100.0 | 100.0 |
| MYO-INOSITOL | g | | | 0.1 | 0.1 | | 0.1 |
| NICOTINIC ACID | mg | | | 0.5 | 0.5 | | |
| PYRIDOXINE•HCL | mg | | | 0.5 | 0.5 | | |
| VITAMIN ASSAY CASAMINTO ACIDS | g | | | 1.0 | | | |
| MES BUFFER | g | | | | 0.5 | | |
| ACETOSYRINGONE | uM | | | | 100.0 | | |
| ASCORBIC ACID 10 MG/ML (7S) | mg | | | | 10.0 | | |
| MS VITAMIN STOCK SOL. | ml | | | | | | 5.0 |
| ZEATIN | mg | | | | | | 0.5 |
| CUPRIC SULFATE | mg | | | | | | 1.3 |
| IAA 0.5 MG/ML (28A) | ml | | | | | | 2.0 |
| ABA 0.1 mm | ml | | | | | | 1.0 |
| THIDIAZURON | mg | | | | | | 0.1 |
| AGRIBIO Carbenicillin | mg | | | | | | 100.0 |
| PPT(GLUFOSINATE-NH4) | mg | | | | | | |
| BAP | mg | | | | | | 1.0 |
| YEAST EXTRACT (BD Difco) | g | | 5.0 | | | | |
| PEPTONE | g | | 10.0 | | | | |
| SODIUM CHLORIDE | g | | 5.0 | | | | |
| SPECTINOMYCIN | mg | 50.0 | 100.0 | | | | |
| FERROUS SULFATE•7H20 | ml | 2.0 | | | | | |
| AB BUFFER 20X (12D) | ml | 50.0 | | | | | |
| AB SALTS 20X (12E) | ml | 50.0 | | | | | |
| Benomyl | mg | | | | | | |
| pH | | | | | | | 5.6 |

| Medium components | Units per liter | 289R | 13158H | 13224B | 13266K | 272X | 272V | 13158 |
|---|---|---|---|---|---|---|---|---|
| MS BASAL SALT MIXTURE | g | 4.3 | 4.3 | | 4.3 | 4.3 | 4.3 | 4.3 |
| N6 MACRONUTRIENTS 10X | ml | | | 4.0 | 60.0 | | | |
| POTASSIUM NITRATE | g | | | | 1.7 | | | |
| B5H MINOR SALTS 1000X | ml | | | | 0.6 | | | |
| NaFe EDTA FOR B5H 100X | ml | | | | 6.0 | | | |
| ERIKSSON'S VITAMINS 1000X | ml | | | 1.0 | 0.4 | | | |
| S&H VITAMIN STOCK 100X | ml | | | | 6.0 | | | |
| THIAMINE•HCL | mg | | | 0.5 | 0.5 | | | |
| L-PROLINE | g | 0.7 | 0.7 | 2.9 | 2.0 | | | |
| CASEIN HYDROLYSATE (ACID) | g | | | | 0.3 | | | |
| SUCROSE | g | 60.0 | 60.0 | 190.0 | 20.0 | 40.0 | 40.0 | 40.0 |
| GLUCOSE | g | | | | 0.6 | | | |
| MALTOSE | g | | | | | | | |
| 2,4-D | mg | | | | 1.6 | | | |
| AGAR | g | | 8.0 | 6.4 | 6.0 | 6.0 | 6.0 | 6.0 |
| PHYTAGEL | g | | | | | | | |
| DICAMBA | g | | | | 1.2 | | | |
| SILVER NITRATE | mg | | | 8.5 | 1.7 | | | |
| AGRIBIO Carbenicillin | mg | | | | 2.0 | | | |
| Timentin | mg | 150.0 | 150.0 | | | | | |
| Cefotaxime | mg | 100.0 | 100.0 | 25 | 25 | | | |
| MYO-INOSITOL | g | 0.1 | 0.1 | | | 0.1 | 0.1 | 0.1 |
| NICOTINIC ACID | mg | | | | | | | |
| PYRIDOXINE•HCL | mg | | | | | | | |
| VITAMIN ASSAY CASAMINTO ACIDS | g | | | | | | | |
| MES BUFFER | g | | | | | | | |
| ACETOSYRINGONE | uM | | | | | | | |
| ASCORBIC ACID 10 MG/ML (7S) | mg | | | | | | | |
| MS VITAMIN STOCK SOL. | ml | 5.0 | 5.0 | | | 5.0 | 5.0 | 5.0 |

TABLE 11-continued

Media formations for maize transformation, selection and regeneration.

| | | | |
|---|---|---|---|
| ZEATIN | mg | 0.5 | 0.5 |
| CUPRIC SULFATE | mg | 1.3 | 1.3 |
| IAA 0.5 MG/ML (28A) | ml | 2.0 | 2.0 |
| ABA 0.1 mm | ml | 1.0 | 1.0 |
| THIDIAZURON | mg | 0.1 | 0.1 |
| AGRIBIO Carbenicillin | mg | | |
| PPT(GLUFOSINATE-NH4) | mg | | |
| BAP | mg | | |
| YEAST EXTRACT (BD Difco) | g | | |
| PEPTONE | g | | |
| SODIUM CHLORIDE | g | | |
| SPECTINOMYCIN | mg | | |
| FERROUS SULFATE•7H20 | ml | | |
| AB BUFFER 20X (12D) | ml | | |
| AB SALTS 20X (12E) | ml | | |
| Benomyl | mg | | 100.0 |
| pH | | 0.5 | 5.6 |

Example 6. Transformation Using the PLTP Promoter

Use of the PLTP promoter to drive expression of the maize ODP2 gene improved transformation and allowed regeneration of phenotypically normal, fertile plants. A Pioneer inbred line used for testing was very sensitive to ectopic ODP2 expression. When a construct was used in Agrobacterium strain LBA4404 THY-, which contained NOS PRO::WUS2::PINII TERM+UBI PRO::ODP2::PINII TERM within the T-DNA, transformation frequencies at the callus level often reached 70% (transgenic calli relative to the number of starting embryos), however, if growth continued into plant regeneration, the continued expression of ODP2 resulted in stunted roots, abnormalities in leaf development and 100% sterility. In contrast, when the same inbred line was transformed with an Agrobacterium carrying the expression cassettes NOS PRO::WUS2::PINII TERM+ PLTP PRO::ODP2::PINII TERM in the T-DNA, transformation frequencies of callus were also very high (>100%). Additionally, all regenerated plants exhibited normal wild-type morphology and all were fertile.

In another set of experiments, the PLTP promoter driving ODP2 and the NOS promoter driving WUS2 expression resulted in rapid, direct somatic embryo formation.

Immature embryos (2-2.5 mm in length) were harvested from Pioneer maize inbred PH184C approximately 11 days after pollination, and were infected with Agrobacterium strain AGL1 containing a T-DNA with the following composition; RB+NOS PRO:Top2:ZM-WUS2::IN2-1 TERM+ ZM-PLTP PRO::ZM-ODP2::OS-T28 TERM+GZ-W64A TERM+UBI PRO:UBI1ZM INTRON:ESR::SB-SAG12 TERM+SB-ALS PRO::HRA::SB-PEPC1 TERM+LTP2 PRO::ZS-YELLOW::PINII TERM-LB (for the PLTP PRO, see SEQ ID NO: 1, and for PHP77833, see SEQ ID NO:28). Agrobacterium was grown in liquid medium to an optical density of 0.5 (at 520 nm) and the immature embryos (53, 52 and 56 embryos from three separate ears) were incubated in the Agrobacterium suspension for 5 minutes before removal from the liquid to be placed on solid 7101 medium.

Figure 4:
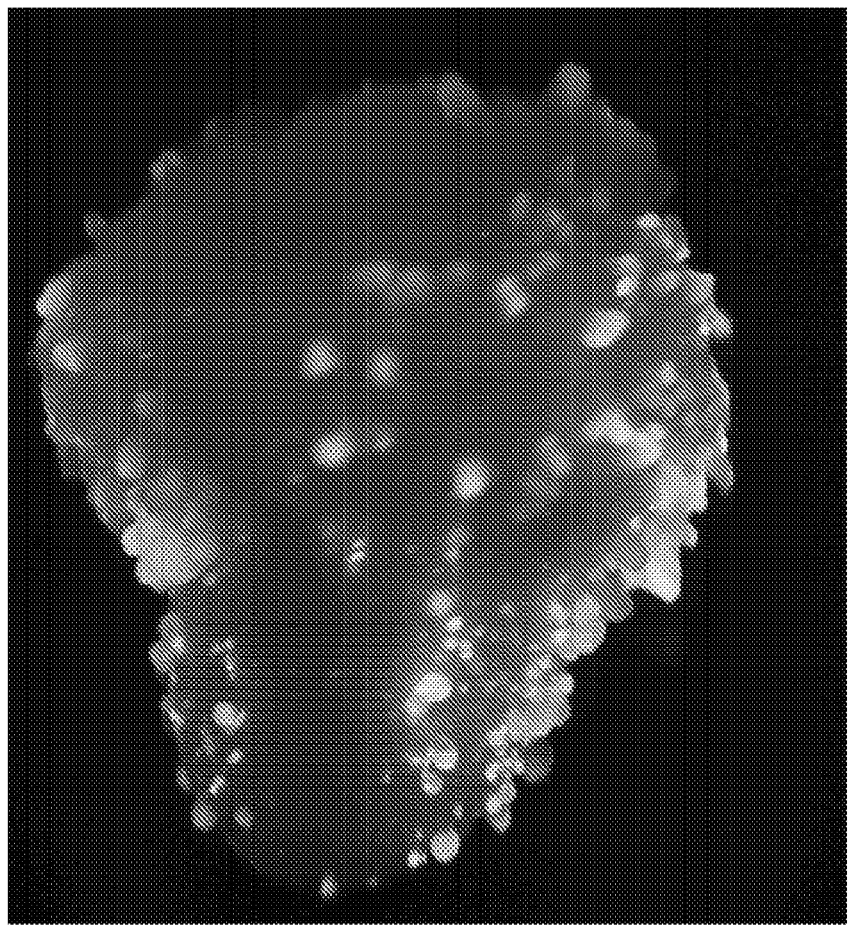
FIG. 4 illustrates that green fluorescence was observed in numerous individual developing somatic embryos on the surface of a zygotic immature embryo transformed with a T-DNA containing NOS PRO::ZM-WUS2::ZM-IN2-1 TERM+ZM-PLTP PRO::ZM-ODP2::OS-T28 TERM+ZM-PLTP PRO::ZS-GREEN1::PINII TERM. The image was taken using an epifluorescence stereo-microscope.

After 24 hours, the embryos were moved to fresh medium to begin selection against the Agrobacterium. After 6 days, numerous small somatic embryos were observed on the surface of each of the 124 treated immature embryos. Each immature embryo contained numerous, distinct, individual somatic embryos, many being supported on clearly-defined suspensors. After Agrobacterium transformation with a T-DNA containing AXIG1::WUS2::IN2 and PLTP::ODP2::OS-T28 expression cassettes, along with a UBI PRO::ZS-GREEN::PINII expression cassette (PHP79024, see SEQ ID NO:29), numerous individual green-fluorescent somatic embryos were observed growing from the scutellum of the originally-infected zygotic embryo (FIG. 4). This image was captured 4 days after the beginning of Agrobacterium infection, using a stereomicroscope with epifluorecence attachments and a standard Leica GFP filter set. For reference, the overall length of the zygotic embryo was approximately 1.5 mm.

Seven days after Agro-infection, the embryos were transferred to maturation medium (289Q medium+0.1 mg/l imazapyr), using the imidazolinone herbicide to select for transgenic embryos. After 14 days on the maturation medium, the mature embryos were moved onto rooting medium (13158H medium; 13158 medium plus 25 mg/l cefotaxime) and leaf pieces were sampled for PCR analysis. From the 53 embryos derived from the first ear, 12 herbicide-resistant plants were PCRed and sent to the greenhouse between 32-34 days after the beginning of the experiment, which was begun when the Agrobacterium transformation was started. Plants were sampled for PCR by taking two samples from each plant, one from each of two opposing ears (from opposite sides of the plant) to check for the possibility of any of the plants being only partially transformed (chimeric). PCR results for each pair of samples from all the plants were consistent with other, indicating that no chimeric plants were produced, and that the TO plants were homogenously transgenic.

Example 7. Expression Patterns for Promoters

Figure 6:
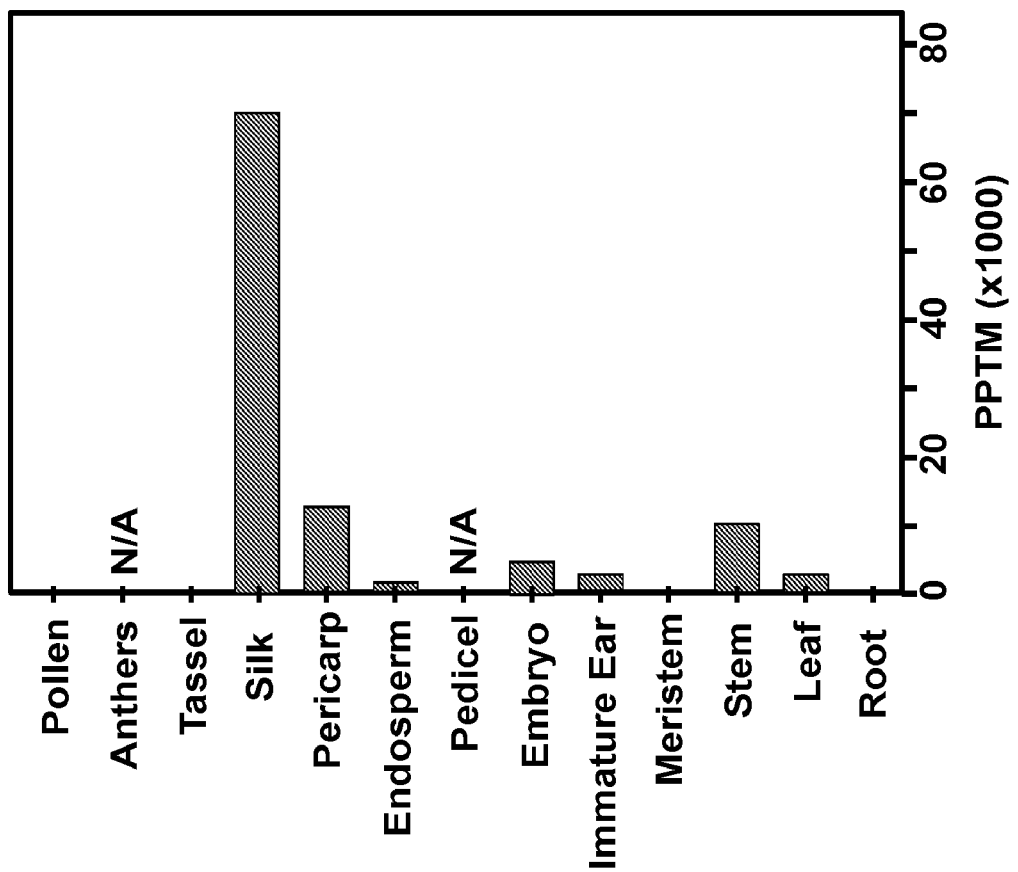
FIG. 6 illustrates expression of the endogenous maize Phospholipid Transfer Protein homolog 1 gene by its native promoter (ZM-PLTP1) (SEQ ID NO:3). Transcript levels based on Massively Parallel Signature Sequencing (MPSS) are shown in Parts Per Ten Million (PPTM).
Figure 7:
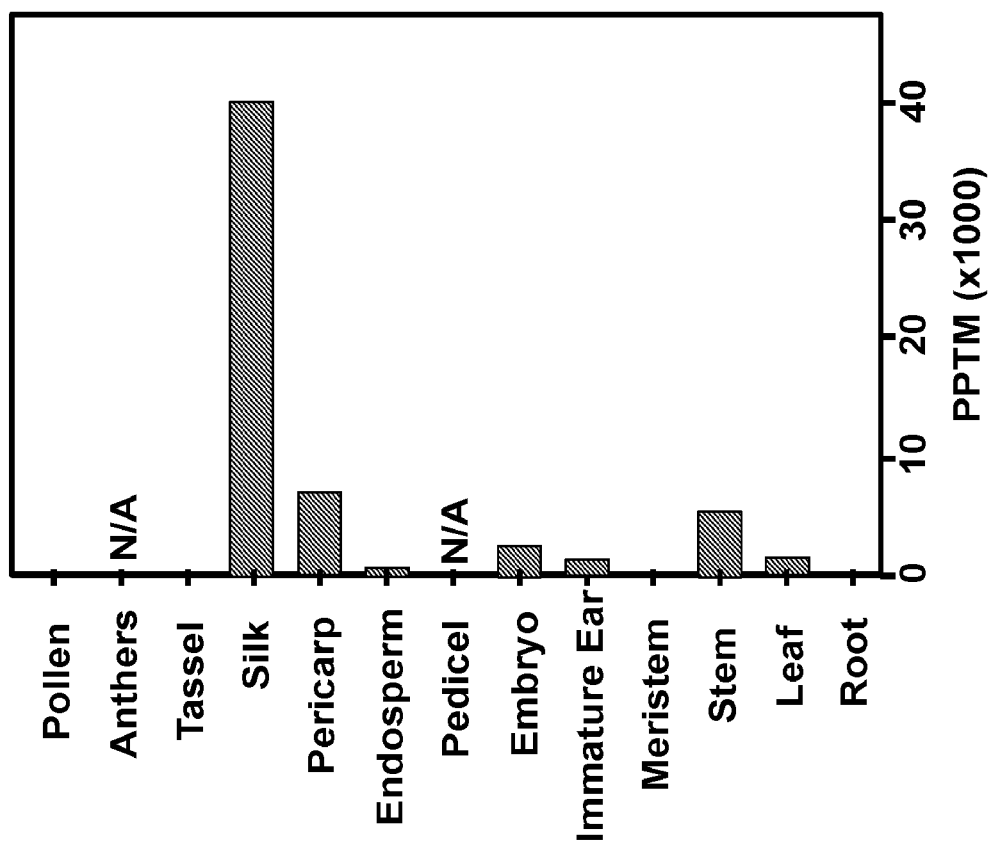
FIG. 7 illustrates expression of the endogenous maize Phospholipid Transfer Protein homolog 2 gene by its native promoter (ZM-PLTP2) (SEQ ID NO: 4). Transcript levels based on Massively Parallel Signature Sequencing (MPSS) are shown in Parts Per Ten Million (PPTM).
Figure 8:
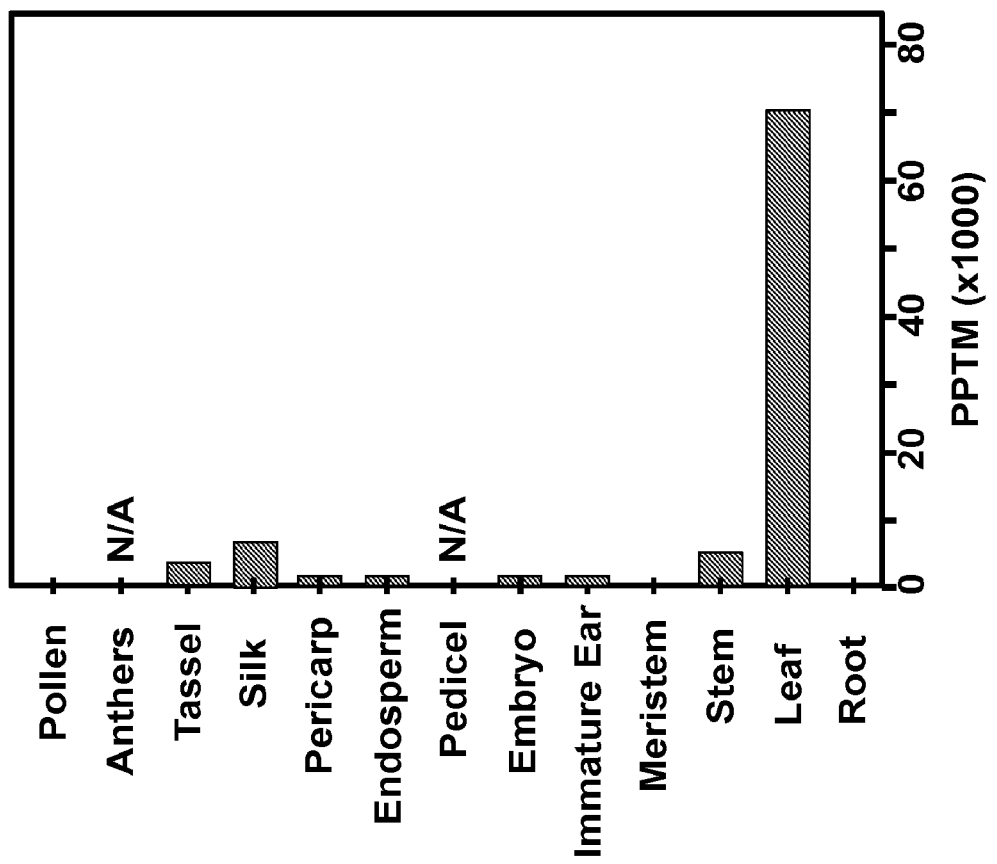
FIG. 8 illustrates expression of the endogenous maize Fructose-1,6-bisphosphatase gene by its native promoter (ZM-FBP) (SEQ ID NO: 10). Transcript levels based on Massively Parallel Signature Sequencing (MPSS) are shown in Parts Per Ten Million (PPTM).
Figure 9:
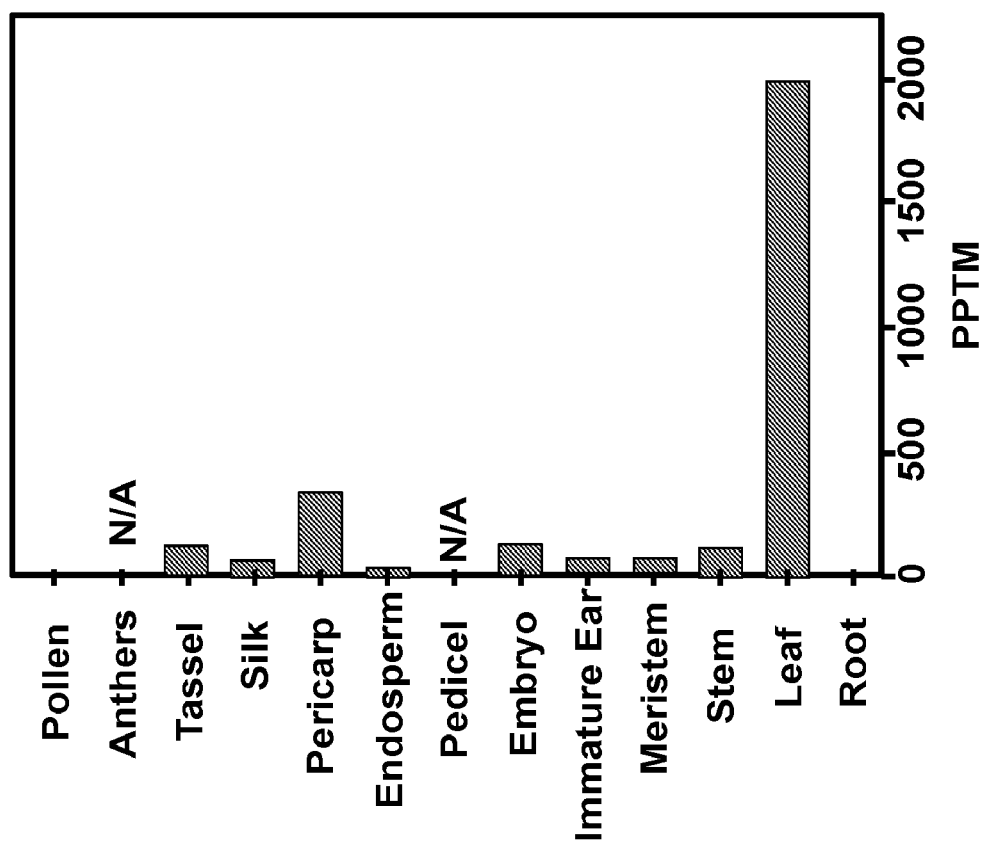
FIG. 9 illustrates expression of the endogenous maize Rossmann-fold NAD(P)-binding domain-containing protein gene by its native promoter (ZM-RFP) (SEQ ID NO: 11). Transcript levels based on Massively Parallel Signature Sequencing (MPSS) are shown in Parts Per Ten Million (PPTM).
Figure 10:
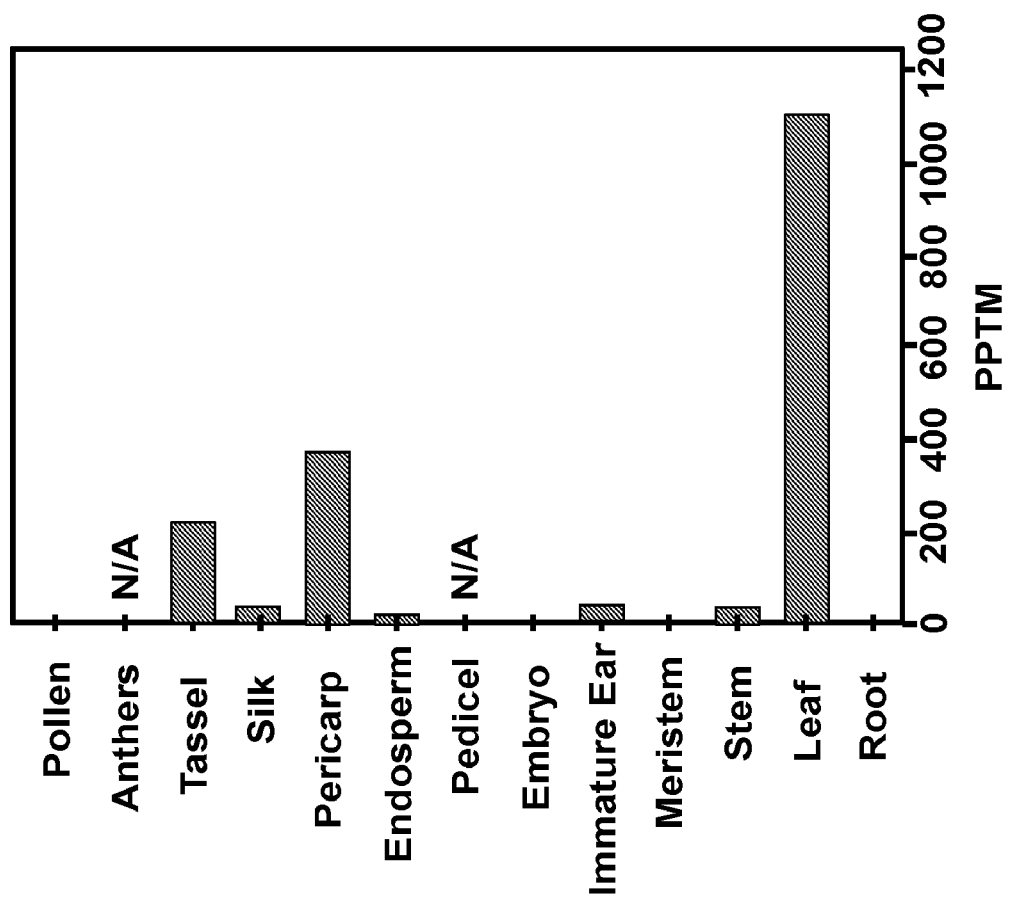
FIG. 10 illustrates expression of the endogenous maize Adipocyte plasma membrane-associated protein-like protein gene by its native promoter (ZM-APMP) (SEQ ID NO: 12). Transcript levels based on Massively Parallel Signature Sequencing (MPSS) are shown in Parts Per Ten Million (PPTM).
Figure 11:
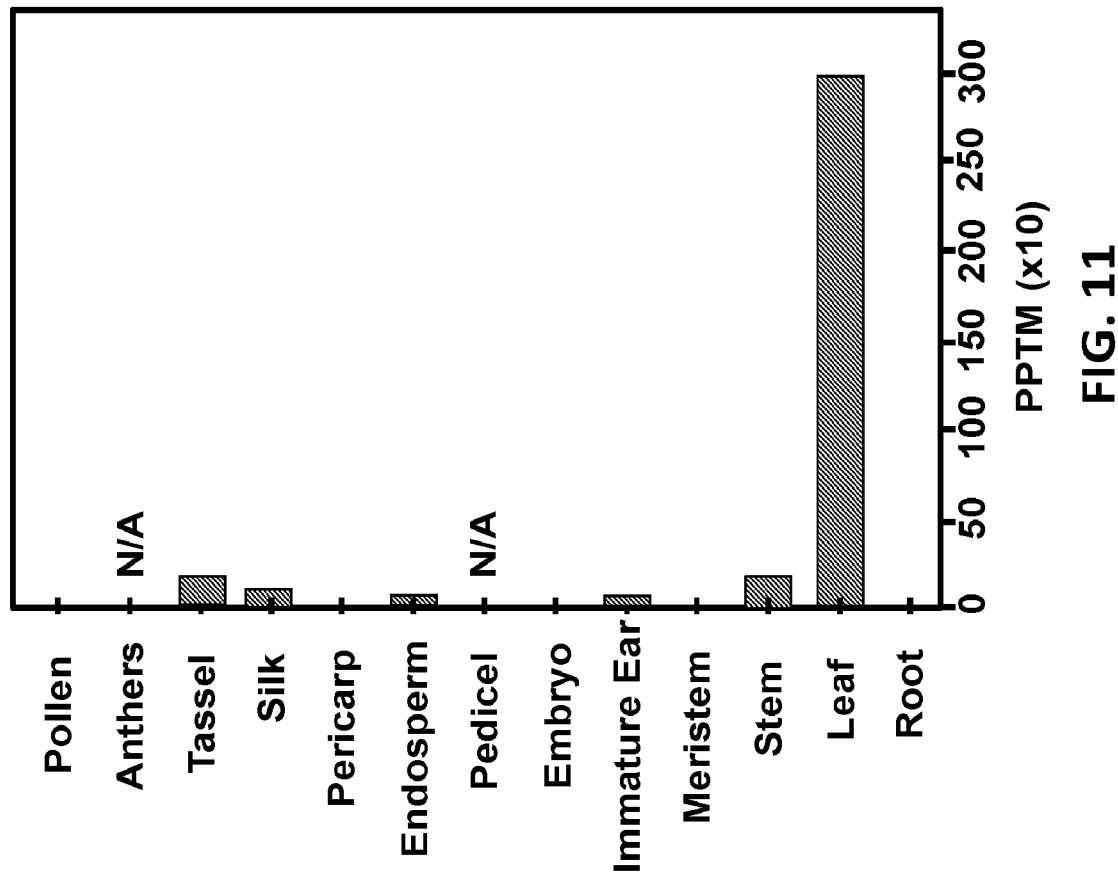
FIG. 11 illustrates expression of the endogenous maize Rieske (2Fe-2S) iron-sulphur domain protein gene by its native promoter (ZM-RfeSP) (SEQ ID NO: 13). Transcript levels based on Massively Parallel Signature Sequencing (MPSS) are shown in Parts Per Ten Million (PPTM).
Figure 12:
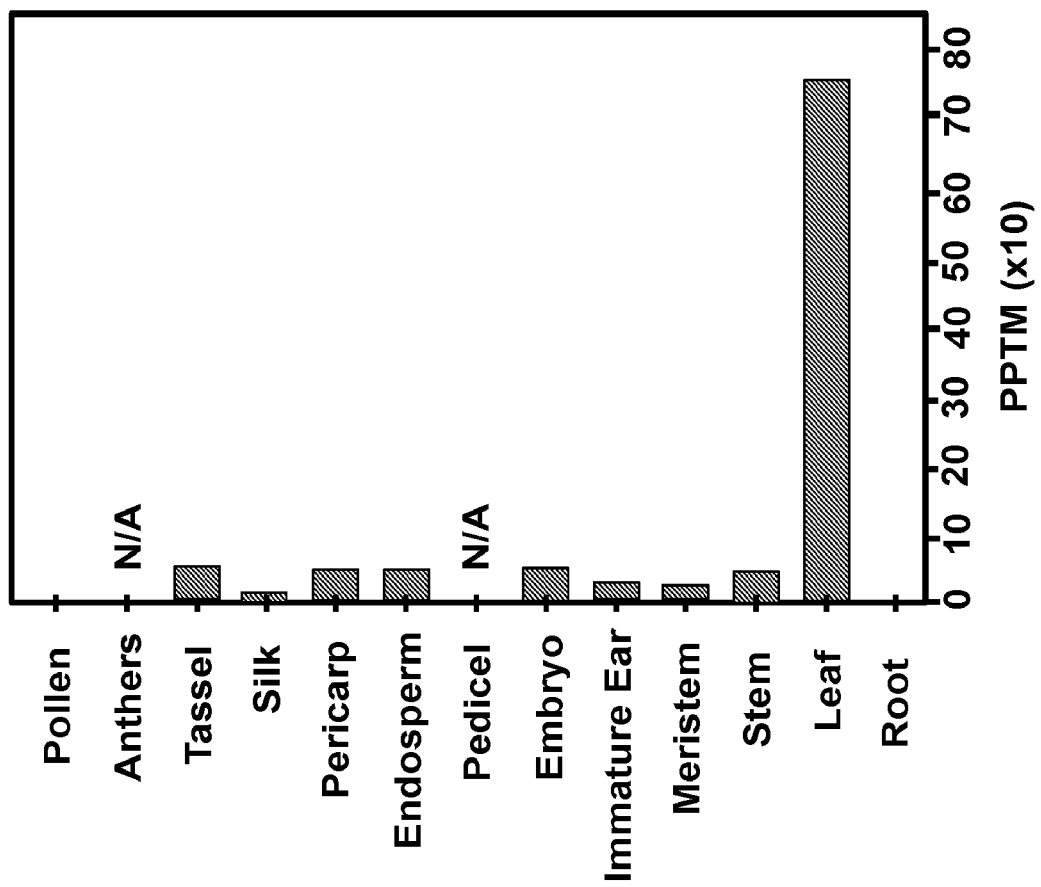
FIG. 12 illustrates expression of the endogenous maize Chlororespiratory reduction 6 gene by its native promoter (ZM-CRR6) (SEQ ID NO: 14). Transcript levels based on Massively Parallel Signature Sequencing (MPSS) are shown in Parts Per Ten Million (PPTM).
Figure 13:
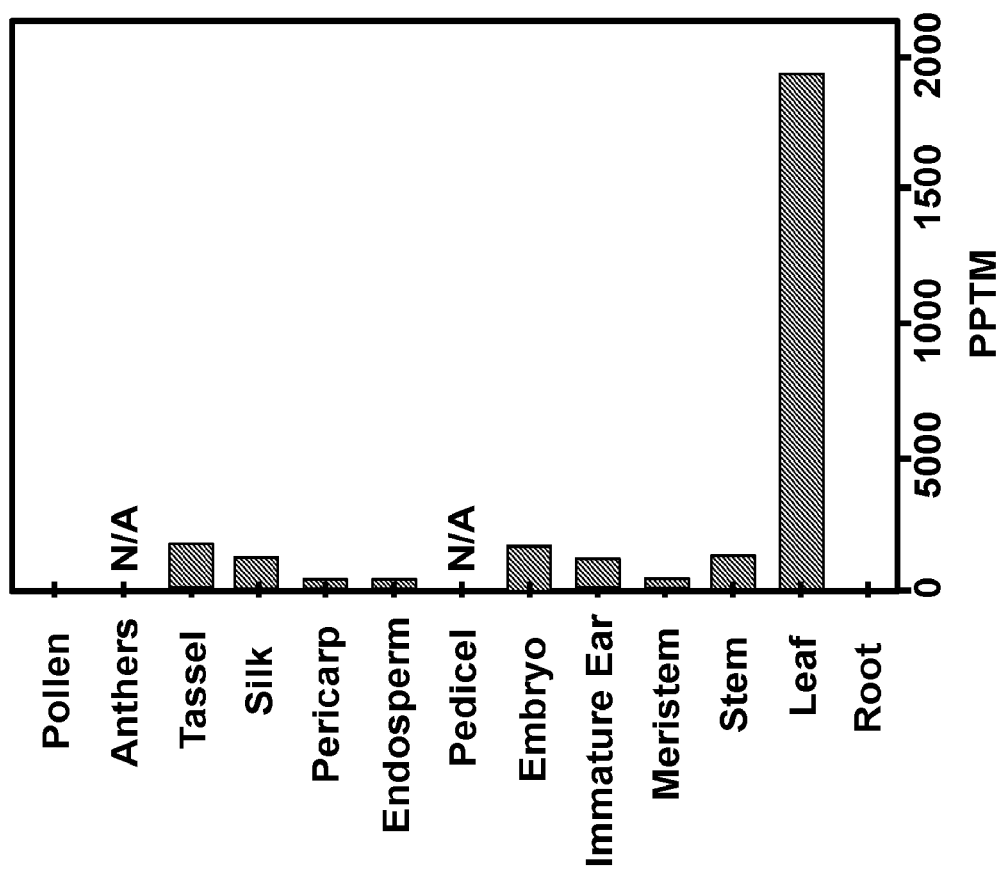
FIG. 13 illustrates expression of the endogenous maize D-glycerate 3-kinase gene by its native promoter (ZM-G3K) (SEQ ID NO: 15). Transcript levels based on Massively Parallel Signature Sequencing (MPSS) are shown in Parts Per Ten Million (PPTM).
Figure 14:
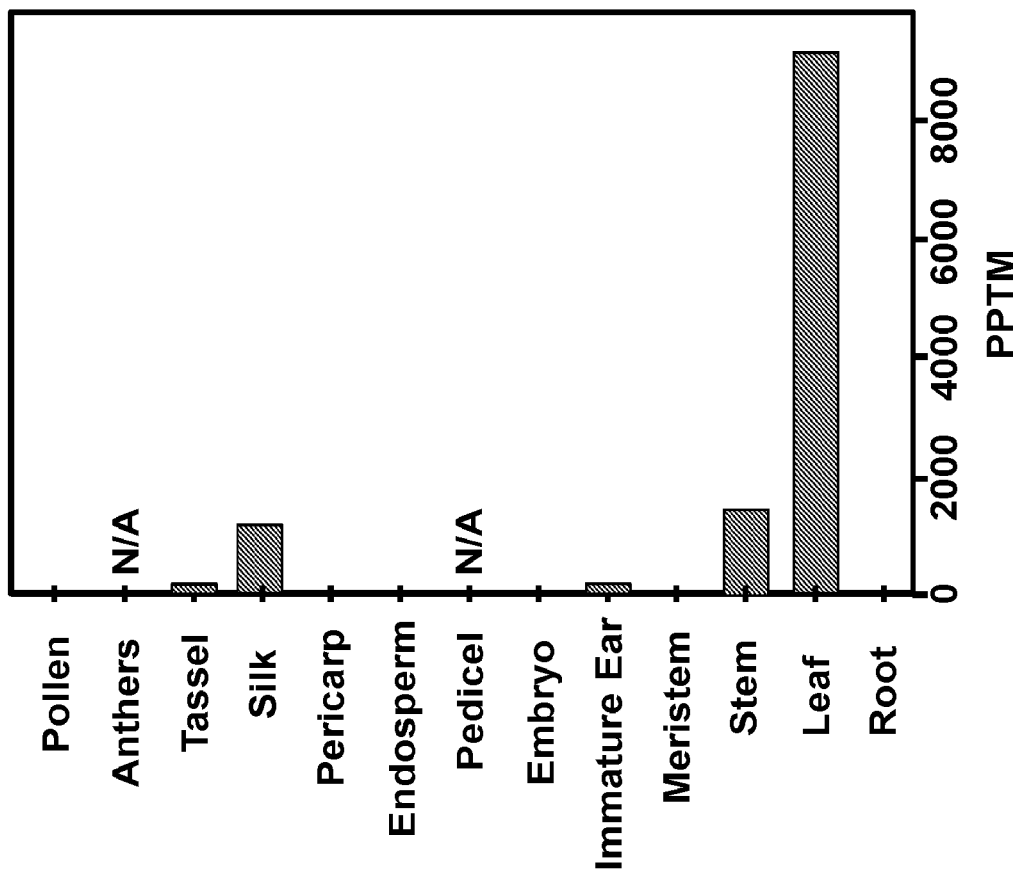
FIG. 14 illustrates expression of the endogenous maize Chlorophyll a-b binding protein 7 gene by its native promoter (ZM-CAB7) (SEQ ID NO: 16). Transcript levels based on Massively Parallel Signature Sequencing (MPSS) are shown in Parts Per Ten Million (PPTM).
Figure 15:
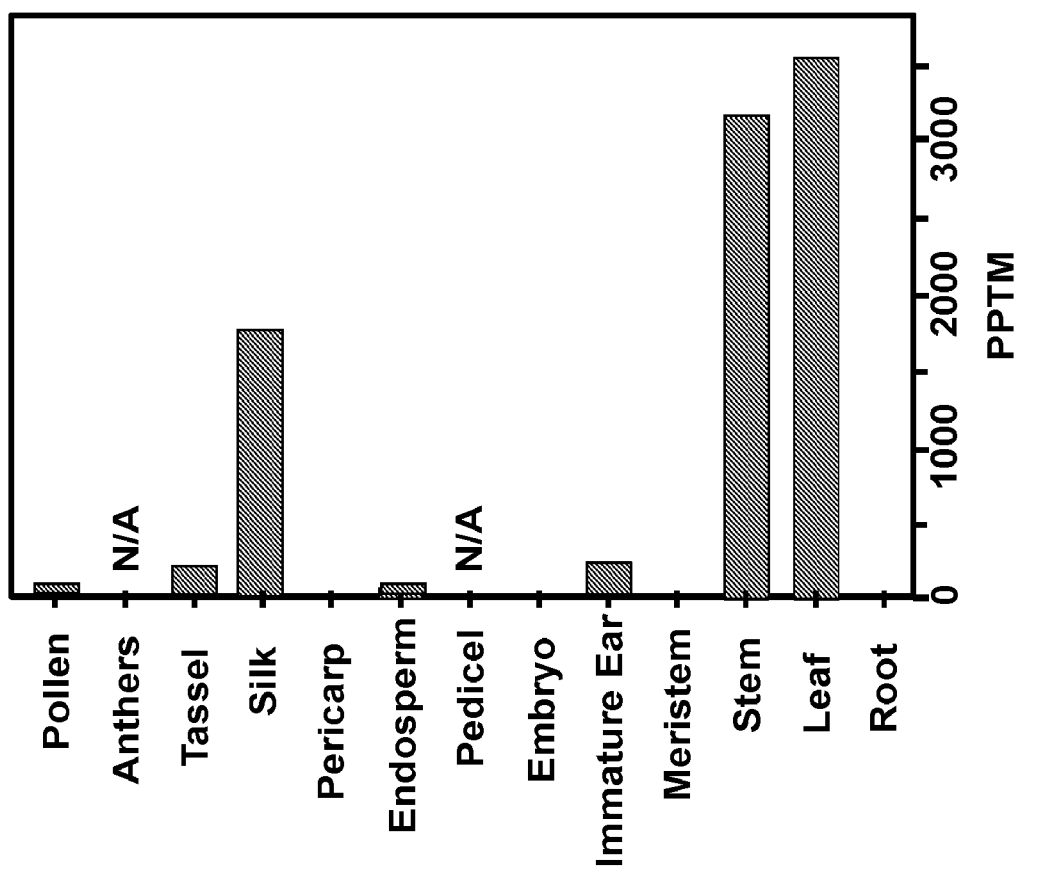
FIG. 15 illustrates expression of the endogenous maize Ultraviolet-B-repressible protein gene by its native promoter (ZM-UBR) (SEQ ID NO: 17). Transcript levels based on Massively Parallel Signature Sequencing (MPSS) are shown in Parts Per Ten Million (PPTM).
Figure 16:
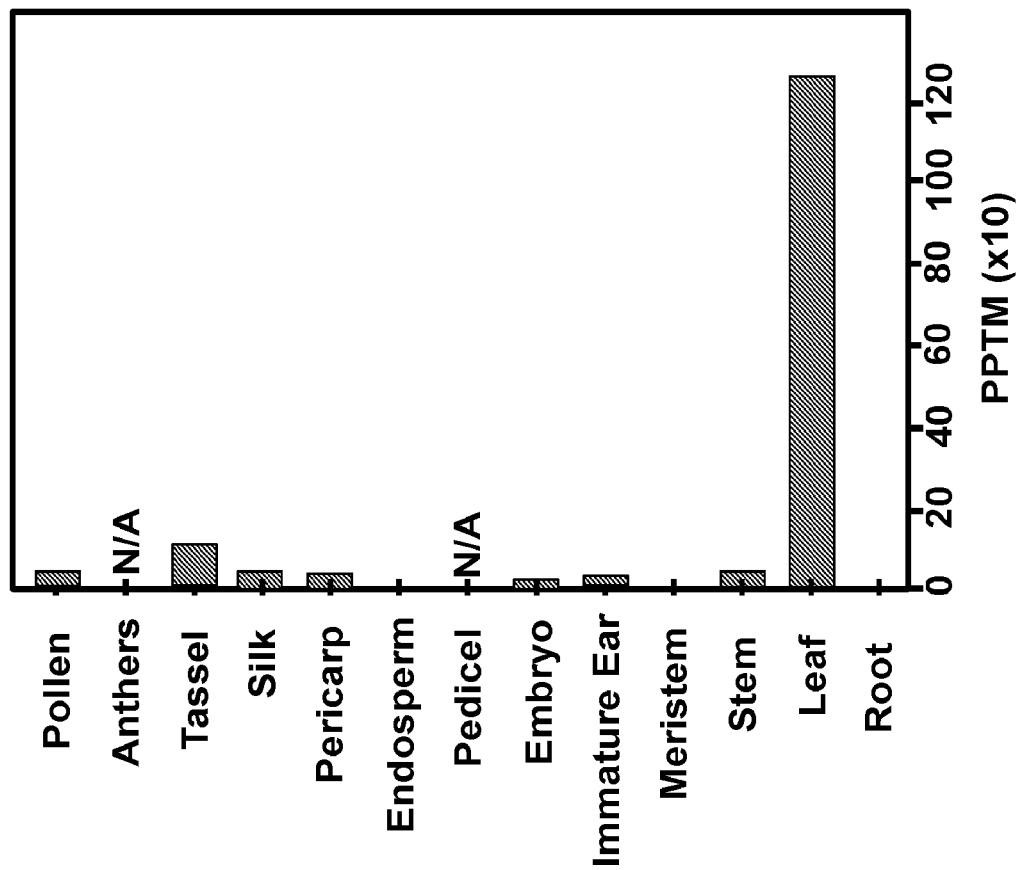
FIG. 16 illustrates expression of the endogenous maize Soul heme-binding family protein gene by its native promoter (ZM-HBP) (SEQ ID NO: 18). Transcript levels based on Massively Parallel Signature Sequencing (MPSS) are shown in Parts Per Ten Million (PPTM).
Figure 17:
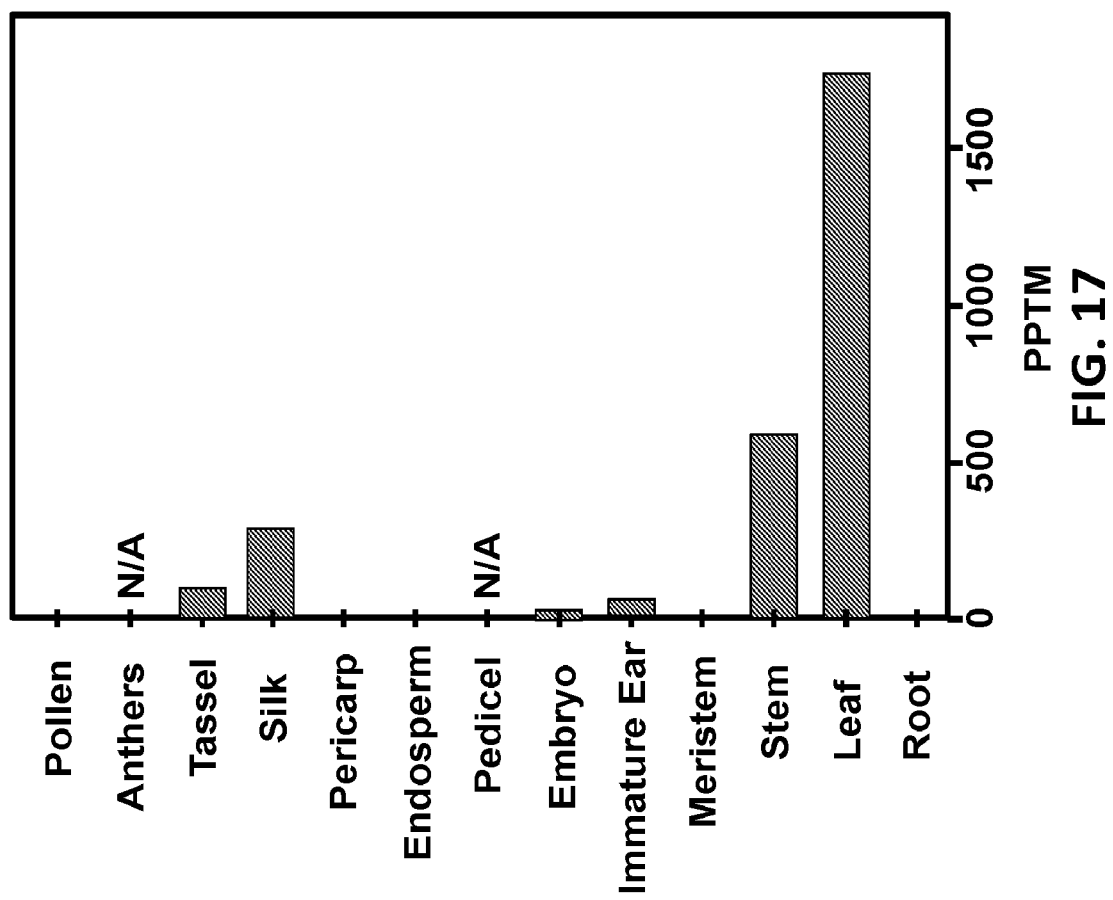
FIG. 17 illustrates expression of the endogenous maize Photosystem I reaction center subunit psi-N gene by its native promoter (ZM-PS1-N) (SEQ ID NO: 19). Transcript levels based on Massively Parallel Signature Sequencing (MPSS) are shown in Parts Per Ten Million (PPTM).
Figure 18:
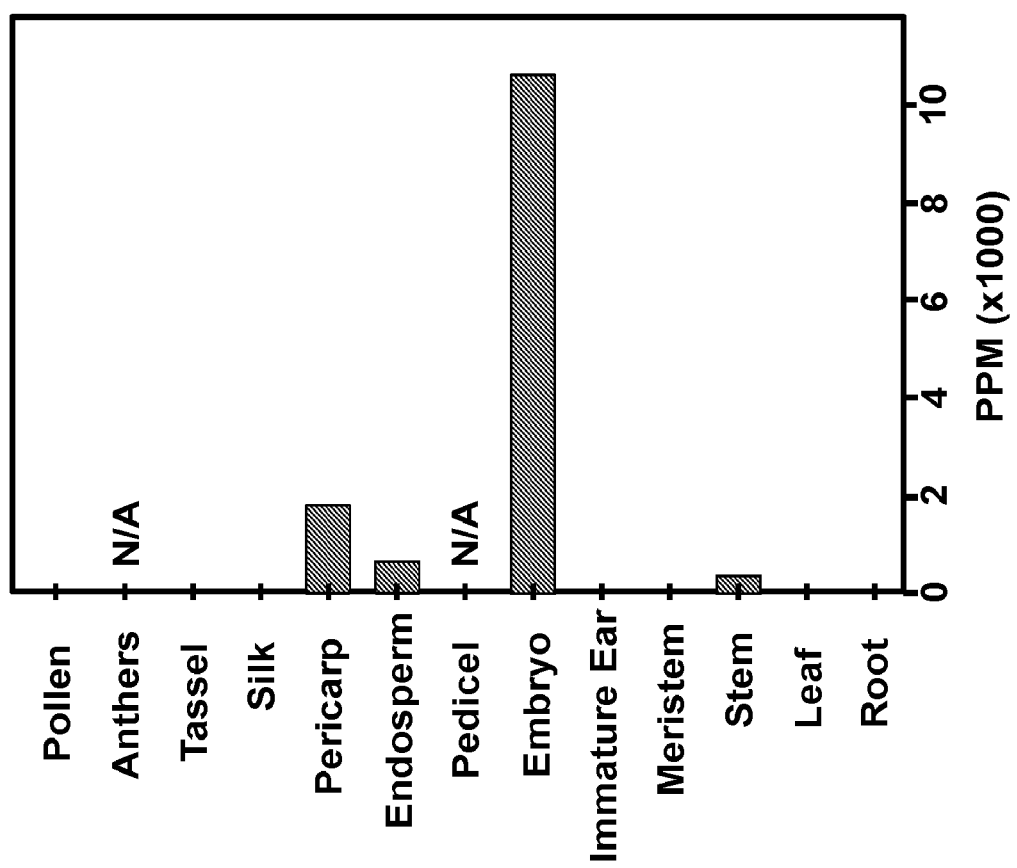
FIG. 18 illustrates expression of the endogenous maize Short-chain dehydrogenase/reductase gene by its native promoter (ZM-SDR) (SEQ ID NO: 20). Transcript levels based on Massively Parallel Signature Sequencing (MPSS) are shown in Parts Per Ten Million (PPTM).
Figure 20:
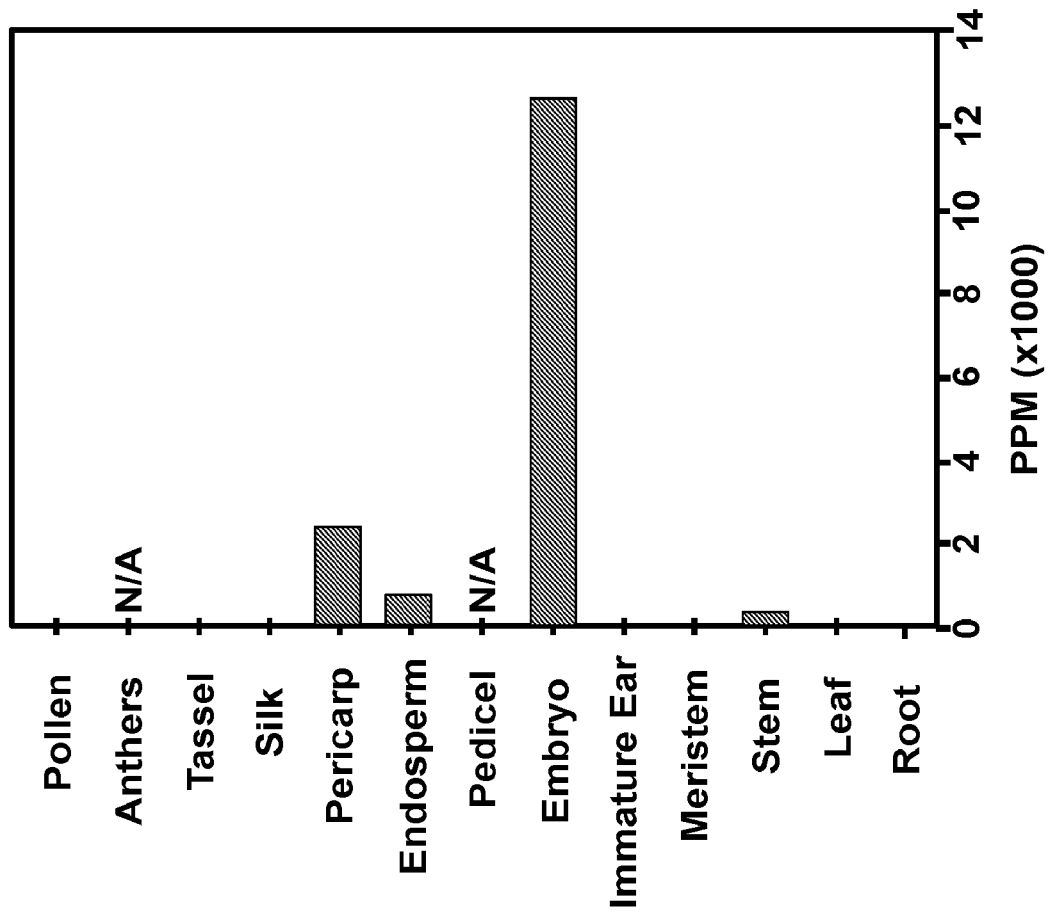
FIG. 20 illustrates expression of the endogenous maize lactoylglutathione lyase gene by its native promoter (ZM-LGL PRO) (SEQ ID NO: 25). Transcript levels based on Massively Parallel Signature Sequencing (MPSS) are shown in Parts Per Ten Million (PPTM).
Figure 21:
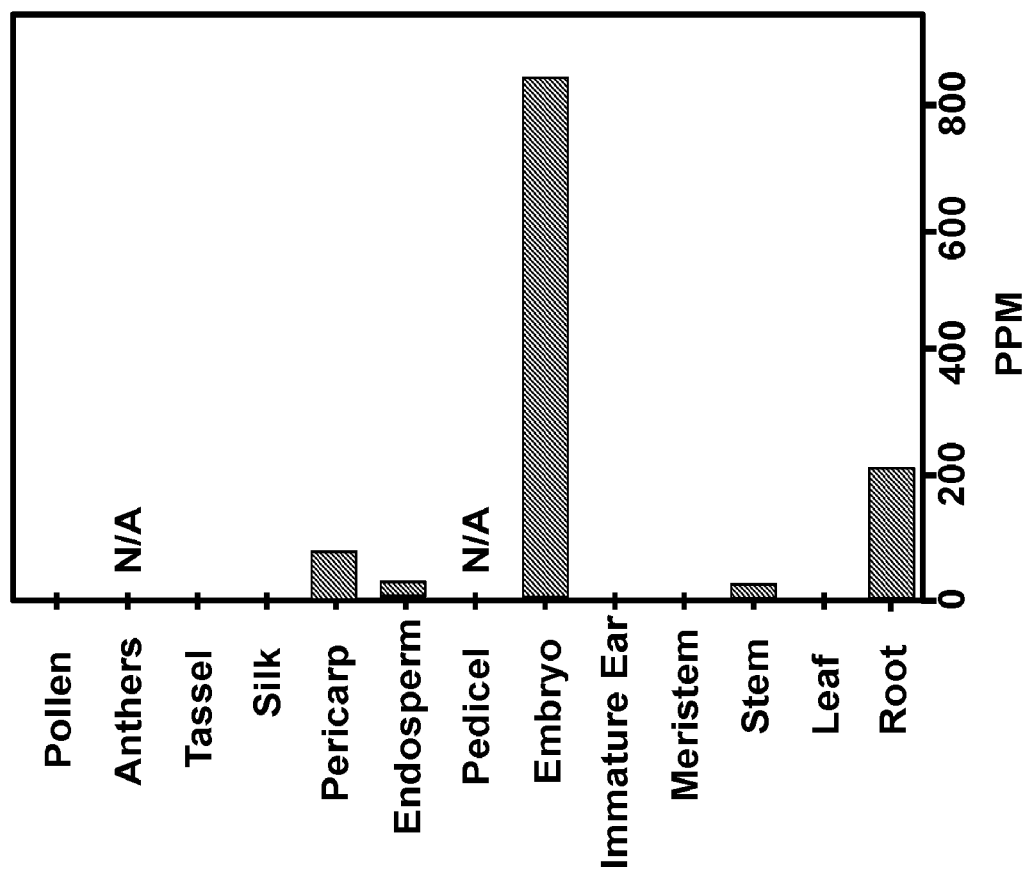
FIG. 21 illustrates expression of the endogenous maize late embryogenic abundant protein Lea-14-A gene by its native promoter (ZM-LEA14-A PRO) (SEQ ID NO: 26). Transcript levels based on Massively Parallel Signature Sequencing (MPSS) are shown in Parts Per Ten Million (PPTM).
Figure 22:
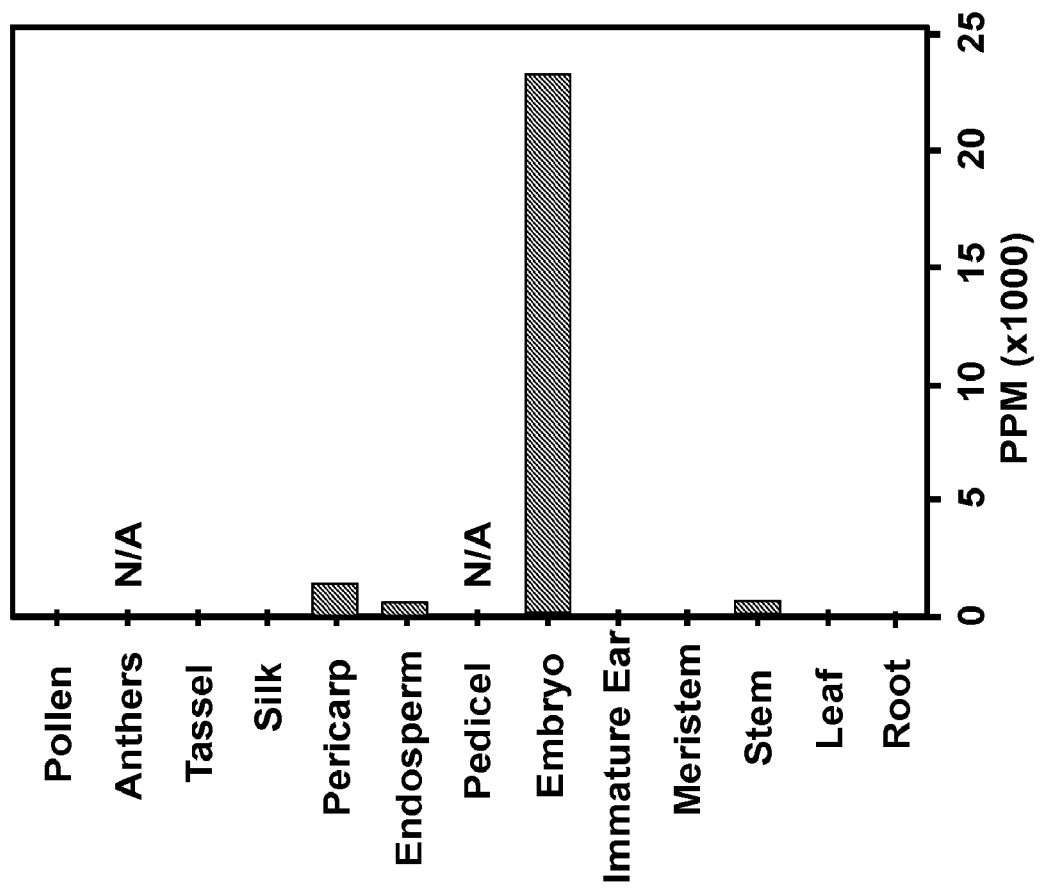
FIG. 22 illustrates expression of the endogenous maize late embryogenic abundant protein Lea34-D gene by its native promoter (ZM-LEA34-D PRO) (SEQ ID NO: 27). Transcript levels based on Massively Parallel Signature Sequencing (MPSS) are shown in Parts Per Ten Million (PPTM).

Data was analyzed to evaluate normal expression patterns in various maize tissues during plant development. Massively parallel signature sequencing (Reinartz J et al. 2002. Brief Funct Genomic Proteomic. 1(1):95-104; Brenner S et al. 2000. Nat Biotechnol. 18(6):630-4; Tones et al., 2008. Gene expression profiling by massively parallel sequencing. Genome Res. 18(1):172-177) was used for evaluation. Various plant tissues at different stages of development were sampled for analysis, and included root, stalk, leaf/shoot, immature ear, embryo, pedicel, endosperm, pericarp, silk, tassel, spikelet, anther, pollen and meristem. Expression data for Massively Parallel Signature Sequencing (MPSS) is shown for ZM-PLTP (SEQ ID NO. 1) in FIG. 5, for ZM-PLTP1(SEQ ID NO. 3) in FIG. 6, for ZM-PLTP2 (SEQ ID NO. 4) in FIG. 7, for ZM-FBP1 (SEQ ID NO. 10) in FIG. 8, for ZM-RFP (SEQ ID NO. 11) in FIG. 9, for ZM-APMP (SEQ ID NO. 12) in FIG. 10, for ZM-RfeSP (SEQ ID NO. 13) in FIG. 11, for ZM-CRR6 (SEQ ID NO. 14) in FIG. 12, for ZM-G3K (SEQ ID NO. 15) in FIG. 13, for ZM-CAB7 (SEQ ID NO. 16) in FIG. 14, for ZM-UBR (SEQ ID NO. 17) in FIG. 15, for ZM-HBP (SEQ ID NO. 18) in FIG. 16, for ZM-PS1-N(SEQ ID NO. 19) in FIG. 17 and ZM-SDR Photosystem I reaction center subunit psi-N(SEQ ID NO. 20) in FIG. 18. For all of these promoters, a distinguishing expression characteristic was that no expression was observed in the roots, and expression in the reproductive structures (except for silks in some promoters) was non-existent or low. Leaf expression was moderate to high for many of these genes, except for ZM-SDR (SEQ ID NO:20) in FIG. 18, ZM-LGL (SEQ ID NO:25) in FIG. 20, ZM-LEA14-A (SEQ ID NO:26) in FIG. 21, and ZM-LEA34-D (SEQ ID NO: 27) in FIG. 22, which showed expression only (or predominantly) in the embryos.

Figure 23:
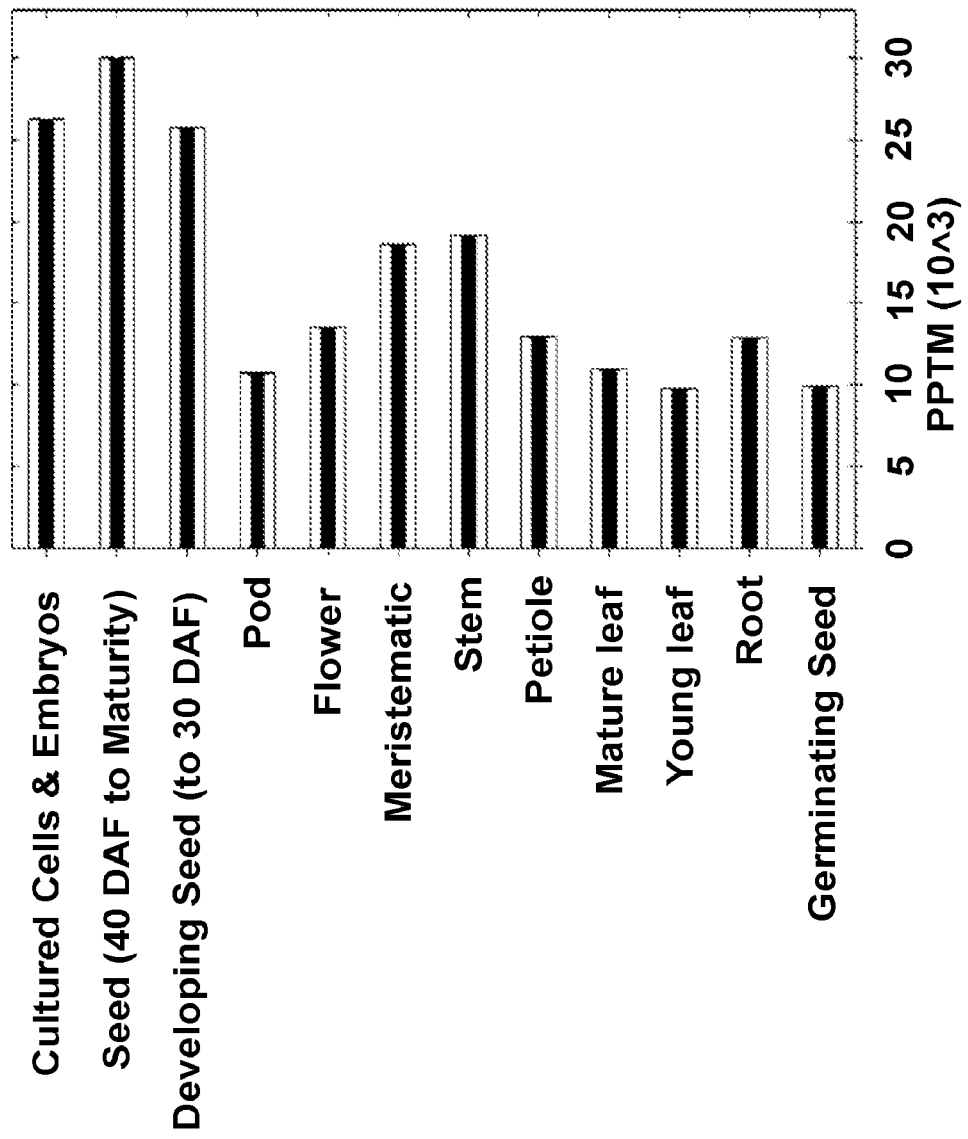
FIG. 23 illustrates expression of the endogenous soybean elongation factor1A gene by its native promoter (GM-EF1A) (SEQ ID NO: 32). Transcript levels based on Massively Parallel Signature Sequencing (MPSS) are shown in Parts Per Ten Million (PPTM).
Figure 24:
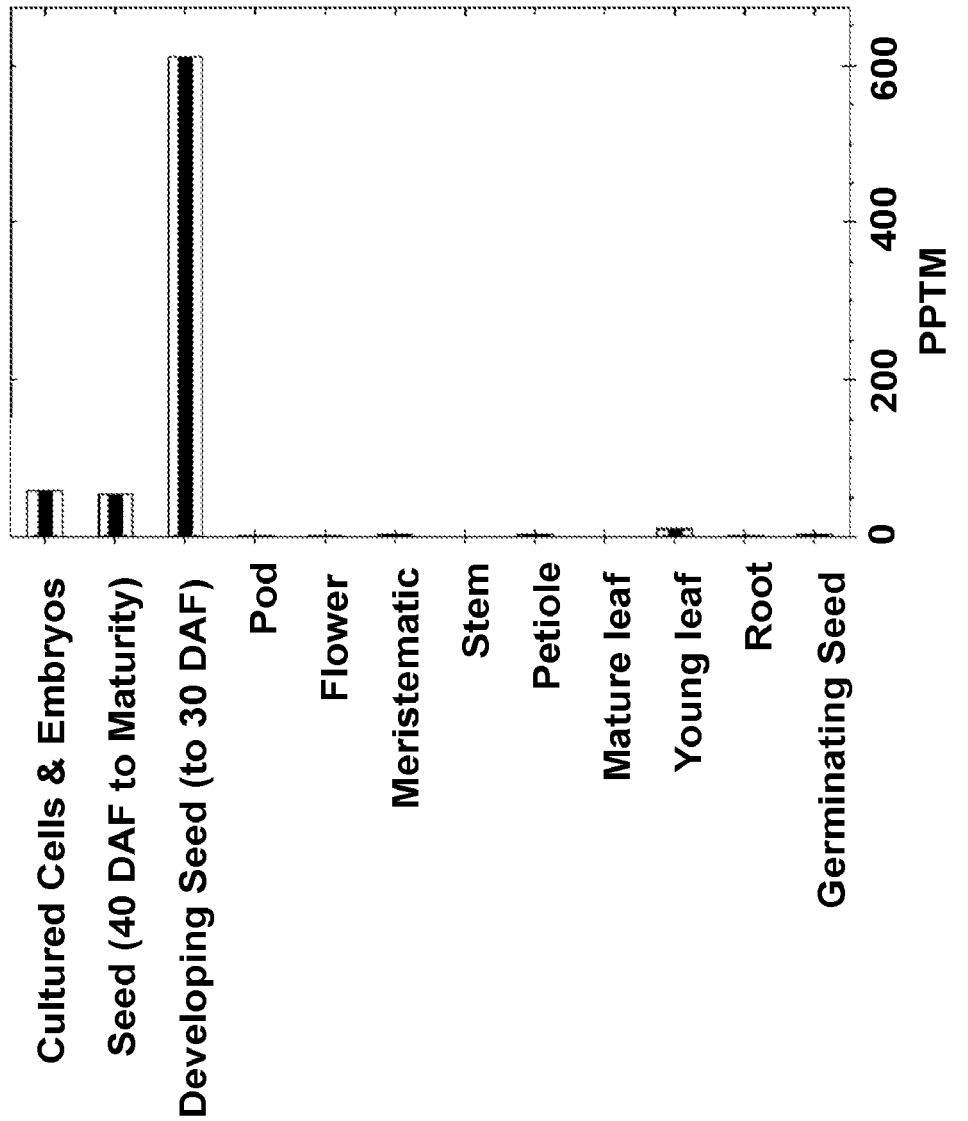
FIG. 24 illustrates expression of the endogenous soybean Lipid Transfer Protein3 gene by its native promoter (GM-LTP3) (SEQ ID NO: 21). Transcript levels based on Massively Parallel Signature Sequencing (MPSS) are shown in Parts Per Ten Million (PPTM).

Example 8. Use of the Soybean LTP3 (Gm-LTP3) Promoter to Control Expression of WUS for Improving Soy Transformation Promoters were identified to improve transformation methods using the *Arabidopsis* WUS gene. High levels of expression for *Arabidopsis* WUS (for example, using the soybean EF1A PRO; SEQ ID NO: 32), expressed immediately after *Agrobacterium*-mediated transformation and throughout callus growth increased the rates of event formation. However, continuing to express this transcription factor at this level hindered event regeneration. Possible solutions would be to excise this gene before regeneration of plantlets and restrict the ectopic expression of *Arabidopsis* WUS in differentiating and maturing somatic embryos. Based on this, new promoters were sought that expressed in cultured cells, embryos and developing immature seeds, with none or much lower expression in other plant tissues. The soybean LTP3 (GM-LTP3; SEQ ID NO: 21) promoter met these criteria. GM-LTP3 (SEQ ID NO: 21) is from a previously unidentified soybean phospholipid transferase gene. When compared to the constitutive expression of the EF1A PRO (FIG. 23), expression of LTP3 (FIG. 24) was i) strong in developing immature seeds and ii) weak or off in other samples and parts of a plant, while expression of EF1A was observed in all tissues.

The *Agrobacterium* strain AGL1, containing a T-DNA with the expression cassettes GM-LTP3 PRO::AT-WUS:: UBI14 TERM+GM-UBQ PRO::TAGRFP::UBQ3 TERM, was used to transform the Pioneer soybean variety 93Y21. Four days after the *Agrobacterium* infection was started, the tissue was washed with sterile culture medium to remove excess bacteria. Nine days later the tissue was moved to somatic embryo maturation medium, and 22 days later the transgenic somatic embryos were ready for dry-down. At this point, well-formed, mature somatic embryos were fluorescing red under an epifluorescence stereo-microscope with an RFP filter set. The somatic embryos that developed were functional and germinated to produce healthy plants in the greenhouse. This rapid method of producing somatic embryos and germinating to form plants reduced the typical timeframe from *Agrobacterium* infection to moving transgenic T0 plants into the greenhouse from 4 months (for conventional soybean transformation) to two months.

As shown in the box plot diagram in FIG. 25 which displays the distribution of somatic embryogenesis responses of immature cotyledon explants 2 weeks after *Agrobacterium* infection, the use of the GM-LTP3 promoter to drive expression of At-WUS (LTP3 PRO) resulted in a substantial improvement in somatic embryogenesis (as compared to other promoters tested, such as the P450, GH, HSD and SSL1 promoters, or to the negative control (NEG CON) with no WUS expression cassette).

The increase in somatic embryo response across the population of infected immature cotyledons was also accompanied by rapid somatic embryo development, which was observed under both light microscopy to assess morphology (FIG. 26A) and epifluorescence to observe red fluorescence (FIG. 26B). It shows mature transgenic soybean somatic embryos that were ready for desiccation and thereafter germination only 5 weeks after *Agrobacterium* infection. When immature cotyledons were transformed without LTP3::At-WUS (control treatment) mature somatic embryos were not only produced at a greatly reduced frequency (see FIG. 25) but the duration from *Agrobacterium* infection to a comparable stage of somatic embryo maturity required nine weeks of culture.

Example 9. Results on Use of Various PLTP Promoters from Homologous Gene Sources to Produce Somatic Embryos in Corn For the studies described below, a single T-DNA configuration was utilized, starting with the following configuration used as the positive control: RB+ZM-AXIG1 PRO::ZM-WUS2::IN2-1 TERM+ZM-PLTP PRO::ZM-ODP2::OS-T28 TERM+GZ-W64A TERM+UBI PRO:UBI1ZM INTRON:ESR::SB-SAG12 TERM+SB-ALS PRO::HRA:: SB-PEPC1 TERM+UBI PRO::ZS-GREEN1::PINII TERM: SB-ACTIN TERM-LB. Within the context of this T-DNA, all the components remained the same except that the ZM-PLTP PRO (SEQ ID NO:1 from the control treatment) was replaced by promoters from two maize paralogs (ZM-PLTP1 and ZM-PLTP2, SEQ ID NO:3 and SEQ ID NO:4, respectively) or from three Poaceae orthologs (*Sorghum bicolor* SB-PLTP1 (SEQ ID NO:2), *Setaria italica* SI-PLTP1 (SEQ ID NO:7) or *Oryza sativa* OS-PLTP1 (SEQ ID NO:8)). Using Pioneer inbreds PH1V5T, PH1V69 and PHHSG as the source of immature embryos, when the control T-DNA (all maize components as shown above) was introduced into the scutellum, for the majority of infected immature embryos approximately half of the scutellar surface area would be covered by newly developed somatic embryos after 7 days and this response would be scored as a "2". At the upper end of the response spectrum, when the scutellum was covered by a "lawn" of individual, developing somatic embryos that were readily discernable under the dissecting microscope 7 days post-infection, this response was given a relative score of "4" and all other treatments were ranked in whole-integer increments from "0" (no response) to "4" (the most prolific production of somatic embryos). In terms of the baseline response for these three inbreds (i.e. with no WUS2 or ODP2 expression cassettes in the T-DNA), PH1V5T produced a low level of somatic embryos (score of 1), while both PH1V69 and PHH5G produce no response (score of 0).

Using various "homologous" promoters produced a range of rapid somatic embryogenesis in three different Pioneer inbreds (Table 12) relative to the control treatment (ZM-PLTP PRO) which produced scores between 1 and 2.

TABLE 12

Inbred transformation response to different PLTP promoter homologs

| ZM-AXIG1 constant for ZM-WUS2 | Promoter for ZM-ODP2 | Response in Inbred | | |
|---|---|---|---|---|
| | | PH1V5T | PH1V69 | PHH5G |
| Zm-Axig1 | ZM-PLTP | 2 | 1 | 2 |
| Zm-Axig1 | ZM-PLTP1 | 3 | 4 | 4 |
| Zm-Axig1 | ZM-PLTP2 | 3 | 3 | 3 |
| Zm-Axig1 | SB-PLTP1 | 2 | 2 | 1 |
| Zm-Axig1 | SI-PLTP1 | 1 | 1 | 2 |
| Zm-Axig1 | OS-PLTP1 | 1 | 2 | 2 |

In this experiment, the ZM-PLTP1 promoter produced the highest somatic embryogenesis scores at seven days post-infection, which ranged from 3 (roughly 75% covered with somatic embryos in PH1V5T) to 4 (totally covered as in PH1V69 and PHHSG). ZM-PLTP2 also produced results better than the control, with a uniform score of 3 across all three inbreds. For PLTP1 promoters from other members of the Poaceae, the sorghum and rice promoters produced an intermediate level response (2) in two inbreds and a low response (1) in one inbred, while the *Setaria* promoter resulted in a low level response in two and an intermediate level response in one inbred. Nonetheless, all the PLTP promoters tested resulted in positive stimulation of somatic embryogenesis after seven days.

As used herein the singular forms "a", "an", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise.

All patents, publications and patent applications mentioned in the specification are indicative of the level of those skilled in the art to which this disclosure pertains. All patents, publications and patent applications are herein incorporated by reference in the entirety to the same extent as if each individual patent, publication or patent application was specifically and individually indicated to be incorporated by reference in its entirety.

Although the foregoing disclosure has been described in some detail by way of illustration and example for purposes of clarity of understanding, certain changes and modifications may be practiced within the scope of the appended claims.

What is claimed is:

1. A DNA construct comprising a first expression cassette comprising a tissue preferred regulatory element having a nucleotide sequence selected from the group consisting of SEQ ID NO: 1 or SEQ ID NO: 3, wherein the regulatory element is operably linked to a heterologous polynucleotide of interest conferring expression of the heterologous polynucleotide of interest in the scutellar epithelium of the embryo, in the accessory cells and cork cells of the leaf epidermis, and in the silk hairs and silk-tip.

2. The DNA construct of claim 1, further comprising a second expression cassette comprising a gene of interest.

3. A vector comprising the DNA construct of claim 2.

4. A plant cell comprising the DNA construct of claim 2.

5. The plant cell of claim 4, wherein the heterologous polynucleotide of interest of the first expression cassette encodes a transcription factor.

6. The plant cell of claim 5, wherein the transcription factor is involved in plant metabolism, organ development, stem cell development, cell growth stimulation, organogenesis, somatic embryogenesis initiation, or development of the apical meristem.

7. The plant cell of claim 6, wherein the DNA construct optionally further comprises a third expression cassette, and wherein the transcription factor involved in plant metabolism, organ development, stem cell development, cell growth stimulation, organogenesis, somatic embryogenesis initiation, or development of the apical meristem is selected from the group consisting of a protein encoded by a Wuschel (WUS) gene and a protein encoded by a BABY BOOM (ODP2 (BBM)) gene, and, optionally both a protein encoded by a Wuschel (WUS) gene and a protein encoded by a BABYBOOM (ODPs (BBM)) gene, wherein one is encoded by the third expression cassette.

8. The plant cell of claim 4, wherein the gene of interest of the second expression cassette encodes a gene product that confers drought tolerance, cold tolerance, herbicide tolerance, pathogen resistance, or insect resistance.

9. The plant cell of claim 4, wherein the heterologous polynucleotide of interest of the first expression cassette is transiently expressed in the plant cell.

10. The plant cell of claim 4, wherein the gene of interest of the second expression cassette is stably integrated into the genome of the plant cell.

11. The plant cell of claim 4, wherein the plant cell is a monocot or a dicot.

12. The plant cell of claim 11, wherein the monocot or the dicot is selected from the group consisting of: maize; sorghum; rice; soybean; wheat; cotton; and Brassica.

13. A plant comprising the DNA construct of claim 2.

14. The plant of claim 13, wherein the heterologous polynucleotide of interest of the first expression cassette encodes a transcription factor.

15. The plant of claim 14, wherein the transcription factor is involved in plant metabolism, organ development, stem cell development, cell growth stimulation, organogenesis, somatic embryogenesis initiation, or development of the apical meristem.

16. The plant of claim 15, wherein the DNA construct optionally further comprises a third expression cassette, and wherein the transcription factor involved in plant metabolism, organ development, stem cell development, cell growth stimulation, organogenesis, somatic embryogenesis initiation, or development of the apical meristem is selected from the group consisting of a protein encoded by a Wuschel (WUS) gene and a protein encoded by a BABY BOOM (ODP2 (BBM)) gene, and, optionally both a protein encoded by a Wuschel (WUS) gene and a protein encoded by a BABYBOOM (ODPs (BBM)) gene, wherein one is encoded by the third expression cassette.

17. The plant of claim 13, wherein the gene of interest of the second expression cassette encodes a gene product that confers drought tolerance, cold tolerance, herbicide tolerance, pathogen resistance, or insect resistance.

18. The plant of claim 13, wherein the heterologous polynucleotide of interest of the first expression cassette is transiently expressed in the plant cell.

19. The plant of claim 13, wherein the gene of interest of the second expression cassette is stably integrated into the genome of the plant cell.

20. The plant of claim 13, wherein the plant is a monocot or a dicot.

21. The plant of claim 20, wherein the monocot or the dicot is selected from the group consisting of: maize; sorghum; rice; soybean; wheat; cotton; and Brassica.

22. A seed of the plant of claim 19, wherein the seed comprises the regulatory element operably linked to the heterologous polynucleotide of interest and the gene of interest of the expression cassette.

23. A method for expressing a polynucleotide in a plant or a plant cell, the method comprising introducing into the plant or the plant cell a DNA construct comprising a firsts expression cassette comprising a heterologous polynucleotide of interest operably linked to a tissue preferred regulatory element, wherein the regulatory element comprises a nucleotide sequence selected from the group consisting of SEQ ID NO: 1 or SEQ ID NO: 3, wherein the regulatory element confers expression of the heterologous polynucleotide of interest in the scutellar epithelium of the embryo, in the accessory cells and cork cells of the leaf epidermis, and in the silk hairs and silk-tip.

24. The method of claim 23, wherein the DNA construct further comprising a second expression cassette comprising a gene of interest.

25. The method of claim 24, wherein the heterologous polynucleotide of interest of the first expression cassette encodes a transcription factor.

26. The method of claim 25, wherein the transcription factor is involved in plant metabolism, organ development, stem cell development, cell growth stimulation, organogenesis, somatic embryogenesis initiation, or development of the apical meristem.

27. The method of claim 26, wherein the DNA construct optionally further comprises a third expression cassette, and wherein the transcription factor involved in plant metabolism, organ development, stem cell development, cell growth stimulation, organogenesis, somatic embryogenesis initiation, or development of the apical meristem is selected from the group consisting of a protein encoded by a Wuschel (WUS) gene and a protein encoded by a BABY BOOM (ODP2 (BBM)) gene, and, optionally both a protein encoded by a Wuschel (WUS) gene and a protein encoded by a BABYBOOM (ODPs (BBM)) gene, wherein one is encoded by the third expression cassette.

28. The method of claim 24, wherein the gene of interest of the second expression cassette encodes a gene product that confers drought tolerance, cold tolerance, herbicide tolerance, pathogen resistance, or insect resistance.

29. The method of claim 24, wherein the heterologous polynucleotide of interest of the first expression cassette is transiently expressed in the plant or the plant cell.

30. The method of claim 24, wherein the gene of interest of the second expression cassette is stably integrated into the genome of the plant or the plant cell.

31. The method of claim 24, wherein the plant or the plant cell is a monocot or a dicot.

32. The method of claim 31, wherein the monocot or the dicot is selected from the group consisting of: maize; sorghum; rice; soybean; wheat; cotton; and *Brassica*.

33. A method for expressing a polynucleotide of interest in a plant or a plant cell, the method comprising introducing into the plant or the plant cell a DNA construct comprising a first expression cassette comprising a heterologous polynucleotide of interest operably linked to a tissue preferred regulatory element, wherein the regulatory element comprises a nucleotide sequence selected from the group consisting of SEQ ID NO: 1 or SEQ ID NO: 3,
  wherein the regulatory element confers expression of the heterologous polynucleotide of interest in the scutellar epithelium of the embryo, in the accessory cells and cork cells of the leaf epidermis, and in the silk hairs and silk tip,
  wherein the DNA construct, optionally, comprises a second expression cassette,
  wherein the heterologous polynucleotide of interest of the first expression cassette encodes a transcription factor involved in plant metabolism, organ development, stem cell development, cell growth stimulation, organogenesis, somatic embryogenesis initiation, or development of the apical meristem is selected from the group consisting of a protein encoded by a Wuschel (WUS) gene and a protein encoded by a BABYBOOM (ODP2 (BBM)) gene, and, optionally both a protein encoded by a Wuschel (WUS) gene and a protein encoded by a BABYBOOM (ODPs (BBM)) gene, wherein one is encoded by the second expression cassette.

34. The method of claim 33, wherein the DNA construct further comprises a third expression cassette comprising a gene of interest.

35. The method of claim 34, wherein the gene of interest of the third expression cassette encodes a gene product that confers drought tolerance, cold tolerance, herbicide tolerance, pathogen resistance, or insect resistance.

36. The method of claim 34, wherein the heterologous polynucleotide of interest of the first expression cassette is transiently expressed in the plant or the plant cell.

37. The method of claim 34, wherein the gene of interest of the third expression cassette is stably integrated into the genome of the plant or the plant cell.

38. The method of claim 34, wherein the plant or the plant cell is a monocot or a dicot.

39. The method of claim 38, wherein the monocot or the dicot is selected from the group consisting of: maize; sorghum; rice; soybean; wheat; cotton; and *Brassica*.

* * * * *

SEQUENCE LISTING

```
<160> NUMBER OF SEQ ID NOS: 43

<210> SEQ ID NO 1
<211> LENGTH: 1062
<212> TYPE: DNA
<213> ORGANISM: Zea mays

<400> SEQUENCE: 1
ccctagctcc ctgcggctgt tacgcggtcc cccatcaatc ttctgttctt gcggttgtag      60
cctgtgtaac agtgctagag tatgtatgat aaataggttt taagtctgct tacatgacat     120
tttttattgt ggaagagaca tataaaaatt agagagagtg gttctcatgc aacggcggac     180
ggcccggtgc taaaagagct tcaagacaaa ataatgaaac aggaagagag tagatttatc     240
taagagccaa ctttattata tgaatgtgtt tattgttggc tttagatgat atggtaagga     300
gttagagcta ataatagata ggctctatta ttattattat taattaaact cgctctaagg     360
aggaaagtgg gaggaaggga cgaggacgaa gactactgga agcatcgtgc atggatgatg     420
gatgtggtgt ctcttaatgt aggtggccgg aggatgtacg tgttaattgc gcgataagca     480
ctcagatcca accgcaaact acctccacac tgacacactg atagagagaa agagagacct     540
ccgacgactg ccgccgcaga tgagccacgt acgtatacga cgtctgccgg ccggctcagg     600
ctgccgccat caccctgctc gaaagtcgcg ttaggcggcg ccagctacat aggagtatct     660
agtctagcca gttagtatac tactactgcg ctgatgatga attaactctg catagatact     720
gtacttgcct ccctccaaca cccaaccacc tcctgctcgg ctcttaataa cttggacacg     780
gatcgatgcc atccaaggaa gaacacgacg acgacgacgg aacatccacc atgcaagctt     840
gcatccatac gccgatacgc gtgcatccat ccatccacca ttatttccat tttccaccga     900
tcacacgtac acaggcctat ttaaggagcg acatcccact gcaactctcc tcaccactca     960
tcaccagcta gctctagcaa agcacttgcc atctaccgac cgccgcattc caaacagccc    1020
```

```
gacgagctag cagagcggca ggcacctccc tcctcaagga ac                    1062
```

<210> SEQ ID NO 2
<211> LENGTH: 1251
<212> TYPE: DNA
<213> ORGANISM: Sorghum bicolor

<400> SEQUENCE: 2

```
aaaatttgtt tgttttgaac aaaaattgag agatttgttt ttgagggtcg gacacatacg    60
agttttggga aaccgtcggt ggtacctgcc tgtgcacaca gaggtagcta gctaggttgg   120
ggacgggatg catgtatgta atacgtggcg gagcttccga tcgagacagc gacatgtggg   180
ctcccatact tgctggacaa cttaatcgct accactgctg caacttcaat ttgtgaatgt   240
gcatgtaacc tcctgcactg tactgatatc tctgtttctg gttgcggccg ggaggaatta   300
acgaagacta ctggaaggat tcatggatga tggacgatcc atatataatt gacgtcttaa   360
tgcaggaaga gtatgtgttt attgtgcgat aagcactcgg atccaactgc aaactacctc   420
acactgacac actagtgaga gagagtgaat acgcctccaa cttcatcaga tgagagccac   480
gtacgtccgt ccctgccgac tgccgccatc accctgcctg ctaagtcgtg ttaggcggct   540
gctatttaag ggcgtgttta aatgtcttta aaattctaaa tgtttataag atttctcgtc   600
gcatcgaatc tttagacgca tgtacgaaac ataaaatata tataaataaa aaaaaaataa   660
ttaactacat agtttgtata tgtaaatcgc gagataaagt acttgttgag tctagttagt   720
ctataattaa atatttattg ctaaatataa acgaaagtgt tatagtataa catacccgtaa  780
taagttgcta ttgctgctgc aaatgaattc actctgcctc gatcatgccc tcatcaacta   840
accgctgtag tattatctgt atctatctgc ctcctgctcc caacacccaa ccacctcctg   900
cccagcaatt aacttcgacg gatggcgacg ataccgtccg tcgtccatgg aagatgatgt   960
tggaacatcc accatattca ttcattcata tgcatgcatc caccattcca ccgactgcct  1020
gcctgaaact gcatgcaatg caacaacacc gtgcatgcat gcatctctgt catcagcaat  1080
gacaagctac tgtagctagc tcccagatca gatcagatca gatcgatcgc aagcctgcct  1140
atttaaggag ccacactcca tctcactctc ctcaccagcg gctagcactt gctcacttgc  1200
attccaaagc tagtacaagc aagtctcaga cacccccaga acatcgacga c           1251
```

<210> SEQ ID NO 3
<211> LENGTH: 1357
<212> TYPE: DNA
<213> ORGANISM: Zea mays

<400> SEQUENCE: 3

```
ttaccctagc tccctgcggc tgttacgcgg tcccccatca atcttctgtt cttgcggttg    60
tagcctgtgt aacagtgcta gagtatgtat gataaatagg ttttaagtct gcttacatga   120
catttttat tgtggaagag acatataaaa attagagaga gtggttctca tgcaacggcg    180
gacggcccgg tgctaaaaga gcttcaagac aaaataatga aacaggaaga gagtagattt   240
atctaagagc caactttatt atatgaatgt gtttattgtt ggctttagat gatatggtaa   300
ggagttagag ctaataatat ataggctcta ttattattat tattaattaa actcgctcta   360
aggaggaaag tgggaggaag ggacgaggac gaagactact ggaagcatcg tccatggatg   420
atggatgtgg tgtctcttaa tgtaggtggc cggaggatgt acgtgttaat tgcgcgataa   480
gcactcagat ccaaccgcaa actacctcca cactgacaca ctgatagaga gaagagaga    540
cctccgacga ctgccgccgc agatgagcca cgtacgtata cgacgtctgc cggccggctc   600
```

```
aggctgccgc catcaccctg ctcgaaagtc gcgttaggcg gcgccagcta cataggagta      660
tctagtctag ccagttagta tactactact gcgctgatga tgaattaact ctgcatatat      720
actgtacatg cctccctcca acacccaacc acctcctgct cggctcttaa taacttggac      780
acggatcgat gccatccaag gaagaagacg acgacgacga cggaacatcc accatgcaag      840
cttgcatcca tacgccgata cgcgtgcatc catccatcca ccattatttc cattttccac      900
cgatcacacg tacacaggcc tatttaagga gcgacatccc actgcaactc tcctcaccac      960
tcatcaccag ctagctctag caaagcactt gccatctacc gaccgccgca ttccaaacag     1020
cccgacgagc tagcagagcg gcaggcacct ccctcctcaa ggaaccttgg acacggatcg     1080
atgccatcca aggaagaaga cgacgacgac gacggaacat ccaccatgca agcttgcatc     1140
catacgccga tacgcgtgca tccatccatc caccattatt tccattttcc accgatcaca     1200
cgtacacagg cctatttaag gagcgacatc ccactgcaac tctcctcacc actcatcacc     1260
agctagctct agcaaagcac ttgccatcta ccgaccgccg cattccaaac agcccgacga     1320
gctagcagag cggcaggcac ctccctcctc aaggaac                              1357

<210> SEQ ID NO 4
<211> LENGTH: 10088
<212> TYPE: DNA
<213> ORGANISM: Zea mays

<400> SEQUENCE: 4
actttggcta aggttagtcg tttgaattga ataactaacc ttagacagaa aagttaggca       60
aagtgtgaca atttaggtag caaaccaaac aacccatcag tactcccgct tcacacatta      120
tgtgggcaag atcagataag caatatacac ttttctttgg atgtcttcaa ttcgatatat      180
ttaaggaact cctaaattat atttatggat gcagaacttt tattgcaaac atttgtgact      240
tttatgtacc taacattttt ctatttctgg tgggactgtt gatgcatctc ttcactgtga      300
gatccaaact gagagtgtgt tgatttcta ggactaattt ttagtccatt cattttattc      360 catttagtc cttaaattgc caaatataga aacttgtatt ggcaatttag gaactaaaat      420
aaaataaaat ggagtgactg aattagtcct aaaaaccaaa caccccttga attggttgag      480
gtagtaggca tttagtaggt gctaagttct ttgagcttgg tcgaacgctg atgatgcttc      540
acactgtata cataatttgt ttttctttcc ttcatgctat gtaactaact ttgtacatgt      600
caccatagtg aaatctttta attccgcagt ctagggctta tgtaaattct aggcctgctg      660
tttatattaa ctccacgaga ccagacccaa tcatggttga ggtgattatt gctacacatt      720
tttcatgtta cttttgatgg cctagagcgc tacaataatc taatcaacaa atttcctttg      780
tgcaaccatc ttttcaaagc acccctcctt tggtgtctc taatatagta gctctaggtg      840
aaatttctgg tgcttttggt attaatggtc cttctcgaca tgtgaatgtg ccaagtaaca      900
gtaaggtcac atttgaatgc ttattaacta ttggttccct cttgttaggg tcatgaaccg      960
gaaaagcgac cacgagatac tgccatttca accctgttgg tacttaagct attcggttca     1020
atggttcaag gaacacatgc caatagtgat cttgaaattt gaaatagagg cttactatgg     1080
tttatttaac ctgaagaatt ggggatgtat tgtttgattg cttatgcatt atacaatttg     1140
ttgtaacaca caattttgc cttggttta ataggtccga taaatgcata gaagcttatc     1200
caacccaaag gacaaaatac caaggtatta atgtcatggt ctctcgtccc tcgacgagaa     1260
attcacgaag caagaaaataa aaaaaatcaa ttggtctcat gccaggggac aaagctccag     1320
```

```
ggccagatgc cttcactggc accttcatca aaacttgctg ggacatcata aaaacaaatg    1380
ttgtggcagt tgccaatgct ttccatgtcc tgcggtgcac taatttgcaa atcgtcaact    1440
tcgcaaaaat agtcttcata ccaaagaaag aaggagcaca tactgtggca aatttttaggc   1500 caatatgtta aatccactct tttattaata tcatcatgaa gactctagca cttcgtataa    1560
cccctcgcat gaatgagatt gtctcgcctg gctaaagtgc cttgatcaag acaaggagta    1620
tccatgacaa ctacatggca gtacatagca tgatctagat atgtaataga aacaaaactc    1680
tcaccctctt cctatagctc gacattgcta aagcatttga ctctgtcaga tgggacttcc    1740
ttcaattctt gagctattgc aacgtcttgg gttcccaaca cgttggcgtg atcgggttgc    1800
gacaattatc tctccatcaa cgtcacgggt gttcgtcaac ggggtcccaa accctcctct    1860
ttggcatgga gaggtcttc ggcagggtga actgctctcc ccctcctctt catcattgct    1920
attgatcctc tataattact tcttcagaag gcgactgagt tgagcatatg aagtaaaatt    1980
cggggacgct gaccaaatct gcgcatttcc ctctacgcag atgactcagc attattcatc    2040
aaaccaaata aggaggagat gaaggggact gtgcaacttc taaatttttt tggccatgcc    2100
ttgggtctca tcacaaattt ccataaatca actgtggtcg taatttgctg cgatggcata    2160
gacctagcta gcgttctgga ggggctaccg gccaaaagga caatgttttc gatcagattt    2220
attggcctac ctttatccaa ctccagactc cgtaaggtgg actttcagtt cttgctagac    2280
aaagtcttga gtatacttaa tagctggaac gaaagaaatt tgaacatggc gagacgcctg    2340
ccttggtcaa gttagtgatt acatctcaaa ctatctacct cctatctgcc ctcaaagcac    2400
caaatgaaat tatggagttc gtggactcaa agcggaggca attatttga gctgaatgg     2460 agagagtcac gagagggaaa tgcaaagtga actggacctg ttcagcaaga ccaaaagccc    2520
taggaggttt gggcatccta cacctgcaat cttttgcatg agcgttgtgc ttgaggtggt    2580
tatggtagga ttggacaacc attatttgtc ctagcctcgg gatcgactcg ccttgcatga    2640
aaattgacag gctgctcttt gcagcagtga ctagcttgac ggtgggggat ggcagtcgcg    2700
tttcattcta cgatagtgcg tggatgcagg gaatgttagt ttgacaaaca atttgtttga    2760
atagtagtca tgtaaacatt gctattatta atgtcttctt ttttctttag aatccaaacc    2820
agttacacga cttcgtcgac gagttgttcg cttctggagg tagtggtcac aactccaatg    2880
accccgatat gtgacggttt gagttttgtg tcgaattgtg agtttgtttt atgttgtaat    2940
gtactatgtg atgtatttgt gaactgtgat gtggtaaacc atttgtgaac tgtgaacttg    3000
attttggtga acttcaatgt ggttgtgaag aagtgtgata ctttgtgtta aatgtgtgta    3060
attctggaat taatgtttct gtcattttat tgtgattata ttgttgctga aattgttgtt    3120
ttttgcattt atttcaaatt tttttctctg aaattgttac ttttcggcgg ccaacagagg    3180
ccgccaaaaa taataatggc acattttcag cggccactat tttcggcggc tagatgccag    3240
ccgccgaaaa taagtgttta ttttcggcgg ccaatgagcc tgaaactggc cgctggaaat    3300
aatggcttat tttcggctaa ttttttctgg tggccagaaa tcaccgaaaa taggcctaaa    3360
gccaccgaaa taagctactt ttggtggcga atgcctcatt ttcggcggcc tcggctgtag    3420
ctgtcgtagt gaacaatgcg aagagacatc gccccaaaca tgttctgaat tccaagaaa    3480 aaatagatca ttgcatgatg ccttatgcaa taataattgg attcgggaca tcaatctgca    3540
acatcatgat ttctcaagca tatatggaca agagtgaaac aggtacagct gcggtcagaa    3600
gcaaacctga cagtatatct tgaagctttc tagaaacaac cagtacacaa tgagatcaac    3660 ataccctagca caatttttgg ggtccataca tactaacctg gaatggatcg tctggaagaa   3720
```

```
ctaggctcca ccaaagtgta agttttttca gctcgctagc gatccaggat aggatttgga    3780
tggccggcca tttggcaagg aggggatggc cacataacct ggtgtgcgcc ctctgtcaca    3840
tctttcaaga aaatggtctg catctcttct ctgattgccg ttcctgttag gcgcatttgg    3900
gcagaggttg aatgctgggc gacaattgaa gatttaggcc cggtttggga acaaagtttt    3960
tgaaaaacac agttttgaa atactacagt atactttagt catgacaata ctgcagttta     4020
caataccaca attttggaaa ctgaggtcca gacctaagtt tagaataccc taaacaact     4080
atagtatttg taatacttca gttttaaaaa cagagatttt agccagcttg tcaaacacca    4140
ttctgtatat aatactgcag tatttgagaa tactgcagta ttcttccaaa actgtgaaaa    4200
aacttcactc ccaaacacgc cccttatctc ctaactcttg gggccaacac gattcagtcc    4260
tccaatggtg gacgttaaga tccaaagcct caatgagaaa tagaagcgac ctgaggagct    4320
tgattatgct agttacttgg gagctttggt gtgagaggaa tacgagaatc tgggacggca    4380
aggagtcatc agtgtagaaa tcagaggcgc gatggaaata ggtggaacgt cggtctccgc    4440
tccagagatc acgacggctt cgtgtttgat atttctggtg gcacaaaaac aaggcgcgag    4500
ttacatatat atagatgagt atggccagct ttagatctat tctaggaaag gataagtttt    4560
acatggttac aattgatcta tttctattaa ctgcctatag atcttagccg acaatatctc    4620
aaccatattt ggaatacaac acatatatgt taacactccc cctcaatcta aatcttctcc    4680
aagttgagat tgcctttgaa caattccaac tgtcgcgccg ccagtggttt tgtaaaccca    4740
tcagccacct gatctcttgt tgacacatgt tctatttcaa gtaattgcct tgcaactctt    4800
tctcgaacaa aatgataatc aacttcaata tgttttgtac gtgcgtgaaa taccggattt    4860
gccgaaagat atttagcccc tatattgtcg caccatagct ttgcctttct tggtgcttga    4920
atcccaattt ctaacagtaa aatctgaatc cacatgatct ctgcagttgc atttgccaac    4980
gccttgtact ctgcttctgt gctagacctt gacactgttg cttgttttct tgctttccag    5040
gaaacaagat ttgatcctag aaaaattgca aaccctcctg tggagcgcct atcatcaaga    5100
cttccagccc aatctgcatc actgaaacca ctaactagaa gtgacgttgt tttaccaatc    5160
tttaagccaa gccttgttgt gtgctttaga tatctcaaga ttcttttgac tgcagcccaa    5220
tgaacagtag taggtgcgtg caaaaactga catactttat taacagcaaa agagatatca    5280
ggccttgtta aagtcaagta ctgcaatgca ccaaccatgc ttctatactg agtagcatca    5340
tttggaccga gtagatctcc ttcatggacc gaaagcttct ctgaagtaga cataggagta    5400
gcgactggtt tacaatcact cattccaatt cttttaata catctgaggc atactttct     5460
tgcgtcaaaa tcagaccatc ggataccttta tttacctcaa ttccaagaaa ataatgcaga    5520
tcacctagat ctttagagc aaactctttg ttaagatcac tgagcaaagc tgaagttgca    5580
cttggtgttg aactagccac aatgatgtca tcaacataaa caagtacata catactgatg    5640
ttacctttat tataaagaa cagagatgtg tctgccttag atgatttgaa acccaagtct    5700
tgtaacttca tactaagtct ggaataccac gctcttggcg cttgtttgag tccatataaa    5760
gccttgtcga gcctgcacac ataacttggc aaagatttgt cctcataccc aggtggttgc    5820
ttcatataaa cttcctcttc tagtaaacca tgtaaaaagg cattttgaac atctagttga    5880
cgaagactcc aacctcttga cacggcaaca gaaagaataa ctctaattgt cgctgcctta    5940
atcacaggac tgaaagtatc ttcatagtct atcccatacc tttgcttgaa gcctttagca    6000
acaagacgag ccttgtacct gtcaagactt ccatctgcct ttctctttat cttatacacc    6060
```

```
catttacagt caataatatt agtgccctttt tttggaggta caagatgcca ggtcttattt    6120
ttcatcaaag cagagtattc tagatccata gcatctttcc aattcttatc ttctaaagct    6180
tcatttatat tatgtggttc ccctgatgat gtaaaacacc catatctaat agtgccatca    6240
gtatatacct ttggtttgcg aattccagct tgtagacgtg tccttggcct tgaatcttca    6300
ggtgcagtag gctgtacaat ttgggacgca gctccctcgg ccataggcga tcccggtgct    6360
ggcggtggca atcctctgt ggaatcggcg ccgatcgggt cataggaatc aggcgcatga     6420
gattctgtct gctgcccaag ctcggtcggc gacgtagctt gatttggttg atcagcgatg    6480
ctggacggga gagcggacac acgtgctggc gacgcggttt ctgcacacac ttcatcacat    6540
agattattag aatcaaacct gtgatcaccc attagttctc ccccttgatc agatggtatt    6600
ggctggagat cagatggaag gagagaaatt tcctgacgaa gtcgagctcc tgcatttgga    6660
tgaagttgtg agaaaggaaa gacattctca tcaaaggcga cgtcccgaga tatgtagacc    6720
cggcctgtgg aaggatctaa gcacttaaag cctttgtgcg agggactata gccaagaaac    6780
acacactgct tagagcgaaa ctgaaattta tgtgtgttgt agggacgtag atgtggccaa    6840
catgcacaac caaacactct aagagaagaa tagtctggtt tttgctgaaa cagacgttca    6900
aggggcgtgt cataatttat gactcgacta ggagttcgat taatcaaata agtggcagct    6960
acaaaagcat cttcccaata tttaagaggg attgaggcgt gagcaaggag agctaaaccg    7020
acctcaataa tatgcctatg ttttcgttct gcagccccgt tttgttgatg agcgtgagga    7080
catgatacaa ggtgagatat cccgacacgc tcaaaaaagg agtgaagctt ctgatattca    7140
cctccccaat cagtttgtat ggcaataatt ttttgattaa atagtctctc gacaaggttt    7200
tgaaattcat tgaatttctg aaaaacttca gatttatgct tgataagata aatccacaca    7260
tatttgctgt aatcatcgat aaagctaaca taatatttgt tctttccaac cgaattaggt    7320
ggaggacccc aaacatctga aaacacaagc tccaaaggtt tactagaaac actatgtgac    7380
ttgggatagg gaagctgatg actctttgcc ttttgacagg catcacacac cgactctttta    7440
tttgattcat ctaaacaagg aagattattt gtgctaataa ctttagaaac aatggggggca   7500
gaagcatgac ccaaacgact gtgccatctt tcgaaagatg gtttgacaac tccaaaggct    7560
tgctttatgg cgggtagagg aagagggtaa agacccttgc ggcatggccc cttaaggatg    7620
gtgttcttcg ttgcctgatc cttgatcaaa aaataatcag gatgaaattc aaggaaagca    7680
gaattatctt tggtgaggcg atgaactgaa acaagatttt tagtggcctt tggaacatga    7740
agaatattgt ttagatgtaa attgcgagtt ggggtgtgaa ctaatgaatg accaatatgt    7800
ttgatttcca tacctgcgcc gcttgctgta tgaatctggt cacttccatg atacttgtca    7860
cgaacggcga gcttctcaag atcactagtg atattgtctg tagcaccaga gtccatgtac    7920
cagtttttgat ccatagaata agggctcatt gcagcagcaa catggcgttc ctctggaaca   7980
tagttttcat caaacctgtg ccaacagtca atcgccgtgt gtcccgtctt gaagcagacc    8040
tgacagattg ggcgcccatt gttgtcgtgg gttgcagttg ggcccgtggg gaagctcctg    8100
cgttgctggt tttgccgtag tggctgctgc tgcccacggc cacggccacc agagctacgg    8160
ccggagttct gccgtccacc tcggccacga tttgggccac gcatttgctg ctcccacca    8220
cggccgccgc ctcttcctgc tgaattcgct gatgacgatg acccgatgcc aagctgtaac    8280
tctaatctag tctcaaagct caaaagttgg gagtacaatt ctgaaggagt aacaggttct    8340
agtctagtta caagagcaga aactagagga ttgtactcaa gatcaagacc gttgcagata    8400
tacatcacca gttcctcatc gtcaaggggt cttcctgctg cagccatctc gtctgcaagc    8460
```

```
ccccttcatct tgccatagta ttgggcaaca gtcatgttgt ccttcttcgt cgtggcgagg      8520
gcaagacgca cattagtagc acgtgcacgc gtgtgagagg cgaacatgtc ggtgatgatc      8580
ttccatgctt cagcggcggt tcttgcaatg gcgacttgtg ccaagatatc cctggacagg      8640
gaggtgagaa gaaatcctag gacttgttgg tccgtggcga accattcgtc gtaggctgga      8700
ttggaaacct tagcgatctt gccgtcgctc tgcttctcat caatttcttc agatggagcg      8760
acggctttgc cgttgacata ccgctccagt cttgcgcctc gtaagatcgc aagaacttgc      8820
gccgaccaca taccgtgatt ctggcgagtg agtttctctg tgacttgaac accaaggaga      8880
ggattcgatg acgagtttga ggacgccatt gctaggatga ttaaccctag gctctggtac      8940
catgtagaaa tcagaggcgc gatggaaata ggtggaacgt cggtctccgc tccagagatc      9000
acgacggctt cgtgtttgat atttctggtg gcacaaaaac aaggcgcgag ttacatatat      9060
atagatgagt atggccagct ttagatctat tctaggaaag gataagtttt acatggttac      9120
aattgatcta tttctattaa ctgcctatag atcttagccg gcaatatctc aaccatattt      9180
ggaatacaac acatatatgt taacaatcag tctagcagct aggttgctgt gtggattcgt      9240
gaagcggcaa attcttggat ggctgcaggt gcccgacatc tttcgagcct ccttgcaaat      9300
tgctagtttt tttcttgttt ttcctctttg acttggtccg agtgtgctat gcagttgctg      9360
tgagagtgca ccttctgctt agtcgcatga tacaaggaac tgttgattct aaaaaaaact      9420 ttatttttaat gtaaaggaga gagaatttaa tatcagtttt ttttcgatat agactttcat      9480
gtgattttgc atcgcccgat acatcagtgt gtttgtttgg ctttagtcca tagcggcttc      9540
tataacgttt tgcctcgata gattacagct agctgcagca gttttaaaag ccgtctttaa      9600
tcggaagcca acatctcgac atatagagcg ttcgatagga tgcttactta ttctagtcta      9660
ttaaatttcc caccgctgct aattaatgct aatgaattaa ctctctctgc ctatccctcg      9720
acatgcacta atgtaggagt atatcccaac gcccaaccac ctcctaataa cttcgacgga      9780
tggcagctac cgtccatgga agatggtgac ggaatgtcca gcattccacc gactgccaga      9840
aactgcacgc acatctgtca tcagcaatcg ctagcctatt taatgagcaa cattccattg      9900
caatctcctc aggccactta cctgcagtca ccactcccaa gccagtaccc acagtcctac      9960
gagcagtcgc acgcaagtgt caagagacga acggtcgac gccacttacc tgcagtcacc     10020
actcccaagc cagtacccac agtcctacga gcagtcgcac gcaagtgtca agagacgaaa     10080
cggtcgac                                                             10088
```

<210> SEQ ID NO 5
<211> LENGTH: 1860
<212> TYPE: DNA
<213> ORGANISM: Sorghum bicolor

<400> SEQUENCE: 5

```
taagtgaaag gaaccatcaa atgtgtagcc aacaaagtat caacaaattc tacactagat        60
ctcatacaaa caagggcaac cacaatgtac tatgatctgt agtacaaaca ttgacctcaa       120
cttagattta acgatccatg cagagatcaa actccacgtt gcaccgaaat cctccaactc       180
ggactcgatt gggagcttaa tcttctcttc gccatacata attaagagtg gtagaaatga       240
gctacagtta agacatcatt gaatagcagc tgcaaggaat tgaatcaaac catccgaaac       300
accgcctcat acatctagag gaaagataaa tgggagcccc tctccgtcgg gaccggatca       360
gttcgagagt atatttgagt tttagcccct ttatataaaa aggtagaggt tcatttagaa       420
```

```
gtttggttga agttgctcta tacgcatcaa ccaatctttt catacaagat ctcatctcta    480
aacattacac acgaatctat ctgttacttt ctagaatata atcccaagtt cttttagaa     540 cggatcgagg tagagcagta ttttttcttg atggtcaaaa gttgtttgtt tttgaatcta    600
aaattttaaa aaatttgttt gttttgaaca aaaattgaga gatttgtttt tgagggtcgg    660
acacatacga gttttgggaa accgtcggtg gtacctgcct gtgcacacag aggtagctag    720
ctaggttggg gacgggatgc atgtatgtaa tacgtggcgg agcttccgat cgagacagcg    780
acatgtgggc tcccatactt gctggacaac ttaatcgcta ccactgctgc aacttcaatt    840
tgtgaatgtg catgtaacct cctgcactgt actgatatct ctgtttctgg ttgcggccgg    900
gaggaattaa cgaagactac tggaaggatt catggatgat ggacgatcca tatataattg    960
acgtcttaat gcaggaagag tatgtgttta ttgtgcgata agcactcgga tccaactgca   1020
aactacctca cactgacaca ctagtgagag agagtgaata cgcctccaac ttcatcagat   1080
gagagccacg tacgtccgtc cctgccgact gccgccatca ccctgcctgc taagtcgtgt   1140
taggcggctg ctatttaagg gcgtgtttaa atgtctttaa aattctaaat gtttataaga   1200
tttctcgtcg catcgaatct ttagacgcat gtacgaaaca taaaatatat ataaataaaa   1260
aaaaaataat taactacata gttttgtatat gtaaatcgcg agataaagta cttgttgagt   1320
ctagttagtc tataattaaa tatttattgc taaatataaa cgaaagtgtt atagtataac   1380 atacccctaat aagttgctat tgctgctgca aatgaattca ctctgcctcg atcatgccct   1440
catcaactaa ccgctgtagt attatctgta tctatctgcc tcctgctccc aacacccaac   1500
cacctcctgc ccagcaatta acttcgacgg atggcgacga taccgtccgt cgtccatgga   1560
agatgatgtt ggaacatcca ccatattcat tcattcatat gcatgcatcc accattccac   1620
cgactgcctg cctgaaactg catgcaatgc aacaacaccg tgcatgcatg cacatctgtc   1680
atcagcaatg acaagctact gtagctagct cccagatcag atcagatcag atcgatcgca   1740
agcctgccta tttaaggagc cacactccat ctcactctcc tcaccagcgg ctagcacttg   1800
ctcacttgca ttccaaagct agtacaagca agtctcagac accccagaa catcgacgac   1860
```

<210> SEQ ID NO 6
<211> LENGTH: 1856
<212> TYPE: DNA
<213> ORGANISM: Sorghum bicolor

<400> SEQUENCE: 6

```
aacatatatc tgcgaataaa cgttgctggc tagcttgatg acgtcgttat aacatagaca     60
tgttttattg ccgttttcct ttagaaaaac aaacctaaaa atacaaagaa aatacgctag    120
tttatttagg ccatatcatc tctgttttaa ctccgttttg tccattgaaa ttgtgttagg    180
ttcgtaatca cgagcactac atgttagtaa tattgttcac tcagtttgaa accttttaat    240
ttcgtgacct taattaatta attacttttc tatataaaat cttagaaaat ccatatcttt    300
tccgttttaa ctccgatttt cgtcatcttt acgtctgtga gatcgtagcg atgcgtagaa    360
ttattttaca aattttttcat attgttttta tatgattggt gtactgttct aattatagcc    420
ttgtttgcta cgtgtatgtt gtgtccgatt gtttgtgtgt tgatgatcga tgatcgagtt    480
tagacggaga gcagtttcgg tgatcaagat caaagctttg gcaacaagtg agaccagcag    540
gaccaaaagg ataagcaaga gcaattggat tgaggcaagt atagcatttg gattttatt     600 ctgtgaccat gatcctgtga ctagattaat gttaagtaat aaatggtaaa aatgactttt    660
taacaacttg atgatttgtc tgtacgtgat cacccgggat aacagtgcaa ccatgagggc    720
```

```
tataatggct ctggctttag ctcagtatga agaccttttc tagcttgtta gaggttaccc      780
gaaagggcgg aggggctgaa ccgacacggg tatagtgcga gccctgtcc ctatgtgtat       840 aggctgcgcg tcattgtgcc attcggaagg ggggtatcta tatctgctcg caaaggaaac     900
cttgcggccc taacatgtta gacgaacttt tgaaaggctt catagtgatc cctgccgacc     960
ttccttggaa gtgggttaag aggctgatca cctcgggcga aagggtaaat catgactcat     1020
gggtaaagat gtgcaacctc tgcagagtgt taaaactagt atactagccg agctcacggt     1080
caggaacggc cttggggaca tctacattaa gggtgatgaa tcttgtgtgt taaatatgct     1140
cattgcttat tgtttaatgc tttacattat ttatgtcaca ttgatcatga gattgtggga     1200
gctatacaat ctagttgcta tacttgtgga gtttgacatg gactcactct tgctatttcc     1260
cccaaacctc aggagaagtt taggcttgtg atcaaccagt cagttggatc ctgtagagag     1320
aagttaatac ccggagtttg gagttgtcta tccgttgttt gctatcaaag gttatctctt     1380
ttatattatg tacgttatat aattttttgca ttgtctttg atattacccc ttatttgtag     1440
ctatatgtga gatttggctt ttaaaactca catatggtgc atatctggtt ttgtccttaa     1500
aatcgggtat tacaacaact aaacaagcat ctgccctcct ccctcaacac caaccacct     1560 cctccccagc agttaacttc gatgcatggc gagagatacc atcgatccat ggacatatac     1620
gcatatgcat gcatccaccg actgaaacag catgcacacc catcccatgc atgcacatca     1680
ctcatcagca atcgctagct agctcacaca tcgatcacaa agcctgccta tttaaggagc     1740
aacattccat tgcaatctcc tcaccagcta gcacttgctc actcactgca tcccaaaagc     1800
tatcagtcac ctacgagcat cagcacatat atcacaggag gtcgatcgag atcgac         1856
```

<210> SEQ ID NO 7
<211> LENGTH: 1588
<212> TYPE: DNA
<213> ORGANISM: Setaria italica

<400> SEQUENCE: 7

```
tacgaagaga gaggggcgga gtttcattaa gaatggcttt atgtacaaca caatgataat      60
ggtctcataa acacatgatc atacgggtga aacgacgaca aaattagtaa atctgtggaa     120
tgatcttatg cacaacaaca gcaacatgac cttaatccaa taatagtgcc atctttatgt     180
ttgttctaga gagggccaa gaggttggtg gcacagggga atgcatgtgc caagcagcta     240
tgactctcca cggtgggacg ccgacccact tgcaaagttg caagccttgc gtgcccgctc     300
tagcaagtgt ccgcgaataa aagttaagta ggccatgaat acatagtact cctacggtgt     360
ataggagacc gctatttgat gcactcgtag gtacacgtgt cacgattagc acttggcagg     420
acattgatgc aggacacgtg tcacctatat gcgaaggtgt cctggacctt cacgactttt     480
tccttgatcc cacgaagcga aaccggacct tctctgctct gtccaaacat catttcctac     540
catcacactt aagtaaacgt cgcggatctc ctttgctctg tccaaacatt atttcctaca     600
atcacgctta agtaaacgtt gcttaccttt ggtgacggtt cagcgagggt ggcatttagt     660
atcccgattc agatccccga cgcagtccga gaccgttctt ctttttttttt cttatggagc     720 atgcagatac atgcatgtag atgcatggac ttggacagat gtcaagtgtg tacgagttgc     780
accgcttccc tcactcgtac tcagcggctt gtacaagcat gtagcggtgt gtcgatccac     840
accacagtcg cgacgtccgg cccatgcagt tgtccatcgc tagcagctcg atggctgcag     900
ctggagggtc tgggtggaca aacgagtttc ggcaaccgtc ggtgcttcct gcttgtgcat     960
```

| | |
|---|---:|
| ctgtctgctg tcactatgct gggtaaattc atcacttaat cagtttacca acggctaacc | 1020 |
| tcctggaaga gtacgtgtct ttaatttgtt tctggttgca gccatgcatt aactattgtg | 1080 |
| ggaagattac agctggaagg atcgatccgt gtaaacgaat ggacggatgg attggtatga | 1140 |
| tgtttaaacg tacaattatc atcgataagc actcgcatcc acccccaaa ccctcgatca | 1200 |
| ctgacactga atgaattgaa tgcgtgctgc ctcaactgca caccgaccat catctgctgg | 1260 |
| cccaactccc aactacctcc tgccggtccc ttaactccca tccggtcgat cgagaccgac | 1320 |
| accaacgaca gggatccacc gacgactgca acacaccatg gcatggcca tgcatgcacc | 1380 |
| catcagctag cagctccccg tctccgtcct cgtcagtcat cgctcacaaa ccacacagag | 1440 |
| agctaggtcg atcgagaccc tatttaaaga ccaacattcc ctcctcacca gcaaagcaaa | 1500 |
| gcacattctt cccaagcagc ttgtagagca catccgatcc atcgaccaca gcgcagctag | 1560 |
| cagctagcac aggaacacgc acatcagc | 1588 |

<210> SEQ ID NO 8
<211> LENGTH: 1798
<212> TYPE: DNA
<213> ORGANISM: Oryza sativa

<400> SEQUENCE: 8

| | |
|---|---:|
| ggttggcagg tagatcgata cgagaatgac atgaacataa tggatcgtcg gcttcaattt | 60 |
| ggaagccacc tgctggcgac cgacagccgt cccggccggg agggataacc tacgtcaacg | 120 |
| ataaataaat actcctacta actggagtag ctagcagctt ggtcttgtga aaagaaaga | 180 |
| taaaattcta ctactccata gtgtacgtgg tcttatctag agcttaattg gattgcaaaa | 240 |
| tagcatacag ctgattgatt aaaaactacg ttaaacttag gaggtgttta gaaattagga | 300 |
| ctaaatttag tccctctcac aaaaatataa gtccctttag tccactttag tccctccaac | 360 |
| caaacaccac cttcaaacac caccttagta actgaaaatt cttagattta attgatcgat | 420 |
| ctgctgagag ctttgcattg tggagcacat gccaggccag ctagtacatt cttgtgataa | 480 |
| gaaacatgaa gtttcggttt aacctcttaa atacatgcat gcatggttga tacaatacac | 540 |
| gtcctgaaca tgaataaata ctattaaata cgttatccga attttatcat atagtaatat | 600 |
| atttggatta gtttcttaat atgactttta ttctttttatc ccaattatat atcaatctct | 660 |
| tgtgtactaa aatgtgatgt gctattgaga tatttcactg tgtttgtacc aactcctgaa | 720 |
| aatactcatc atatcgtcgt tgttggttgg cattcatagt ttatttttgta gcagctgagc | 780 |
| aattttaatt agtctttta gcttgtaaga ttcttatatt tcttagcaat agccgagcgc | 840 |
| attattgggc tatagtgtaa ccaggtgaag cgtacgcgtg tgcataagtt gtccttgtgg | 900 |
| ttgaaagaag aatactggaa ggatcgttgg atgttactgc tgatatgatg gacacttgga | 960 |
| tccaaacatc atgaatgcgc tcaactactt gcatgttcca aatgtacaac atgcatgcta | 1020 |
| gctgctacaa cgactagct ccgttaggcc gctgctaatc attttctcat cactaatact | 1080 |
| aacactgtgt gactagctag ctaaaccagc cctaacaacc aaccaccctg attcaattga | 1140 |
| attgaattga ataacattag acgcaccgac gactaagaac ggtgcctaaa cactagcact | 1200 |
| ccaagcttaa ttacactatg cgtacaccaa ttaaaaatg tcacgaaaca ttctataaac | 1260 |
| aaattagata tttactccta atagtattat acatatgtgc aaagtctcat attcaaattc | 1320 |
| aatatatttt agctgtaaca aaaagtgaaa aaaacccgaa ttttagctgt aacaaaaagt | 1380 |
| gaaaaaaaac ccgacagttt taagggtaaa aatatcagga ttttgtcttt tttatggcta | 1440 |
| aaatataatg aaattgaaga taagatttca catgtaggtg taaaactatt ggaagtatgt | 1500 |

```
gtccaattttt ttctaaaatt ttttatgaca tttgctaatt gatatgtata gtgtgtacat    1560
aagtaaagct tgtgtgtata ggatatgttc tctaattata ggtggactat atattccacg    1620
tagtaactac atttgacttg gtcgatgcat cggcacagat gaaatcatag ctatttaaag    1680
ccccctacat tcccgggaat tctcatcgat cgatctcacc tgcagcagca aacgagcacc    1740
acacaccagc agcagcagca aagtcgatcg atcgtcagca cacacgacca agatcgag     1798
```

<210> SEQ ID NO 9
<211> LENGTH: 1500
<212> TYPE: DNA
<213> ORGANISM: Oryza sativa

<400> SEQUENCE: 9

```
ttaaagatga tttctccacc agtgtaaaat gtgatgtgct attgagatat ttcactgtgt     60
ttcctaaaaa tactcatcgt cgttaattgt tggttggcat tcgtagttta ttttgtagca    120
gctgagcaat tttaattagt ctatttagct tgtaagattc ttatatttct tagcaatagc    180
cgagcgcatt attgggctat agtgtaacca ggtgaagcgt acgcgtgtgc ataagttgtc    240
cttgtggttg aaagaagaat actggaagga tcgttggatg ttactgctga tatgatggac    300
acttggatcc aaacatcatg aatgcgctca actacttgca tgttccaagt gtacaacatg    360
catgctagct gctacaaacg actagctctg ttaggccgct gctaatcatt ttctcatcac    420
taatactaac actgtgtgac tagctagcta aaccagccct aacaaccaac caccctgatt    480
caattgaatt gaattgaata acattagacg caccgacgac taagtgcagt cccaaccctc    540
cacctaaaat ggtgtctata tatggcatta actaaattgt catgtatgac ttttaactta    600
tgtggcacta tattaatata ttaattaaga aggagagtga agagaggaag aaactgggtc    660
tcatgcaaga cacagcttca acacgagaat ctatgcacta gacactatca agttttgcat    720
tggaagagaa tagtgtcttt ataatagttg aagaataaat atgattggta gagaagagag    780
atgatgtatt tattaatggc ccactttaag aaatcatggg ttgtggagtg tagttttat    840 tgtgatgtct tattgacatg acaccataga cactgcttat ggacattatg ggttggaact    900
gccctaagaa cggtgcctaa acactagcac tccaagctta attacactat gtgtacgcca    960
attagaaaat gtcatgaaac attctataaa caaattagat atttactcct aatagtatta   1020
tacatatctg gaaagtctca tactcaaatt taatatattt tagctgtaac ataaagtgaa   1080
aaaacccgac agttttaagg gtaaaaatgt caggatttta tctttcttgt tatggctaaa   1140
atataatgaa actaaagata agatttcaca ataggtgta aaactattgg aagtatgtgt    1200
ctaatttttt ctagaacttt tgtggcattt gctaattgat atgtatagtg tgtacataag   1260
taaagcttct gtgtatagga tatgttctct aattataatt ataggtggac tatatattcc   1320
acgtagtaac tacatttgac ttggtcgatg catcggcaca gatgaaatca tagctactta   1380 aagccccta cattcccggg aattctcatc gatcgatctc acctgcagca gcaaacgagc    1440
accacacacc agcagcagca gcaagtcgat cgatcgtcag cacacgac caagatcgag     1500
```

<210> SEQ ID NO 10
<211> LENGTH: 1804
<212> TYPE: DNA
<213> ORGANISM: Zea mays

<400> SEQUENCE: 10

```
acgccggcgc cacgacagcc ggcagcttga aggagccaga gaagtacagc gcggccgcgc     60
```

| | |
|---|---|
| gcgggcatcc gctggcgctg ggccgccgcc ctgctgccgc ggaggatctt ggagagcagg | 120 |
| agctggagga tgccgccggc agcctgctgc cgggcgggct tcagctcggt cgccttgttc | 180 |
| ttcttgaagc aaaatcgccc cgccgccacc ttccttggat cgcgcggaca tccggcggcg | 240 |
| ccctccggtg acgcgaggt gggctggagt ggagggaggg ggcggcggcg gctagggttt | 300 |
| tggccgcccg tgtcgcccca gtgggaggcg accgagcggg acagttttcg cagccccgac | 360 |
| aaccctttttg tcgatatggt ctgattaatt gcttagcgta aacgtgtgca gtgtcttagt | 420 |
| atttgattat actgcacagg caagttacat tgatatatg tttcgttgtt tatgttatcc | 480 |
| atattctagc tacgaggatt ttggatgaga gcatgtctct tttttacgct atcggctatg | 540 |
| tgcacatcct tactgtctgt ctgtctaata cgatcaaatc tagcatacta agttactaac | 600 |
| taatacagta cgtcattaga tctgctttga gcactgtgaa aaaaaaacta taagagcc | 660 |
| tatacagtta accaaacaca attttatcaa aaatgtaaat tatgggcaag gtacaatttc | 720 |
| attagctccc acattagtac gtgtcaatca aaatttagaa gatacggccg tcaacgtctc | 780 |
| gtcgagtttc agcaatatgc ttgtgcatag ccgtataggc aatccgagcg agcactagca | 840 |
| ctttgcaaat tcgaatgaca gctcagtcaa ttctttttg attgcagctc agtcaattct | 900 |
| gattggccta atcgaatatg cgctgcaagg atccggtaaa ctactcagga attttgtgtg | 960 |
| acttacaaat acccgacaca cttgggccgg tttggatacg gtccatggaa ggaagaaggc | 1020 |
| ccaacttccg tctactctcc ccccgcacgc tcggcccctc gtagtcgccg aatggctact | 1080 |
| ggcgaacggc ggccagggc agcgagcagc cggtggcacg ccagcgacgc actcgagact | 1140 |
| cgagaggttg ccgttccagc gccctctccc tctctcccag ctctcagccc gatgtccctc | 1200 |
| tctgcgccag tcttctactg tccacagctg cagcctttgc gccttagctc cgagcgcgag | 1260 |
| cagagcaggg cagcgagcgg ccgccggcgt ccgttccaag tcccacagca cttagctgta | 1320 |
| gctccgaccc ccagcatccc tacatgagat tagctgattt gtgatgtgct tcgatctaaa | 1380 |
| atttttgttcc attttatctt tgttactagt tcgagtagat ggccccgcgt aacgaacgtg | 1440 |
| ctgaacatgt tgatgacctt attaagttgt gaaacacctt gtatatactg ccttgctggt | 1500 |
| actagaaata tactgttttt ttggaggata gcctatctgc gtatctgatg ggtaccgtat | 1560 |
| ccgtatgtat gtaaacaaca tagggtgcag ccatgcaagt ctgatactct gatgatggct | 1620 |
| acaacgtaaa gctggtgaag caacgccgtc ctcacaattc ttcccccaat ccacattctc | 1680 |
| tcccaggctc ccaaaaccac acaaacctca acccgaaaaa agacaagatc aagccaccac | 1740 |
| caccgccagc aagagcagag gcgagaccgc gagagtgtac gtgccaccag gagcagcagc | 1800 |
| agca | 1804 |

<210> SEQ ID NO 11
<211> LENGTH: 4263
<212> TYPE: DNA
<213> ORGANISM: Zea mays

<400> SEQUENCE: 11

| | |
|---|---|
| cctagggaaa ggggcaagta ttgtgcagat aagaaaaata ttgaatacat aacatgatag | 60 |
| ttcataaaat aacttattct cgttaatctg aatggtttac caagtttgct caattctgcc | 120 |
| tgcaaagaac gaaattctga atgcgaaaca gaaaagtaaa aaaaaaaaac taatcctact | 180 |
| aatctgaaat tctgaacggt tttacaaatt gagttcaacc ccacctcatc atataacaca | 240 |
| agacctttttc atggacactt caaatataca acatcctaaa aattgatttc tgtaacaatc | 300 |
| ttgttatcca ttttctgcc attgctacaa cagtaaaccg aatcatcaca taaatgcttg | 360 |

```
ttaagaggct acagaatggc aaggcaaagc tactcagctt ccaatatgaa caaacaagcc      420
cacatgtagc aggaagagaa cagtttatta ggacatgagg taacttcagt aataataagg      480
acaagataaa ggaaacaaga aaccatattt tgcaccttac aatttagaaa actagacaag      540
gttcattttc tctgcaagta gggcttgact gattccaaga caacctgacc atcagagaag      600
ctcatgaatg tttaggacat gtaaggcaaa gttcgacaag gcaataaagc atgtgagcac      660
ataccctccc atcatatgac aaagaagcga ataatgatgg atcatgggag ctccatgcaa      720
tacctacaat tttagttaac cctgtcattc cttgtcaaag ttctaattga taagcgaagt      780
atgaaggttg gaggatacca tagatgctgt cttcatagtc agtatatgag ttgagtaatg      840
gtacttcttg cctattggat aaagcagaag ggctgtgcaa aatgaccagg gcatcaatac      900
cacaacttta aacaaaatga tctaacaagc acaagaatag agacctatca gattcaggat      960
cgtcactgct aactttagcc aaccataaat ttacagttga atctgttcca gcactctaca     1020
gaaggtccaa tatcatcagt acacaataaa accaatgcat cattatgtta accctgccaa     1080
aaaagttaca tgtggacgga ggtaggaagg agacaaacca gaaggagctc atcatacgca     1140
ggattgtgcc aacagcccca tgtcctgtaa aaataatgag accataaaaa accccgatc      1200 tttgctagat aagaaaggca aaacaaatct gtaatcacaa ttgttaatga ccgaaccatt     1260
tccggaaact aactctgaat tggatgaaat ttgcttttt tggaaggtaa gtgtcaaacc      1320
gacattcacc gcatatatac aaacagaatg attgagaaca tttaaagatt gcacattgca     1380
gtgaaaagat tctggtttga gtatattatt acagtactta ccaatgtgag tgcccaggga     1440
gatcttttag aggatactta agcattctga gatcccacaa gcgaattcca aattcctctt     1500
ctgctgttgc ctgatgttta tattcgacta cttatcagaa gcaaacattt tatttgggag     1560
caacaatata aataagttga taataattca ataatgaact agcaatagat gtcattgtta     1620
atgaacttga acacgggtgt ccaatttgac agactctatg aattggattg ggacttgcta     1680
gattatatta atacaactct aaaccaaaaa aaatgaattt gttggtagaa cacaatcaag     1740
agttataatc ggttatttaa taataacgaa gcaaaaaccc atgtcatatg ccatacccag     1800
tgtgaacatg atatttaact actgaagcaa gaaaaaaaat gcaaaatcca taatcaaata     1860
taaaaaaata aaattgaaat gtaaccaaga aacaaaagat actacaaagt tgatgtcttc     1920
aatgctacta agaaagcta attcataaga atgttcgttt tatgtaaagg caacaactaa      1980
tatgcaatta gccaatcaag tcttgtgtgc aagtgtgcaa gcgaggttcc tgattcgtta     2040
gataatgatc caaccatgaa tcatatttaa cacttaaacc cttccaccac cagctcgtgt     2100
agatttatag aaaaccccat aacaaaccac gatcatgtct acaattagat cataatctaa     2160
cagactaaga ggctcgcttg caagcttgca cataaggtct gattgcatat tagttgttgc     2220
cttatgtaaa tatatatgat gtattgcttg atatatggga acaagaaag tgtcaaactc      2280 acaacaatgt tttgcttctt ggggttataa tccacatccc gtatatgtgc atgttcaatt     2340
gcagttgatt ttctgggaat gatacatttta aagataaata taactgcaac atttcaataa     2400
aatgaactat agataaaagc atagtaaaca atagatcaag ataatatatt aactccatag     2460
aacgtagatc ccacagctga agtgatgaat cagatattgc agcaactaaa ttatgattgt     2520
gtggatccca agctccacca cgtaaatttg gaagcatgtc agttgatccc tgtgagatca     2580
cctgtaatgc atgacattgt gaagcattaa gtatataaac agatggtgtg tagattcttg     2640
acatttcata atctggtact taagctaatg tttgaaaaca gagtaagtat tttgcaagta     2700
```

| | |
|---|---:|
| ctctaatgat atattgataa agaaggatg gtgacacacc ttagctattt tttttgacgt | 2760 |
| gtctatgttc caaagaaaaa tatttcggtc atcaatgcta attagtttat catgctttcc | 2820 |
| aagtggccac cagatcacac tacaaaataa ccagcttaga ggtgtcaaga accaataaag | 2880 |
| atgttacaca tatcactagc agcttttaag aatacgaagc aagcaagact agtttaaaag | 2940 |
| attcatatag aaataactgt agagttaaaa taaaatattc taatctatta tcccttcatg | 3000 |
| agcactgtgg gaaataatcc tactatattg cttaaatggt gctcatggaa tgtgaaacag | 3060 |
| gcgcaacatg ctagacagga aacatgttca attgtcaatt gcaccttcct tggtaactat | 3120 |
| gctctcatgt gtagtgaaca cgcgatatag tcacacaagt gaggccacaa taatctaacc | 3180 |
| acaaataaag gccatgtgaa tcaggaaaga attcaccaca caccacagag ttgcatttca | 3240 |
| gctaacaaag ttggacgcaa ctccgaaatt caaaatatag gaagaatcta gcacagtaag | 3300 |
| tagatcaaac atctctagaa caacaaaaaa aatcaacaga aacaggagtg caccgtctaa | 3360 |
| tcttgcccgt atgcccacta agctcaaaga gctgctcaag ttgtggtgag tttgattgcc | 3420 |
| cattgagctc cgggatcttc caaactgatg caccatagcc ctcacctggt attcatatca | 3480 |
| cgaattttca aattacaaga aaactacaca ctacatttt ttttgttatg caaattacaa | 3540 |
| tgctcacgag tcacgaacag agacaacttt tgcgttcttt accagacgtg tagactgtgg | 3600 |
| agaaaaccct gtgatcgaag gggcatgatt tgaggtccca aatctcgttg gggtggtaga | 3660 |
| agaggccatc gcacaccagc tcgctctccg ccggcgaaaa ccggatcagg tgcacctact | 3720 |
| tgtatgcacg cagaggaatc gagatccaaa tcaaatccca cgccatttca cctggcagaa | 3780 |
| aaagtactac tcgatcgcaa tcccaccagg cgcgatgagc cttcatgaac gcgagacacg | 3840 |
| cacctcgttc tcctccttga ggctgagggt gccggcgagg aaggtggtcg agccggcgtc | 3900 |
| cgcgcgtatg tcgcgatac accgcgcctg caagagccga gacccgagag agcaggaaga | 3960 |
| ggttaagaca ggtcgttcaa gaatgtttca gaaggcgctg cttgcttgct tgcctggtac | 4020 |
| ttgaggccac catacacgat gccgctggat ccgccctgca ttttctcgcg cgctttggat | 4080 |
| ccacccggcg acgccgctga tcgctctctc ccacctccga gacggaagag accgcgggag | 4140 |
| caggcagccg ccttccacac gagtacacga cgaaccaaaa gtacgatatc gcgagtgaaa | 4200 |
| acgtaattca ctggaatacg tgtttaggag cagacagcgt agtagcagag aataacgaag | 4260 |
| cgg | 4263 |

<210> SEQ ID NO 12
<211> LENGTH: 1900
<212> TYPE: DNA
<213> ORGANISM: Zea mays

<400> SEQUENCE: 12

| | |
|---|---:|
| aaatttcgga cgaagcaatg atgaaacgct cacctgtcat cttcccatat tgagatgcga | 60 |
| gcaccttctg agcttcgttc tttttttta tttactagac ttgctgtgtg ggtgagggaa | 120 |
| attgaacgaa cgaaattttg tgggtaattg tcatagtgga tgaagattta aaagtttata | 180 |
| tttaaaggtg cgttttgttg gagtaactag ttttttaaaa aaagagttat tttattatac | 240 |
| gtttgctaaa tagaatagag ttaacgatcc tgaggtcgag agttcgagcc tctctcaccc | 300 |
| caaatttcgg acgaagcaat gatgaaacgc tcacctgtca tcttcccata ttgagatgcg | 360 |
| agcaccttct gagcttcgtt ctttttttt tatttactag acttgctgtg tgggtgaggg | 420 |
| aaattgaacg aacgaaattt tgtgggtaat tgtctctcga gcctctctca ccccaaattt | 480 |
| cggacgaagc aatgatgaaa cgctcacctg tcatcttccc atattgagat gcgagcacct | 540 |

```
tctgagcttc gttcttttt ttttatttac tagacttgct gtgtgggtga gggaaattga    600
acgaacgaaa ttttgtgggt aattgtcata gtggatgaag atttaaaagt ttatatttaa    660
aggtgcgttt tgttggagta actagttttt taaaaaaaga gttatttat tatacgtttg    720 ctaaatagaa tagagttact ttattttttt ggttagaggg tagaatagaa cagagttgct    780
ccgagatgtg agaaccttct gagcttcgtt cattttttt tatttactag acttgctgtg    840
tggggtgagg aaattgaacg aacgaaaatt tgtgggtagt tgtcatagtg gatgaagatt    900
taaaagttta gatttaaagg tgcgtttggt tggagtaact agaattgtgt ggtttcattc    960 tagtttttt taaaaagagt tattctatgc gtttgctaaa tagaatagag ttactctatt   1020
ttttttggtt gaagagtaga atagaacaga gttgctccgt tctctattta gttggagaac   1080
catatgagtg tagatggtag gagagagatg agagcgctcg tatccgatgg tattttggag   1140
cgggagtatt tcaattattt atgatagagt ttcacatgaa gattctagga gtcaatctgc   1200
tccttttgtt gaaaactaac catccaaaaa atagtaataa agtcactcta ttttttctcc   1260
acggctcaat caagcacacg attaaggttg aatgtgcaca acacctcca taaaattttc    1320 gaatttaacg atggtcggta tccatcggtt gagattggta ttgatggagc catccaacca   1380
aaaaaaaaat ataacgtcgc gtgaaaccga tcgatcgaca ccgacgaaac catccgagag   1440
accgatcggt ggcacccccaa ctgaccggtc agtcccgatc ctggaccaaa tcacaaccga   1500
tccgcgctgg ttgtctgatg ctcatgcagg cgaccgaaaa cgagagatca caccgctgtg   1560
cagcagcgct gagccatatc cctgaccctg acgccgctct tggctgctat tgaggtgtct   1620
tctctctttg gagtggacaa gtcctctttg cgtgcgaatc cggcgcaaac ggtgaatttc   1680
agccactctc tagtttcgtt ctctctgtct tccgaaagtg aagtgcagga ccggaaaaca   1740
cagcgatttg gcagggtaaa aagctccaac agccacagcc gtgatcatta tatcctatct   1800
atctacgctc caggctttga ggtgggtatt cgaccgccaa gcgccaactg cttagctcac   1860
tcgtacatcg ccacatcggt gaagtggtgt cgtggtgacc                         1900

<210> SEQ ID NO 13
<211> LENGTH: 2936
<212> TYPE: DNA
<213> ORGANISM: Zea mays

<400> SEQUENCE: 13
taggcgattc tagagattcg ttaacacact acaagccggg gttagcgtta gaataaaaat     60
ccgagtccga gagagagggg aaaaacaaat caaccaaaaa tataaagcgg atgacacggt    120
gatttgtttt accgaggttc ggttccaaag aacctagtcc ccgttgaggt ggtcacaaag    180
actgggtctc tttcaaccct ttccctctct gaaacggtca cttagaccga gtgagctttc    240
tccttaacca atcgggtcac ttagaccctc acaaggacca ccacacactt ggtgtctctt    300
gctttgatta caagtgtctt gagaacaaga atgaggatga agaaagccaa ccaagcaaca    360
agagctacaa agaaacacaa atgatcctcc cacaagtcta aatgcgctag agttgaatag    420
gagactttga gcggatcgat cacttgaatt gtgtctttgg agtggagtct attactcttg    480
tattgaatga gtagtgaatg cttcgatggt tggagtggag gtggttgtgt ggtatttata    540
gcccccaacc accaattcaa ccgttggggt aggctgctgt cgatgggcgc accggacagt    600
gtccggtgcg ctagccacgt cacccaactg ttagggttct gcggtttcg accgttggag    660 ctttgtccta ttgtgacacc ggatagtccg gtgccgcacc ggacagacac tgttcactgt    720
```

| | |
|---|---|
| ttggtgcccc tctgacaggc ggctctaact ctacgcccat tgttcttcat tgttcatctg | 780 |
| acttcacggc ttttgcagtc gaccattgcg cgaagtagcc gttgctccgc tggtgcaccg | 840 |
| gacagtccgg tggcacaccg gacagtccgg tgaattatag cggagcgtct tttctgaaac | 900 |
| ccgaaggtgg caagttcaga gtggtacggc cctggtgcac cagacattgt ccgatggcac | 960 |
| accggacagt ccggtgcgcc agaccagggt tctcttcggt ttcttttgct cctttctttt | 1020 |
| gaaccttaac ttgatctttt tattggtttg tgttgaactt ttagcacctg tagaatatat | 1080 |
| aatctagagc aaactagtta gtccaattat ttgtgttggg cattcaacca ccaaaatcat | 1140 |
| ttatgggaaa aggttaaacc ctatttccct ttcaatctcc cccttttggg tgattgatgc | 1200 |
| caacacaaac caaagcaaat atataagtgc agaattgaac tagtttgcat aaagtaagtg | 1260 |
| cataggttgc ttggaattta aaccaatatt ttacttttac tggatatgca tggttggttt | 1320 |
| cttttattta acattttgga ccacttgttt tttttgcaaa ttctattgga aaatcttttc | 1380 |
| aaagtatttt tgcaaatagt caatggtata tgaataagat ttcgagaagc attttcaaga | 1440 |
| ttttgaaatt ttctcccct gtttcaaatg ctttccttt gacttaaaca aaactccccc | 1500 |
| tgaatagaat tcacctctaa gttttcaaga gggttttact aatttgaaca agatttagat | 1560 |
| accaatttga aaaattcttg aaagttaaca taccaaaata tatcaattga aaattttgaa | 1620 |
| attggtggtg gtggtgcggt cctttttgctt tgggctaata cttcccccc tttggcatga | 1680 |
| atcgccaaaa aacgaagact ttgtgagccc ttaaactttc ttcccattgg tacaagtaaa | 1740 |
| tatgagcgaa agattatacc aatttgagag tgatgtggag tgatggtgaa gggtaaatga | 1800 |
| taccgataga gtggagtgga agccttgtct tcaccgaaga ctccattcc ctttcaatct | 1860 |
| atgactttcg cccttgcgtt cagcctccac tgctgctctc ctcactagca tccctcacgc | 1920 |
| tgtataccctt acctcagtcg tctcctccct gaagaaacca cccaaagaaa ctgcccaatc | 1980 |
| tccaccttag tcgtctcctc tcaggctctc catgatctcg ctccctcacc tcaatcggct | 2040 |
| caacgatctc catgttctgc tagctcgagg cgtcacgaat ggagataaat acggaggtcc | 2100 |
| gagcgcgcgc agacgaggga gacgacatcg acgtgattcg gtattttttat cattaactat | 2160 |
| tatatgaaaa catcatcaca cgtaagttta atgggtcccc atggggaatg gcatcctca | 2220 |
| tcaccgggga gaatttttct tcgtttatat ccctgtgggg gaagaaactt cctcatcccc | 2280 |
| atctcctaat ggaagaattc tccacggaga atcggcgatc agagccccat tgccatctgt | 2340 |
| aagtataact aacggattag gagcatacaa cattttgttt aaaaaaacag gggcaaatct | 2400 |
| acagttacac tctaaaacag agacactgaa acaattgcat atatttctta aataataatt | 2460 |
| aaacattcaa aagcgtcgag gaggtcccat gcataggttt aggagcgatg ataatcattc | 2520 |
| taattttcat caaactaatt tatcgaggca aaaattagtt ttagataagg aagaccaact | 2580 |
| tcttggtttt ttaaaaaact aacaatccag ttttgcaaaa tctaaagcat aaattagcat | 2640 |
| attaggaagc atcccagttt ctaaaaattg gatgctttga ggctctaaaa tagttgaaaa | 2700 |
| aagagtgtga aaaacactaa aaaactatct tgggagttac aaaaccggat gaaattggag | 2760 |
| agaataaaat tctcttctta ttcaatttca aataagaaag atatcttaaa atttataatc | 2820 |
| atctccaatt ttatggcact ctatagaaaa tcggaggaga tttgagagtc taaaatcaat | 2880 |
| atgattttag atctttgaac cactcctttc tttggctaca aactagctct aaaata | 2936 |

<210> SEQ ID NO 14
<211> LENGTH: 1339
<212> TYPE: DNA
<213> ORGANISM: Zea mays

<400> SEQUENCE: 14

```
agtgttgtgt tttcattgtt ttagacttca gaacttatgt ataatactta tgtctgtgtt      60
tgatacttat gtgagagctt gcggcgtttg agacttatgt ttgtgtttaa tacttatgtt     120
gaacacttat gtttgtgatg gatatttatg tttgtggtga cagttttatg tttgtgttgg     180
ctatttatgt ctgtgatgat atctgtgatg tatatatgtg atatatatgt gatatcttct     240
gtttgtgtgg atggaataca aaaaacaaat aaaaaaggta tatactagtc actttgccga     300
gtgtaacact cggcaaagag gcgctttgcc gagtgtcagg gtcataacac tcggcaaaga     360
gcacagacct gggcaccggc ttaggttctt tgccgagtgt tatgtcgttg cactcggca      420
aagaggtcgg ctttgccgag tgccgcacag aacactcgac aaagagcctg acatggggac     480
cctccctggc gggttctttg ccacttggga cactcggcaa agatggattc tttgccgagt     540
gctgcctgga agacactcgg caaatataac ttctttgccg agtgtcacca gggacactcg     600
gcaaagccgc cgtctccgtc acccggcgtc gtaacggccg ctttcttg  ccgagtgctc      660
tctggcactc ggcaaagagg tttgccgagt gcccgagaaa aagcactcga caaagaaggc     720
tttgccgatg cactgtttgc cgagccttct tgccgagtg  taacactcgg caaagccttt     780
gccgagtgtt tttaaggctt cgccgagtac ttcaggcact cggcaaagcg attgattccg     840
gtagtggatg tggtaacatc gatgcacctg aagagctatc acaagtgttg attctgacac     900
ggaagtcatc ctatgatgaa ttaaacatta tataaaatgg tatatttaga ttttaaaagt     960
tcaccataaa aatttacgaa atagtgagcc catacaaatc ttaacagact tacagtacac    1020
aaagggcaaa aactactatg cacgcttgta cataaagact gtttgcatag cagtcgttgc    1080
ctacacaaag gctttaatta aatatgtcat aaaaaatgtc caaacagata aaagtttttt    1140
tttctgacgt gaaacgttct atagagaatc ccatccgtcc atctggcctc acaacagacc    1200
tgcccgttgt tctgctaaaa ccaccagggg aaaaagtaaa gagataaacg gatagaacag    1260
gcgtggagcg cgcgaccccg tacgtctcca ccgctgcagg aactccccc  ctccccggcg    1320
gcccgcgcgc ccaccaacc                                                 1339
```

<210> SEQ ID NO 15
<211> LENGTH: 3067
<212> TYPE: DNA
<213> ORGANISM: Zea mays

<400> SEQUENCE: 15

```
agttaggtca cggttgaaca accatggttt gtaaaagcct tgcctgtcc  cttcttctcc      60
ttggcttgat atctctatgg actttgtttt gggcttgcct aaatctaaaa aggggaggga     120
tagtatttt  gtggttgttg atagattctc taaaatggct cactttatcc cttgtcataa     180
aaactgatga tgctagcatt gttgctgaat tgttctttag aaaaatttat tcgtttacat     240
ggtattccaa aacacaatag tctctgatcg cgatgctaag tttctaagcc atttgtgga     300
gatctctttg gaataaattg ggaaactaaa ttgttgttta gcactacttg tcaccctcag     360
actgatggac aaactgaggt agtaaataga actttatcta ccatgcttag ggctgtttta     420
gacaagaatt tgagacgttg ggaggattgc ttgcctcatg ttgaatttgc ttacaatcat     480
gccacgcatt cttctacaaa gatgtgccct ttccagattg tttatgggta cattcctagg     540
gcacctattg atttgatttc acttaatgcc gcgaacgccc cacatgtaga tgcttctgca     600
catgttgaac aaatgattac catacatgaa caaacgaaac agaacattgc tgctactaat     660
```

-continued

```
gcaaaaaatc aggttgctgg tagtaaagga agaaaacatg ttacttttga gccaggtgat      720
atggtttggt tgcacttgag aaaggatcgg tttcctactt tgcggcgttc taaattaatg      780
cctcgtgctg ctggtccttt taaggtgcta acaaagatta atgataatgc ttatatcctt      840
gacctgcctg cggaatttgg tgtttccact agttttaatg ttgcagattt gaaaccatat      900
atggccgagg atgaggagtt gtcgtcgagg acgacttcac ttcaagaagg ggaggatgat      960
gaggacatca ctatgagtac gaatacacca acagcacctc cacatcaaga gccacttcct     1020
tcattagctg ggccaatcac tcgggcccgt gccagagatc ttaacttagt catgctactg     1080
aagaatgagg gccagaaaga atagacgacc agcccaactg cggcccatag tggacgacct     1140
agggttggcc gccctaggg gctgcgcccc ctctatttat ccaggagctg cgtctccttt      1200
attttcgagt tttgttttac gttagcctta gctactctca aacacgcgca aatctgcgct     1260
gtcttcgtgt attcagaact ccaccctcga gtaatagatt agattgctcg catctttttt     1320
cttgttcgtt cttcgattgc gcacaggaaa cgatcttcgt gatcaggccg atctcgcatc     1380
agcaaggtcg ataaccacag ggagttggtt cagcgattgc attggcgcct cgggcttgct     1440
cgtcgtagtc ggatcgcaag ggtcatcttc cgccaaatcg gaattatctc tactcgccga     1500
aagatcgggc acctcagctt catcaccggt ggcgcactgg acagtccggt gtgacctggt     1560
gaccgtcggc acaaggcacg cgtcgcccgc tgattgcacg ttgattgcgc taccgaccgt     1620
tggcgcgggt gtggctagct caccggacag tctggtgcac accgggcagt ccggtgaatt     1680
atagtcgtga ctcctccaac ttttccaaga gcaccgagtt cgtcgagcgc gccagccttg     1740
gcaccggaca ctgtccggtg cacaccggac agtccggtgc actgcagact ggtgcaagtc     1800
tggctggatg cagccaacct tctccaatcc aatctcattt gatttgacaa ggttcctaac     1860
acttagagga atatgttagt accaaaaaca attcactaag gctagagtta taccttgatt     1920
cttgatttgc atctctttaa cccttaacat atcaaccaaa acaatatgag ttgggcatct     1980
aatcaccaaa acatttataa aaatggccca agggcacatt tcccttttcat gatcaaaggc     2040
aactgccagt acaagggcca tcccggaggc tatactgcta caggggctcg ggctcgcctc     2100
tccatattac gacaatcctt gtactgctgg gttccctcct tgcgactata aaaggggggag     2160
tccagagcct gtaagggaca tgggtcaaca cttcaccgtt tgccctccat gttcgatact     2220
ggcacttgcc tcaagcactc acaagatact tgtgatctac tccctctctt ggatagcttg     2280
taccccgtac tacgagcact taagtgcaag ataatataag tctcatcctc ctattataag     2340
tatgccttc tattgctcga accaagataa atcttgtgtc ttgttatatc acccatctga     2400
actgggacag gtagcacaaa tttgctggtt ggttaggacc cttacattga caccattctt     2460
ggagatggtt tgcattcagg ttttgtcctg gatggaagga gggttttgt tgcatataca      2520
aggctgatca ttagggaggg aagtagtaaa acgaaggaag acaggaagaa caaaacaagg     2580
actcccaatc gattgccttc tccatttcat caaggctctt ttgcgggagg cgaggcatct     2640
cgccgaacac cttcccgctc ggtcgttcac agccccggc tcgtgtcgtc tgactgactg      2700
tgagtctgtg acgtcgctgc cagtaaacca cataccaacc attgaacatc ttctgtggcc     2760
agccggcatc cgtgcagccg ccagcaccag caggccatga catggcacca tgtttgagct     2820
gacagctgac tagctgagcg tgccgccttg ccgtgtcggg gagctgagct gagcctagag     2880
acgccaaacg gaatggcgaa agcgaccggc cgcgcggcgg gcagcaggag ctgcatcgag     2940
aggctgcctg cgccccgcgc ccaatcctct tcctaaatcc taatcccctc cgcctcatcc     3000
ccttcaaccc cacgtctctc tcgccgaagg ctccggcctc gtcgggatcc ggtgctggat     3060
``` tgacgca                                                                3067

<210> SEQ ID NO 16
<211> LENGTH: 1407
<212> TYPE: DNA
<213> ORGANISM: Zea mays

<400> SEQUENCE: 16
gtgctaggtt ttcatttttt tgaatttctt ttcttttcta gaaaacatat aaataactat      60
atttaactat ttcaaaaata taataaattc actaaaaata tttacaaata aaattactag     120
atatatattt ttagaccaaa gtctattata taaattaatt ggatttcgca ataaagaaat     180
actacaaata aaatcctcaa caatcattag caaacaaaat catgctttca aaaaaatgaa     240
tagatcaaac acttaattaa aaaataattt attcaaaaga ttatatatat acatatatat     300
atatgacatt attttcttta ttttaaaatt gttttctctc tactagtttt agcaactaat     360
gtttaatttc tttaagttt taattgatgg atttgaggtg ttacatattc tatatatcgg      420
ggagaatgca tgtaacttgt attatccatt ggtaggtcct caatttgctt ccaccatttg     480
attcacctaa aaggccacca cccaccagta gccgagcctc agcttttct ggagctggca       540 agcagccctc atggacctca tgtgatttat attcacccaa aaaagtttt tcagaaaaga       600 atttgtatat attttcgtca actctatttt atctctcttg ccattaacat cgtgtcactg     660
gatctaatac gtgatacgtt gtgttaaaac attgcgagaa cttatttttt ttcttctttt     720
gtgatatggg aggcaaatct gtctttttt tttgtcatgg ggttttgatt tatatggagg       780
ggaagtgaaa tgaaaccttt ttttttgcc accgatgcct tctattctat ctggtgcctc       840
ttgttcgccg cggggctgca gcctgcaggt agtcaggcat cgccggcagt tccatttcca     900
tgacaacgcg tcgtccgccc ggggtactgg cctgattcgg gcacccagaa agtttggcct     960 ttctttttgac agttgaaaca agttttccaa attttttttg gccatgtatt actataaaca    1020
aggtttcgcc atttgcctat gtttattagg aagttacatc cggtttgctg ctgccaccat    1080
tttgtcagcc cgtcacattc atatctttta tatggctatt gctcttcctt tttgtaaagc    1140
cgaatgaatc cgcgcgcgac atggcacttt gccgatagct gagcaccctc cacgtcagcg    1200
cgatccggcg cgccagagcc aaacgagcag attctcccgc gccgcgtggc acgaggcggc    1260
cgcgcccgct atccctcgc ggataaagcc ggacccactc cggcgcgcgc gcaccacgag      1320
atcccttaaa ctgccgggca tcacccacca gcccaccgcc accacacagc tcccacgctc    1380
accgacgcca cagcttgtgc gcgcgca                                         1407

<210> SEQ ID NO 17
<211> LENGTH: 10000
<212> TYPE: DNA
<213> ORGANISM: Zea mays

<400> SEQUENCE: 17
acaactacaa gccgggttag cgttagaaat ataaacgagt tcgcaagaga gggtgaaaaa      60
caaatcgcaa gcaaatgaag tgtgtgacac gcggatttgt tttaccgagg ttcggttctc     120
gcaaacctac tccccgttga ggaggccaca aaggtcgggt ctctttcaac ccttccctct     180
ctcaaacgat ccctcggacc gagtgagctt ctcttctcaa atcaaaaccg ggatcaaaac     240
ttccccacaa gggccaccac acacttggtg cctcttgcct tgattacaat ggaatttga      300 tcacaagaac aagtgagaaa gaaagaagc aatccaagcg caagagctca aaagaacacg      360

-continued

```
ggaaatctct ctcgctaatc acttaagcct tgagtggaat tggagaggat ttgatctctt    420
tggtgtgtct agaattgaat gcctagctct tgtaagtggt tgagaagtgg aaaacttgga    480
tgcaatgaat ggtgggggtg gttggggtat ttatagcctc aaccaccaaa cttgaccatt    540
ggtggaggct gtctgtcgat ggcgcaccgg acagtccggt gcacaccgga catgtccggt    600
gccccagcca cgtcaccaat gccgttggat tccgaccgtt ggagttctga tttctgggcc    660
cgccttgatg tccggtggcg caccggacat gtactgttga gtgttcggtg cgccagtatg    720
ggcacgcctg acttctgcgc cctagcgcg cgcatttaat gcgtcgcagg tagccgttgg    780
cgcgaagtag ccgttgctcc ggagttgcac cggacagtcc ggtgtacacc ggacatgtcc    840
ggtgaattat agcggagcag ccgttctgat ttcccgaggc tggcgagttc ctgaggcagc    900
tcttcagagg agcaccggac actgtccggt gtacaccgga cagtccggtg aattatagcg    960
cgagtgcctc tggaaattcc cgaaggtggc aagtttgagt tggagtcctc tggtgcaccg   1020
gacactgtcc ggtgccccag accagagatg ccttcggttg tccctttgct cctttgttga   1080
atccaatatt tgatcttttt attggctaag tgtgaacctt ttacacctgt ataacttata   1140
cactagagca aactagttag tccaattatt tgtgttgggc aattcaacca ccaaaattat   1200
ttgggaacta ggtgtaagcc taattccctt tcaatctccc ccttttggt gattgatgcc    1260 aacacaaacc aaagcaaata tagaagtgca taattgaact agtttgcata atgtaagtgc   1320
aaaggttgct tggaattgag ccaatataaa tacttacaag atatgcatgg atcgtttctt   1380
tgtttttaac attttggacc acgctcgcac cacatgtttt gtttttgcaa attctttttt   1440
gtaaatcctt ttcaaagttc ttttgcaaat agtcaaaggt aaatgaataa gattttgcaa   1500
agcattttca agatttgaaa ttttctcccc ctgtttcaaa tgcttttctt ttgactaaac   1560
aaaactcccc ctaaatgaga tcctcctctt agtgttcaag agggttttga tatatcattt   1620
tgaaatacta ttttctcccc cttttgaaca caataggata ccaattgaaa atactatttg   1680
gaaaactaag tttttgaaat tggtggtggt gcggtccttt tgctttgggc tcttactctc   1740
tccccctttg gcatgaatcg ccaaaaacgg aatcattaga gccctcgaag tgctttcttc   1800
ctcttttggt cataaataaa tgagttaaga ttataccaaa gacgaagtcc ttttgctttg   1860
tgctcatgct ttctccccca agaatggaga gaggcgtgga gcgacggcga aggatgagat   1920
acgtagtgga agcctttgtc ttcgccgaag actccaattc cctttcaata ttcctatgac   1980
ttggtttgaa atagacttgg aaacatatta gtcatagcat atgaaggaga catgatcaaa   2040
ggtatataaa agagctatgt gtgcaatcta gcaaaagaaa ttgcgcgaat caagaatatt   2100
gagctcatgc ctaagtgtgt tgaaagtttg ttcatcaaga ggcttggtaa agatatcggc   2160
taattgatct ttagtattaa tgtaagaaat ctcgatatct cccttttgtt ggtgatccct   2220
aagaaaatga taccgaatgg ctatgtgttt agtgcggcta tgctcgacgg gattatccgc   2280
catcttgatt gcactctcat tatcacatag caaagggact ttggttaatt tgtaaccgta   2340
gtcccgcagg gtttgcctca tccaaagcaa ttgcgcgcaa caatggcctg cggcaatgta   2400
ctcggcttcg gcggtggaaa gagcaaccga attttgcttc tttgaagccc aagacaccaa   2460
ggatcttccc aagaactggc aagtcccga tgtgctcttt ctattgattt tgcaccctgc   2520
ccaatcggca tccgaatagc caatcaagtc aaatgtggat ccctaggat accaaagccc    2580 aaacttagga gtataagcca aatatctcaa gattcgtttc acggccataa ggtgagcttc   2640
cttaggatcg gcttggaatc ttgcacacat gcatacggaa agcataatat ccggtcgaga   2700
tgcacataag tagagtaaag aacctatcat cgaccggtat accttttgat ccacagactt   2760
```

```
acctcctgtg tcgaggtcga gatgcccatt agttcccatg ggtgtcttga tgggcttggc    2820
atccttcatt ccaaacttgc ttagaatatc ttgagtgtac ttggtttggc ttaggaaggt    2880
gccctcttgg aattgcttta cttgaaatcc taagaaatac ttcaactccc ccatcataga    2940
catctcgaac ttttgtgtca tgatcctact aaattcttca catgtagact tgttagtaga    3000
cccaaatata atatcatcaa cataaatttg gcatacaaac aagtcattat caagagtttt    3060
ggtaaagagc gtaggatcgg cttttccgac tttgaagcca ttagcaataa ggaaatctct    3120
aaggcattca taccatgctc ttggtgcttg cttgagccca taaagcgcct tagagagctt    3180
atagacatgg ttagggtact cactgtcttc aaagccggga ggttgctcaa catagacctc    3240
ttccttgatt ggtccattga ggaaggcact tttcacgtcc atttgataaa gcttaaagcc    3300
atggttagta gcataggcca ataatatgcg aattgactca agtctagcta cgggtgcata    3360
ggtttcaccg aaatccaaac cttcgacttg ggagtatccc ttggccacaa gtcgggcttt    3420
gttccttgtc accacaccat gctcatcttg cttgttgcgg aagacccatt tggttcctac    3480
aacattttga ttaggacgtg aactaaatg ccatacctta ttcctagtga agttgttgag    3540
ctcctcttgc atcgccacca cccaatccga atcttggagt gcttcctcta ccctgtgtgg    3600
ctcaatagag gaaacaaaag agtaatgctc acaaaaatgt gcaactcgat atctagtagt    3660
taccccctta tgaatgtcgc cgaggatggt gtcgacgggg tgatctcgtt ggattgcttg    3720
gtggactctc gggtgtggcg gtcttgctc ttcatcctcc ttgtcttctt catttgcatc    3780
tccccttga tcattgccat cattttgagg tggctcattt gcttgatctt ctacttcatc    3840
aacttgagct tcatcctcat tttgagttgg tggagatgct tgcatggagg aggatggttg    3900
atcttgtgta tttggaggct cttcggattc cttaggacac acatccccaa tggacatgtt    3960
ccttagcgcg atgcatggag cctcttcatc accggttagg agttcatagg atgtcttctt    4020
gaggattcgg tgtagatata accggttgat ggcgtagcag gcggtgttga ccgcctcggc    4080
ccaaaaccga tccaaagtct tgtactcatc aagcatggtc cttgccatgt ccaatagagt    4140
tcgattcttc ctctccacta caccattttg ttgtggcgtg tagggagaag agaactcatg    4200
tttgatgccc tcctcctcaa gaaaaccttc aatttgagag ttcttgaact ccgtcccgtt    4260
gtcgcttctt atttcttga tccttaagcc gaactcattt tgagcccgtc tcaagaatcc    4320
ctttaaggtc tcttgggttt gagatttttc ttgcaaaaag aatacccaag tgaaacgaga    4380
ataatcatcc actattacaa gacaatactt actcccgccg atgcttatgt aagcaatcga    4440
gccgaataga tccatgtgga gtagctcaag cggcctgtcg gtcgtcatga tgttcttgtg    4500
tggatgatgg gcaccaactt gctttcctgc ttggcatgcg ctacaaaccc tgtctttctc    4560
aaaatgaaca ttggttagtc ctaaaacgtg ctctcccttt agaagcttat gaagattctt    4620
catcccaaca tgggctagtc ggcggtgcta gagccaaccc atgttagtct tagcaattaa    4680
gcatgtgtcg agttcagctc tatcaaaatc tactaagtat agctgaccct ctaacacacc    4740
cttaaatgct attgaatcat cacttcttct aaagacagtg acacctgtat cagtgaaaag    4800
acagttgtag cccattttgc ataattgaga tacagaaagc aaattgtaat ctaatgaatc    4860
tacaagaaaa acgttggaaa tagaatggtc aggagatata gcaatcttac caagacccttt   4920
gaccaaagct tgatttccat ccccgaatgt gatagctcgt tggggatctt ggttttctc    4980
ataggaggag aacattttct tctcccctgt catgtggttt gtgcaccctc tgtcgatgat    5040
ctaacttgag cccccggatg cataaaccta caaaacaatt ttagttcttg actttaggta    5100
```

```
cccaaacggt tttgggtcct tggcattag aaacaagaac tttgggtacc caaacacaag    5160
tcttggagcc cctgtgtttg cccccaacaa acttggcaac tactttgccg gatttgttag    5220
tcaaaacata agatgcatca aaagtcttaa atgaaatgtc atgctcattt gatgcactag    5280
gagttttcct tttaggcaac ttagcacggg ttggttgcct agagctagat gtctcacact    5340
tatacaaaaa tgcatgatta gggccagagt gagacttcct agaatgaatt ctcctaatct    5400
tgctctcagg ataaccggca ggatataaaa tgtaactctc gttatcctga ggcatgggag    5460
ccttgccctt tacaaaatta gacaatcttt taggaggggc attaagtttg acattgtctc    5520 cccttttggaa gccaatgcca tccttgatgc cagggcgtct cccattatag agcatacttc    5580
tagcaaattt aaatttttca ttttctaagt tatgctcggc aattttagca cctaatattg    5640
ctatgtgatc attttgttgt ttaattaaag ccatgtgatc atgaatagca ttgatatcaa    5700
catctctaca tctagtacaa atagaagtgt gctcaacggt agatgtagag ggtttgcagg    5760
atttgagttc tacaaccta gcatgcaaca tatcattctt agttctaagg tcggaaattg    5820
tagcattgca aacatcaaaa tctttagcct tagcaatcaa attttcattt tctactctaa    5880
gactagcaag agaattgttc aattcttcaa tcctagcaag caaatcaaca ttatcatctc    5940
taggattgga agttgaaaca atacaaacat gagaatcaac cttagctaac aaattagcat    6000
tttcatttct aaggttgtct attgtttcat ggcaagtgct tagctcacta gataatttt    6060 cacttttctc aatttctaga gcataagcat ttttaacctt aacatgtttc ttattttcct    6120
taatcaggaa gtcctcttgg gaatccaaaa ggtcatcctt ttcatgaatg gcactaatta    6180
attcatttaa tttttccttt tgttccatgt taaggttggc aaaaagggta cgcaaattat    6240
cttcctcatc actagcatta tcatcactag aggactcata tctagtggag gatttagatt    6300
taaccttctt cctttttgccg tcctttgcca tgaggcactt gtggccaacg ttggggaaga    6360 ggagtcctt ggtgacggcg atgttggcgg cgtcctcgtc gtcggaggag tcggtggagc    6420
tctcgtcgga gtcccactca cggcacatgt gggcatcgcc gccctcttc ttgtggtacc    6480 tcttctttc tctcctcttg cccttttgt cgttatccct gtcactgtca cttgataatg    6540
gacatttagc tataaagtga ccgggcttac cacacttgta gcaaaccttc ttggaatggg    6600
atttgtaatc cttccccttc cgttgcttga ggatttggcg aaagcttttg atgattaaag    6660
ccatctcctc gttgtcgagc tttgaagcgt cgattggttg tctactcggt gtagactcct    6720
ccttcttctc ctccgtcgcc ttgaatgcca ccggttgtgc ttcggacgtg gagggatcat    6780
caagctcgtt gatcttcttt gagcccttga tcatacattc aaagctcaca aaattcccga    6840
taacttcctc gggggtcatt gatgtatatc taggattacc acgaattaat tgaacttgag    6900
tggggttaag gaagatgagt gatctaagaa taaccttaac cacctcgtgg tcatcccatt    6960
tcttgctccc gaggttgcgc acttggttca ccaaagtttt gagccggttg tacatatctt    7020
gtggctcctc cccttggcga agacggaagc gaccgagctc cccctcgatc gtttcccgct    7080
tggtaatctt ggtgagttca tctccctcgt gcgcggtctt gagtaagtcc caaatttcct    7140
ttgcattctt caacccttgc accttgttat attcctcctt gcttagagag gcgaggagta    7200
tggttgtagc ttgagagttg aagtgctcga tttgggccac ttcgtcctca tcatagtctt    7260
catcccctac ggatggtacc tatgcaccaa actcaacaac atcccatatg cttttgtgg    7320 agtgaggtta gatgaaatcg cattaaatca ctccacctag agtaatcttc accatcaaat    7380
gttggtggtt tgcctaatgg aacgaaaagc aaaggtgtat gtttgaaat gcagggtag    7440 cgtaggggga tcttactata cttcttgcgc tcttggcgct tagaagtgac ggatgccgcg    7500
```

```
tcggagccgg aggtggatgg cgatgaagaa tcggtctcgt agtagaccac tttcctcatc   7560
ctcttttcct tgtccccact ccgacgcgtc ttgtgagaag aggatttctc cttcttctcc   7620
ttttggtgtg aagaagactt cttctccttc cctttggagg agttcttctt ctccttcctc   7680
ttggtgcggg actcttccga tgaagtgctc ccatggcttg tagtgggctt ttcgctggtc   7740
tccatctcct tcttggcgtg atctcccgac atcacttcga gcggttaggc tctaatgaag   7800
caccgggctc tgataccaat tgatagtcgc ctagaggggg ggtgaatagg gcgaaactga   7860
aatttacaaa tataaacaca actacaagcc gggttagcgt tagaaatata aacgagttcg   7920
caagagaggg tgaaaaacaa atcgcaagca aatgaagtgt gtgacacgcg gatttgtttt   7980
accgaggttc ggttctcgca aacctactcc ccgttgagga ggccacaaag gccgggtctc   8040
tttcaaccct tccctctctc aaacgatccc tcggaccgag tgagcttctc ttctcaaatc   8100
aaaaccggga acaaaacttc cccacaaggg ccaccacaca cttggtgcct cttgccttga   8160
ttacaatgga gttttgatca caagaacaag tgagaaagaa aagaagcaat ccaagcgcaa   8220
gagctcaaaa gaacacggca aatctctctc gctaatcact aaagccttga gtggaattgg   8280
agaggatttg atctctttgg tgtgtctaga attgaatgcc tagctcttgt aagtggttga   8340
gaagtggaaa acttggatgc aatgaatggt ggggtggttg gggtatttat agcctcaacc   8400
accaaacttg accgttggtg gaggttgtct gtcgatggcg caccggacag tccggtgcac   8460
accggacatg tccggtgccc cagccacatc accaatgccg ttggattccg accgttggag   8520
ttctgatttc tgggcccgcc ttgatgtccg gtggcgcacc ggacatgtac tgttgagtgt   8580
ccagtgcgcc agtatgggca cgcctgactt ctgcgcgcgc atttaatgcg tcgcaggtag   8640
ccgctggcgc gaagtagccg ttgctccgga gttgcaccgg acagtccggt gtacaccgga   8700
catgtccggt gaattatagc ggagcagccg ttctgatttc ccgaggctgg cgagttcctg   8760
aggcagctct tcagaggagc accgacact gtccggtgta caccggacag tccggtgaat   8820
tatagcgcga gtgcctctgg aaattcccga atgtggcaag tttgagttgg agtcctctgg   8880
tgcaccggac actgtccggt ggtgcaccgg acattgtccg gtgtacaccg gacagtccgg   8940
tgccccagac cagagatgcc ttcggttgtc cctttgctcc tttgttgaat ccaatatttg   9000 atcttttat tggctaagtg tgaaccttt acacctgtat aacttataca ctagagcaaa   9060
ctagttagtc caattatttg tgttgggcaa ttcaaccacc aaaattattt gggaactagg   9120
tgtaagccta attccctttc agtttggcgg tggtaaaagt tggttcggcg gtggtaaaag   9180
gaacgtgtgc gcctaatagc gaggtaaatt aggacaacta tttccgcact aatctatgac   9240
ttctattttt tgcttaaata aaatctatgc aaatattcaa gcatccaaag agttgtaact   9300
aaggttttat tcaagtgttg atatatgtat tgtaaaggt cttttgtaac ctagatcacc   9360
gattgttttc tgagcattta gatgtctaga gctatgttat taaagtctca actcacttat   9420
tatgtttgtc agctcctaca tttgagaaat gacccgttag agtggagtca acaacattgg   9480
cattcaaacc ccagagtggc cattacgatt tatgtgtagc tgtgcgcctg tgccttaagt   9540
cttactctct ccgtttcttt ttatttgtcg ctggatagcg caatttttta cactatccag   9600
cgacaaataa aaagaaacgg agggagtaac aatctgtaac atgctgctaa catttgggtg   9660
gctttgcgtt ctgcttgttg ggccggctc tgaaatgagc agtctagaag ccaacggccc   9720
aacacagagc agctaattcg ggcctccacg ctacggctat ggcttctcag ttctcatctc   9780
caactacgca ccagatgcca ggtggcgata agaccttatc ctgcgcggct acttggcgcg   9840
```

| agggcggcca tccacgtcag acgagcgcgc tgacctggcg ccccctccagc tcatcctatc | 9900 |
| tacatatcag tgtccctctc cctggcccag ccgctcctac catcagaatc agaccaccac | 9960 |
| acgcccgagg cccgactgca agcgcctgag cccaagaccc | 10000 |

<210> SEQ ID NO 18
<211> LENGTH: 1663
<212> TYPE: DNA
<213> ORGANISM: Zea mays

<400> SEQUENCE: 18

| gatattgaag tctagaatta gaaattggaa ccaagattcc taaattatgt tgtttgcttg | 60 |
| tataatgaat ttatagttta aattaaagtt caattcctca gtattagact ataactagaa | 120 |
| gttgtctcac ataatttaga gaatagacct tctgtattgg ttggaattgc aattccagat | 180 |
| acatccaaac aacagattta tattgcaact catttccaat atcaagaaga tttagtatta | 240 |
| atctaattta attctaccat ccttaatgcc tacatccaaa cagacactga agggaatttt | 300 |
| tttggttggt catagggttg aaaacgaacg ggtaaaatct cgtcccgatc cgtaccgttt | 360 |
| tccatatttg attctctcgt tttttaaatt tgtggaaaat ccataaatag ttcgaaaacg | 420 |
| agagacggtc gggttgaacc cgtatttgag aaatccaaga tcagcccaat atatattagt | 480 |
| gcattagtta aagcctcata tccttatatg acaaattata tcacaagagg tcgttatagc | 540 |
| catcgactca gtgacaagtg gtctaaagac ttaaacaaca ccactcatag ctataagtac | 600 |
| atcataaaca agcaaacaac aactaagtgt tacctctatg tatctatttg tttcatgtta | 660 |
| ttatcttgcc attcaataac taactaacca ccaatattag tgtgtttgta taagttacaa | 720 |
| gtttcggctt aatattcacg tccctttttt acacccatt attctacatc tattttcgtt | 780 |
| cctggctatt ctagacctgg tctcgttttc accaataaaa tacggaaatg gaaacgagag | 840 |
| gggttttctg tctatttcg ttcgttttta tagtcggtca tgtgttgcaa gtataggtga | 900 |
| ccagatgggt caagttatat gggacgacac gaggcaccac cattttggcc ggcatgagac | 960 |
| ccatcatggg tcgtgcttgg acttaggtac aagcccattg ggcgacacag gcacgaccta | 1020 |
| tttactgtca gctcatttag cacgatgcta atcacggata gcccatcaaa ccgaccacga | 1080 |
| cttagcatga cccgtttgtg gcctagtctt gtcctaatct aggccaccat aatatatata | 1140 |
| aatatgacca actcaatccc cactttcatc tattttcgag ttctgtaaaa aaatgagaaa | 1200 |
| aataagcaac aaaaaatagg aaaaataaat tattttcaag ctatgttata aggcagacct | 1260 |
| ttggtcactc agaaccttag cacgatacga catgatagtc tatcataacc cgttttaaat | 1320 |
| tagtagggtt atgtttgggc tcagacttcg gctcacggac agacaccata accccgcccg | 1380 |
| ctatttatct gtaccgtgtc tcggatcgat taaatcggca cggccatga cgggctccgg | 1440 |
| ccgtgcttgc acggcactgt ccattagcca cgtgtagttg caaggtgtga cgagtgttaa | 1500 |
| cttcacccgt ccaatcgatt ttaacacgcg ggggcctgcg gttagagatt ggacaaggcc | 1560 |
| cgccagtaat cttctggtcc aaatgttaac acgcgcgcaa ttgtaaaaga aatatatgtc | 1620 |
| tatatagtaa aacgcgaaga gagagatact tctgcggaaa cga | 1663 |

<210> SEQ ID NO 19
<211> LENGTH: 919
<212> TYPE: DNA
<213> ORGANISM: Zea mays

<400> SEQUENCE: 19

| ttggggaggt ggagtccgac ggtgcggtgg gggaggagat ggagtccaat ggtggggtgg | 60 |

```
aggagaggga ggggaggccg ccggagttga gcacagtgga ggaagctgcg cgagcccgtg    120
gctgcaaccg ccggcggtga ttaggtcaaa tgcgagaacg cggtcggcca tgggctgcac    180
gctaggatgg tgggctgcac gatgggacga tgggccttag gcccacacga aaatcattgg    240
accgcccgaa ccgctgccac aggcgcgctg gtatgctatc tattttatta gtgccacatc    300
gtccattgag agtgacggaa catggcttat aagcgcagtt gtgtattgtg tgttgctcac    360
taagagagat ggaactggat gtggctcaaa aacttgtgta tgtactgttt attttgttac    420
tcaggactgc atggtgcgta tggccggtgg ggcccacatg tagcggctgt tggaggcaga    480
acaacagttg gcagaacgcg tcggaggcag aacacgtcag aggcagacta ctattgcagt    540
cttaataagt agtagagaaa tagaagtgaa atggagttag agcatctgaa agccagaggc    600
ttccatgcag gccacctaag caataccttc ctctatattt gcatgcccaa gagtcacctg    660
cacgtgtcac acggacccat cgccatttgg ataatgggtg ccacgtgtga aaaagcccag    720
ccaatgggat ggaagcagag cctcacgccc tatccatacg acaaccacaa ccccctccc    780 gcctcagttt cctccaccgg acacctgctg ccacccacac gatcaaaaac aaaaccaagc    840
tccaagcacc catagccaca caccacacca ggtcaaagca aggagctcga tcgagagcaa    900
caagccaaca acggccatc                                                919

<210> SEQ ID NO 20
<211> LENGTH: 751
<212> TYPE: DNA
<213> ORGANISM: Zea mays

<400> SEQUENCE: 20
cccacagaga taaagttct ccactatgta tgtatgttgt tttaaactgt agtcatagaa     60
gaagtcaccg tgctcactga taggagggtc taaaagtaga tgcattaatc aaaaacaaaa   120
catacatcat tgaactttaa aagcatataa ccttcaatac taaataaaaa gattagtatt   180
gtttaaatat tagatactac tgataaaaaa gataaacacc attagctata ttaccaccct   240
ctccaactgt tttctgaact aattgtaaat gggcccatag tgtagtcgtc aagcatggag   300
gcccgctcga ccgacctcct cgatcgctca aatttggaaa cagcggttgc tactgaccgg   360
ggtgagtgct gcgttgttgg cgactgccct gttttttaat ggattcagtg agagctaaaa   420
agtgcgagac tgccagagaa atccagcagg tgtacgtacg taaagcgaga gtcgacgcgt   480
gggcgcggca gacgcgagcc tcccgccacg ttggcctcgt tcccgcgcca cgcggccacg    540
cctgcctgcc tcctcaccctt gtttatatgc ctcgcgcctc cctcaccgtg ccaatgccgc    600
aggtgtacgt acgtaaagcg agagtcgacg cgtgggcgcg gcagacgcga gcctcccgcc    660
acgttggcct cgttcccgcg ccacgcggcc acgcctgcct gcctcctcac cttgtttata    720
tgcctcgcgc ctccctcacc gtgccaatgc c                                   751

<210> SEQ ID NO 21
<211> LENGTH: 2000
<212> TYPE: DNA
<213> ORGANISM: Glycine max

<400> SEQUENCE: 21
acatagcccc aaaaccacta ttgaatatca attagaaatt ggaagggtta cttaaccttc     60
cattaaacat acaagtttcc ccatgataat agggatcaaa ataatgatc agggattcat    120 tccaaagaaa agtttacaaa atcaattttc gctcatttta taggagttaa acccattttt    180
```

```
aagccaaaaa cctttacgta taaacaacat tttaaaagtt attttttcaat aaaagcatct        240 tttagagttt actgttttta tggcatattc accccagtac agtttatatt gctttcgttt        300
aaacaggagt tcatgaattt ctaaaaaaaa tgtttatgat acttgtcatt tcgattgttc        360
atatggtgcc tgtcagataa ttaatgtctc cgtggtgttt aactgttaag tagttgattt        420
tttgtcatgt aatcttgtaa atgacaattc tatcgttaat caaacaatcc gtatacacac        480
acacacacgg agaaactagt gtgggtttga ccaaggaccc tgaattcttc ttctttgtat        540
aaggtcaggc aagtggtaga gttcgaatag taagttttga agtttaaagc ttgtacacaa        600
aatatatata tatatatatt gataaagaat ggataatt gttttacaac gtgcagcgag          660
ggaacccttc aatacgcacc tctctaccaa gtctaactta aaaacacaga attatcaaac        720
acccaattta tgtgttagaa tgtcttgctt ttcgctacta ctattgtctg gtgggcatga        780
tgattttctc acaaaataat tggaatattc cacttatctc tggctgatct ttttttcttac       840 atttaagaca atagagagta ttaaatttgt tataatcgta atatttatat attaaatagt        900
atttatggta tatttaaata tatatatata tagaatatta ttttatatat gcatattata        960
gttattgtta attcagcatg tgttctggtt tctgaaataa aataaaaaaa caaaaatttg       1020
aaaaatagaa actagaataa aaaaaatcaa taaaaaggac ctcacttatt attttgactg       1080
ttactaatta cggaaataag ttacttaaat gtattaaatt aattttgaa aattaatgca        1140 ttaaagaaac ttatttaatg tattaaataa gtatttaatg catttcagga aaagcatttt      1200
aatgtattaa atacagttta gaaattaatt tttgtttcat ttttttattta taaaattatg     1260 ttttctttttt acatatttgt aaaattattt ggagagatga aaaaaaatgt gtaaaagaa      1320 agagtctacc aacaagtagt tagtccaaat agtattgaat tcaaatttttt taaataaagt     1380 tttgttaaaa ttaattatga ataaaattga tagataattc taacataatt acacaaaaaa     1440
atctttaatc ataatactcc ctttagacct caaatgtaaa aaaataaaa aaaaaatcaa       1500 ttgtgttaga ttaaaatata aacaaatttt aattaactat cacctacttt atcacctact     1560
taatgatgta ttttcaaaac atcattcgtt taattgagtt ttattttttaa taatcttatt   1620 ttttttttctt atataatcaa tatagatgat attttaagga ataaattaac ttttattga    1680 aattatcaaa attaaataat attaactaat tttttgtcta atggttgagt ccagagagag    1740
taatatttgt gggtggagtt ttactggtgg atgtggacag gtgtgagcca catgttacca    1800
tgcagtgagt cagaaaaaag aagtggcagg atatccggcg ggttcacggc ttggaagttg    1860
caataaatat taaatgagga tgcagatatt cttcttctgt cggtggtatg atatatatat    1920
atatataagg ccgggcagaa aggaaggaa atactattac atagcagaag caaagaaaat     1980
actattacta gctaatgagt                                                  2000
```

<210> SEQ ID NO 22
<211> LENGTH: 2222
<212> TYPE: DNA
<213> ORGANISM: Zea mays

<400> SEQUENCE: 22

```
cctcttcctg taccgcggcg gggtgcacgt gcgtgccgac aacgacgacg acccggcgtg         60
tgtgatccgc cgcgcgctcg gcgaggcgct ggtgccgttc tacccgctcg cggggcggct        120
gcgggaggtg gagggccgga agctggtcgt cgactgcacc ggcgaggggg tgctgttcgt        180
ggaggccgac gctgacgtgc ggctggacga actggaggcg accggctga ggccgccgtt         240 cccgtgcatg gaccagctgc tgttcgacgt ggacggctcc agcggcgtgc tccactgccc        300
```

-continued

```
cctgctgctc atccaggtac cccaccagtt ttgccgcaaa caaaaaaaaa aaagctttca      360
gacaatcagt ggtgtgcgat atgatatgat acgatggtct cgtcgatcac caggtgaccc      420
ggctgctctg cggcggcttc gtcctcgcgc tccgcctcaa ccacaccatc tgcgacgcca      480
tcggcctcgc ccagttcatg tccgccgtgg ccgagctcgc ccgcggcctc ccgcgccga       540 ccgtggcgcc cgcatggtcc cgcgagctcc tcgaagcgcg caacccaccg aagccggcgt      600
tccctcaccg cgagttcgac gtggcgccac ctccgccacc cccaccgccg ggcgacatgg      660
tgacgcggac cttcaccttc agcccagccg acgtcgccgc gatcaagcgc gccctcccgc      720
tggctctccg cgaggcggcc acgaccttcg aggcgctgac ggcggccctc tggcgcgcgc      780
gcacggcggc gctggcgccc cctcacgacg cggaggcgcg gctggtgtcc attgtcagct      840
ttcgtggcct tcccgagctg gcgctccccg cgggttacta cggcaacgcg tgcgtgcccg      900
tggccgcgct caccaccgcg ggggcactgc tggcggggtc gctgggcgac gcggtggcgc      960
tggtgcgggg gaccaaggcg gcggtcaccg ccgagtacgt gcggtccacg ctggacctgc     1020
tggtgctgcg ggggcggccg tgcgtggcgc tcgcgaacct gttcctcgtg tccgacaacc     1080
ggcgcgcgga gttccaccgg ctggacttgg ggtggggcgt gccggcgtac ggggtcctg      1140 ccgtggcgct cttcgggttg agcttcttcg tccaggcagg gaacggtgac gacgtcgccg     1200
tgttgatggc gctgccgcgg ccggctatgg accacttcgc gtcggaagtg gagacgttgt     1260
tgaaggctta gttgggtgtt cttgaatctt gacgagcgag cgagagagcg gcagagcgcc     1320
gcctgttctt gctaatgcta actgtcttcg ctcaaatttg tcgtctattc gtcgccaacg     1380
actctctccg atcgttcagt cagattcgct tggccatgtc aggtctggtc tagatggacc     1440
atgccggctt gggcccaatc ttgacaacgc cgtgtttggt ttggaccgaa ataacaggcc     1500
tctgagccat cgccattcac tgggaactta aaatggtgca gggttgttgt tattgtccac     1560
gctaatccaa gtgtgttgtg cttccgaata cagctatcaa gagagtaaaa ttttaagatg     1620
aaaacccaca gagataaaag ttctccacta tgtatgtatg ttgttttaaa ctgtagtcat     1680
agaagaagtc accgtgctca ctgataggag ggtctaaaag tagatgcatt aatcaaaaac     1740
aaaacataca tcattgaact ttaaaagcat ataaccttca atactaaata aaaagattag     1800
tattgtttaa atattagata ctactgataa aaaagataaa caccattagc tatattacca     1860
ccctctccaa ctgttttctg aactaattgt aaatgggccc atagtgtagt cgtcaagcat     1920
ggaggcccgc tcgaccgacc tcctcgatcg ctcaaatttg gaaacagcgg ttgctactga     1980 ccgggggtgag tgctgcgttg ttggcgactg ccctgttttt taatggattc agtgagagct     2040
aaaaagtgcg agactgcgag agaaatccag caggtgtacg tacgtaaagc gagagtcgac     2100
gcgtgggcgc ggcagacgcg agcctcccgc cacgttggcc tcgttcccgc gccacgcggc     2160
cacgcctgcc tgcctcctca ccttgtttat atgcctcgcg cctccctcac cgtgccaatg     2220
cc                                                                    2222
```

<210> SEQ ID NO 23
<211> LENGTH: 2101
<212> TYPE: DNA
<213> ORGANISM: Oryza sativa

<400> SEQUENCE: 23

```
ttttttaagg acaggggag tatgaagtag tcacatgaat gcccaaggaa ttaggaattt       60
ttcccgtgct acagatttta agtgagaaac acatgaattt ttccattcac tctgaactta      120
```

```
tttttctatt catttgcgta ggatccagac aaacatgcag ctaatccaaa caccttcata      180
tgtttttcaa ttatctgttt tgcatttata ttcttatcat atttctatgt ttttttatgt      240
ttctgtattt ttttttttcaa tgatgcgttc gaataagcc ctctgcaagc agcaggtaac      300
aatgggttgc aacagtcact gtcatagctg aagcctcggc gagcgacatg ttcggaacgg      360
agcagaatga atagtgtgct acctaatgat tacattattc gagtagcacc ttaagatctt      420
aaatttaacc gatttggcta tatctcactc gaaagatttt tttcttatct cactcgattt      480
tctcactcaa atttacaggg tatttttcttg taaattacag tgtaacttat gaaacttaca      540 ttgtaattttt tgtaagttgc agtgtaattt tttaatcttt gcatgtaagt tttaaaattt      600
atattggatt tggtcttttt cttgaagata tggtaattta ttgtccatta tggtgtttct      660
tagttgcttt ttatcttttta ctgtgtctat tggattttaa tccaaaaatt aaaaatctgt      720
gtgatatggt cataaaaatc ttttgaaaga tgcataggta ctcccaatttt aattcttcat      780 ccgagcgaat tttaaggctt agttaaagaa aaaaaaactt actaataaag gcccaccaat      840
aaaaccacgc gcgatcggaa taagttcact tcgtcaccct taactgtgat cgaaatctaa      900
tccatgaccc taaaccacaa aaccagatat atcgaccccc aaacttatgg gcgccggcaa      960
ctagcaagga gaggatggca cggaggaagg cccgcccgcc gccgtcgtcg ccgcctccgc     1020
tcgggcctcc ctggcgccca tcgctatcgc ctctgctcga tcctcctctg caccaccgc      1080 cgctcgagtc gggtggccgc cgccgttttgg gatgccccgt cgcccggcgt cgtcgcctct     1140
gctcgagccg agcggcctcc gcccatgagg cgcgcggcga ggctaggtgt gcgcggcgtg     1200
ttggcctcgg agggtggcgc ggacggcctg ggccgcgcga gagcgccaga ggccggctcg     1260
atctggacgc cgatctggat gtcgccgcgg aggaggttgg cgtcgaggtc gaggctgttg     1320
cgtggcgcct ggaggcctcc gtcgtttgtg ccgccccgtc gcccgacgcc gtcacctccg     1380
ctcgacctgc ctctagcgcc gccgccgctc tagccgggtg gccgccgccg tttggcctcc     1440
ccgttgcccg gcgccatcgc ccatcaccgc ctgtgggaga cgtaggggaa gaaggggga       1500 gagagagaag ggagaaaggg aggaggaaga aggaaggagg atgacatgtg gggtccacat     1560
gtcagtggga cccacaattt tttttatgtg tgtgaatgac aaacgggtcc cacaattgta      1620
atgccatgta agtgccacgt caacgccacg tggatcgaag actcggtcaa tattgccacg     1680
taggcgccac gtaagcaaaa ccgcctccca aaaccgcgca gggagtcaaa ttgcaccggt     1740
tttagaagtt tgggggtcga gatatctggt tttgtggttt agggtcatgg attagatttc      1800
gaccacagtt gagggtcatg aagtgaactt attcccgcgc gatcaaacgt gttaaggatc     1860
cacgttgcgg cccataaagg cccagatgtc tctactattt cttcttctag tgagctccat     1920
cgaagctttt aggcgaggcc taccgctgtg gctaagcggc ggcgtgtgcc agcccaaccc     1980
ccgacgacga cgacgcgtgg cgacggccgc cgcgacaccc gccgccacgt cgccccgcca     2040
cgcgccgccc ccggcgagc tcctcctcct ctttttataat cccagcctcg tctccccgc      2100 g                                                                    2101
```

<210> SEQ ID NO 24
<211> LENGTH: 2137
<212> TYPE: DNA
<213> ORGANISM: Sorghum bicolor

<400> SEQUENCE: 24

```
cggaattcat accttgttta gttcgcaaaa atttccaaga ttcaccgtca catcaaatct       60
ttagtcgcat gtatagagta ttaaaaatag acgaaaacaa aaactaactg tatagtttac      120
```

```
ttgtaatttg tgagatgaat cttttaagtc tagttactct gtgattggat aatatttgtc      180
aaataaaaac gaaatgctag agtatctaaa aacaaaaaaa atttacgaac caaattgcaa      240
gatctcgcag tcgcccgggt ctccgccgcc gccatcatag tcgctgcctg ctctttgata      300
gcgacgtccc ggctgccggc aacccgcagg cgctcgtcca cgaagcagga gccatgacgc      360
caccccacca ctggtctgct tcctgcaccc gcacgccagg cgctgagggt atccgccgcc      420
gcacgctacg cgctcgatcc ttcgccggtt ccatcggatc ttcgtcgggt acccggccag      480
caggtatgtc caccccttct cttcccttta cttctgaaat atgtatttag catataagga      540
tgattttgtg tagaccccat tcagatgaaa tatgtattta gcacagtcaa aaatttagca      600
gatgcctctt gtttagcttt tgagtgtgat ctaacagttg catttggagc ataatgcttt      660
ttaacaaatt ttaactgaat agctaacgtc aaaatggagc aatgcagcca catagggtca      720
ttattcttac aaggaaggac ctggattcag cattcaaact tcaaagtagg catatttaac      780
acaaaaaatg atttctgatt tctgaatcgt cttcatggat gcagacttga gtacttgata      840
tttgttggca tataaatgat aaaactagat ttacagaaaa taacatatag ttcatcaaat      900
tatttcagtt gacgggcctt tcatagtata ttcattagta tactaccact gattgctgac      960
agggtgcaag ccttctttgt gctttgatct gctttgctct taatgttcat aggccttgtg     1020
tgctcctcat ccaccccacc gtggcggcat ttggataggc agatcgaaag ggatcaggat     1080
atgtgcccag taagaattat cgtggagtgc acagagctat atgtatggtt gtttacaagt     1140
ggccaaatag gcttgctcaa cttgggatta acttatttat ctttctaaaa tgaaggtagc     1200
attccagttt atggccacca gggattgact tatttatcct cttgaaatat attccctcca     1260
tctcaaattg taagttattt caaaaatctt ggagagttaa acttttctaa gtttgaccca     1320
atttatatga taaaataatt attattatga tacaaactaa gtatcattaa attctttttt     1380
aattatattt ttatagtata ctcactttac gttacaattc ttagtatttc tctctataat     1440
tttggtcaaa tgtaaaaata cttttaactct ccaagattct tggaatgact tacaatttag     1500
gatggaggga gtaggtagca ttccagtttg tggctatcat gcaagtacac atgcaatggt     1560
ttccagttca gccatctaat tgcttttaaaa cttagtgctg atcatagatg cagcaaaatg     1620
gttcctattt agagctcata tactatattt gtttcatgaa cttaattatg attgcaggac     1680
tactacaaag ttctagaggt tgactatgac gcatcttaca ataccatcaa atcaagttat     1740
cgaaaattac ctttggtaag atgttgtaca acctccactc gtcaaactag aagataatta     1800
tgtgcacacc tgacgatgtt ctatcttttc tgaattgtat ggcattaagc ggttgacaca     1860
gttgtaagta tctaattatc cccaagtgca ctaccatct ctattaaaac tgtcaattca     1920
gaatttcaga cagtgatgct actagcgagg tcgagtgggt gtaataagcg gcggccggcg     1980
tgcgttggtt ggttctccga gcggccggac tggacgcgtg ggcgaggcag atgccagcct     2040
cccgccacgt ccgccgccac gcgcccacgc ctgcctgcct ccctctcttg tttatatgcc     2100
ctcctcccct ccaccccctc gtctccctca ccgtgcc                              2137

<210> SEQ ID NO 25
<211> LENGTH: 2105
<212> TYPE: DNA
<213> ORGANISM: Zea mays

<400> SEQUENCE: 25
atggcttcaa accaaacaca tgcctaactt ggtcaaactt gtctaacctt aggcgtggta       60
```

```
aactatggca agttaggcag caaaccaaac agccccttag tcgtcttact tcatgccaca      120
atattataaa atgtcatata gttactctag ctagccttct tgttgttctt ggcctaaacc      180
ctgattttag atcaggcaac aacaacctct cgaaagagga ctacaacaaa actatgtga       240 accctaccaa caacagcaac accctagcaa taggaacaca caacagctct gacaccacga      300
gcacacaaca aaaagaact  ttgcgtaacc aaagtagctt catcctcatc taatgcatcc      360
tccaccacaa catcctcaac agaggtgaca acctaaagca acgtgaatgt atctaaaggc      420
acctcaatgg tctactcggt ggacatcatt cagtgagaat tagcttcaaa tgcccattcc      480
atcacctcat tagtggtaag gttcgtctct ctatgaatct cttctctatg aatctttgta      540
ccagaggtcc tagtgggcat ctcgccaagg acagagactc cagtgtttgt actggtgtcc      600
ggacacacca aggagtcgat agtcgcgcag gccaacgtga gagaggcaag gatagacgat      660
ggtgaatctt gcttcactgg agaacatggg ccaaagagct cgagcaagtc agagacagaa      720
gcatgcttct catgcgcctc cccatgatcc aaatagttgg ccacacatgg tagccacacc      780
ttgatgatag aagcctcctc cttgacaggt tgaaacactt ccttcaaaca agctgaaaac      840
atatgttgaa actctaaccg caacgactcg gccaaagggg tgaccaagga atgaaggtgc      900
aaaggtgtcg aggcaagaga ggcacaacac caacgacaaa catgatcgtc gtcctcacca      960
cggaaaccga tggttgagaa gccgacgggg gattgagatg tccatgtgat tgagacttgg     1020
cgacggtgtc agctgacaac aacgtacttg gcgaagactt ggccactacc tcagtactcc     1080
aagtccctga ttgttcagga tgatcacatt ggacagagga cttaactcga cgagcacgag     1140
aggaagaccg aaagtgacaa tgccgctcct gatgaccaag gcagcgacac cgaatgcaac     1200
ggaagaaagt tcttgcgtga gctaacttgg tgatcatgtg cgaggtagcg ataacacctg     1260
gccgagccca cctctcgaag tcaaagctcc tctttgactt gctctttgca caacatccg      1320 atgacattgg caatatggtc tgaagaggga gtactttga  cgacgacgtg tccggtgata     1380
acgggtagcc cagatgacgg ctcctgctag agacgaggcc tctgttagca ctaagatcgg     1440
ccactgtcat cgatgacggt agccaatcta ggtaggagtg cggccctaca tgaagggaca     1500
tgcgctcgag aacgagcact cggcgagctc gaacggtggg cttgaggccg gcagatgct      1560 ctccttccac tctggtgtct tgctctcctt ccacgagctg agcgcagatg aatggcggag     1620
tggcaatact gggtctcctt cctcgagctt gatggcccag cggaggagcg agcacatgct     1680
gtagccccca atctggggtt gggacttggg agggtggagg aactgatctg aacaagcatg     1740
gatctggctg gagataggtg gtgacgagta ccatgcgttg acggcagcag agagtcgaca     1800
accggcgcgc ggggacaagt cggccttacc tgcgaagtcg tcccggacgg caacagcagc     1860
atgctcccgg ccccggcggt ggcggcgaaa atagcgagat gatgcactag acgcagcctg     1920
tacacggggc acggaggggc gtagttgtta aagtatgccg ctgcagctag tatttgtctc     1980
agcgcagttt tctagctagc taaaaatagt tgaagaaata tacatacatg aatcggaaag     2040
gaaatcgtac acaggattac ctaatatgtc gcatgtgaca ccgaggcacc gagtaacggt     2100
gacaa                                                                 2105
```

<210> SEQ ID NO 26
<211> LENGTH: 2123
<212> TYPE: DNA
<213> ORGANISM: Zea mays

<400> SEQUENCE: 26

```
taggtggtgt tcggctgagt gggacgaggc gcacaacgct agccgggaac ggcgtatgat      60
```

```
gatgcaaggt ccctcccacc accaaggcag ccggagcctg ggccaatatg cagaagcatg      120
gatacgccct attttttatt taggtatata gcactggatt agatattatt tcttactatc      180
tcgttggttt tcttgcagtc ggcatcacat ggtggtcggc cttgctccac cttcttggtc      240
tatgctatgg cccataaggg caaggcgacg tccgacgtca cctacaaccc ggatgacagg      300
tcggaggagg caagagacat gggcgttact ggattgccga tggggcaatc gactcatcct      360
ccactcccac tctgtctcag gtgaccactc ccactctgtc tcaggtgaga gcaaggagca      420
tgagctcgag tccagccata cgacctcgac acgatagctc acagcatcgc atacaacaac      480
tcgaggttag tgcttctata actcatcctt ccttgagtta tataccttct ctttgagtta      540
ctataacgtt ggcttgtaat attacagacc caactagaag aagagaggag ggaacgtcaa      600
gagatggagg cgaggataat ggcggagcgg gaggcagagc gggaggctcg cctggcggct      660
gatcagagga tggcggagat gttccagtac atgcagagcc ttggcgccgc atagggcttc      720
gctccgccac ctccattgtt ccctgcagtt gaccctgcta tgttccatac tcctgtgagt      780
atcaaaattg tagttacatg ttggtaatgc atctggtata acacatgcaa tctcttctct      840
atgcagggcc aatttgggc ggcatccaac aaccctcatg aagggttcag cccaacgtag      900
caccagtcca acagccacct ccatgagagt tatgttttag tgtttagact ttagaacatg      960
tgttgaatac tcatgtttgt gttggatact tatgtcagag cttgagactt atgagactta     1020
tgttcttgat acttatgttt gccttgagaa cttggatatt tatgtttgtg ttggatattt     1080
atgtttgtga tgatatatgt gatgtatata tgtgatatat gtgatgtata tatggtatct     1140
tttgtttgtt tggatggaat ataaaaaaca aataaaaagg tgtatactgg tcactttgcc     1200
gagtgtgaca ctcggtaaat aggtgctttg tcgagtatca gagacatagc actcggtaaa     1260
gaaccaagac ctgggcaccg gtataggttc tttgccgagt gtaatggctc tggcactcgg     1320
caaagaagca cgctttgccg agtgccatac caagcactcg gcaaagtacc taacatgggg     1380 accctctgg cggattcttt gtcgagtgct gtcaggcaga cactcggcaa aggtaacttc     1440
tttgccgagt gtcacctggg acactcggca aagatgctgt ctctgtcacc cggcgccgta     1500
acggctgctt tctttgccg agtgctccct gatactcggc aaacctattt gccgagtgtc     1560
cgataaaaag tactcggcaa agaaggcttt gccgatgcac tgtgtaccga gccctctttg     1620
ccgagtgcga cactcggtaa agccttgcc gagtgttttt aatggtttac cgagtgcttc     1680
agacactcgg caaagccgtc gattccgata gtgttttcta tattttggtt ttattgtttt     1740
tagaatatat ttagacataa tgtgtaccaa gtatatctag aaaaaaatat aagttagaat     1800
aaagagaaaa tacttgaata aaaaatcttg tttaaatctc attttttaa acctaattca     1860 cattttttaa agatccacct gcatgacctt attgatgttc aaatgtcaag ctagctagaa     1920
ttgccatgta cgttgtggca gcgagttcga aaatgattag caggacgcca cgaatcacgc     1980
taaatttatt tatcttctac tgttccttgg ccggagatcg actcatcgcg tgctgccacg     2040
aatccaacac gcaaaccccc aacgtgtcag ccggctagat gcgacggctg actatttaaa     2100
gcggtagatc gcgcggtcgc atc                                              2123
```

<210> SEQ ID NO 27
<211> LENGTH: 2145
<212> TYPE: DNA
<213> ORGANISM: Zea mays

<400> SEQUENCE: 27

```
gacgtttaaa aagccagtac actatgaaaa ttaagggata gtaccatcac acgcctcctt      60
atatagcaat atagcaaaag gataaacact acaagaggca atatccaatt tttttttaagt    120
accttctaaa gagagcggtg aagattaatg aaccttaatt tatagatgag ttattatata    180
tagaatatgt aagtcattca tggtatagca atttcataac tattcttgtt gaactctcta    240
tagcaatttc ataccagaca aaaacttcca aatgaccaaa gaacaattag agtggctatc    300
aaagtttaaa cacccgtcaa agccattaga gatttacctc taacaccaga tgatgactat    360
gtactactcg ttagagatag tttatttgta ttctcattga ggagaaattt gatttcatat    420
ttgagactag atgattagaa catttattgt tagtttgttg accatataaa tatattatcc    480
aagttgacaa taacaatatg gatctctcta ttcgataaga catactttat ttaatattta    540
atgcaatgat gcaaatgtaa ctgaaatagt atattcactg ccaacaaaaa aaggcaacaa    600
aaggaaaaat aaatgatgga aaaatctcat ccaaattata acactatcat ttaggctatg    660
ttttgagaga ataaaacatc atattagagg agagactcta ttctttggat tttatagatt    720
tagaacattg cttagattgt gttaaggata aattttcaaa acaatttaat aaaacaacca    780
agcgtaatac acgagtatta taaattattc acacaaacat ttatgcatgg ttctttctca    840
ataagaggag tagatggtta tgatttattt atgaccttca tagatgatta tgactatatt    900
taccttgtta aagaaagatc ataattctta taaaagctca agttttttaa aataaaagtt    960
gagaatcaag ataatttaaa gatcaacata gtgatatatg accgtgggag ggagtatatt   1020
agagacacca tatattatat atggacaagt actagaaccc tttgcaagat ttctccaaga   1080
aagtagcatt gtatcctact ataggaaaac attgagaaat cgtcggctaa ttaaatcaag   1140
aatgaagtta cagaagaag aaaccatact tcaatggaca tgacatgttg tatgttgagt   1200
tactctatt taccatattg tttatagatg gaggtttaaa ccgctatcca cgtactcaac   1260
aaagttccta ctaaattagt gcctaaaact caatatgagt tatagtctgg aagaaatcca   1320
aacttgaact atttgtatat ttggggatct ttagcagctg agtcaataat ctttaacccct   1380
aaacaaagga aagtgaataa aagggcaaga agttgccatt ttattagcta tcacagaagt   1440
cgaaagagtt tcgattttac tgtctaaaca aacacaataa atttgtagaa acacgacata   1500
aaatattact ccacatgttc taaaataata accgttttag ctcttgtttt ttatgtctat   1560
atttagatgg atgatgataa atctagacac atatataaaa catatatatc aagtattgta   1620
tgatctatta attgtctaaa acgaatttaa attgatacag atgggagatg gaggagtatt   1680
agagaatgag taatcaaggg aagcatggta cccagaaata aaccttgagg aaaagaagat   1740
gtacgtccca attctaatag tttaagaacc atattttgaa catgttgagg tttttaccatc   1800
agttcctcga gttgtcaata aaaccccttgc tacaaatttc gagtcatcga gcacgacaat   1860
tgatgagccc caaataatgg tgagtcgcgc ataccctgcac gcgacacgac ggtacgaggg   1920
cacgggcgca cctgctcgag tgcatgccgc atgcctctac cgcgagcgtt ccacgacgtt   1980
ccgcatgcat ggctggcacc tgtcggagca agggaaaacc agggcatgtc gtggacgcac   2040
cccacgaaaa ccaaacgcct ccacgtagcc tcgccggctc ccttgcgtgt ctccgctttt   2100
cgcgcctccc tacctatata agggcgcacc aacgtactcg accgg                    2145
```

<210> SEQ ID NO 28
<211> LENGTH: 17306
<212> TYPE: DNA
<213> ORGANISM: Artificial sequence
<220> FEATURE:
<223> OTHER INFORMATION: Synthetic construct

<400> SEQUENCE: 28

```
gtttacccgc caatatatcc tgtcaaacac tgatagttta aactgaaggc gggaaacgac      60
aatctgatca tgagcggaga attaagggag tcacgttatg accccgccg atgacgcggg     120
acaagccgtt ttacgtttgg aactgacaga accgcaacgt tgaaggagcc actcagcaag    180
ctggtacgat tgtaatacga ctcactatag ggcgaattga gcgctgttta aacgctcttc    240
aactggaaga gcggttacgc tgtttaaacg ctcttcaact ggaagagcgg ttactaccgg    300
ttcactagct agctgctaat cgagctagtt accctatgag gtgacatgaa gcgctcacgg    360
ttactatgac ggttagcttc acgactgttg gtggcagtag cgtacgactt agctatagtt    420
ccggacttac ccttaagcga tttaaatcct gaggatatcg ctatcaactt tgtatagaaa    480
agttgggccg aattcgagct cggtacggcc agaatggccc ggaccgaagc ttcggccgca    540
cactgatagt ttaaactgaa ggcgggaaac gacaatctga tcatgagcgg agaattaagg    600
gagtcacgtt atgaccccg ccgatgacgc gggacaagcc gttttacgtt tggaactgac    660
agaaccgcaa cgttgaagga gccactcagc cgcgggtttc tggagtttaa tgagctaagc    720
acatacgtca gaaaccatta ttgcgcgttc aaaagtcgcc taaggtcact atcagctagc    780
aaatatttct tgtcaaaaat gctccactga cgttccataa attcccctcg gtatccaatt    840
actctatcag tgatagagta ctggcgcgcc actctatcag tgatagagtc tagaggatcg    900
ctcaggaagg ccgctgagat agaggcatgg cggccaatgc gggcggcggt ggagcgggag    960
gaggcagcgg cagcggcagc gtggctgcgc cggcggtgtg ccgccccagc ggctcgcggt   1020
ggacgccgac gccggagcag atcaggatgc tgaaggagct ctactacggc tgcggcatcc   1080
ggtcgcccag ctcggagcag atccagcgca tcaccgccat gctgcggcag cacggcaaga   1140
tcgagggcaa gaacgtcttc tactggttcc agaaccacaa ggcccgcgag cgccagaagc   1200
gccgcctcac cagcctcgac gtcaacgtgc ccgccgccgg cgcggccgac gccaccacca   1260
gccaactcgg cgtcctctcg ctgtcgtcgc cgccgccttc aggcgcggcg cctccctcgc   1320
ccaccctcgg cttctacgcc gccggcaatg gcggcggatc ggctgtgctg ctggacacga   1380
gttccgactg gggcagcagc ggcgctgcca tggccaccga gacatgcttc ctgcaggact   1440
acatgggcgt gacggacacg ggcagctcgt cgcagtggcc acgcttctcg tcgtcggaca   1500
cgataatggc ggcggccgcg gcgcgggcgg cgacgacgcg ggcgcccgag acgctccctc   1560
tcttcccgac ctgcggcgac gacggcggca gcggtagcag cagctacttg ccgttctggg   1620
gtgccgcgtc cacaactgcc ggcgccactt cttccgttgc gatccagcag caacaccagc   1680
tgcaggagca gtacagcttt tacagcaaca gcaacagcac ccagctggcc ggcaccggca   1740
accaagacgt atcggcaaca gcagcagcag ccgccgccct ggagctgagc ctcagctcat   1800
ggtgctcccc ttaccctgct gcagggagta tgtgagagca acgcgagctg ccactgctct   1860
tcactggtac cgttaacaga tcattcgaca aagcagcatt agtccgttga tcggtggaag   1920
accactcgtc agtgttgagt tgaatgtttg atcaataaaa tacggcaatg ctgtaagggt   1980
tgttttttat gccattgata atacactgta ctgttcagtt gttgaactct atttcttagc   2040
catgccaagt gcttttctta ttttgaataa cattacagca aaaagttgaa agacaaaaaa   2100
aaaaaccccc gaacagagtg ctttgggtcc caagcttctt tagactgtgt tcggcgttcc   2160
ccctaaattt ctcccctat atctcactca cttgtcacat cagcgttctc tttcccccta   2220
tatctccacg ctctacagca gttccaccta tatcaaacct ctataccca ccacaacaat   2280
```

```
attatatact ttcatcttca actaactcat gtaccttcca attttttct actaataatt      2340 atttacgtgc acagaaactt agcaaggaga gagagagcgg ggtgacccac cttgctagtt      2400
ggatattacc tcttctcttc aaagtatcct tgaacgctca ccggttatca aatctctaca      2460
ctatagctct gtagtcttgc tagatagtta gttctttagc tctcggtgac caagcttggc      2520
gcgatcaagc ttatcgatac cgtcgacctc gaagcttggt cacccggtcc gggcctagaa      2580
ggccagcttc aagtttgtac aaaaaagcag gctccggcca gaatggcccg gaccgggtta      2640
ccgaattctt accctagctc cctgcggctg ttacgcggtc ccccatcaat cttctgttct      2700
tgcggttgta gcctgtgtaa cagtgctaga gtatgtatga taaataggtt ttaagtctgc      2760
ttacatgaca ttttttattg tggaagagac atataaaaat tagagagagt ggttctcatg      2820
caacggcgga cggcccggtg ctaaaagagc ttcaagacaa aataatgaaa caggaagaga      2880
gtagatttat ctaagagcca actttattat atgaatgtgt ttattgttgg ctttagatga      2940
tatggtaagg agttagagct aataatagat aggctctatt attattatta ttaattaaac      3000
tcgctctaag gaggaaagtg ggaggaaggg acgaggacga agactactgg aagcatcgtg      3060
catggatgat ggatgtggtg tctcttaatg taggtggccg gaggatgtac gtgttaattg      3120
cgcgataagc actcagatcc aaccgcaaac tacctccaca ctgacacact gatagagaga      3180
aagagagacc tccgacgact gccgccgcag atgagccacg tacgtatacg acgtctgccg      3240
gccggctcag gctgccgcca tcaccctgct cgaaagtcgc gttaggcggc gccagctaca      3300
taggagtatc tagtctagcc agttagtata ctactactgc gctgatgatg aattaactct      3360
gcatagatac tgtacttgcc tccctccaac acccaaccac ctcctgctcg gctcttaata      3420
acttggacac ggatcgatgc catccaagga agaacacgac gacgacgacg aacatccac       3480 catgcaagct tgcatccata cgccgatacg cgtgcatcca tccatccacc attatttcca      3540
ttttccaccg atcacacgta cacaggccta tttaaggagc gacatcccac tgcaactctc      3600
ctcaccactc atcaccagct agctctagca aagcacttgc catctaccga ccgccgcatt      3660
ccaaacagcc cgacgagcta gcagagcggc aggcacctcc ctcctcaagg aacccatggc      3720
cactgtgaac aactggctcg cttttctccct ctccccgcag gagctgccgc cctcccagac     3780
gacggactcc acactcatct cggccgccac cgccgaccat gtctccggcg atgtctgctt      3840
caacatcccc caagattgga gcatgagggg atcagagctt tcggcgctcg tcgcggagcc      3900
gaagctggag gacttcctcg gcggcatctc cttctccgag cagcatcaca aggccaactg      3960
caacatgata cccagcacta gcagcacagt ttgctacgcg agctcaggtg ctagcaccgg      4020
ctaccatcac cagctgtacc accagcccac cagctcagcg ctccacttcg cggactccgt      4080
aatggtggct tcctcggccg gtgtccacga cggcggtgcc atgctcagcg cggccgccgc      4140
taacggtgtc gctggcgctg ccagtgccaa cggcggcggc atcggctgt ccatgattaa       4200 gaactggctg cggagccaac cggcgcccat gcagccgagg gtggcggcgg ctgagggcgc      4260
gcaggggctc tctttgtcca tgaacatggc ggggacgacc caaggcgctg ctggcatgcc      4320
acttctcgct ggagagcgcg cacgggcgcc cgagagtgta tcgacgtcag cacagggtgg      4380
agccgtcgtc gtcacggcgc cgaaggagga tagcggtggc agcggtgttg ccggcgctct      4440
agtagccgtg agcacggaca cgggtggcag cggcggcgcg tcggctgaca acacggcaag      4500
gaagacggtg gacacgttcg ggcagcgcac gtcgatttac cgtggcgtga caaggcatag      4560
atggactggg agatatgagg cacatctttg ggataacagt tgcagaaggg aagggcaaac      4620
tcgtaagggt cgtcaagtct atttaggtgg ctatgataaa gaggagaaag ctgctagggc      4680
```

```
ttatgatctt gctgctctga agtactgggg tgccacaaca acaacaaatt ttccagtgag    4740
taactacgaa aaggagctcg aggacatgaa gcacatgaca aggcaggagt ttgtagcgtc    4800
tctgagaagg aagagcagtg gtttctccag aggtgcatcc atttacaggg gagtgactag    4860
gcatcaccaa catggaagat ggcaagcacg gattggacga gttgcaggga acaaggatct    4920
ttacttgggc accttcagca cccaggagga ggcagcggag gcgtacgaca tcgcggcgat    4980
caagttccgc ggcctcaacg ccgtcaccaa cttcgacatg agccgctacg acgtgaagag    5040
catcctggac agcagcgccc tccccatcgg cagcgccgcc aagcgcctca aggaggccga    5100
ggccgcagcg tccgcgcagc accaccacgc cggcgtggtg agctacgacg tcggccgcat    5160
cgcctcgcag ctcggcgacg gcggagccct ggcggcggcg tacggcgcgc actaccacgg    5220
cgccgcctgg ccgaccatcg cgttccagcc gggcgccgcc agcacaggcc tgtaccaccc    5280
gtacgcgcag cagccaatgc gcggcggcgg gtggtgcaag caggagcagg accacgcggt    5340
gatcgcggcc gcgcacagcc tgcaggacct ccaccacctg aacctgggcg cggccggcgc    5400
gcacgacttt ttctcggcag ggcagcaggc cgccgccgct gcgatgcacg gcctgggtag    5460
catcgacagt gcgtcgctcg agcacagcac cggctccaac tccgtcgtct acaacgcgg    5520 ggtcggcgac agcaacggcg ccagcgccgt cggcggcagt ggcggtggct acatgatgcc    5580
gatgagcgct gccggagcaa ccactacatc ggcaatggtg agccacgagc aggtgcatgc    5640
acgggcctac gacgaagcca agcaggctgc tcagatgggg tacgagagct acctggtgaa    5700
cgcggagaac aatggtggcg gaaggatgtc tgcatggggg actgtcgtgt ctgcagccgc    5760
ggcggcagca gcaagcagca acgacaacat ggccgccgac gtcgggcatg gcggcgcgca    5820
gctcttcagt gtctggaacg acacttaagc gtacctagtg gtacctgaca tcttatagtc    5880
tgcaacctct cgtgtctgaa ttcctatctt tatcaagtgt tattgcttcc acgactatag    5940
gacagctttc gtcgaaagct tttgctcatg tgatctcgaa ggattcatct agtctgattt    6000
ttcgtgactt gtatcggttt tattggattc atccaacata tatcaataaa aaatgagttg    6060
tgtttccttt cttcctagtt cagttaaaat tatttccctc ctgcgcttgt gctgtaattg    6120
tctgtgtacc tgttgtttgt gactgtgtta gttcccttgg atatgatttc gtatttgata    6180
tgtacatgga gatagcttag cttcattatt ggagtatgaa gttagtatga catagtcact    6240
ctcctggaaa attgacactg caaaccatat ttttattctg aaccacaaat cctagtcagt    6300
ccgctggcat atgccgtccg tttgctgaat ccagaacgtg ggtttggaga tgtacggctg    6360
agatgcctct atgcgaaggg gatttcgtgg tgaaacgaga tgggagtaga gcaacgcccg    6420
tggaagatgc ttcaaacttc cacacttttg agcaacgatc ggcagtagta aggtagacga    6480
tttcaagatc aaagcatatg aagataaaca acatcaacaa caaatttgt tggggttcta    6540 tagagagaaa cagagctaca tacatacact gttttgtatc taccatctga gatgatgaaa    6600
agatgaaaaa ctaaagaatg ccccggcgcc aacgccagga cacgccgcgc gcgcgtcacc    6660
cgagccatct cttgacccag ccggcgctgt atatttacac acgttgcagc atcgatcacc    6720
acctgttcga tcgcgtcgcc gtcaccggta ccgagctcga attccggtcc gggcctagaa    6780
ggccgatctc ccgggcaccc agctttcttg tacaaagtgg ccgttaacgg atcggccaga    6840
atggcccgga ccgggttacc gaattcgagc tcggtaccct gggatcggcc gctctagaac    6900
tagtggatcc cggccgtgat ccccggcggt gtccgccact gaagaaacta tgtgctgtag    6960
tatagccgct gcccgctggc tagctagcta gttgagtcat ttagcggcga tgattgagta    7020
```

```
ataatgtgtc acgcatcacc atgcatgggt ggcagtgtca gtgtgagcaa tgacctgaat    7080
gaacaattga aatgaaaaga aaaaagtatt gttccaaatt aaacgtttta acctttaat    7140 aggtttatac aataattgat atatgttttc tgtatatgtc taatttgtta tcatccattt    7200
agatatagac aaaaaaaatc taagaactaa acaaatgct aatttgaaat gaagggagta    7260
tatattggga taatgtcgat gagatccctc gtaatatcac cgacatcaca cgtgtccagt    7320
taatgtatca gtgatacgtg tattcacatt tgttgcgcgt aggcgtaccc aacaattttg    7380
atcgactatc agaaagtccg gtccgctcga ggcatgcctg cagtgcagcg tgacccggtc    7440
gtgcccctct ctagagataa tgagcattgc atgtctaagt tataaaaaat taccacatat    7500 ttttttttgtc acacttgttt gaagtgcagt ttatctatct ttatacatat atttaaactt    7560
tactctacga ataatataat ctatagtact acaataatat cagtgtttta gagaatcata    7620
taaatgaaca gttagacatg gtctaaagga caattgagta ttttgacaac aggactctac    7680
agttttatct ttttagtgtg catgtgttct ccttttttttt tgcaaatagc ttcacctata    7740
taatacttca tccattttat tagtacatcc attagggtt tagggttaat ggttttata    7800 gactaatttt tttagtacat ctattttatt ctattttagc ctctaaatta agaaaactaa    7860
aactctattt tagttttttt atttaataat ttagatataa aatagaataa aataagtga    7920 ctaaaaatta aacaaatacc ctttaagaaa ttaaaaaaac taaggaaaca ttttcttgt    7980 ttcgagtaga taatgccagc ctgttaaacg ccgtcgacga gtctaacgga caccaaccag    8040
cgaaccagca gcgtcgcgtc gggccaagcg aagcagacgg cacggcatct ctgtcgctgc    8100
ctctggaccc ctctcgagag ttccgctcca ccgttggact tgctccgctg tcggcatcca    8160
gaaattgcgt ggcggagcgg cagacgtgag ccggcacggc aggcggcctc ctcctcctct    8220
cacggcaccg gcagctacgg gggattcctt tcccaccgct ccttcgcttt ccttcctcg    8280 cccgccgtaa taaatagaca ccccctccac accctctttc cccaacctcg tgttgttcgg    8340
agcgcacaca cacacaacca gatctccccc aaatccaccc gtcggcacct ccgcttcaag    8400
gtacgccgct cgtcctcccc ccccccctc tctaccttct ctagatcggc gttccggtcc    8460
atgcatggtt agggcccggt agttctactt ctgttcatgt ttgtgttaga tccgtgtttg    8520
tgttagatcc gtgctgctag cgttcgtaca cggatgcgac ctgtacgtca gacacgttct    8580
gattgctaac ttgccagtgt ttctctttgg ggaatcctgg gatggctcta gccgttccgc    8640
agacgggatc gatttcatga tttttttttgt ttcgttgcat agggtttggt ttgcccttt    8700 cctttatttc aatatatgcc gtgcacttgt ttgtcgggtc atcttttcat gcttttttt    8760 gtcttggttg tgatgatgtg gtctggttgg gcggtcgttc tagatcggag tagaattctg    8820
tttcaaacta cctggtggat ttattaattt tggatctgta tgtgtgtgcc atacatattc    8880
atagttacga attgaagatg atggatggaa atatcgatct aggataggta tacatgttga    8940
tgcgggtttt actgatgcat atacagagat gcttttgtt cgcttggttg tgatgatgtg    9000
gtgtggttgg gcggtcgttc attcgttcta gatcggagta gaatactgtt tcaaactacc    9060
tggtgtattt attaattttg gaactgtatg tgtgtgtcat acatcttcat agttacgagt    9120
ttaagatgga tggaaatatc gatctaggat aggtatacat gttgatgtgg gttttactga    9180
tgcatataca tgatggcata tgcagcatct attcatatgc tctaaccttg agtacctatc    9240
tattataata aacaagtatg ttttataatt attttgatct tgatatactt ggatgatggc    9300
atatgcagca gctatatgtg gatttttta gccctgcctt catacgctat ttatttgctt    9360
ggtactgttt cttttgtcga tgctcaccct gttgtttggt gttacttctg caggtcgact    9420
```

```
ctagaggatc catggccaga ctcgacaaga gcaaggtgat caacagcgca ctggagctgc    9480
tgaacgaggt cggaatcgaa ggcctcacaa cccgtaagct cgcccagaag ctcggggttg    9540
agcagcctac attgtactgg cacgtcaaga acaagcgagc tctgctagac gctatggcca    9600
tagagatgct cgatccgcac aagattcact acttaccctt ggaaggggaa agctggcaag    9660
atttcttgag gaacagggct aagtccatga gaaatgcttt gctcagtcac cgtgatggag    9720
ccaaggtctg tctaggtacg ggcttcacgg agcgacaata tgaaactgct gagaacacgc    9780
ttgccttcct gacacaacaa ggtttctccc ttgagaacgc cctctacgca ttccaagcag    9840
tggggatcta cactctgggt tgtgtcttgc tggatcaaga gctgcaagtc gctaaggagg    9900
agagggaaac acctactact gatagtatgc cgccactggt tcgacaagct tacgaactcg    9960
cggatcacca aggtgcagag ccagccttcc tgttcggcct tgaactgatc atatcaggat   10020
tggagaagca gctgaaggcc gaaagtgggt cttaatgata gctgcagaag gtacctcagc   10080
cgtcaacagc cagggtgatt agagcccag catgcaaaat gatcacctgg tcgctcatcc    10140
ttgactaaag catggctcgg cggtcgctgt ttacctatat ccctatagta ggtactcctg   10200
tacataaagc ctgaaaaaat gggttcagtt gtttatcgaa ctctgccaaa tttgcttttg   10260
catataatgt aaaattcagc tagctctgct aagctcctcg cttcagttcg acagaactgc   10320
aattgatatt gatgttatgg aaattgatat tggaacaatc agcaatatta tgcttatatt   10380
catttcttgg gcgtgctcta ctctgtgccg atgatatcat ccgatgggtt ttgtacttct   10440
tacttatgaa gtgaacgata ataggttgcc tggtcccagt tctcagcttg atgttatgat   10500
aatcatatgt gatttcagtt ctttgtctgg cattggtctg ttttgtgtc tgtgtctgtg    10560 ggctgtggct ctgtgtgttg ataactcgag cttgattgca tcagtgaact gcgacttaca   10620
acagcagaca gagtgttagc agcagggaag gagaatagag aaattaggga gtaaagagaa   10680
catagttgcc tttcagagga cagcttagca agataacaaa attatgttct ctccttttaa   10740
ggattacaga ggcatagcct cagcgacgcg cgtgctagcg gatccagtta tcatcatcgt   10800
gttgggcttc ctgggcctgg cctgcctagc aggcctgtcg acagcttcag aaggggaact   10860
cgttggcgga ttgtccacag tagcacgtac tatatgcaga aaaagtcctt atgtctctct   10920
tatcattagc ctattaatca tattaattca gtccacatag gaccgaattt ataacttaac   10980 aatctttttag tttcctgagc aatatcgtta aatcaaaaca tattcttgta ccaaattttg   11040
ctatcaacgg ttcaacgcct agttagttag cggaccgaag cttcctgaat tccaggtgga   11100
gctcgaattc ctgcagcccc tcggtaccct gggatctgcc cttactttaa cgcctctaac   11160
caacacccct ttatctttat aaggaacaat aaacagaatt tgccccactg ttctaaatca   11220
cctaataata tccccagcta aaacaataa aggtttccta gaattaagac aagcatgact    11280
gttcctccag gagggtttgg aacattgttg cagtcttgca gatacgggcg aagggtgaga   11340
aacagagcgg agggctggag gtgacctcgg tagtcgacgc cggagttgag cttgacaacg   11400
acggggcggc ccctgatgga cttgaggaag tccgatggcg tcttcaccgt cccgccggcg   11460
cccgaggcgg gcctgtcgct gccgccgccg ccgctgctca tcttgcgcgc tgtgcccccg   11520
gcggtgtccc tgtgttgcgg atcgcgggtg ggccaggtga tgcgagggc gacccgtttg    11580 gactccggcc ggagccgccg gatccctggt cggtgtcagt gccgtttact ctgggcccca   11640
cgtgtcagta ccgtctgtag atgacaacaa cccgtcgtcc acagtcatgt ccaaaatatc   11700 cttcttctt tttttcgat tcggatatct atcttccttt tttttttcca aaaatcttct    11760
```

```
tgacgcacca gcgcgcacgt ttgtggtaaa cgccgacacg tcggtcccac gtcgatagac    11820
cccacccacc agtgagtagc gtgtacgtat tcggggggtga cggacgtgtc gccgtcgtct    11880
tgctagtccc attcccatct gagccacaca tctctgaaca aaaaaaagga gggaggcctc    11940
cacgcacatc cccctccgtg ccacccgccc caaaccctcg cgccgcctcc gagacagccg    12000
ccgcaaccat ggccaccgcc gccgccgcgt ctaccgcgct cactggcgcc actaccgctg    12060
cgcccaaggc gaggcgccgg gcgcacctcc tggccacccg ccgcgccctc gccgcgccca    12120
tcaggtgctc agcggcgtca cccgccatgc cgatggctcc cccggccacc ccgctccggc    12180
cgtggggccc caccgagccc cgcaagggtg ctgacatcct cgtcgagtcc ctcgagcgct    12240
gcggcgtccg cgacgtcttc gcctaccccg gcggcgcgtc catggagatc caccaggcac    12300
tcacccgctc ccccgtcatc gccaaccacc tcttccgcca cgagcaaggg gaggcctttg    12360
ccgcctccgg ctacgcgcgc tcctcgggcc gcgtcggcgt ctgcatcgcc acctccggcc    12420
ccggcgccac caacctagtc tccgcgctcg ccgacgcgct gctcgattcc gtccccatgg    12480
tcgccatcac gggacaggtg gcgcgacgca tgattggcac cgacgccttc caggagacgc    12540
ccatcgtcga ggtcacccgc tccatcacca agcacaacta cctggtcctc gacgtcgacg    12600
acatcccccg cgtcgtgcag gaggcttttct tcctcgcctc ctctggtcga ccagggccgg    12660
tgcttgtcga catccccaag gacatccagc agcagatggc ggtgcctgtc tgggacaagc    12720
ccatgagtct gcctgggtac attgcgcgcc ttcccaagcc cctgcgact gagttgcttg    12780 agcaggtgct gcgtcttgtt ggtgaatcgc ggcgccctgt tctttatgtg ggcggtggct    12840
gcgcagcatc tggtgaggag ttgcgacgct tgtggagct gactggaatc ccggtcacaa    12900
ctactcttat gggcctcggc aacttcccca gcgacgaccc actgtctctg cgcatgctag    12960
gtatgcatgg gacggtgtat gcaaattatg cagtggataa ggccgatctg ttgcttgcac    13020
ttggtgtgcg gtttgatgat cgcgtgacag ggaagattga ggcttttgca agcagggcta    13080
agattgtgca cgttgatatt gatccggctg agattggcaa gaacaagcag ccacatgtgt    13140
ccatctgtgc agatgttaag cttgcttgc agggcatgaa tgctcttctt gaaggaagca    13200
catcaaagaa gagctttgac tttggctcat ggaacgatga gttggatcag cagaagaggg    13260
aattccccct tgggtataaa acatctaatg aggagatcca gccacaatat gctattcagg    13320
ttcttgatga gctgacgaaa ggcgaggcca tcatcggcac aggtgttggg cagcaccaga    13380
tgtgggcggc acagtactac acttacaagc ggccaaggca gtggttgtct tcagctggtc    13440
ttggggctat gggatttggt ttgccggctg ctgctggtgc ttctgtggca acccaggtg    13500 tcactgttgt tgacatcgat ggagatggta gctttctcat gaacgttcag gagctagcta    13560
tgatccgaat tgagaacctc ccagtgaagg tctttgtgct aaacaaccag cacctgggga    13620
tggtggtgca gttggaggac aggttctata aggccaacag agcgcacaca tacttgggaa    13680
acccagagaa tgaaagtgag atatatccag atttcgtgac gatcgccaaa gggttcaaca    13740
ttccagcggt ccgtgtgaca aagaagaacg aagtccgcgc agcgataaag aagatgctcg    13800
agactccagg gccgtaccctc ttggatataa tcgtcccaca ccaggagcat gtgttgccta    13860
tgatccctag tggtgggggct ttcaaggata tgatcctgga tggtgatggc aggactgtgt    13920
actgactagc tagtcagtta acagatctgc cagatcctcg gtgtacaaat aacccgtctt    13980
atcctatgag acgggccggc gtcagtgtgt tctggaggaa tttttatgtc agagccttt    14040 tctttgtgtg cttgatgtag atgccaaggg aagcttattg gctgttgaag cttgatgcaa    14100
aataaattat ggaactctgt tttttgttta tctaataata actagcaaat atgcttccat    14160
```

```
tgcattgaaa ctaacagcct tttgtgtttc caagttttat tttgtgacaa tgtcatctat    14220
ttcaattagt tgtggaatcg gaaacttgca ggactaactt ggaaactcca atccctcagc    14280
atcctggact ttttcctggt gtaatccatg tagatattat tttaatcatc attttagttc    14340
tggaggtttt tccatctccg gttttgctcc cctttcttca aaaaaaaaaa aaaaatgccg    14400
taggcgccgc aacgcccacc tgttgttcaa actcatgggc acgagtggct cgaagatttt    14460
atacaacaat tgctgtagtt tcaccgttgc tggtgaagaa gcattttttt aaaaaaatat    14520
agtggtattc attttaatta gtttagttgt gcagcgagca aatttggac atgctctgct     14580 cggaatctga tcgacctaga cacagattag cagcagtagc tttgtcatct gttccaagag    14640
ttgcgatctg atagaagaaa aaaaaacctt cccttcaatg taaaaccgaa actaacaaga    14700
aagaagcaca gtgccgttta ggcaagtatg gagtacgtat taagcatgta gaaggccatg    14760
catgaaccac taacaagaaa gaagcgcagt gccattcagg caagcataag catgtagatt    14820
ggcatgcatg aacaactaac agtagatcgt ctctggtctg attagaagtt ttttgggaag    14880
ccaagaaatc atgtacaact ggttccatct caaattccgt ggcaaaaaga ggcctaagca    14940
acataaagct tcggtccggg cctagaaggc cattgggtca tcggatcccg ggcaacttta    15000
ttatacaaag ttgatagata tctggtctaa ctaactagtc ctaaggaccc ggcggaccga    15060
agctggccgc tctagaacta gtggatctcg atgtgtagtc tacgagaagg gttaaccgtc    15120
tcttcgtgag aataaccgtg gcctaaaaat aagccgatga ggataaataa aatgtggtgg    15180
tacagtactt caagaggttt actcatcaag aggatgcttt tccgatgagc tctagtagta    15240
catcggacct cacataccte cattgtggtg aaatattttg tgctcattta gtgatgggta    15300
aattttgttt atgtcactct aggttttgac atttcagttt tgccactctt aggttttgac    15360
aaataatttc cattccgcgg caaaagcaaa acaatttat tttacttta ccactcttag       15420 ctttcacaat gtatcacaaa tgccactcta gaaattctgt ttatgccaca gaatgtgaaa    15480
aaaaacactc acttatttga agccaaggtg ttcatggcat ggaaatgtga cataaagtaa    15540
cgttcgtgta taagaaaaaa ttgtactcct cgtaacaaga gacggaaaca tcatgagaca    15600
atcgcgtttg gaaggctttg catcaccttt ggatgatgcg catgaatgga gtcgtctgct    15660
tgctagcctt cgcctaccgc ccactgagtc cgggcggcaa ctaccatcgg cgaacgaccc    15720
agctgacctc taccgaccgg acttgaatgc gctaccttcg tcagcgacga tggccgcgta    15780
cgctggcgac gtgcccccgc atgcatggcg gcacatggcg agctcagacc gtgcgtggct    15840
ggctacaaat acgtaccccg tgagtgccct agctagaaac ttacacctgc aactgcgaga    15900
gcgagcgtgt gagtgtagcc gagtagatcc cccgggctgc aggtcgactc tagaggatcc    15960
accggtcgcc accatggccc acagcaagca cggcctgaag gaggagatga ccatgaagta    16020
ccacatggag ggctgcgtga acggccacaa gttcgtgatc accggcgagg gcatcggcta    16080 cccccttcaag ggcaagcaga ccatcaacct gtgcgtgatc gagggcggcc ccctgccctt    16140
cagcgaggac atcctgagcg ccggcttcaa gtacggcgac cggatcttca ccgagtaccc    16200
ccaggacatc gtggactact tcaagaacag ctgccccgcc ggctacacct ggggccggag    16260
cttcctgttc gaggacggcg ccgtgtgcat ctgtaacgtg acatcaccg tgagcgtgaa     16320 ggagaactgc atctaccaca agagcatctt caacggcgtg aacttccccg ccgacggccc    16380
cgtgatgaag aagatgacca ccaactggga ggccagctgc gagaagatca tgcccgtgcc    16440
taagcagggc atcctgaagg gcgacgtgag catgtacctg ctgctgaagg acggcggccg    16500
```

```
gtaccggtgc cagttcgaca ccgtgtacaa ggccaagagc gtgcccagca agatgcccga    16560
gtggcacttc atccagcaca agctgctgcg ggaggaccgg agcgacgcca agaaccagaa    16620
gtggcagctg accgagcacg ccatcgcctt ccccagcgcc ctggcctgaa gcggcccatg    16680
gatattcgaa cgcgtaggta ccacatggtt aacctagact tgtccatctt ctggattggc    16740
caacttaatt aatgtatgaa ataaaaggat gcacacatag tgacatgcta atcactataa    16800
tgtgggcatc aaagttgtgt gttatgtgta attactagtt atctgaataa agagaaaga    16860 gatcatccat atttcttatc ctaaatgaat gtcacgtgtc tttataattc tttgatgaac    16920
cagatgcatt tcattaacca aatccatata catataaata ttaatcatat ataattaata    16980
tcaattgggt tagcaaaaca aatctagtct aggtgtgttt tgcgaatgcg ccgccaccg    17040 cggtggagct cgaattccgg tccgaagctt aagccatggc ccgggaatct tagcggccgc    17100
ctgcagagtt aacggcgcgc cgactagcta gctaaggtac cgagctcgaa ttcattccga    17160
ttaatcgtgg cctcttgctc ttcaggatga agagctatgt ttaaacgtgc aagcgctact    17220
agacaattca gtacattaaa aacgtccgca atgtgttatt aagttgtcta agcgtcaatt    17280
tgtttacacc acaatatatc ctgcca                                        17306

<210> SEQ ID NO 29
<211> LENGTH: 20236
<212> TYPE: DNA
<213> ORGANISM: Artificial sequence
<220> FEATURE:
<223> OTHER INFORMATION: Synthetic construct

<400> SEQUENCE: 29
gtttacccgc caatatatcc tgtcaaacac tgatagttta aactgaaggc gggaaacgac      60
aatctgatca tgagcggaga attaagggag tcacgttatg accccgccg atgacgcggg     120 acaagccgtt ttacgtttgg aactgacaga accgcaacgt tgaaggagcc actcagcaag     180
ctggtacgat tgtaatacga ctcactatag ggcgaattga gcgctgttta acgctcttc     240 aactggaaga gcggttacgc tgtttaaacg ctcttcaact ggaagagcgg ttactaccgg     300
ttcactagct agctgctaag gttaccgag ctggtcacct ttgtccacca acttattaag     360
tatctagttg aagacacgtt cttcttcacg taagaagaca ctcagtagtc ttcggccaga     420
atggcctctt gattcagcgg gcctagaagg ccggatcact gactagctaa tttaaatcct     480
gaggatatcg ctatcaactt tgtatagaaa agttgggccg agctcggtac ggccagaatg     540
gcccggaccg ggttaccgaa ttcaggcgac ccatcgctgc tttgtctaca tcatgttctt     600
catcatcctc cccaggcgac gcgtgctgct gttcttattc agactaccgt tcgagtgact     660
gcatggcgta catctttctg catcgacttt gtacggctac atcgaacata tacacgagat     720
gtctcgtgtg aatagagtca ctaatgcctt aagcatcggt tactccgtag ggtacattct     780
gttcttctta tttgtgcata ttttattgt tgtttactga ttatcgagt agttatacat     840 acatgcacat acatatcatc acatatatca caatattttt ctaaattaaa ttaaaactaa     900
aaatgactaa atttctaaca ccaacgacat tgtaatgttt tctccaacaa ctttacctat     960
tctacattgt tctatttcga atttcactct ataacaaca tagtctacaa tggaaaacag    1020
tgctttgtac gactatatac gcgatgtgtg gctacaacat aagacaatat agtcgtttga    1080
agattgaacc tatatatcgg tacggttaat ccgtctatgt acgtgggcat gacgaacacc    1140
cgtgataacg aaggattaac gtgcacaatc ataaatccaa gtaggagcg gtgcatgatg    1200 agaatcgctc tcagtactcg acataatgaa ccttacgagg tacaacaggc aggcaggcag    1260
```

```
ggaccagggg ccgcctttat ttcaggctcg ctggcccac gggcgtgctg cgtgcacgaa      1320
gggcactacc ccaacctctc accgaaaacc gcgctggatc ggcaaatcaa acgaggtggt      1380
gccccgtgcc cactctccac gtccacggca ccatccctct gcagccgctc accagccatg      1440
ccgtgtcgcg gaacggcaca accacccca acccactcac gaaacccgt cccggccgtg       1500 cccgtgtcgg tccgcgctcg gcaacgaggc ggcccgcgct gctgagtccc ctggacaccc      1560
gacaccctgt cggccctttg tttattcatc ccgaaatctc atctgccccc acggccgact      1620
gcgctgcgcc gcccggatat atatacccat cgttatcgat cgactgggga ctctatcagt      1680
gatagagtct agaggatcgc tcaggaaggc cgctgagata gaggcatggc ggccaatgcg      1740
ggcggcggtg gagcgggagg aggcagcggc agcggcagcg tggctgcgcc ggcggtgtgc      1800
cgccccagcg gctcgcggtg gacgccgacg ccggagcaga tcaggatgct gaaggagctc      1860
tactacggct gcggcatccg gtcgcccagc tcggagcaga tccagcgcat caccgccatg      1920
ctgcggcagc acggcaagat cgagggcaag aacgtcttct actggttcca gaaccacaag      1980
gcccgcgagc gccagaagcg ccgcctcacc agcctcgacg tcaacgtgcc cgccgccggc      2040
gcggccgacg ccaccaccag ccaactcggc gtcctctcgc tgtcgtcgcc gccgccttca      2100
ggcgcggcgc ctccctcgcc cacccctcggc ttctacgccg ccggcaatgg cggcggatcg      2160
gctgtgctgc tggacacgag ttccgactgg ggcagcagcg gcgctgccat ggccaccgag      2220
acatgcttcc tgcaggacta catgggcgtg acggacacgg gcagctcgtc gcagtggcca      2280
cgcttctcgt cgtcggacac gataatggcg gcggccgcgg cgcgggcggc gacgacgcgg      2340
gcgcccgaga cgctccctct cttcccgacc tgcggcgacg acggcggcag cggtagcagc      2400
agctacttgc cgttctgggg tgccgcgtcc acaactgccg gcgccacttc ttccgttgcg      2460
atccagcagc aacaccagct gcaggagcag tacagctttt acagcaacag caacagcacc      2520
cagctggccg gcaccggcaa ccaagacgta tcggcaacag cagcagcagc gccgccctg       2580 gagctgagcc tcagctcatg gtgctcccct taccctgctg cagggagtat gtgagagcaa      2640
cgcgagctgc cactgctctt cactggtacc gttaacagat cattcgacaa agcagcatta      2700
gtccgttgat cggtggaaga ccactcgtca gtgttgagtt gaatgtttga tcaataaaat      2760
acggcaatgc tgtaagggtt gtttttatg ccattgataa tacactgtac tgttcagttg       2820
ttgaactcta tttcttagcc atgccaagtg ctttcttat tttgaataac attacagcaa       2880
aaagttgaaa gacaaaaaa aaaacccccg aacagagtgc tttgggtccc aagcttcttt       2940
agactgtgtt cggcgttccc cctaaatttc tccccctata tctcactcac ttgtcacatc      3000
agcgttctct ttccccctat atctccacgc tctacagcag ttccacctat atcaaacctc      3060
tataccccac cacaacaata ttatatactt tcatcttcaa ctaactcatg taccttccaa      3120
tttttttcta ctaataatta tttacgtgca cagaaactta gcaaggagag agagagcggg      3180
gtgacccacc ttgctagttg gatattacct cttctcttca aagtatcctt gaacgctcac      3240
cggttatcaa atctctacac tatagctctg tagtcttgct agatagttag ttctttagct      3300
ctcggtgacc aagcttggcg cgatcaagct tatcgatacc gtcgacctcg aagcttggtc      3360
acccggtccg ggcctagaag gccagcttca agtttgtaca aaaaagcagg ctccggccag      3420
aatggcccgg accgggttac cgaattctta ccctagctcc ctgcggctgt tacgcggtcc      3480
cccatcaatc ttctgttctt gcggttgtag cctgtgtaac agtgctagag tatgtatgat      3540
aaataggttt taagtctgct tacatgacat tttttattgt ggaagagaca tataaaaatt      3600
```

```
agagagagtg gttctcatgc aacggcggac ggcccggtgc taaaagagct tcaagacaaa    3660
ataatgaaac aggaagagag tagatttatc taagagccaa ctttattata tgaatgtgtt    3720
tattgttggc tttagatgat atggtaagga gttagagcta ataatagata ggctctatta    3780
ttattattat taattaaact cgctctaagg aggaaagtgg gaggaaggga cgaggacgaa    3840
gactactgga agcatcgtgc atggatgatg gatgtggtgt ctcttaatgt aggtggccgg    3900
aggatgtacg tgttaattgc gcgataagca ctcagatcca accgcaaact acctccacac    3960
tgacacactg atagagagaa agagagacct ccgacgactg ccgccgcaga tgagccacgt    4020
acgtatacga cgtctgccgg ccggctcagg ctgccgccat caccctgctc gaaagtcgcg    4080
ttaggcggcg ccagctacat aggagtatct agtctagcca gttagtatac tactactgcg    4140
ctgatgatga attaactctg catagatact gtacttgcct ccctccaaca cccaaccacc    4200
tcctgctcgg ctcttaataa cttggacacg gatcgatgcc atccaaggaa gaacacgacg    4260
acgacgacgg aacatccacc atgcaagctt gcatccatac gccgatacgc gtgcatccat    4320
ccatccacca ttatttccat tttccaccga tcacacgtac acaggcctat ttaaggagcg    4380
acatcccact gcaactctcc tcactctatc agtgatagag tctctagcaa agcacttgcc    4440
atctaccgac cgccgcattc caaacagccc gacgagctag cagagcggca ggcacctccc    4500
tcctcaagga acccatggcc actgtgaaca actggctcgc tttctccctc tccccgcagg    4560
agctgccgcc ctcccagacg acggactcca cactcatctc ggccgccacc gccgaccatg    4620
tctccggcga tgtctgcttc aacatccccc aagattggag catgagggga tcagagcttt    4680
cggcgctcgt cgcggagccg aagctggagg acttcctcgg cggcatctcc ttctccgagc    4740
agcatcacaa ggccaactgc aacatgatac ccagcactag cagcacagtt gctacgcga    4800 gctcaggtgc tagcaccggc taccatcacc agctgtacca ccagcccacc agctcagcgc    4860
tccacttcgc ggactccgta atggtggctt cctcggccgg tgtccacgac ggcggtgcca    4920
tgctcagcgc ggccgccgct aacggtgtcg ctggcgctgc cagtgccaac ggcggcggca    4980
tcgggctgtc catgattaag aactggctgc ggagccaacc ggcgcccatg cagccgaggg    5040
tggcggcggc tgagggcgcg caggggctct ctttgtccat gaacatggcg gggacgaccc    5100
aaggcgctgc tggcatgcca cttctcgctg gagagcgcgc acgggcgccc gagagtgtat    5160
cgacgtcagc acagggtgga gccgtcgtcg tcacggcgcc gaaggaggat agcggtggca    5220
gcggtgttgc cggcgctcta gtagccgtga gcacggacac gggtggcagc ggcggcgcgt    5280
cggctgacaa cacggcaagg aagacggtgg acacgttcgg gcagcgcacg tcgatttacc    5340
gtggcgtgac aaggcataga tggactggga gatatgaggc acatctttgg gataacagtt    5400
gcagaaggga agggcaaact cgtaagggtc gtcaagtcta tttaggtggc tatgataaag    5460
aggagaaagc tgctagggct tatgatcttg ctgctctgaa gtactggggt gccacaacaa    5520
caacaaattt tccagtgagt aactacgaaa aggagctcga ggacatgaag cacatgacaa    5580
ggcaggagtt tgtagcgtct ctgagaagga agagcagtgg tttctccaga ggtgcatcca    5640
tttacagggg agtgactagg catcaccaac atggaagatg gcaagcacgg attggacgag    5700
ttgcagggaa caaggatctt tacttgggca ccttcagcac ccaggaggag gcagcggagg    5760
cgtacgacat cgcggcgatc aagttccgcg gcctcaacgc cgtcaccaac ttcgacatga    5820
gccgctacga cgtgaagagc atcctggaca cagcgccct cccatcggc agcgccgcca    5880 agcgcctcaa ggaggccgag gccgcagcgt ccgcgcagca ccaccacgcc ggcgtggtga    5940
gctacgacgt cggccgcatc gcctcgcagc tcggcgacgg cggagccctg cggcggcgt    6000
```

-continued

```
acggcgcgca ctaccacggc gccgcctggc cgaccatcgc gttccagccg ggcgccgcca    6060
gcacaggcct gtaccacccg tacgcgcagc agccaatgcg cggcggcggg tggtgcaagc    6120
aggagcagga ccacgcggtg atcgcggccg cgcacagcct gcaggacctc caccacctga    6180
acctgggcgc ggccggcgcg cacgactttt tctcggcagg gcagcaggcc gccgccgctg    6240
cgatgcacgg cctgggtagc atcgacagtg cgtcgctcga gcacagcacc ggctccaact    6300
ccgtcgtcta caacgcggg gtcggcgaca gcaacggcgc cagcgccgtc ggcggcagtg    6360
gcggtggcta catgatgccg atgagcgctg ccggagcaac cactacatcg caatggtga    6420 gccacgagca ggtgcatgca cgggcctacg acgaagccaa gcaggctgct cagatggggt    6480
acgagagcta cctggtgaac gcggagaaca atggtggcgg aaggatgtct gcatggggga    6540
ctgtcgtgtc tgcagccgcg gcggcagcag caagcagcaa cgacaacatg gccgccgacg    6600
tcgggcatgg cggcgcgcag ctcttcagtg tctggaacga cacttaagcg tacctagtgg    6660
tacctgacat cttatagtct gcaacctctc gtgtctgaat tcctatcttt atcaagtgtt    6720
attgcttcca cgactatagg acagctttcg tcgaaagctt ttgctcatgt gatctcgaag    6780
gattcatcta gtctgatttt tcgtgacttg tatcggtttt attggattca tccaacatat    6840
atcaataaaa aatgagttgt gtttcctttc ttcctagttc agttaaaatt atttccctcc    6900
tgcgcttgtg ctgtaattgt ctgtgtacct gttgtttgtg actgtgttag ttcccttgga    6960
tatgatttcg tatttgatat gtacatggag atagcttagc ttcattattg gagtatgaag    7020
ttagtatgac atagtcactc tcctggaaaa ttgacactgc aaaccatatt tttattctga    7080
accacaaatc ctagtcagtc cgctggcata tgccgtccgt ttgctgaatc cagaacgtgg    7140
gtttggagat gtacggctga gatgcctcta tgcgaagggg atttcgtggt gaaacgagat    7200
gggagtagag caacgcccgt ggaagatgct tcaaacttcc acactttga gcaacgatcg    7260 gcagtagtaa ggtagacgat ttcaagatca aagcatatga agataaacaa catcaacaac    7320
aaaatttgtt ggggttctat agagagaaac agagctacat acatacactg ttttgtatct    7380
accatctgag atgatgaaaa gatgaaaaac taaagaatgc cccggcgcca acgccaggac    7440
acgccgcgcg cgcgtcaccc gagccatctc ttgacccagc cggcgctgta tatttacaca    7500
cgttgcagca tcgatcacca cctgttcgat cgcgtcgccg tcaccggtac cgagctcgaa    7560
ttccggtccg ggcctagaag gccgatctcc cgggcaccca gctttcttgt acaaagtggc    7620
cgttaacgga tcggccagaa tggcccggac cgggttaccg aattcgagct cggtaccctg    7680
ggatcggccg ctctagaact agtggatccc ggccgtgatc cccggcggtg tccgccactg    7740
aagaaactat gtgctgtagt atagccgctg cccgctggct agctagctag ttgagtcatt    7800
tagcggcgat gattgagtaa taatgtgtca cgcatcacca tgcatgggtg gcagtgtcag    7860
tgtgagcaat gacctgaatg aacaattgaa atgaaagaa aaagtattg ttccaaatta    7920 aacgttttaa ccttttaata ggtttataca ataattgata tatgttttct gtatatgtct    7980
aatttgttat catccatta gatatagaca aaaaaaatct aagaactaaa acaaatgcta    8040
atttgaaatg aagggagtat atattgggat aatgtcgatg agatccctcg taatatcacc    8100
gacatcacac gtgtccagtt aatgtatcag tgatacgtgt attcacattt gttgcgcgta    8160
ggcgtaccca acaatttga tcgactatca gaaagtccgg tccgctcgag gcatgcctgc    8220
agtgcagcgt gacccggtcg tgcccctctc tagagataat gagcattgca tgtctaagtt    8280
ataaaaaatt accacatatt tttttgtca cacttgtttg aagtgcagtt tatctatctt    8340
```

| | | | | | |
|---|---|---|---|---|---|
| tatacatata | tttaaacttt | actctacgaa | taatataatc | tatagtacta | caataatatc | 8400 |
| agtgttttag | agaatcatat | aaatgaacag | ttagacatgg | tctaaaggac | aattgagtat | 8460 |
| tttgacaaca | ggactctaca | gttttatctt | tttagtgtgc | atgtgttctc | ctttttttt | 8520 |
| gcaaatagct | tcacctatat | aatacttcat | ccattttatt | agtacatcca | tttagggttt | 8580 |
| agggttaatg | gttttatag | actaatttt | ttagtacatc | tattttattc | tattttagcc | 8640 |
| tctaaattaa | gaaaactaaa | actctatttt | agttttttta | tttaataatt | tagatataaa | 8700 |
| atagaataaa | ataaagtgac | taaaaattaa | acaaataccc | tttaagaaat | taaaaaaact | 8760 |
| aaggaaacat | ttttcttgtt | tcgagtagat | aatgccagcc | tgttaaacgc | cgtcgacgag | 8820 |
| tctaacggac | accaaccagc | gaaccagcag | cgtcgcgtcg | ggccaagcga | agcagacggc | 8880 |
| acggcatctc | tgtcgctgcc | tctgaccccc | tctcgagagt | tccgctccac | cgttggactt | 8940 |
| gctccgctgt | cggcatccag | aaattgcgtg | gcggagcggc | agacgtgagc | cggcacggca | 9000 |
| ggcggcctcc | tcctcctctc | acggcaccgg | cagctacggg | ggattccttt | cccaccgctc | 9060 |
| cttcgctttc | ccttcctcgc | ccgccgtaat | aaatagacac | ccctccaca | ccctctttcc | 9120 |
| ccaacctcgt | gttgttcgga | gcgcacacac | acacaaccag | atctccccca | aatccacccg | 9180 |
| tcggcacctc | cgcttcaagg | tacgccgctc | gtcctccccc | cccccctct | ctaccttctc | 9240 |
| tagatcggcg | ttccggtcca | tgcatggtta | gggcccggta | gttctacttc | tgttcatgtt | 9300 |
| tgtgttagat | ccgtgtttgt | gttagatccg | tgctgctagc | gttcgtacac | ggatgcgacc | 9360 |
| tgtacgtcag | acacgttctg | attgctaact | tgccagtgtt | tctctttggg | gaatcctggg | 9420 |
| atggctctag | ccgttccgca | gacgggatcg | atttcatgat | tttttttgtt | tcgttgcata | 9480 |
| gggtttggtt | tgccctttc | ctttatttca | atatatgccg | tgcacttgtt | tgtcgggtca | 9540 |
| tcttttcatg | cttttttttg | tcttggttgt | gatgatgtgg | tctggttggg | cggtcgttct | 9600 |
| agatcggagt | agaattctgt | ttcaaactac | ctggtggatt | tattaatttt | ggatctgtat | 9660 |
| gtgtgtgcca | tacatattca | tagttacgaa | ttgaagatga | tggatggaaa | tatcgatcta | 9720 |
| ggataggtat | acatgttgat | gcgggtttta | ctgatgcata | tacagagatg | ctttttgttc | 9780 |
| gcttggttgt | gatgatgtgg | tgtgttggg | cggtcgttca | ttcgttctag | atcggagtag | 9840 |
| aatactgttt | caaactacct | ggtgtattta | ttaattttgg | aactgtatgt | gtgtgtcata | 9900 |
| catcttcata | gttacgagtt | taagatggat | ggaaatatcg | atctaggata | ggtatacatg | 9960 |
| ttgatgtggg | ttttactgat | gcatatacat | gatggcatat | gcagcatcta | ttcatatgct | 10020 |
| ctaaccttga | gtacctatct | attataataa | acaagtatgt | tttataatta | ttttgatctt | 10080 |
| gatatacttg | gatgatggca | tatgcagcag | ctatatgtgg | atttttttag | ccctgccttc | 10140 |
| atacgctatt | tatttgcttg | gtactgtttc | ttttgtcgat | gctcaccctg | ttgtttggtg | 10200 |
| ttacttctgc | aggtcgactc | tagaggatcc | atggccagac | tcgacaagag | caaggtgatc | 10260 |
| aacagcgcac | tggagctgct | gaacgaggtc | ggaatcgaag | gcctcacaac | ccgtaagctc | 10320 |
| gcccagaagc | tcgggggttga | gcagcctaca | ttgtactggc | acgtcaagaa | caagcgagct | 10380 |
| ctgctagacg | ctatggccat | agagatgctc | gatccgcaca | agattcacta | cttacccttg | 10440 |
| gaagggaaa | gctggcaaga | tttcttgagg | aacaggcta | agtccatgag | aaatgctttg | 10500 |
| ctcagtcacc | gtgatggagc | caaggtctgt | ctaggtacgg | gcttcacgga | gcgacaatat | 10560 |
| gaaactgctg | agaacacgct | tgccttcctg | acacaacaag | gtttctccct | tgagaacgcc | 10620 |
| ctctacgcat | tccaagcagt | ggggatctac | actctgggtt | gtgtcttgct | ggatcaagag | 10680 |
| ctgcaagtcg | ctaaggagga | gagggaaaca | cctactactg | atagtatgcc | gccactggtt | 10740 |

```
cgacaagctt acgaactcgc ggatcaccaa ggtgcagagc cagccttcct gttcggcctt   10800
gaactgatca tatcaggatt ggagaagcag ctgaaggccg aaagtgggtc ttaatgatag   10860
ctgcagaagg tacctcagcc gtcaacagcc agggtgatta gagccccagc atgcaaaatg   10920
atcacctggt cgctcatcct tgactaaagc atggctcggc ggtcgctgtt tacctatatc   10980
cctatagtag gtactcctgt acataaagcc tgaaaaatg gttcagttg tttatcgaac    11040 tctgccaaat ttgcttttgc atataatgta aaattcagct agctctgcta agctcctcgc   11100
ttcagttcga cagaactgca attgatattg atgttatgga aattgatatt ggaacaatca   11160
gcaatattat gcttatattc atttcttggg cgtgctctac tctgtgccga tgatatcatc   11220
cgatgggttt tgtacttctt acttatgaag tgaacgataa taggttgcct ggtcccagtt   11280
ctcagcttga tgttatgata atcatatgtg atttcagttc tttgtctggc attggtctgt   11340
ttttgtgtct gtgtctgtgg gctgtggctc tgtgtgttga taactcgagc ttgattgcat   11400
cagtgaactg cgacttacaa cagcagacag agtgttagca gcagggaagg agaatagaga   11460
aattagggag taaagagaac atagttgcct ttcagaggac agcttagcaa gataacaaaa   11520
ttatgttctc tccttttaag gattacagag gcatagcctc agcgacgcgc gtgctagcgg   11580
atccagttat catcatcgtg ttgggcttcc tgggcctggc ctgcctagca ggcctgtcga   11640
cagcttcaga aggggaactc gttggcggat tgtccacagt agcacgtact atatgcagaa   11700
aaagtcctta tgtctctctt atcattagcc tattaatcat attaattcag tccacatagg   11760
accgaattta taacttaaca atcttttagt ttcctgagca atatcgttaa atcaaaacat   11820
attcttgtac caaattttgc tatcaacggt tcaacgccta gttagttagc ggaccgaagc   11880
ttcctgaatt ccaggtggag ctcgaattcc tgcagcccct cggtaccctg ggatctgccc   11940
ttactttaac gcctctaacc aacacccctt tatctttata aggaacaata aacagaattt   12000
gccccactgt tctaaatcac ctaataatat ccccagctaa aaacaataaa ggtttcctag   12060
aattaagaca agcatgactg ttcctccagg aggtttgga acattgttgc agtcttgcag   12120
atacgggcga agggtgagaa acagagcgga gggctggagg tgacctcggt agtcgacgcc   12180
ggagttgagc ttgacaacga cggggcggcc cctgatggac ttgaggaagt ccgatggcgt   12240
cttcaccgtc ccgccggcgc ccgaggcggg cctgtcgctg ccgccgccgc cgctgctcat   12300
cttgcgcgct gtgcccccgg cggtgtccct gtgttgcgga tcgcgggtgg gccaggtgga   12360
tgcgagggcg accgtttgg actccggccg gagccgccgg atccctggtc ggtgtcagtg    12420
ccgtttactc tgggcccccac gtgtcagtac cgtctgtaga tgacaacaac ccgtcgtcca   12480
cagtcatgtc caaaatatcc tttcttcttt tttttcgatt cggatatcta tcttcctttt   12540
ttttttccaa aaatcttctt gacgcaccag cgcgcacgtt tgtggtaaac gccgacacgt   12600
cggtcccacg tcgatagacc ccacccacca gtgagtagcg tgtacgtatt cgggggtgac   12660
ggacgtgtcg ccgtcgtctt gctagtccca ttcccatctg agccacacat ctctgaacaa   12720 aaaaaggag ggaggcctcc acgcacatcc ccctccgtgc cacccgcccc aaaccctcgc    12780
gccgcctccg agacagccgc cgcaaccatg gccaccgccg ccgccgcgtc taccgcgctc   12840
actggcgcca ctaccgctgc gcccaaggcg aggcgccggg cgcacctcct ggccaccgc    12900 cgcgccctcg ccgcgcccat caggtgctca gcggcgtcac ccgccatgcc gatggctccc   12960
ccggccaccc cgctccggcc gtggggcccc accgagcccc gcaagggtgc tgacatcctc   13020
gtcgagtccc tcgagcgctg cggcgtccgc gacgtcttcg cctaccccgg cggcgcgtcc   13080
```

```
atggagatcc accaggcact cacccgctcc ccgtcatcg ccaaccacct cttccgccac    13140
gagcaagggg aggcctttgc cgcctccggc tacgcgcgct cctcgggccg cgtcggcgtc    13200
tgcatcgcca cctccggccc cggcgccacc aacctagtct ccgcgctcgc cgacgcgctg    13260
ctcgattccg tccccatggt cgccatcacg ggacaggtgg cgcgacgcat gattggcacc    13320
gacgccttcc aggagacgcc catcgtcgag gtcacccgct ccatcaccaa gcacaactac    13380
ctggtcctcg acgtcgacga catccccgc gtcgtgcagg aggctttctt cctcgcctcc    13440
tctggtcgac cagggccggt gcttgtcgac atccccaagg acatccagca gcagatggcg    13500
gtgcctgtct gggacaagcc catgagtctg cctgggtaca ttgcgcgcct tcccaagccc    13560
cctgcgactg agttgcttga gcaggtgctg cgtcttgttg gtgaatcgcg cgccctgtt    13620 ctttatgtgg gcggtggctg cgcagcatct ggtgaggagt tgcgacgctt tgtggagctg    13680
actggaatcc cggtcacaac tactcttatg ggcctcggca acttcccag cgacgaccca    13740 ctgtctctgc gcatgctagg tatgcatggg acggtgtatg caaattatgc agtggataag    13800
gccgatctgt tgcttgcact tggtgtgcgg tttgatgatc gcgtgacagg gaagattgag    13860
gcttttgcaa gcagggctaa gattgtgcac gttgatattg atccggctga gattggcaag    13920
aacaagcagc cacatgtgtc catctgtgca gatgttaagc ttgctttgca gggcatgaat    13980
gctcttcttg aaggaagcac atcaaagaag agctttgact ttggctcatg gaacgatgag    14040
ttggatcagc agaagaggga attccccctt gggtataaaa catctaatga ggagatccag    14100
ccacaatatg ctattcaggt tcttgatgag ctgacgaaag gcgaggccat catcggcaca    14160
ggtgttgggc agcaccagat gtgggcggca cagtactaca cttacaagcg gccaaggcag    14220
tggttgtctt cagctggtct tggggctatg ggatttggtt tgccggctgc tgctggtgct    14280
tctgtggcaa acccaggtgt cactgttgtt gacatcgatg gagatggtag ctttctcatg    14340
aacgttcagg agctagctat gatccgaatt gagaacctcc cagtgaaggt ctttgtgcta    14400
aacaaccagc acctggggat ggtggtgcag ttggaggaca ggttctataa ggccaacaga    14460
gcgcacacat acttgggaaa cccagagaat gaaagtgaga tatatccaga tttcgtgacg    14520
atcgccaaag ggttcaacat tccagcggtc cgtgtgacaa agaagaacga agtccgcgca    14580
gcgataaaga agatgctcga actccaggg ccgtacctct tggatataat cgtcccacac    14640
caggagcatg tgttgcctat gatccctagt ggtggggctt tcaaggatat gatcctggat    14700
ggtgatggca ggactgtgta ctgactagct agtcagttaa cagatctgcc agatcctcgg    14760
tgtacaaata acccgtctta tcctatgaga cgggccggcg tcagtgtgtt ctggaggaat    14820
ttttatgtca gagccttttt ctttgtgtgc ttgatgtaga tgccaaggga agcttattgg    14880
ctgttgaagc ttgatgcaaa ataaattatg gaactctgtt ttttgtttat ctaataataa    14940
ctagcaaata tgcttccatt gcattgaaac taacagcctt ttgtgtttcc aagtttttatt   15000 ttgtgacaat gtcatctatt tcaattagtt gtggaatcgg aaacttgcag gactaacttg    15060
gaaactccaa tccctcagca tcctggactt tttcctggtg taatccatgt agatattatt    15120
ttaatcatca ttttagttct ggaggttttt ccatctccgg ttttgctccc cttttcttcaa   15180 aaaaaaaaaa aaaatgccgt aggcgccgca acgcccacct gttgttcaaa ctcatgggca    15240
cgagtggctc gaagatttta tacaacaatt gctgtagttt caccgttgct ggtgaagaag    15300 catttttta aaaaaatata gtggtattca ttttaattag tttagttgtg cagcgagcaa    15360
aatttggaca tgctctgctc ggaatctgat cgacctagac acagattagc agcagtagct    15420
ttgtcatctg ttccaagagt tgcgatctga tagaagaaaa aaaaaccttc ccttcaatgt    15480
```

```
aaaaccgaaa ctaacaagaa agaagcacag tgccgtttag gcaagtatgg agtacgtatt     15540
aagcatgtag aaggccatgc atgaaccact aacaagaaag aagcgcagtg ccattcaggc     15600
aagcataagc atgtagattg gcatgcatga acaactaaca gtagatcgtc tctggtctga    15660
ttagaagttt tttgggaagc caagaaatca tgtacaactg gttccatctc aaattccgtg    15720
gcaaaaagag gcctaagcaa cataaagctt cggtccgggc ctagaaggcc attgggtcat    15780
cggatcccgg gcaactttat tatacaaagt tgatagatat ctggtctaac taactagtcc    15840
taaggacccg gcggaccgaa gcttgcatgc ctgcagtgca gcgtgacccg gtcgtgcccc    15900
tctctagaga taatgagcat tgcatgtcta agttataaaa aattaccaca tattttttt     15960 gtcacacttg tttgaagtgc agtttatcta tctttataca tatatttaaa ctttactcta    16020
cgaataatat aatctatagt actacaataa tatcagtgtt ttagagaatc atataaatga    16080
acagttagac atggtctaaa ggacaattga gtattttgac aacaggactc tacagtttta    16140 tcttttagt gtgcatgtgt tctccttttt ttttgcaaat agcttcacct atataatact     16200
tcatccattt tattagtaca tccatttagg gtttagggtt aatggttttt atagactaat    16260 tttttagta catctatttt attctatttt agcctctaaa ttaagaaaac taaaactcta    16320
ttttagtttt tttatttaat aatttagata taaaatagaa taaaataaag tgactaaaaa    16380
ttaaacaaat accctttaag aaattaaaaa aactaaggaa acatttttct tgtttcgagt    16440
agataatgcc agcctgttaa acgccgtcga cgagtctaac ggacaccaac cagcgaacca    16500
gcagcgtcgc gtcgggccaa gcgaagcaga cggcacggca tctctgtcgc tgcctctgga    16560
cccctctcga gagttccgct ccaccgttgg acttgctccg ctgtcggcat ccagaaattg    16620
cgtggcggag cggcagacgt gagccggcac ggcaggcggc ctcctcctcc tctcacggca    16680
ccggcagcta cgggggattc ctttcccacc gctccttcgc tttcccttcc tcgcccgccg    16740
taataaatag acaccccctc cacaccctct ttccccaacc tcgtgttgtt cggagcgcac    16800
acacacacaa ccagatctcc cccaaatcca cccgtcggca cctccgcttc aaggtacgcc    16860
gctcgtcctc cccccccccc ctctctacct tctctagatc ggcgttccgg tccatgcatg    16920
gttagggccc ggtagttcta cttctgttca tgtttgtgtt agatccgtgt ttgtgttaga    16980
tccgtgctgc tagcgttcgt acacggatgc gacctgtacg tcagacacgt tctgattgct    17040
aacttgccag tgtttctctt tggggaatcc tgggatggct ctagccgttc cgcagacggg    17100
atcgatttca tgatttttt tgtttcgttg catagggttt ggtttgccct tttcctttat     17160
ttcaatatat gccgtgcact tgtttgtcgg gtcatctttt catgcttttt tttgtcttgg    17220
ttgtgatgat gtggtctggt tgggcggtcg ttctagatcg gagtagaatt ctgtttcaaa    17280
ctacctggtg gatttattaa ttttggatct gtatgtgtgt gccatacata ttcatagtta    17340
cgaattgaag atgatggatg gaaatatcga tctaggatag gtatacatgt tgatgcgggt    17400
tttactgatg catatacaga gatgcttttt gttcgcttgg ttgtgatgat gtggtgtggt    17460
tgggcggtcg ttcattcgtt ctagatcgga gtagaatact gtttcaaact acctggtgta    17520
tttattaatt ttggaactgt atgtgtgtgt catacatctt catagttacg agtttaagat    17580
ggatggaaat atcgatctag gataggtata catgttgatg tgggttttac tgatgcatat    17640
acatgatggc atatgcagca tctattcata tgctctaacc ttgagtacct atctattata    17700
ataaacaagt atgttttata attattttga tcttgatata cttggatgat ggcatatgca    17760
gcagctatat gtggattttt ttagccctgc cttcatacgc tatttatttg cttggtactg    17820
```

```
tttcttttgt cgatgctcac cctgttgttt ggtgttactt ctgcaggtcg actctagagg    17880
atccatggcc cagtccaagc acggcctgac caaggagatg accatgaagt accgcatgga    17940
gggctgcgtg gacggccaca agttcgtgat caccggcgag ggcatcggct accccttcaa    18000
gggcaagcag gccatcaacc tgtgcgtggt ggagggcggc cccttgccct cgccgaggaa    18060
catcttgtcc gccgccttca tgtacggcaa ccgcgtgttc accgagtacc cccaggacat    18120
cgtcgactac ttcaagaact cctgccccgc cggctacacc tgggaccgct ccttcctgtt    18180
cgaggacggc gccgtgtgca tctgcaacgc cgacatcacc gtgagcgtgg aggagaactg    18240
catgtaccac gagtccaagt tctacggcgt gaacttcccc gccgacgcc ccgtgatgaa     18300
gaagatgacc gacaactggg agccctcctg cgagaagatc atccccgtgc caagcaggg     18360
catcttgaag ggcgacgtga gcatgtacct gctgctgaag gacggtggcc gcttgcgctg    18420
ccagttcgac accgtgtaca aggccaagtc cgtgccccgc aagatgcccg actggcactt    18480
catccagcac aagctgaccc gcgaggaccg cagcgacgcc aagaaccaga gtggcacct     18540
gaccgagcac gccatcgcct ccggctccgc cttgccctcc ggactcagat ctcgatagag    18600
tcaacctaga cttgtccatc ttctggattg gccaacttaa ttaatgtatg aaataaaagg    18660
atgcacacat agtgacatgc taatcactat aatgtgggca tcaaagttgt gtgttatgtg    18720
taattactag ttatctgaat aaaagagaaa gagatcatcc atatttctta tcctaaatga    18780
atgtcacgtg tctttataat tctttgatga accagatgca tttcattaac caaatccata    18840
tacatataaa tattaatcat atataattaa tatcaattgg gttagcaaaa caaatctagt    18900
ctaggtgtgt tttgcgaatt gcggcaagct tgttttttctc agacagtttt ctaaaaaaag    18960
ggcgtttctg gggaagttcg agatggttcg taaggtgtta ctggctcctg tgaaccaata    19020
catgatactg ccatgataag ggttataatt agtcaagcag agtaagaaga aacaacagta    19080
gcagtgactc cgattcctga agatgagtca tatttgtctt gtgctcctgc tgtatgaaat    19140
ggatcgcatg tgtatattcg tcgccgcgcc gcactggtgt aacctgttgc ctcagagttt    19200
gcttttagct ggttctgttt taaaaataag tactgttttt tggttggctg caagccattc    19260
tgaacttcag tttaccaatt gttttttatgt tgtggttgaa tattttaatt ttttatttaa    19320
tgtttggttc ttttttttata tatatttgca aaaatgatac aagtggtcaa gttttcatat    19380
agtatgggct ctatttccta gagctctacc tctaggaacg aattttgtgg aggttttctt    19440
ttggctagtt aggcaaagtc cccatatctt gcaggctaaa tcaagaagaa gctctgtcaa    19500
acagtttttt ttactgaaaa gtgattaaag agtagtttct cctagatcac ttcagagttt    19560
atcctagaga atcatgggaa tcaaattcag ttagaggatc atttcttaca aagaatcaac    19620
tttcgtagag aatctaaagc agaaagagct ttgacaaact tacccttaga gcaattccaa    19680
cattctcgcg tgagtttctt cgcgccgttg ttttgcggtg acttcatctg gacgtcccgc    19740
gacatagaga cgcttgtatt gatcatgaga gcttgtgtgg tcatacacaa tataattgtt    19800
aaagatgaaa gagatgtgga ccttaatgag cgattcgact tgatggtga aaatgtgcaa     19860
ccttctcatg gtatttctac tcgcacacta gctgaattta ttgaagctca taaaaagatc    19920
cgagacaaag aaatacattt tcaattgaaa gaagacctaa tcaagcactt atggaagctt    19980
ggtcacccgg tccgaagctt aagccatggc ccgggaatct tagcggccgc ctgcagagtt    20040
aacggcgcgc cgactagcta gctaaggtac cgagctcgaa ttcattccga ttaatcgtgg    20100
cctcttgctc ttcaggatga agagctatgt ttaaacgtgc aagcgctact agacaattca    20160
gtacattaaa aacgtccgca atgtgttatt aagttgtcta gcgtcaatt tgtttacacc     20220
```
acaatatatc ctgcca 20236

<210> SEQ ID NO 30
<211> LENGTH: 14504
<212> TYPE: DNA
<213> ORGANISM: Artificial sequence
<220> FEATURE:
<223> OTHER INFORMATION: Synthetic construct

<400> SEQUENCE: 30

| | | | | | |
|---|---|---|---|---|---|
| caaacaaaca | tacacagcga | tttattcaca | cgaacccgaa | ttacaacggt | atatatcctg | 60 |
| tcagccaaca | ccaaaacatc | aaaaaaatcg | ggatcaggat | caggatctgc | ggccgcatcc | 120 |
| tgcaggttta | aacggccggc | cttcactagc | tagctgctaa | gctcaaacga | gcaggaagca | 180 |
| acgagagggt | ggcgcgcgac | cgacgtgcgt | acgtagcatg | agcctgagtg | gagacgttgg | 240 |
| acgtgtatgt | atataccctct | ctgcgtgtta | actatgtacg | taagcggcag | gcagtgcaat | 300 |
| aagtgtggct | ctgtagtatg | tacgtgcggg | tacgatgctg | taagctactg | aggcaagtcc | 360 |
| ataaataaat | aatgacacgt | gcgtgttcta | taatctcttc | gcttcttcat | ttgtcccctt | 420 |
| gcggagtttg | gcatccattg | atgccgttac | gctgagaaca | gacacagcag | acgaaccaaa | 480 |
| agtgagttct | tgtatgaaac | tatgacccctt | catcgctagg | ctcaaacagc | accccgtacg | 540 |
| aacacagcaa | attagtcatc | taactattag | cccctacatg | tttcagacga | tacataaata | 600 |
| tagcccatcc | ttagcaatta | gctattggcc | ctgcccatcc | caagcaatga | tctcgaagta | 660 |
| ttttttaatat | atagtatttt | taatatgtag | cttttaaaat | tagaagataa | ttttgagaca | 720 |
| aaaatctcca | agtattttttt | tgggtatttt | ttactgcctc | cgttttttctt | tatttctcgt | 780 |
| cacctagttt | aatttttgtgc | taatcggcta | taaacgaaac | agagagaaaa | gttactctaa | 840 |
| aagcaactcc | aacagattag | atataaatct | tatatcctgc | ctagagctgt | taaaaagata | 900 |
| gacaacttta | gtggattagt | gtatgcaaca | aactctccaa | atttaagtat | cccaactacc | 960 |
| caacgcatat | cgttcccttt | tcattggcgc | acgaactttc | acctgctata | gccgacgtac | 1020 |
| atgttcgttt | tttttgggcg | gcgcttactt | tcttccccgt | tcgttctcag | catcgcaact | 1080 |
| caatttgtta | tggcggagaa | gcccttgtat | cccaggtagt | aatgcacaga | tatgcattat | 1140 |
| tattattcat | aaaatcgagc | tagttacccct | atgaggtgac | atgaagcgct | cacggttact | 1200 |
| atgacggtta | gcttcacgac | tgttggtggc | agtagcgtac | gacttagcta | tagttccgga | 1260 |
| cttacctaac | tgactagagt | cacacttagc | tgaccctagt | cacttaggcg | cgccgtcgac | 1320 |
| ggatccgtac | catcaacttt | gtaataaaa | gttgcccgcg | gccgccggta | cctctgttaa | 1380 |
| tgaacgtaag | gagcttctgg | atgacggctg | ggacttcttt | gacaaagaga | cagagctcta | 1440 |
| agtgtcttct | tttcagtaga | ttatcggtgc | tagaataaaa | gagatatgaa | gggattctgg | 1500 |
| gttctgctct | atgtagagta | aagcttggat | ctttgatcta | atctaccgtt | agtataaaac | 1560 |
| atctattgag | ctctcttta | ttttttcttct | cagtgtatag | tttgcttatt | gttttttttgg | 1620 |
| tgttttttttc | cacctctttg | tggtactgac | ataaacaaag | actatcgttt | tgtcatagaa | 1680 |
| ttttgagatt | ttgaagaaaa | gttggataat | ttagtatact | ttttaactga | ctttataaaa | 1740 |
| cgaattagct | tcaattagag | cttcacaatt | ctcggatttt | actgaatgac | aagttaacaa | 1800 |
| tttaagctag | aaaaaaatat | gctctaagcc | tggacatgtt | gttagtcatg | ccagcgtat | 1860 |
| gtgtacatta | ggtaaatgaa | aacaaaaaca | aaaactttga | aggtttctgt | taagaaagga | 1920 |
| actaatttag | caataagaga | catgatatta | caagctcaac | actgtcgcta | tatctaccag | 1980 |

```
aagccaacaa atcttccagt gcgtaccatt ggagccactt ttcaggctca ttagacaaaa    2040
gtagcacata taatgtaaag acgaaacgat gataaagaga ctcacaagga cataatttca    2100
atacagaaga agtttgatgt cattactcat tagaaagaaa ggtataacac aggaacggaa    2160
acatagttga acaattattc atcagggggct ttacaaggcc ccaaaacaca aaccaccaaa    2220
gttttaaatg aaacgagaca tgaacttctt ctgattcata acagagataa gtttcctagg    2280
tcccaatcta gttcagtctc aattccaggg aagcgcatgg tctgacctcg gactgtccat    2340
acttccagat agcgccagat cctccgttga tgtggtcctc accgtgcatt ggaaagagag    2400
ggagagtcct tctgtgttcc aagtaagcat cacctccgca ttcctcttct tcttggtgtc    2460
cctccaagcc gaagagaggt ttagccctat cgaagaagtt gtagggagcg gaggagtagt    2520
ggtgatccat gtttgcccat ccgcctccaa cgttgttgta gttcatggag caatcttgct    2580
ccatagagcc gtacacgtgg gaagacatgt agccgttgga ggcgttgaca actccacatt    2640
cggttccaga ggaggcatgg ttgagattcc cgttgttgaa agagggtag  ggcttgttgt    2700 ggtggtagag gtgatggtcc tggttcaact tcacgttgac ggagtttgcg ggtctttgca    2760
taggaactcc gtggtggtga tgaagcaaag gatggtagtg gtcgttggcg gccatcataa    2820
cagaattggg tgatgaggaa ggagtggtca tgttagtccc gttgaaacgc ttcttctgcc    2880
tctcacgagc cttgtggttc tggaaccagt agaagacgtt cttaccctcg atcttaccga    2940
attgacgcag gcgagcggtg atcttctgaa tctgatcagc agtaggggag cggatggcat    3000
tgttgtagta caactccttc aggatcttga tctgctcagt ggtaggtgtc catctggtgg    3060
aggtctgtct gcaagtgtac cctccggaac cggacttgtt gttgttgttg ttcccggact    3120
cttgatcggc ctgatggtgg tgatgttggt gctgaggagg ctccatggac tcattagcta    3180
gtaatagtat tttctttgct tctgctatgt aatagtattt cctttccttt ctgcccggcc    3240
ttatatatat atatatatca taccaccgac agaagaagaa tatctgcatc ctcatttaat    3300
atttattgca acttccaagc cgtgaacccg ccggatatcc tgccacttct tttttctgac    3360
tcactgcatg gtaacatgtg gctcacacct gtccacatcc accagtaaaa ctccacccac    3420
aaatattact ctctctggac tcaaccatta gacaaaaaat tagttaatat tatttaatttt   3480 tgataatttc aataaaaagt taatttattc cttaaaatat catctatatt gattatataa    3540
gaaaaaaaaa taagattatt aaaaataaaa ctcaattaaa cgaatgatgt tttgaaaata    3600
catcattaag taggtgataa agtaggtgat agttaattaa aatttgttta tattttaatc    3660
taacacaatt gattttttttt ttattttttt tacatttgag gtctaaaggg agtattatga    3720
ttaaagattt ttttgtgtaa ttatgttaga attatctatc aatttttattc ataattaatt   3780 ttaacaaaac tttatttaaa aaatttgaat tcaatactat ttggactaac tacttgttgg    3840
tagactcttt cttttttacac attttttttc atctctccaa ataattttac aaatatgtaa    3900
aaagaaaaca taattttata aataaaaaat gaaacaaaaa ttaatttcta aactgtattt    3960
aatacattaa atgcttttttc ctgaaatgca ttaaatactt atttaataca ttaaataagt    4020
ttctttaatg cattaatttt caaaattaa tttaatacat ttaagtaact tatttccgta     4080
attagtaaca gtcaaaataa taagtgaggt ccttttattt gatttttttt attctagttt    4140
ctatttttca aattttttgtt tttttatttt atttcagaaa ccagaacaca tgctgaatta   4200
acaataacta atatatgcat atataaaata atattctata tatatatata tttaaatata    4260 ccataaaatac tatttaatat ataaatatta cgattataac aaatttaata ctctctattg   4320
tcttaaatgt aagaaaaaag atcagccaga gataagtgga atattccaat tatttttgtga  4380
```

```
gaaaatcatc atgcccacca gacaatagta gtagcgaaaa gcaagacatt ctaacacata   4440
aattgggtgt ttgataattc tgtgttttta agttagactt ggtagagagg tgcgtattga   4500
agggttccct cgctgcacgt tgtaaaacaa ttatatccat tctttatcaa tatatatata   4560
tatatatttt gtgtacaagc tttaaacttc aaaacttact attcgaactc taccacttgc   4620
ctgaccttat acaaagaaga agaattcagg gtccttggtc aaacccacac tagtttctcc   4680
gtgtgtgtgt gtgtatacgg attgtttgat taacgataga attgtcattt acaagattac   4740
atgacaaaaa atcaactact taacagttaa acaccacgga gacattaatt atctgacagg   4800
caccatatga acaatcgaaa tgacaagtat catcaaacatt ttttttagaa attcatgaac   4860
tcctgtttaa acgaaagcaa tataaactgt actggggtga atatgccata aaaacagtaa   4920
actctaaaag atgcttttat tgaaaaataa cttttaaaat gttgtttata cgtaaaggtt   4980
tttggcttaa aaatgggttt aactcctata aaatgagcga aaattgattt tgtaaacttt   5040
tctttggaat gaatccctga tcattatttt tgatccctat tatcatgggg aaacttgtat   5100
gtttaatgga aggttaagta acccttccaa tttctaattg atattcaata gtggttttgg   5160
ggctatgtcc cgggccattc tggcccactt tgtacaagaa agctgggtct agatatctcg   5220
agtgcggccg cgaattcggt accggatcca gtcgactgaa ttggttccgg cgccagcctg   5280
cttttttgta caaacttgaa gcttcggccg gggccgcatt cgcaaaacac acctagacta   5340
gatttgtttt gctaacccaa ttcgagctcg gtacctcgcg aatgcatcta gatatcggat   5400
cccggggtta accttcagct tagaaatgat gtgttttcta cacttttctc ttctttttt   5460 tcttttcatc tcacatgaat caaaagaga aagcttaatt acattaaagg ttgatgtgat   5520
atttactttc taaatatttg ctagaagaaa ttataatgat aacattaaat taagttatag   5580
tcatttctat ttcggttgtc tcccactttc tgctatgctt ttacaacaac agttcaagat   5640
ttggaatcgt tttctttctc caccaatcgt agtaatactt cttttttgtgt ttgttgaaat   5700 tttgcaagat tctctcttcc tctggttaat acacataact tacttggtaa gcttggctgc   5760
attttctttt caagctttta atcaaagact cactagaaat tgcaaaggca aacataaaat   5820
tatgtgatca aactcctact gtgagttttt ggttacaaac aaaagttaaa aacaaaagct   5880
tgatatttaa aagataaact caacacatat gcatttgact ggcgcacaga agacaattca   5940
agacttggga aaacagtgag ccatcaaaat cgtcagataa ttcagggaat atattgaatg   6000
tggagatgtg gtaatcacac tattgcacac aaagagtggc aaacaagcgg cgcccttggt   6060
ttggtatagt aagagacaat tgttttggac tgtttgtgtt gccatattca caaaaatact   6120
attgagctat gtatgttaaa cattatggtc aatgagtagt agtgaacatt caagtttttt   6180
ttttttccca cttcaagttt ttcatcttat tattattttt cgttgtgatg cagtagtacg   6240
gcccatcttc accagtagta tatcaaagcc gaaacagatg acaaattgtt taacatgcac   6300
ttggattatt attgagagtt gaaatacaaa ggcccgttac aagcccaaac gaaggtacat   6360
aaaagaaaag cagaaaatga aaacgaaatc gatagggata agttttccaa actgacggaa   6420
acacaaacta caccaggtga aatagatcac ctcccaagtg catgagacac gaaccaacca   6480
cttatcatca gatcacaaaa gagctcaaag atctagcgat cgcctaattc agtttgtggc   6540
caagctttga tggcaagtcg caatatctag cgacggccac ctcgtgctgc tccacataag   6600
tctccttgtc ggcctctttt atgcgctcga gtctatggtc cacgtaatac acgccgggca   6660
ttttcaagtt tttggcaggc ttttttggagc ggtaggtggt cttgaagtta cagatgagat   6720
```

```
ggcctccgcc gacaagcttc aaggccatgt cggatctacc ttcaagacca ccgtcggctg    6780
ggtaaagcat ttcagtattg gcttcccagc cgagagtctt cttctgcatc acgggaccgt    6840
ttgatgggaa gttcacgccg cggatcttga cgttgtagat caagcagccg tcttgaagac    6900
tagtgtcttg ggtggcggtc aagactcctc cgtcttcgta ggtggtcact ctctcccagg    6960
tgaatccctc tgggaatgac tgtttgaaga agtctgggat gccctgggtg tggttgatga    7020
aggttctact cccgtacatg aaggaggtgg ctagtatgtc gaaggcgaat gggagtggac    7080
ctccttcgac caccttgatt ctcatagtct gggttccctc atagggcttg ccctcaccct    7140
cagaggtaca cttgaagtgg tgattattca cggtgccctc catgtataac ttcatgtgca    7200
tgttctcttt aatgagctcc tcccccttgg acaccatggc tgtagagtca acaatcacaa    7260
gataaatcag aatcaaaatc catcacgtaa tttcaagaag caatttcgtg aaaaaaaatc    7320
ctaatctatg gccacagaat caacaaataa ggtagttgct aaaggacctg agcaatatct    7380
cttgaaatac catacagaat caacgaataa ggcttttatc aacggatctg aacaatttct    7440 tgaaaacga ctgaagtatc aacaaataag gctgttgttt aacggatctg aagtagttca    7500 tgaaaaaac cttaatctac gactacagaa tcaacaatta aggcttgttg taaacggatc    7560
tgaaaatctt tatgaaaaaa actctaatta gacctaattt acggttataa aatcatcaat    7620
taaggacgtt cttgcattaa taaaagctga atcttctgat tatgaaaatt tataatcgat    7680
gaaacgatag aaaacacaat caaatcaaca tcatgctgat gtagaacaaa caataaagaa    7740
gaagaaaaaa aaacggaaga aatctacgaa ccttgaaagg agaggtaggg aactgcgcaa    7800
agagaatgaa ctaatttgat tgcaattgaa gtgcgattag ggtcgagggg tgtggggggca    7860 ttttatagca tatgcggtgg aaccgttctc caatcatatt gtgacgcgtg cccatgtatg    7920
gtgtgacttg gtgtttatga cacagatgat atttcgggga gtccttcgta gttgacggtt    7980
tcgtaatctt gacggagtca gagatgtacc ttcaccgctt cacgcttggc tttatccgtt    8040
accacggcgt tattaaattg ggcccgcacc cgttgcaagt taggaccaca gtgtccatta    8100
cctgaacggt cggctgctac cagtattttta cattattaaa atctatggaa aagctgtcac    8160
gctagatttt tttttttttt ttatggata agaaaagact aataggaaag ctttcttact    8220
ccactaaagt ctttaataat tatttttttca attttcaaat aaaatcataa tcatcccact    8280
aaattctttc tcatttgttt ttcacttttgt aagatattct tccgtagatt tttataagta    8340 attcttttaag atacatagca taataaattg tatactttta gttacagtct atataaaatt    8400
agtcatttaa aaaatatagc cttaatgatt tttttaaaat gaagttattt ttttctaatt    8460
tttctttctt atttattatc gaatgatttt ttctactaat cgtttaggga agagttttat    8520
ttttctaatg acgagatgtg ttaaatgatg caacttgaag gcgacatatt ttttaccaat    8580
aaaataaaac taaaagatag cttgttgaca aaaacaataa ttgatgttaa agaaaacgta    8640
agggcaatgg gtatcatcta attgttggac aagttgtctt ctaaggctag gtaagctttt    8700
gttttttatt agctgaaata tttatttaat tgttctataa ataaattttt taaaatgatt    8760
tttaatgttt ttaaatatta tttaaaataa tttttttaaa attttaacat tttagttttt    8820 aattatttt tatcttactt aaattaatta taatttatta ttttctacca ttttatactt    8880
tccaattaat tttatcgaag cattaatacc atctggtatt ttgtcactgc ttcgtatgat    8940 tgttttattaa attttagctt ctttcacatt ggagatgctg ggcggtgtga gttacagcat    9000
ggtgtgaagt taaggtggtt tgattatgga acccgaaggt gttggtgcaa ggtggataaa    9060
attgcttgcc aggagataca taaaatgatt tacaaaatga aataagaat aaataaatag    9120
```

```
tcaagttcaa atttaaatca aggattagaa ttattttcc  gtacatgatg taaccgcaat    9180 cacccctgc  tgaatccaga tggccattct ggccgaattt aagtgactag ggtcaccctg    9240
ctgaatccag atggccattc tggccgaatt taagtgacta gggtcacgtg accctagtca    9300
cttaccggat tctggccgta ccgagctcga attcggccca acttttctat acaaagttga    9360
ggtacgagat ccgcccatcc ggccggccag atcctgcagg agatccaagc ttggcgcgcc    9420
gcggacctga attccagcac actggcggcc gttactagta acggccgcca gtgtgctgga    9480
attcgccctt cccaagcttt gctctagatc aaactcacat ccaaacataa catggatatc    9540
ttccttacca atcatactaa ttattttggg ttaaatatta atcattattt ttaagatatt    9600
aattaagaaa ttaaaagatt ttttaaaaaa atgtataaaa ttatattatt catgattttt    9660
catacatttg attttgataa taaatatatt tttttaatt  tcttaaaaaa tgttgcaaga    9720
cacttattag acatagtctt gttctgttta caaaagcatt catcatttaa tacattaaaa    9780
aatatttaat actaacagta gaatcttctt gtgagtggtg tgggagtagg caacctggca    9840
ttgaaacgag agaaagagag tcagaaccag aagacaaata aaaagtatgc aacaaacaaa    9900
tcaaaatcaa agggcaaagg ctggggttgg ctcaattggt tgctacattc aattttcaac    9960
tcagtcaacg gttgagattc actctgactt ccccaatcta agccgcggat gcaaacggtt   10020
gaatctaacc cacaatccaa tctcgttact taggggcttt tccgtcatta actcaccct    10080 gccacccggt ttccctataa attggaactc aatgctcccc tctaaactcg tatcgcttca   10140
gagttgagac caagacacac tcgttcatat atctctctgc tcttctcttc tcttctacct   10200
ctcaaggtac ttttcttctc cctctaccaa atcctagatt ccgtggttca atttcggatc   10260
ttgcacttct ggtttgcttt gccttgcttt ttcctcaact gggtccatct aggatccatg   10320
tgaaactcta ctcttcttt  aatatctgcg gaatacgcgt ttgactttca gatcagtcg    10380 aaatcatttc ataattgcct ttcttcttt  tagcttatga gaaataaaat cactttttt    10440 ttatttcaaa ataaaccttg ggccttgtgc tgactgagat ggggtttggt gattacagaa   10500
ttttagcgaa ttttgtaatt gtacttgttt gtctgtagtt ttgttttgtt ttcttgtttc   10560
tcatacattc cttaggcttc aattttattc gagtataggt cacaatagga attcaaactt   10620
tgagcagggg aattaatccc ttccttcaaa tccagtttgt ttgtatatat gtttaaaaaa   10680
tgaaactttt gctttaaatt ctattataac ttttttatg  gctgaaattt ttgcatgtgt   10740
ctttgctctc tgttgtaaat ttactgttta ggtactaact ctaggcttgt tgtgcagttt   10800
ttgaagtata acaacagaag ttcctattcc gaagttccta ttctctagaa agtataggaa   10860
cttccaccac acaacacaat ggcggccacc gcttccagaa ccacccgatt ctcttcttcc   10920
tcttcacacc ccaccttccc caaacgcatt actagatcca cctcccctct ctctcatcaa   10980
accctcacca aacccaacca cgctctcaaa atcaaatgtt ccatctccaa acccccacg    11040 gcggcgccct tcaccaagga agcgccgacc acggagccct tcgtgtcacg gttcgcctcc   11100
ggcgaacctc gcaagggcgc ggacatcctt gtggaggcgc tggagaggca gggcgtgacg   11160
acggtgttcg cgtaccccgg cggtgcgtcg atggagatcc accaggcgct cacgcgctcc   11220
gccgccatcc gcaacgtgct cccgcgccac gagcagggcg cgtcttcgc  cgccgaaggc   11280 tacgcgcgtt cctccggcct ccccggcgtc tgcattgcca cctccggccc cggcgccacc   11340
aacctcgtga gcggcctcgc cgacgcttta atggacagcg tcccagtcgt cgccatcacc   11400
ggccaggtcg cccgccggat gatcggcacc gacgccttcc aagaaccccc gatcgtggag   11460
```

```
gtgagcagat ccatcacgaa gcacaactac ctcatcctcg acgtcgacga catcccccgc    11520
gtcgtcgccg aggctttctt cgtcgccacc tccggccgcc ccggtccggt cctcatcgac    11580
attcccaaag acgttcagca gcaactcgcc gtgcctaatt gggacgagcc cgttaacctc    11640
cccggttacc tcgccaggct gcccaggccc ccgccgaggg cccaattgga acacattgtc    11700
agactcatca tggaggccca aaagcccgtt ctctacgtcg gcggtggcag tttgaattcc    11760
agtgctgaat tgaggcgctt tgttgaactc actggtattc ccgttgctag cactttaatg    11820
ggtcttggaa cttttcctat tggtgatgaa tattcccttc agatgctggg tatgcatggt    11880
actgtttatg ctaactatgc tgttgacaat agtgatttgt tgcttgcctt tggggtaagg    11940
tttgatgacc gtgttactgg gaagcttgag gcttttgcta gtagggctaa gattgttcac    12000
attgatattg attctgccga gattgggaag aacaagcagg cgcacgtgtc ggtttgcgcg    12060
gatttgaagt tggccttgaa gggaattaat atgattttgg aggagaaagg agtggagggt    12120
aagtttgatc ttggaggttg gagagaagag attaatgtgc agaaacacaa gtttccattg    12180
ggttacaaga cattccagga cgcgatttct ccgcagcatg ctatcgaggt tcttgatgag    12240
ttgactaatg gagatgctat tgttagtact ggggttgggc agcatcaaat gtgggctgcg    12300
cagttttaca agtacaagag accgaggcag tggttgacct caggggggtct tggagccatg    12360 ggttttggat tgcctgcggc tattggtgct gctgttgcta accctggggc tgttgtggtt    12420
gacattgatg gggatggtag tttcatcatg aatgttcagg agttggccac tataagagtg    12480
gagaatctcc cagttaagat attgttgttg aacaatcagc atttgggtat ggtggttcag    12540
ttggaggata ggttctacaa gtccaataga gctcacacct atcttggaga tccgtctagc    12600
gagagcgaga tattcccaaa catgctcaag tttgctgatg cttgtgggat accggcagcg    12660
cgagtgacga agaaggaaga gcttagagcg gcaattcaga gaatgttgga cacccctggc    12720
ccctaccttc ttgatgtcat tgtgccccat caggagcatg tgttgccgat gattcccagt    12780
aatggatcct tcaaggatgt gataactgag ggtgatggta gaacgaggta ctgattgcct    12840
agaccaaatg ttccttgatg cttgttttgt acaatatata taagataatg ctgtcctagt    12900
tgcaggattt ggcctgtggt gagcatcata gtctgtagta gttttggtag caagacattt    12960
tattttcctt ttatttaact tactacatgc agtagcatct atctatctct gtagtctgat    13020
atctcctgtt gtctgtattg tgccgttgga ttttttgctg tagtgagact gaaaatgatg    13080
tgctagtaat aatatttctg ttagaaatct aagtagagaa tctgttgaag aagtcaaaag    13140
ctaatggaat caggttacat attcaatgtt tttctttttt tagcggttgg tagacgtgta    13200
gattcaactt ctcttggagc tcacctaggc aatcagtaaa atgcatattc cttttttaac    13260
ttgccattta tttactttta gtggaaattg tgaccaattt gttcatgtag aacggatttg    13320
gaccattgcg tccacaaaac gtctcttttg ctcgatcttc acaaagcgat accgaaatcc    13380
agagatagtt ttcaaaagtc agaaatggca aagttataaa tagtaaaaca gaatagatgc    13440
tgtaatcgac ttcaataaca agtggcatca cgtttctagt tctagaccca tcagctgagg    13500
tacaaattaa ttaataagtg actagggtca cgtgacccta gtcacttatg attccgatga    13560
cttcgtaggt tcctagctca agccgctcgt gtccaagcgt cacttacgat tagctaatga    13620
ttacggcatc taggaccgac tagttcttat gtgcttctag tctccaaatg tggttgatag    13680
ttattttgct ctaagatcaa cagtaatgaa gtataaatca tcgttgtggt gtgctactcg    13740
gttaattgag cattaacaca cacaaacatg acgaggatgg tataatctcc aaaaatgtgt    13800
actttgttag gtgggaccct atagccttga ttaatgtgct atgttaggca tgcctggaaa    13860
```

| | |
|---|---:|
| cgtgtgacgc atatgttttg tgaacctgtt gatattatat gtgcttttat attaccatat | 13920 |
| tttattaaaa tactaatatt tattactagt aagatataac attctatcta gcttaaaaac | 13980 |
| taaccataaa tattccataa taactagatt taccaaacta atatactaaa tatacataat | 14040 |
| aaatacaaaa ttaacaagac aataatcaat atttatgagc ttaatatatt tagacattat | 14100 |
| ggttggtcga cgataatcat gctaactttt cgtaattgct tgattgaaat atgcttagaa | 14160 |
| taatgcctct ttgttctaca tggcaaatag ggaccattat ggtgtaacac cctgggaacc | 14220 |
| acaaacaccc cgaaatgcta ctaaactaca caactaacct tcatatataa aatttcgaca | 14280 |
| gcatctcctt tgaaaatttg catagacgtg gaagcaacag agtataaaca gatctagcta | 14340 |
| gctaagttta aacggccggc catttacaat tgaatatatc ctgccatttt acacctcgat | 14400 |
| atatcctgcc acaaattcca tgtacacagt acattaaaaa cgtccgcaat gtgttattaa | 14460 |
| gttgtctaag cgtcaatttg tttacaccac aatatatcct gcca | 14504 |

<210> SEQ ID NO 31
<211> LENGTH: 896
<212> TYPE: DNA
<213> ORGANISM: Zea mays

<400> SEQUENCE: 31

| | |
|---|---:|
| gtgcagcgtg acccggtcgt gcccctctct agagataatg agcattgcat gtctaagtta | 60 |
| taaaaaatta ccacatattt tttttgtcac acttgtttga agtgcagttt atctatcttt | 120 |
| atacatatat ttaaacttta ctctacgaat aatataatct atagtactac aataatatca | 180 |
| gtgttttaga gaatcatata aatgaacagt tagacatggt ctaaaggaca attgagtatt | 240 |
| ttgacaacag gactctacag ttttatcttt ttagtgtgca tgtgttctcc ttttttttg | 300 |
| caaatagctt cacctatata atacttcatc cattttatta gtacatccat ttagggttta | 360 |
| gggttaatgg ttttttataga ctaattttt tagtacatct attttattct attttagcct | 420 |
| ctaaattaag aaaactaaaa ctctatttta gttttttat ttaataattt agatataaaa | 480 |
| tagaataaaa taaagtgact aaaaattaaa caaatccct ttaagaaatt aaaaaaacta | 540 |
| aggaaacatt tttcttgttt cgagtagata atgccagcct gttaaacgcc gtcgacgagt | 600 |
| ctaacggaca ccaaccagcg aaccagcagc gtcgcgtcgg gccaagcgaa gcagacggca | 660 |
| cggcatctct gtcgctgcct ctggacccct ctcgagagtt ccgctccacc gttggacttg | 720 |
| ctccgctgtc ggcatccaga aattgcgtgg cggagcggca gacgtgagcc ggcacggcag | 780 |
| gcggcctcct cctcctctca cggcaccggc agctacgggg gattcctttc ccaccgctcc | 840 |
| ttcgctttcc cttcctcgcc cgccgtaata aatagacacc ccctccacac cctctt | 896 |

<210> SEQ ID NO 32
<211> LENGTH: 1346
<212> TYPE: DNA
<213> ORGANISM: Glycine max

<400> SEQUENCE: 32

| | |
|---|---:|
| ccgggcaatc aaattatata tgtaaagcaa ttcagtttta tcaaacttta tttatggaaa | 60 |
| taatttatta tcacatttat tttggtttat aaattttaaa ttaaaatatc acctaaataa | 120 |
| aaataatttt taacatgact tattgtccta aataaattat ttccgtaaat taaataaaat | 180 |
| gaagttttt tctttcaaag aatctaaatg gtcataatga gaattctcta aaaaaataca | 240 |
| taatgagaat aattatggaa tttatttatt aataaaaatt aatagcattt tgatagacaa | 300 |

-continued

```
ttaataaaat tttaaaaata accatataga aataataatt tttttactat cggttccaat    360
taaaataatg ataaaaaata aaatagatta ttaattgata ttgatatgaa atttaaataa    420
agaatataat catatatttt attgatatat gatatgatat agattaattg atattgattt    480
tgatatggaa tttaaaaata atataataat tgttttttatt tattaatacg tgtaatcaaa   540
taattctcac ttttttgaatc aatcagtgta cttaaagata atatcagttg aatattttttt  600 atccttttac gtgtgctgtg agacattatc atcaattgtg ttgtatatga tatatagata   660
tagatatata aatatataga ttgagtgata taatatattt aaaatataaa ttatatatat   720
gttttaatat atttttgcat atatatatat atttgtaaaa actagaagta tttttcatga   780
gataattatt atcgagttga ataagtctat tatttgtgag agccaaccat atttatatat   840
gtgattaaat tttatctttg tgaaattaaa aataataaaa aataccttaa aatcataata   900
atagaaaaac ttatatttat aatttaccat tatacttaaa aaaaattaaa taaatattat   960
aaatataaat actatcgagt aatggccgcg ctagggtttt tgagaaaaaa tcttcccacg  1020
cactcaactg cactgtacgg cgtcgttttc acagccgcat aatagaagcc gcgttcccca  1080
acccttcctc acaacattct cggaccctcc agcaccgtca cccaaacaaa tatccacgcg  1140
gtagtaggcg cgtgaaacaa actctaatcc gaactacgag acgtgagaag cacgcgcttt  1200
agcgagcgtt tcaattgtcg ctacgaaagc agagaaggat acaaacggaa ctagggtaaa  1260
ttagtaaggg taatttcgta aacagaagaa aagagttgta gctataaata aaccctctaa  1320
ccctcgtcgc attacttctc ttcaca                                       1346
```

<210> SEQ ID NO 33
<211> LENGTH: 22
<212> TYPE: DNA
<213> ORGANISM: Artificial Sequence
<220> FEATURE:
<223> OTHER INFORMATION: Shared Element

<400> SEQUENCE: 33
aacacccaac cacctcctgc tc                                             22

<210> SEQ ID NO 34
<211> LENGTH: 12
<212> TYPE: DNA
<213> ORGANISM: Artificial Sequence
<220> FEATURE:
<223> OTHER INFORMATION: Shared Element

<400> SEQUENCE: 34 ccwaccccctc ct                                                       12

<210> SEQ ID NO 35
<211> LENGTH: 10
<212> TYPE: DNA
<213> ORGANISM: Artificial Sequence
<220> FEATURE:
<223> OTHER INFORMATION: Shared Element

<400> SEQUENCE: 35
ggaacatcca                                                           10

<210> SEQ ID NO 36
<211> LENGTH: 11
<212> TYPE: DNA
<213> ORGANISM: Artificial Sequence
<220> FEATURE:
<223> OTHER INFORMATION: Shared Element

```
<400> SEQUENCE: 36
catccaccat t                                                       11

<210> SEQ ID NO 37
<211> LENGTH: 15
<212> TYPE: DNA
<213> ORGANISM: Artificial Sequence
<220> FEATURE:
<223> OTHER INFORMATION: Shared Sequence

<400> SEQUENCE: 37
gcctatttaa ggagc                                                   15

<210> SEQ ID NO 38
<211> LENGTH: 10
<212> TYPE: DNA
<213> ORGANISM: Artificial Sequence
<220> FEATURE:
<223> OTHER INFORMATION: Shared Sequence
<220> FEATURE:
<221> NAME/KEY: misc_feature
<222> LOCATION: (3)..(4)
<223> OTHER INFORMATION: n is a, c, g, or t

<400> SEQUENCE: 38 canntgyact                                                         10

<210> SEQ ID NO 39
<211> LENGTH: 10
<212> TYPE: DNA
<213> ORGANISM: Artificial Sequence
<220> FEATURE:
<223> OTHER INFORMATION: Shared Sequence

<400> SEQUENCE: 39
gcattccaaa                                                         10

<210> SEQ ID NO 40
<211> LENGTH: 15
<212> TYPE: DNA
<213> ORGANISM: Artificial Sequence
<220> FEATURE:
<223> OTHER INFORMATION: Shared Sequence

<400> SEQUENCE: 40
atgtacgaag cgtac                                                   15

<210> SEQ ID NO 41
<211> LENGTH: 24
<212> TYPE: DNA
<213> ORGANISM: Artificial Sequence
<220> FEATURE:
<223> OTHER INFORMATION: Shared Sequence

<400> SEQUENCE: 41
agttagttac agttagttaa aaga                                         24

<210> SEQ ID NO 42
<211> LENGTH: 12
<212> TYPE: DNA
<213> ORGANISM: Artificial Sequence
<220> FEATURE:
<223> OTHER INFORMATION: Shared Sequence
<220> FEATURE:
<221> NAME/KEY: misc_feature
<222> LOCATION: (2)..(2)
```

```
<223> OTHER INFORMATION: n is a, c, g, or t

<400> SEQUENCE: 42
cnaacaccaa ca                                                            12

<210> SEQ ID NO 43
<211> LENGTH: 10
<212> TYPE: DNA
<213> ORGANISM: Artificial Sequence
<220> FEATURE:
<223> OTHER INFORMATION: Shared Sequence
<220> FEATURE:
<221> NAME/KEY: misc_feature
<222> LOCATION: (3)..(4)
<223> OTHER INFORMATION: n is a, c, g, or t

<400> SEQUENCE: 43 canntgyact                                                               10
```